United States Patent
Lancaster et al.

(10) Patent No.: US 9,074,015 B2
(45) Date of Patent: Jul. 7, 2015

(54) RECOMBINANTLY EXPRESSED INSULIN POLYPEPTIDES AND USES THEREOF

(75) Inventors: Thomas M. Lancaster, Stoneham, MA (US); Sylaja Murikipudi, Medford, MA (US); Rassol Laleau, Woburn, MA (US); Todd C. Zion, Marblehead, MA (US)

(73) Assignee: SMARTCELLS, INC., Whitehouse Station, NJ (US)

( * ) Notice: Subject to any disclaimer, the term of this patent is extended or adjusted under 35 U.S.C. 154(b) by 0 days.

(21) Appl. No.: 13/811,910

(22) PCT Filed: Jul. 22, 2011

(86) PCT No.: PCT/US2011/045008
§ 371 (c)(1),
(2), (4) Date: Jan. 24, 2013

(87) PCT Pub. No.: WO2012/015692
PCT Pub. Date: Feb. 2, 2012

(65) Prior Publication Data
US 2013/0190476 A1 Jul. 25, 2013

Related U.S. Application Data

(60) Provisional application No. 61/368,607, filed on Jul. 28, 2010.

(51) Int. Cl.
*C07K 14/62* (2006.01)
*A61K 38/28* (2006.01)

(52) U.S. Cl.
CPC *C07K 14/62* (2013.01); *A61K 38/28* (2013.01)

(58) Field of Classification Search
CPC .......... A61K 38/28; C07K 14/62; C07K 5/00; C07K 7/00; C07K 16/00; C07K 17/00
See application file for complete search history.

(56) References Cited

U.S. PATENT DOCUMENTS

| | | |
|---|---|---|
| 3,591,574 A | 7/1971 | Fenichel et al. |
| 3,684,791 A | 8/1972 | Geiger et al. |
| 3,847,890 A | 11/1974 | Green et al. |
| 4,348,387 A | 9/1982 | Brownlee et al. |
| 4,372,948 A | 2/1983 | Yoshikumi et al. |
| 4,377,567 A | 3/1983 | Geho |
| 4,444,683 A | 4/1984 | Kim et al. |
| 4,603,044 A | 7/1986 | Geho et al. |
| 4,863,896 A | 9/1989 | Geho et al. |
| 5,239,062 A | 8/1993 | Blattler et al. |
| 5,395,924 A | 3/1995 | Blattler et al. |
| 5,461,031 A | 10/1995 | De Felippis |
| 5,478,575 A | 12/1995 | Miyazaki et al. |
| 5,527,524 A | 6/1996 | Tomalia et al. |
| 5,563,056 A | 10/1996 | Swan et al. |
| 5,723,589 A | 3/1998 | Miljkovic et al. |
| 5,830,506 A | 11/1998 | Taylor |
| 5,843,886 A | 12/1998 | Weiner et al. |
| 5,854,208 A | 12/1998 | Jones et al. |
| 5,866,538 A | 2/1999 | Norup et al. |
| 5,902,607 A | 5/1999 | Taylor |
| 5,905,140 A | 5/1999 | Hansen |
| 5,922,675 A | 7/1999 | Baker et al. |
| 5,948,751 A | 9/1999 | Kimer et al. |
| 5,994,517 A | 11/1999 | Ts'o et al. |
| 6,034,054 A | 3/2000 | DeFelippis et al. |
| 6,180,757 B1 | 1/2001 | Bogsnes |
| 6,214,547 B1 | 4/2001 | Kjeldsen et al. |
| 6,323,311 B1 | 11/2001 | Liu et al. |
| 6,342,225 B1 | 1/2002 | Jones et al. |
| 6,410,053 B1 | 6/2002 | Taylor |
| 6,500,645 B1 | 12/2002 | Kjeldsen et al. |
| 6,521,738 B2 | 2/2003 | Kjeldsen et al. |
| 6,551,992 B1 | 4/2003 | DeFelippis et al. |
| 6,777,207 B2 | 8/2004 | Kjeldsen et al. |

(Continued)

FOREIGN PATENT DOCUMENTS

| | | |
|---|---|---|
| CN | 101273961 | 10/2008 |
| EP | 009842 | 4/1980 |

(Continued)

OTHER PUBLICATIONS

UniProtKB/Swiss-Prot Accession No. P01314 (accessed Aug. 20, 2014 at URL uniprot.org/uniprot/P01314).*
UniProtKB/Swiss-Prot Accession No. C9JNR5 (accessed Aug. 20, 2014 at URL uniprot.org/uniprot/C9JNR5).*
UniProtKB/Swiss-Prot Accession No. P30410 (accessed Aug. 20, 2014 at URL uniprot.org/uniprot/P30410).*
Zion, Bringing the Cure Home, Slideshare.net, PowerPoint presentation-2-1319001 (Apr. 6, 2009).
Chu, Smart Insulin, MIT Technology Review, p. 2, (Oct. 30, 2008).
Baudys, et al., "Physical Stabilization of Insulin by Glycosylation" *J Pharma Sci* (1995) 64: 28-33.
Brownlee & Cerami, "A Glucose-Controlled-Insulin-Delivery-System: Semisynthetic Insulin Bound to Lectin" *Diabetes* (1983) 32:499-504.

(Continued)

*Primary Examiner* — Julie Ha
*Assistant Examiner* — Kristina M Hellman
(74) *Attorney, Agent, or Firm* — Immac J. Thampoe; John David Reilly

(57) ABSTRACT

The present disclosure provides recombinantly expressed insulin polypeptides that comprise an N-linked glycan motif. The N-linked glycan motif is not present in wild-type insulins and enables the recombinant expression of glycosylated insulin polypeptides (e.g., in yeast cells). Based on results obtained with synthetic glycosylated insulin conjugates we predict that when these recombinant glycosylated insulin polypeptides are administered to a mammal, at least one pharmacokinetic or pharmacodynamic property of the glycosylated insulin polypeptide will be sensitive to serum concentrations of glucose (or an exogenous saccharide such as alpha-methyl mannose). Exemplary insulin polypeptides, polynucleotides encoding these insulin polypeptides, glycosylated insulin polypeptides, pharmaceutical formulations and sustained release formulations are provided in addition to methods of use and preparation.

7 Claims, 50 Drawing Sheets

(56) References Cited

U.S. PATENT DOCUMENTS

| | | |
|---|---|---|
| 6,844,166 B1 | 1/2005 | Wolf |
| 6,869,930 B1 | 3/2005 | Havelund et al. |
| RE39,055 E | 4/2006 | Jones et al. |
| 7,063,863 B2 | 6/2006 | Taylor |
| 7,087,408 B2 | 8/2006 | Kjeldsen et al. |
| 7,101,971 B2 | 9/2006 | Meade et al. |
| 7,105,314 B2 | 9/2006 | Kjeldsen |
| 7,138,371 B2 | 11/2006 | DeFrees et al. |
| 7,316,999 B2 | 1/2008 | Hoeg-Jensen et al. |
| 7,317,000 B2 | 1/2008 | Hoeg-Jensen et al. |
| 7,423,014 B2 | 9/2008 | Ekwuribe et al. |
| 7,531,191 B2 | 5/2009 | Zion et al. |
| 7,687,608 B2 | 3/2010 | Lancaster et al. |
| 8,062,668 B2 | 11/2011 | Ying et al. |
| 2006/0019874 A1 | 1/2006 | Radhakrishnan et al. |
| 2006/0216265 A1 | 9/2006 | Goodman et al. |
| 2006/0247154 A1 | 11/2006 | Palmieri et al. |
| 2007/0099820 A1 | 5/2007 | Lancaster et al. |
| 2007/0207498 A1 | 9/2007 | Palmieri et al. |
| 2009/0053167 A1 | 2/2009 | DeFrees |
| 2009/0137454 A1 | 5/2009 | Fynbo et al. |
| 2010/0130726 A1 | 5/2010 | Lancaster et al. |
| 2010/0266698 A1 | 10/2010 | Filvaroff et al. |
| 2010/0298212 A1 | 11/2010 | Miao et al. |
| 2011/0275560 A1 | 11/2011 | Zion et al. |
| 2011/0281791 A1 | 11/2011 | Zion et al. |
| 2011/0281792 A1 | 11/2011 | Zion et al. |
| 2011/0281939 A1 | 11/2011 | Zion et al. |
| 2011/0301083 A1 | 12/2011 | Zion et al. |
| 2012/0046223 A1 | 2/2012 | Zion et al. |

FOREIGN PATENT DOCUMENTS

| | | |
|---|---|---|
| EP | 0119650 | 9/1984 |
| EP | 0725648 | 8/1996 |
| RU | 2381238 | 8/2009 |
| WO | WO81/00354 | 2/1981 |
| WO | WO84/01896 | 5/1984 |
| WO | WO90/10645 | 9/1990 |
| WO | WO 9211378 A1 * | 7/1992 |
| WO | WO99/52934 | 10/1999 |
| WO | WO01/92334 | 12/2001 |
| WO | WO03/018636 | 3/2003 |
| WO | WO03/035011 | 5/2003 |
| WO | WO03/047462 | 6/2003 |
| WO | WO03/048915 | 6/2003 |
| WO | WO03/074087 | 9/2003 |
| WO | WO2004/057002 | 7/2004 |
| WO | WO2006/008238 | 1/2006 |
| WO | WO2006/082184 | 8/2006 |
| WO | WO2006/088473 | 8/2006 |
| WO | WO2006/102762 | 10/2006 |
| WO | WO2007/042470 | 4/2007 |
| WO | WO2007/043050 | 4/2007 |
| WO | WO2008/012440 | 1/2008 |
| WO | WO2008/012528 | 1/2008 |
| WO | WO2008/036147 | 3/2008 |
| WO | WO2008/065372 | 6/2008 |
| WO | WO2009/033588 | 3/2009 |
| WO | WO2009/059450 | 5/2009 |
| WO | WO92/11378 | 7/2009 |
| WO | WO2009/089396 | 7/2009 |
| WO | WO2009/104199 | 8/2009 |
| WO | WO2010/001134 | 1/2010 |
| WO | WO 2010001134 A2 * | 1/2010 |
| WO | WO2010088294 | 8/2010 |
| WO | WO2011/000823 | 1/2011 |

OTHER PUBLICATIONS

Brownlee & Cerami, "Glycosylated Insulin Complexed to Concanavalin A" *Science* (1979) 206:1190-1191.

Dea, et al., "Albumin Binding of Acylated Insulin (NN304) Does Not Deter Action to Stimulate Glucose Uptake" *Diabetes* (2002) 51: 762-769.

Eggert, et al., "A New Glucose Selective Fluorescent Bisboronic Acid" *J Org Chem* (1999) 64:3846-3852.

Heinnemann, et al., "Time-action profile of the soluble, fatty acid acylated, long acting insulin analogue NN304" *Diabetic Med* (1999) 16: 332-338.

Jeong, et al., "Self Regulating Insulin Delivery Systems I. Synthesis and Characterization of Glycosylated Insulin" *J of Controlled Release* (1984) 1: 57-66.

Lee et al., "Biochemistry of crbohydrate-protein interaction" *FASEB J* (1992) 3193-3200.

Monsigny, et al., "Endogenous Lectins and Drug Targeting" *Annals NY Acad Sci* (1988) 551: 399-414.

Ruziak, et al., "Basal activity profiles of NPH and [Ne-palmitoyl Lys (B29) human insulins in subjects with IDDM" *Diabetologia* (1998) 41: 116-120.

Shojaee-Moradie, "Novel Hepatoselective Insulin Analog" *Diabetes Care* (2000) 23: 1124-1129.

Yamazaki, et al., "Endogenous lectins as targets for drug delivery" *Adv Drug Delivery Rev* (2000) 43: 225-244.

Yang et al., Tissue Targeting of Multivalent GalNAc Lex Terminated N-Glycans in Mice, Glycbiology 2000, vol. 10, p. 1341-1345.

Office Action for U.S. Appl. No. 13/145,532 dated Sep. 15, 2014.

Response to Office Action for U.S. Appl. No. 13/145,532 dated Dec. 4, 2014.

* cited by examiner

Conjugate I-6
TSAT-C6-AETM-2 (B29)

Conjugate I-1
TSAT-C6-AEM-2 (B1)

Conjugate I-2
TSAT-C6-AETM-2 (B1)

Conjugate I-3
TSAT-C6-AEBM-2 (B1)

Conjugate I-4
TSAT-C6-AEBM-1-AETM-1 (B1)

Conjugate I-5
TSAT-C6-GA-2 (B29)

Conjugate I-7
TSAT-C6-AEM-2 (B29)

Conjugate I-8
TSAT-C6-AETM-2 (A1)

Conjugate I-9
TSAT-C6-AEM-2 (A1)

Conjugate I-10
TSAT-C6-Di-sub-AEM-2 (A1,B29)

Conjugate I-11
TSAT-C6-Di-sub-AETM-2 (A1,B29)

Conjugate I-12
TSAT-C6-Di-sub-AETM-2 (A1,B1)

Conjugate I-13
TSAT-C6-Di-sub-AETM-2 (B1,B29)

Conjugate I-14
TSPE-AEM-3 (B29)

Conjugate I-15
TSPE-AETM-3 (B29)

Conjugate I-16
TSPE-AETM-3 (A1)

Conjugate I-17
TSPE-AEM-3 (A1)

Conjugate I-18
TSPE-AEM-3 (B1)

| Formulation | β-phase half-line (min) for each type of infusion | | |
| --- | --- | --- | --- |
| | Saline | Glucose | α-methyl mannose |
| RHI | 2.7 | 2.3 | 3.3 |
| I-7: AEM-2 | 5.5 | 5.8 | 5.4 |
| I-6: AETM-2 | 4.8 | 3.3 | 8.1 |
| I-11: Di-sub-AETM-2 | 2.5 | n/a | 20.3 |

FIG.20

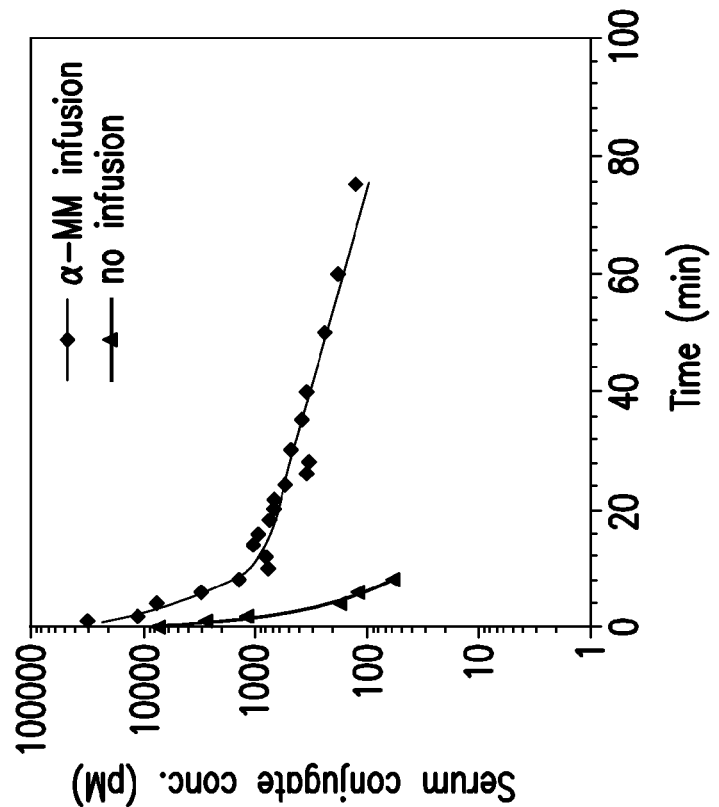
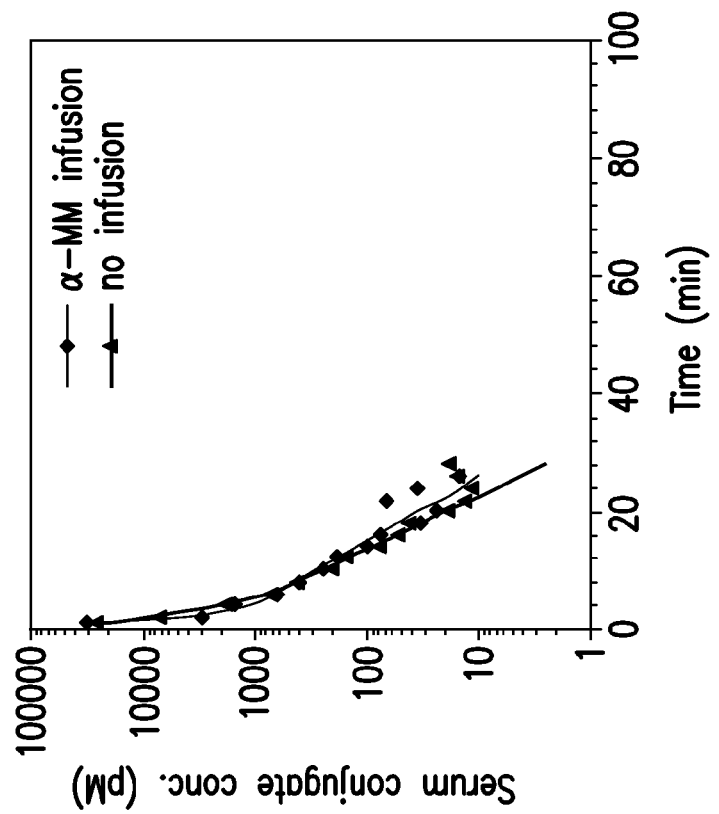
FIG. 21A
FIG. 21B

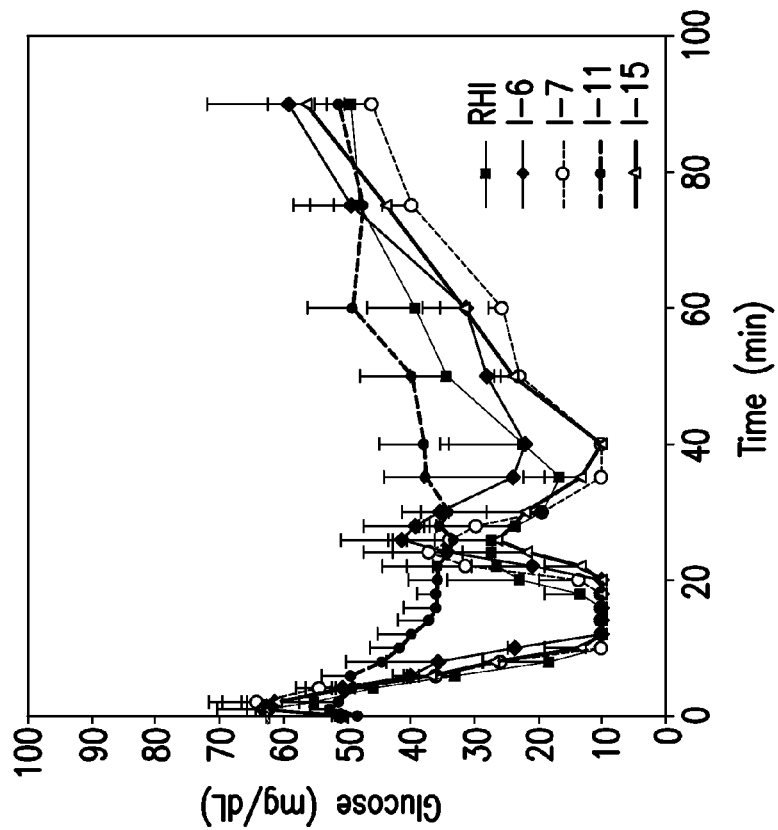
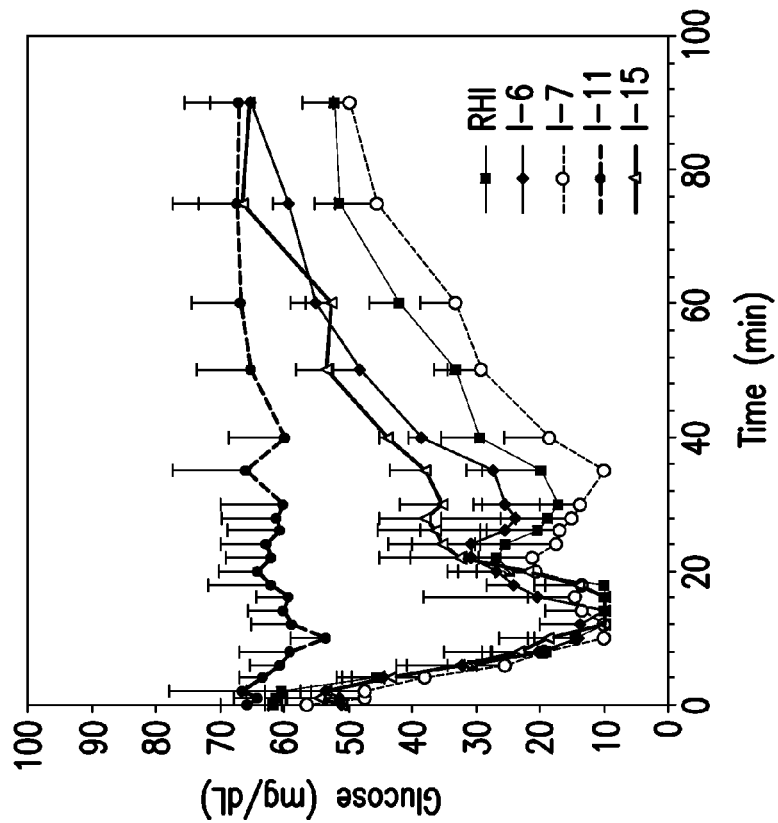
FIG. 22A
FIG. 22B

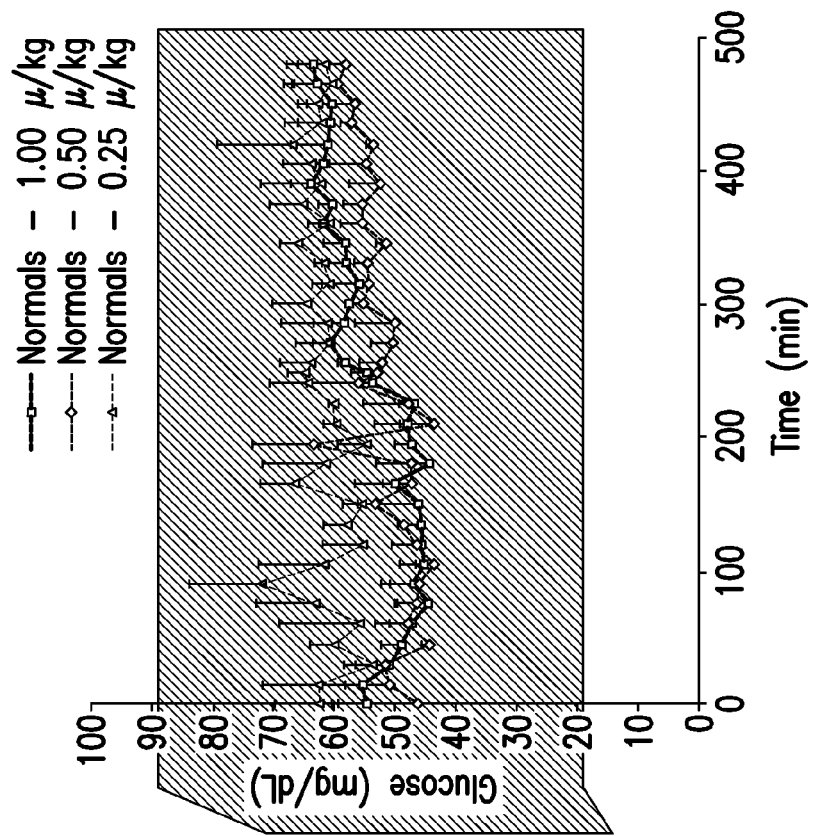
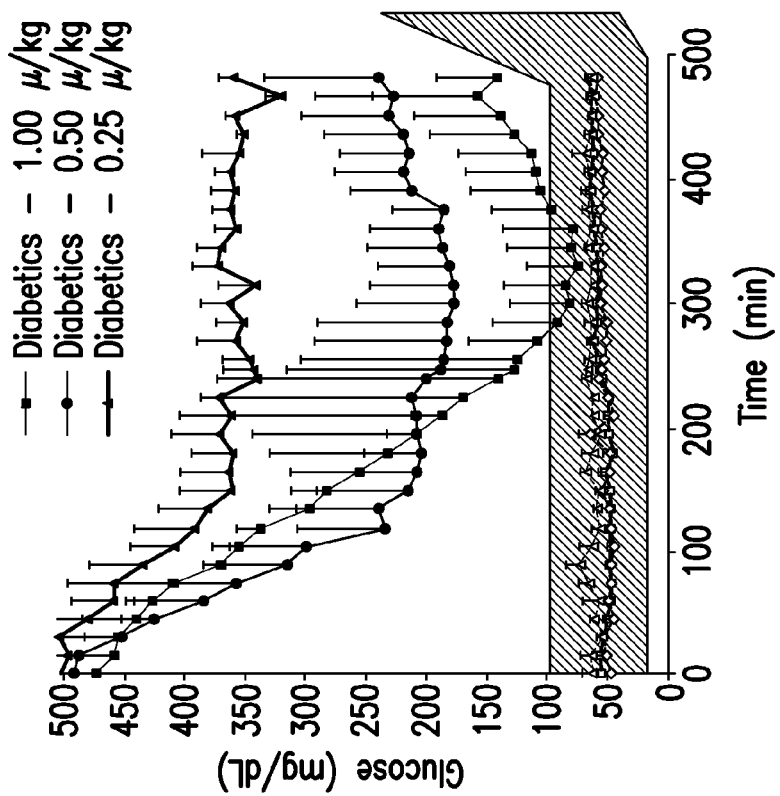
FIG. 23A
FIG. 23B

| Insulin-conjugate | Sugar composition | $t_{1/2,\beta}$ (α-MM) / $t_{1/2,\beta}$ (No Inf) |
|---|---|---|
| I-11 | B29: AETMx2, A1: AETMx2 | 8.1 |
| I-8 | A1: AETMx2 | 2.3 |
| I-6 | B29: AETMx2 | 1.7 |
| I-10 | B29: AEMx2, A1: AEMx2 | 1.5 |
| RHI | n/a | 1.2 |
| I-7 | B29: AEMx2 | 0.9 |

SEQUENCE LISTING

<160> NUMBER OF SEQ ID NOS: 54

<210> SEQ ID NO 1
<211> LENGTH: 23
<212> TYPE: PRT
<213> ORGANISM: Artificial Sequence
<220> FEATURE:
<223> OTHER INFORMATION: Insulin analog A-chain of I'
<220> FEATURE:
<221> NAME/KEY: VARIANT

```
<222> LOCATION: (1)..(1)
<223> OTHER INFORMATION: Xaa= any codable amino acid or missing
<220> FEATURE:
<221> NAME/KEY: DISULFID
<222> LOCATION: (7)..(12)
<223> OTHER INFORMATION: disulfide between Cys7 and Cys12
<220> FEATURE:
<221> NAME/KEY: DISULFID
<222> LOCATION: (8)..(8)
<223> OTHER INFORMATION: disulfide between Cys8 and Cys8 of SEQ ID NO:2
<220> FEATURE:
<221> NAME/KEY: VARIANT
<222> LOCATION: (10)..(10)
<223> OTHER INFORMATION: Xaa= any codable amino acid; or T or A
<220> FEATURE:
<221> NAME/KEY: VARIANT
<222> LOCATION: (16)..(16)
<223> OTHER INFORMATION: Xaa= any codable amino acid;
<220> FEATURE:
<221> NAME/KEY: VARIANT
<222> LOCATION: (19)..(19)
<223> OTHER INFORMATION: Xaa= any codable amino acid
<220> FEATURE:
<221> NAME/KEY: DISULFID
<222> LOCATION: (21)..(21)
<223> OTHER INFORMATION: disulfide between Cys21 and Cys20 of
      SEQ ID NO:2
<220> FEATURE:
<221> NAME/KEY: VARIANT
<222> LOCATION: (22)..(22)
<223> OTHER INFORMATION: Xaa= any codable amino acid; or N, D, E, G, or
      A
<220> FEATURE:
<221> NAME/KEY: VARIANT
<222> LOCATION: (22)..(22)
<223> OTHER INFORMATION: Xaa= any codable amino acid
<220> FEATURE:
<221> NAME/KEY: VARIANT
<222> LOCATION: (23)..(23)
<223> OTHER INFORMATION: Xaa= any codable amino acid or missing

<400> SEQUENCE: 1

Xaa Gly Ile Val Glu Gln Cys Cys Xaa Xaa Xaa Cys Ser Leu Tyr Xaa
1               5                   10                  15

Leu Glu Xaa Tyr Cys Xaa Xaa
            20

<210> SEQ ID NO 2
<211> LENGTH: 32
<212> TYPE: PRT
<213> ORGANISM: Artificial Sequence
<220> FEATURE:
<223> OTHER INFORMATION: Insulin analog B-chain of I'
<220> FEATURE:
<221> NAME/KEY: VARIANT
<222> LOCATION: (1)..(1)
<223> OTHER INFORMATION: Xaa= any codable amino acid or missing
<220> FEATURE:
<221> NAME/KEY: VARIANT
<222> LOCATION: (2)..(2)
<223> OTHER INFORMATION: Xaa= any codable amino acid
<220> FEATURE:
<221> NAME/KEY: VARIANT
<222> LOCATION: (3)..(3)
<223> OTHER INFORMATION: Xaa= any codable amino acid
<220> FEATURE:
<221> NAME/KEY: VARIANT
<222> LOCATION: (4)..(4)
<223> OTHER INFORMATION: Xaa= any codable amino acid; or N, K, D, or E,
      or missing
<220> FEATURE:
<221> NAME/KEY: VARIANT
<222> LOCATION: (5)..(5)
<223> OTHER INFORMATION: Xaa= any codable amino acid; or N, K, D, or E,
      or missing
<220> FEATURE:
```

```
<221> NAME/KEY: misc_feature
<222> LOCATION: (6)..(6)
<223> OTHER INFORMATION: Xaa can be any naturally occurring amino acid
<220> FEATURE:
<221> NAME/KEY: DISULFID
<222> LOCATION: (8)..(8)
<223> OTHER INFORMATION: disulfide between Cys8 and Cys8 of SEQ ID NO:1
<220> FEATURE:
<221> NAME/KEY: VARIANT
<222> LOCATION: (10)..(14)
<223> OTHER INFORMATION: Xaa= any codable amino acid
<220> FEATURE:
<221> NAME/KEY: DISULFID
<222> LOCATION: (20)..(20)
<223> OTHER INFORMATION: disulfide between Cys20 and Cys21 of SEQ ID
      NO:1
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: VARIANT
<222> LOCATION: (22)..(22)
<223> OTHER INFORMATION: Xaa= any codable amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: VARIANT
<222> LOCATION: (27)..(31)
<223> OTHER INFORMATION: Xaa= any codable amino acid
<220> FEATURE:
<221> NAME/KEY: VARIANT
<222> LOCATION: (32)..(32)
<223> OTHER INFORMATION: Xaa= any codable amino acid or missing

<400> SEQUENCE: 2

Xaa Xaa Xaa Xaa Xaa Xaa Leu Cys Gly Xaa Xaa Xaa Xaa Ala Leu Tyr
1               5                   10                  15

Leu Val Cys Gly Xaa Arg Gly Phe Phe Xaa Xaa Xaa Xaa Xaa Xaa
            20                  25                  30

<210> SEQ ID NO 3
<211> LENGTH: 447
<212> TYPE: DNA
<213> ORGANISM: Artificial Sequence
<220> FEATURE:
<223> OTHER INFORMATION: Encodes RHI-1

<400> SEQUENCE: 3
atgagattcc catctatctt cactgctgtt tgttcgctg cttcttctgc tttggctgct      60
cctgttaaca ctactactga agacgaaact gctcaaatcc cagctgaagc ggttatcggt    120
tactctgact tggaaggtga cttcgacgtt gctgttttgc cttctctaa ctctactaat    180 aatggtttgt tgttcatcaa cactactatc gcttctatcg ctgctaagga gagggtgtt    240 tctatggcta agagagaaga agctgaagct gaagctgaac caaagtttgt taaccaacac    300
ttgtgtggtt ctcacttggt tgaagctttg tacttggttt gtggtgaaag aggtttcttc    360
tacactccaa aggctgctaa gggtatcgtt gaacaatgtt gtacttctat ctgttctttg    420
taccaattgg aaaactactg taactaa                                        447

<210> SEQ ID NO 4
<211> LENGTH: 435
<212> TYPE: DNA
<213> ORGANISM: Artificial Sequence
<220> FEATURE:
<223> OTHER INFORMATION: Encodes RHI-2
```

<400> SEQUENCE: 4

```
atgagattcc catctatctt cactgctgtt ttgttcgctg cttcttctgc tttggctgct    60
cctgttaaca ctactactga agacgaaact gctcaaatcc cagctgaagc ggttatcggt   120
tactctgact tggaaggtga cttcgacgtt gctgttttgc ctttctctaa ctctactaat   180
aatggtttgt tgttcatcaa cactactatc gcttctatcg ctgctaagga gagggtgtt    240
tctatggcta agagagacga cggtgaccca gatttgttaa ccaacacttg tgtggttct    300
cacttggttg aagctttgta cttggtttgt ggtgaaagag gtttcttcta cactccaaag   360
gacgaaagag gtatcgttga acaatgttgt acttctatct gttctttgta ccaattggaa   420
aactactgta actaa                                                     435
```

<210> SEQ ID NO 5
<211> LENGTH: 447
<212> TYPE: DNA
<213> ORGANISM: Artificial Sequence
<220> FEATURE:
<223> OTHER INFORMATION: Encodes RHI-3

<400> SEQUENCE: 5

```
atgagattcc catctatctt cactgctgtt ttgttcgctg cttcttctgc tttggctgct    60
cctgttaaca ctactactga agacgaaact gctcaaatcc cagctgaagc ggttatcggt   120
tactctgact tggaaggtga cttcgacgtt gctgttttgc ctttctctaa ctctactaat   180
aatggtttgt tgttcatcaa cactactatc gcttctatcg ctgctaagga gagggtgtt    240
tctatggcta agagagaaga agctgaagct gaagctgaac aaagtttgt taaccaacac   300
ttgtgtggtt ctcacttggt tgaagctttg tacttggttt gtggtgaaag aggtttcttc   360
tacactccaa aggacgaaag aggtatcgtt gaacaatgtt gtacttctat ctgttctttg   420
taccaattgg aaaaactactg taactaa                                       447
```

<210> SEQ ID NO 6
<211> LENGTH: 447
<212> TYPE: DNA
<213> ORGANISM: Artificial Sequence
<220> FEATURE:
<223> OTHER INFORMATION: Encodes RAT-1

<400> SEQUENCE: 6

```
atgagattcc catctatctt cactgctgtt ttgttcgctg cttcttctgc tttggctgct    60
cctgttaaca ctactactga agacgaaact gctcaaatcc cagctgaagc ggttatcggt   120
tactctgact tggaaggtga cttcgacgtt gctgttttgc ctttctctaa ctctactaat   180
aatggtttgt tgttcatcaa cactactatc gcttctatcg ctgctaagga gagggtgtt    240
tctatggcta agagagaaga agctgaagct gaagctgaac aaagtttgt taagcaacac   300
ttgtgtggtc tcacttggt tgaagctttg tacttggttt gtggtgaaag aggtttcttc    360
tacactccaa aggctgctaa gggtatcgtt gaccaatgtt gtacttctat ctgttctttg   420
taccaattgg aaaaactactg taactaa                                       447
```

<210> SEQ ID NO 7
<211> LENGTH: 435
<212> TYPE: DNA
<213> ORGANISM: Artificial Sequence
<220> FEATURE:
<223> OTHER INFORMATION: Encodes RHI-4

<400> SEQUENCE: 7

```
atgagattcc catctatctt cactgctgtt tgttcgctg cttcttctgc tttggctgct      60
cctgttaaca ctactactga agacgaaact gctcaaatcc cagctgaagc ggttatcggt    120
tactctgact tggaaggtga cttcgacgtt gctgttttgc ctttctctaa ctctactaat    180
aatggtttgt tgttcatcaa cactactatc gcttctatcg ctgctaagga gagggtgtt    240 tctatggcta agagagacga cggtgaccca agatttgtta accaacactt gtgtggttct    300
cacttggttg aagctttgta cttggttgt ggtgaaagag gtttcttcta cactccaaag    360
gctgctaagg gtatcgttga acaatgttgt acttctatct gttctttgta ccaattggaa    420
aactactgta actaa                                                     435
```

<210> SEQ ID NO 8
<211> LENGTH: 66
<212> TYPE: PRT
<213> ORGANISM: Artificial Sequence
<220> FEATURE:
<223> OTHER INFORMATION: pro-leader peptide

<400> SEQUENCE: 8

Ala Pro Val Asn Thr Thr Thr Glu Asp Glu Thr Ala Gln Ile Pro Ala
1               5                   10                  15

Glu Ala Val Ile Gly Tyr Ser Asp Leu Glu Gly Asp Phe Asp Val Ala
            20                  25                  30

Val Leu Pro Phe Ser Asn Ser Thr Asn Asn Gly Leu Leu Phe Ile Asn
        35                  40                  45

Thr Thr Ile Ala Ser Ile Ala Ala Lys Glu Glu Gly Val Ser Met Ala
    50                  55                  60

Lys Arg
65

<210> SEQ ID NO 9
<211> LENGTH: 10
<212> TYPE: PRT
<213> ORGANISM: Artificial Sequence
<220> FEATURE:
<223> OTHER INFORMATION: leader peptide

<400> SEQUENCE: 9

Glu Glu Ala Glu Ala Glu Ala Glu Pro Lys
1               5                   10

<210> SEQ ID NO 10
<211> LENGTH: 6
<212> TYPE: PRT
<213> ORGANISM: Artificial Sequence
<220> FEATURE:
<223> OTHER INFORMATION: leader peptide

<400> SEQUENCE: 10

Asp Asp Gly Asp Pro Arg
1               5

<210> SEQ ID NO 11
<211> LENGTH: 53
<212> TYPE: PRT
<213> ORGANISM: Artificial Sequence
<220> FEATURE:
<223> OTHER INFORMATION: B-C-A peptides

<400> SEQUENCE: 11

Phe Val Asn Gln His Leu Cys Gly Ser His Leu Val Glu Ala Leu Tyr

```
1               5                   10                  15
Leu Val Cys Gly Glu Arg Gly Phe Phe Tyr Thr Pro Lys Ala Ala Lys
            20                  25                  30

Gly Ile Val Glu Gln Cys Cys Thr Ser Ile Cys Ser Leu Tyr Gln Leu
        35                  40                  45

Glu Asn Tyr Cys Asn
    50

<210> SEQ ID NO 12
<211> LENGTH: 53
<212> TYPE: PRT
<213> ORGANISM: Artificial Sequence
<220> FEATURE:
<223> OTHER INFORMATION: B-C-A peptides

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Asp Glu Arg
            20                  25                  30

Gly Ile Val Glu Gln Cys Cys Thr Ser Ile Cys Ser Leu Tyr Gln Leu
        35                  40                  45

Glu Asn Tyr Cys Asn
    50

<210> SEQ ID NO 13
<211> LENGTH: 29
<212> TYPE: PRT
<213> ORGANISM: Artificial Sequence
<220> FEATURE:
<223> OTHER INFORMATION: B peptide

<400> SEQUENCE: 13

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 14
<211> LENGTH: 35
<212> TYPE: PRT
<213> ORGANISM: Artificial Sequence
<220> FEATURE:
<223> OTHER INFORMATION: B peptide

<400> SEQUENCE: 14

Asp Gly Gly Asp Pro Arg Phe Val Asn Gln His Leu Cys Gly Ser His
1               5                   10                  15

Leu Val Glu Ala Leu Tyr Leu Val Cys Gly Glu Arg Gly Phe Phe Tyr
            20                  25                  30

Thr Pro Lys
        35

<210> SEQ ID NO 15
<211> LENGTH: 29
<212> TYPE: PRT
<213> ORGANISM: Artificial Sequence
<220> FEATURE:
<223> OTHER INFORMATION: B peptide

<400> SEQUENCE: 15

Phe Val Lys Gln His Leu Cys Gly Pro His Leu Val Glu Ala Leu Tyr
```

```
                1               5                   10                  15
Leu Val Cys Gly Glu Arg Gly Phe Phe Tyr Thr Pro Lys
            20                  25

<210> SEQ ID NO 16
<211> LENGTH: 3
<212> TYPE: PRT
<213> ORGANISM: Artificial Sequence
<220> FEATURE:
<223> OTHER INFORMATION: C peptide

<400> SEQUENCE: 16

Ala Ala Lys
1

<210> SEQ ID NO 17
<211> LENGTH: 3
<212> TYPE: PRT
<213> ORGANISM: Artificial Sequence
<220> FEATURE:
<223> OTHER INFORMATION: C peptide

<400> SEQUENCE: 17

Asp Glu Arg
1

<210> SEQ ID NO 18
<211> LENGTH: 21
<212> TYPE: PRT
<213> ORGANISM: Artificial Sequence
<220> FEATURE:
<223> OTHER INFORMATION: A peptide

<400> SEQUENCE: 18

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 19
<211> LENGTH: 21
<212> TYPE: PRT
<213> ORGANISM: Artificial Sequence
<220> FEATURE:
<223> OTHER INFORMATION: A peptide

<400> SEQUENCE: 19

Gly Ile Val Asp Gln Cys Cys Thr Ser Ile Cys Ser Leu Tyr Gln Leu
1               5                   10                  15

Glu Asn Tyr Cys Asn
            20

<210> SEQ ID NO 20
<211> LENGTH: 21
<212> TYPE: PRT
<213> ORGANISM: Homo sapiens

<400> SEQUENCE: 20

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 21
```

```
<211> LENGTH: 30
<212> TYPE: PRT
<213> ORGANISM: Homo sapiens

<400> SEQUENCE: 21

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 22
<211> LENGTH: 35
<212> TYPE: PRT
<213> ORGANISM: Homo sapiens

<400> SEQUENCE: 22

Arg Arg Glu Ala Glu Asp Leu Gln Val Gly Gln Val Glu Leu Gly Gly
1               5                   10                  15

Gly Pro Gly Ala Gly Ser Leu Gln Pro Leu Ala Leu Glu Gly Ser Leu
            20                  25                  30

Gln Lys Arg
        35

<210> SEQ ID NO 23
<211> LENGTH: 10
<212> TYPE: PRT
<213> ORGANISM: Artificial Sequence
<220> FEATURE:
<223> OTHER INFORMATION: leader peptide

<400> SEQUENCE: 23

Glu Glu Ala Glu Ala Glu Ala Glu Pro Lys
1               5                   10

<210> SEQ ID NO 24
<211> LENGTH: 6
<212> TYPE: PRT
<213> ORGANISM: Artificial Sequence
<220> FEATURE:
<223> OTHER INFORMATION: leader peptide

<400> SEQUENCE: 24

Asp Asp Gly Asp Pro Arg
1               5

<210> SEQ ID NO 25
<211> LENGTH: 4
<212> TYPE: PRT
<213> ORGANISM: Artificial Sequence
<220> FEATURE:
<223> OTHER INFORMATION: C peptide

<400> SEQUENCE: 25

Thr Ala Ala Lys
1

<210> SEQ ID NO 26
<211> LENGTH: 24
<212> TYPE: PRT
<213> ORGANISM: Artificial Sequence
<220> FEATURE:
<223> OTHER INFORMATION: insulin analog A chain of formula I with the
      proviso that SEQ ID NO:26 and/or SEQ ID NO:27 includes a motif
      Asn-Xaa-Ser/Thr where Xaa is not Pro
<220> FEATURE:
<221> NAME/KEY: VARIANT
```

```
<222> LOCATION: (1)..(1)
<223> OTHER INFORMATION: Xaa= a codable amino acid or missing
<220> FEATURE:
<221> NAME/KEY: VARIANT
<222> LOCATION: (9)..(9)
<223> OTHER INFORMATION: Xaa= a codable amino acid
<220> FEATURE:
<221> NAME/KEY: VARIANT
<222> LOCATION: (10)..(10)
<223> OTHER INFORMATION: Xaa= a codable amino acid
<220> FEATURE:
<221> NAME/KEY: VARIANT
<222> LOCATION: (11)..(11)
<223> OTHER INFORMATION: Xaa= a codable amino acid
<220> FEATURE:
<221> NAME/KEY: VARIANT
<222> LOCATION: (16)..(16)
<223> OTHER INFORMATION: Xaa= a codable amino acid
<220> FEATURE:
<221> NAME/KEY: VARIANT
<222> LOCATION: (19)..(19)
<223> OTHER INFORMATION: Xaa= a codable amino acid
<220> FEATURE:
<221> NAME/KEY: VARIANT
<222> LOCATION: (22)..(22)
<223> OTHER INFORMATION: Xaa= a codable amino acid
<220> FEATURE:
<221> NAME/KEY: VARIANT
<222> LOCATION: (23)..(23)
<223> OTHER INFORMATION: Xaa= a codable amino acid
<220> FEATURE:
<221> NAME/KEY: VARIANT
<222> LOCATION: (24)..(24)
<223> OTHER INFORMATION: Xaa= a codable amino acid or missing

<400> SEQUENCE: 26

Xaa Gly Ile Val Glu Gln Cys Cys Xaa Xaa Xaa Cys Ser Leu Tyr Xaa
1               5                   10                  15

Leu Glu Xaa Tyr Cys Xaa Xaa Xaa
            20

<210> SEQ ID NO 27
<211> LENGTH: 32
<212> TYPE: PRT
<213> ORGANISM: Artificial Sequence
<220> FEATURE:
<223> OTHER INFORMATION: insulin analog B chain of formula I with the
      proviso that SEQ ID NO:26 and/or SEQ ID NO:27 includes a motif
      Asn-Xaa-Ser/Thr where Xaa is not Pro
<220> FEATURE:
<221> NAME/KEY: VARIANT
<222> LOCATION: (1)..(1)
<223> OTHER INFORMATION: Xaa= a codable amino acid or missing
<220> FEATURE:
<221> NAME/KEY: VARIANT
<222> LOCATION: (2)..(2)
<223> OTHER INFORMATION: Xaa= a codable amino acid
<220> FEATURE:
<221> NAME/KEY: VARIANT
<222> LOCATION: (3)..(3)
<223> OTHER INFORMATION: Xaa= a codable amino acid
<220> FEATURE:
<221> NAME/KEY: VARIANT
<222> LOCATION: (4)..(4)
<223> OTHER INFORMATION: Xaa= a codable amino acid
<220> FEATURE:
<221> NAME/KEY: VARIANT
<222> LOCATION: (5)..(5)
<223> OTHER INFORMATION: Xaa= a codable amino acid
<220> FEATURE:
<221> NAME/KEY: VARIANT
<222> LOCATION: (6)..(6)
<223> OTHER INFORMATION: Xaa= a codable amino acid
<220> FEATURE:
<221> NAME/KEY: VARIANT
<222> LOCATION: (10)..(10)
```

```
<223> OTHER INFORMATION: Xaa= a codable amino acid
<220> FEATURE:
<221> NAME/KEY: VARIANT
<222> LOCATION: (11)..(11)
<223> OTHER INFORMATION: Xaa= a codable amino acid
<220> FEATURE:
<221> NAME/KEY: VARIANT
<222> LOCATION: (12)..(12)
<223> OTHER INFORMATION: Xaa= a codable amino acid
<220> FEATURE:
<221> NAME/KEY: VARIANT
<222> LOCATION: (13)..(13)
<223> OTHER INFORMATION: Xaa= a codable amino acid
<220> FEATURE:
<221> NAME/KEY: VARIANT
<222> LOCATION: (14)..(14)
<223> OTHER INFORMATION: Xaa= a codable amino acid
<220> FEATURE:
<221> NAME/KEY: VARIANT
<222> LOCATION: (22)..(22)
<223> OTHER INFORMATION: Xaa= a codable amino acid
<220> FEATURE:
<221> NAME/KEY: VARIANT
<222> LOCATION: (27)..(27)
<223> OTHER INFORMATION: Xaa= a codable amino acid
<220> FEATURE:
<221> NAME/KEY: VARIANT
<222> LOCATION: (28)..(28)
<223> OTHER INFORMATION: Xaa= a codable amino acid
<220> FEATURE:
<221> NAME/KEY: VARIANT
<222> LOCATION: (29)..(29)
<223> OTHER INFORMATION: Xaa= a codable amino acid
<220> FEATURE:
<221> NAME/KEY: VARIANT
<222> LOCATION: (30)..(30)
<223> OTHER INFORMATION: Xaa= a codable amino acid
<220> FEATURE:
<221> NAME/KEY: VARIANT
<222> LOCATION: (31)..(31)
<223> OTHER INFORMATION: Xaa= a codable amino acid
<220> FEATURE:
<221> NAME/KEY: VARIANT
<222> LOCATION: (32)..(32)
<223> OTHER INFORMATION: Xaa= a codable amino acid or missing

<400> SEQUENCE: 27

Xaa Xaa Xaa Xaa Xaa Xaa Leu Cys Gly Xaa Xaa Xaa Xaa Xaa Ala Leu
 1               5                  10                  15

Tyr Leu Val Cys Gly Xaa Arg Gly Phe Phe Xaa Xaa Xaa Xaa Xaa Xaa
                20                  25                  30

<210> SEQ ID NO 28
<211> LENGTH: 23
<212> TYPE: PRT
<213> ORGANISM: Artificial Sequence
<220> FEATURE:
<223> OTHER INFORMATION: insulin analog A chain of II
<220> FEATURE:
<221> NAME/KEY: VARIANT
<222> LOCATION: (1)..(1)
<223> OTHER INFORMATION: Xaa= a codable amino acid or missing
<220> FEATURE:
<221> NAME/KEY: VARIANT
<222> LOCATION: (9)..(9)
<223> OTHER INFORMATION: Xaa= a codable amino acid
<220> FEATURE:
<221> NAME/KEY: VARIANT
<222> LOCATION: (10)..(10)
<223> OTHER INFORMATION: Xaa= a codable amino acid
<220> FEATURE:
<221> NAME/KEY: VARIANT
<222> LOCATION: (11)..(11)
<223> OTHER INFORMATION: Xaa= a codable amino acid
<220> FEATURE:
<221> NAME/KEY: VARIANT
```

-continued

<222> LOCATION: (19)..(19)
<223> OTHER INFORMATION: Xaa= a codable amino acid
<220> FEATURE:
<221> NAME/KEY: VARIANT
<222> LOCATION: (22)..(22)
<223> OTHER INFORMATION: Xaa= a codable amino acid
<220> FEATURE:
<221> NAME/KEY: VARIANT
<222> LOCATION: (23)..(23)
<223> OTHER INFORMATION: Xaa= a codable amino acid or missing

<400> SEQUENCE: 28

Xaa Gly Ile Val Glu Gln Cys Cys Xaa Xaa Xaa Cys Ser Leu Tyr Gln
1               5                   10                  15

Leu Glu Xaa Tyr Cys Xaa Xaa
            20

<210> SEQ ID NO 29
<211> LENGTH: 33
<212> TYPE: PRT
<213> ORGANISM: Artificial Sequence
<220> FEATURE:
<223> OTHER INFORMATION: insulin analog B chain of II
<220> FEATURE:
<221> NAME/KEY: VARIANT
<222> LOCATION: (1)..(1)
<223> OTHER INFORMATION: Xaa= a codable amino acid or missing
<220> FEATURE:
<221> NAME/KEY: VARIANT
<222> LOCATION: (4)..(4)
<223> OTHER INFORMATION: Xaa= a codable amino acid
<220> FEATURE:
<221> NAME/KEY: VARIANT
<222> LOCATION: (29)..(29)
<223> OTHER INFORMATION: Xaa= a codable amino acid
<220> FEATURE:
<221> NAME/KEY: VARIANT
<222> LOCATION: (30)..(30)
<223> OTHER INFORMATION: Xaa= a codable amino acid
<220> FEATURE:
<221> NAME/KEY: VARIANT
<222> LOCATION: (31)..(31)
<223> OTHER INFORMATION: Xaa= a codable amino acid
<220> FEATURE:
<221> NAME/KEY: VARIANT
<222> LOCATION: (32)..(32)
<223> OTHER INFORMATION: Xaa= a codable amino acid or missing
<220> FEATURE:
<221> NAME/KEY: misc_feature
<222> LOCATION: (33)..(33)
<223> OTHER INFORMATION: Xaa can be any naturally occurring amino acid

<400> SEQUENCE: 29

Xaa Phe Val Xaa Gln His Leu Cys Gly Ser His Leu Val Glu Ala Leu
1               5                   10                  15

Tyr Leu Val Cys Gly Glu Arg Gly Phe Phe Tyr Thr Xaa Xaa Xaa Xaa
            20                  25                  30

Xaa

<210> SEQ ID NO 30
<211> LENGTH: 4
<212> TYPE: PRT
<213> ORGANISM: Artificial Sequence
<220> FEATURE:
<223> OTHER INFORMATION: C peptide
<220> FEATURE:
<221> NAME/KEY: VARIANT
<222> LOCATION: (3)..(3)
<223> OTHER INFORMATION: Xaa= Lys/Arg
<220> FEATURE:
<221> NAME/KEY: VARIANT
<222> LOCATION: (4)..(4)

<223> OTHER INFORMATION: Xaa= Lys/Arg

<400> SEQUENCE: 30

Gly Asn Xaa Xaa
1

<210> SEQ ID NO 31
<211> LENGTH: 450
<212> TYPE: DNA
<213> ORGANISM: Artificial Sequence
<220> FEATURE:
<223> OTHER INFORMATION: encodes RHI-5G

<400> SEQUENCE: 31

| atgagattcc catctatctt cactgctgtt tgttcgctg cttcttctgc tttggctgct | 60 |
| cctgttaaca ctactactga agacgaaact gctcaaatcc cagctgaagc ggttatcggt | 120 |
| tactctgact tggaaggtga cttcgacgtt gctgttttgc cttctctcaa ctctactaat | 180 |
| aatggtttgt tgttcatcaa cactactatc gcttctatcg ctgctaagga gagggtgtt | 240 |
| tctatggcta agagagaaga agctgaagct gaagctgaac caaagtttgt taaccaacac | 300 |
| ttgtgtggtt ctcacttggt tgaagctttg tacttggttt gtggtgaaag aggtttcttc | 360 |
| tacactaaca agactgctgc taagggtatc gttgaacaat gttgtacttc tatctgttct | 420 |
| ttgtaccaat tggaaaacta ctgtaactaa | 450 |

<210> SEQ ID NO 32
<211> LENGTH: 450
<212> TYPE: DNA
<213> ORGANISM: Artificial Sequence
<220> FEATURE:
<223> OTHER INFORMATION: encodes RHI-6G

<400> SEQUENCE: 32

| atgagattcc catctatctt cactgctgtt tgttcgctg cttcttctgc tttggctgct | 60 |
| cctgttaaca ctactactga agacgaaact gctcaaatcc cagctgaagc ggttatcggt | 120 |
| tactctgact tggaaggtga cttcgacgtt gctgttttgc cttctctcaa ctctactaat | 180 |
| aatggtttgt tgttcatcaa cactactatc gcttctatcg ctgctaagga gagggtgtt | 240 |
| tctatggcta agagagaaga agctgaagct gaagctgaac caaagtttgt taaccaacac | 300 |
| ttgtgtggtt ctcacttggt tgaagctttg tacttggttt gtggtgaaag aggtttcttc | 360 |
| tacactaaca ctactaaggc tgctaagggt atcgttgaac aatgttgtac ttctatctgt | 420 |
| tctttgtacc aattggaaaa ctactgtaac | 450 |

<210> SEQ ID NO 33
<211> LENGTH: 450
<212> TYPE: DNA
<213> ORGANISM: Artificial Sequence
<220> FEATURE:
<223> OTHER INFORMATION: encodes RHI-7G

<400> SEQUENCE: 33

| atgagattcc catctatctt cactgctgtt tgttcgctg cttcttctgc tttggctgct | 60 |
| cctgttaaca ctactactga agacgaaact gctcaaatcc cagctgaagc ggttatcggt | 120 |
| tactctgact tggaaggtga cttcgacgtt gctgttttgc cttctctcaa ctctactaat | 180 |
| aatggtttgt tgttcatcaa cactactatc gcttctatcg ctgctaagga gagggtgtt | 240 |
| tctatggcta agagagaaga agctgaagct gaagctgaac caaagaacac tacttttgtt | 300 |

```
aaccaacact tgtgtggttc tcacttggtt gaagctttgt acttggtttg tggtgaaaga      360
ggtttcttct acactccaaa ggctgctaag ggtatcgttg aacaatgttg tacttctatc      420
tgttctttgt accaattgga aaactactgt                                      450
```

<210> SEQ ID NO 34
<211> LENGTH: 450
<212> TYPE: DNA
<213> ORGANISM: Artificial Sequence
<220> FEATURE:
<223> OTHER INFORMATION: encodes RHI-8G

<400> SEQUENCE: 34

```
atgagattcc catctatctt cactgctgtt ttgttcgctg cttcttctgc tttggctgct      60
cctgttaaca ctactactga agacgaaact gctcaaatcc cagctgaagc ggttatcggt      120
tactctgact tggaaggtga cttcgacgtt gctgttttgc cttttctctaa ctctactaat     180 aatggtttgt tgttcatcaa cactactatc gcttctatcg ctgctaagga agagggtgtt     240
tctatggcta agagagaaga agctgaagct gaagctgaac aaagtttgt taaccaacac      300 ttgtgtggtt ctcacttggt tgaagctttg tacttggttt gtggtgaaag aggtttcttc     360
tacactccaa ggctgctaa gaacactact ggtatcgttg aacaatgttg tacttctatc      420
tgttctttgt accaattgga aaactactgt                                      450
```

<210> SEQ ID NO 35
<211> LENGTH: 462
<212> TYPE: DNA
<213> ORGANISM: Artificial Sequence
<220> FEATURE:
<223> OTHER INFORMATION: encodes RHI-9G2

<400> SEQUENCE: 35

```
atgagattcc catctatctt cactgctgtt ttgttcgctg cttcttctgc tttggctgct      60
cctgttaaca ctactactga agacgaaact gctcaaatcc cagctgaagc ggttatcggt      120
tactctgact tggaaggtga cttcgacgtt gctgttttgc cttttctctaa ctctactaat     180 aatggtttgt tgttcatcaa cactactatc gcttctatcg ctgctaagga agagggtgtt     240
tctatggcta agagagaaga agctgaagct gaagctgaac aaagaacac tacttttgtt      300 aaccaacact tgtgtggttc tcacttggtt gaagctttgt acttggtttg tggtgaaaga     360
ggtttcttct acactaacac tactaaggct gctaaggta tcgttaaca atgttgtact       420 tctatctgtt ctttgtacca attggaaaac tactgtaact aa                        462
```

<210> SEQ ID NO 36
<211> LENGTH: 462
<212> TYPE: DNA
<213> ORGANISM: Artificial Sequence
<220> FEATURE:
<223> OTHER INFORMATION: encodes RHI-10G2

<400> SEQUENCE: 36

```
atgagattcc catctatctt cactgctgtt ttgttcgctg cttcttctgc tttggctgct      60
cctgttaaca ctactactga agacgaaact gctcaaatcc cagctgaagc ggttatcggt      120
tactctgact tggaaggtga cttcgacgtt gctgttttgc cttttctctaa ctctactaat     180 aatggtttgt tgttcatcaa cactactatc gcttctatcg ctgctaagga agagggtgtt     240
tctatggcta agagagaaga agctgaagct gaagctgaac aaagtttgt taaccaacac      300 ttgtgtggtt ctcacttggt tgaagctttg tacttggttt gtggtgaaag aggtttcttc     360
```

```
tacactaaca ctactaaggc tgctaagaac actactggta tcgttgaaca atgttgtact    420
tctatctgtt ctttgtacca attggaaaac tactgtaact aa                       462
```

<210> SEQ ID NO 37
<211> LENGTH: 54
<212> TYPE: PRT
<213> ORGANISM: Artificial Sequence
<220> FEATURE:
<223> OTHER INFORMATION: RHI-5G B-C-A peptide

<400> SEQUENCE: 37

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asn Lys Thr Ala Ala
                20                  25                  30

Lys Gly Ile Val Glu Gln Cys Cys Thr Ser Ile Cys Ser Leu Tyr Gln
            35                  40                  45

Leu Glu Asn Tyr Cys Asn
    50

<210> SEQ ID NO 38
<211> LENGTH: 55
<212> TYPE: PRT
<213> ORGANISM: Artificial Sequence
<220> FEATURE:
<223> OTHER INFORMATION: RHI-6G B-C-A peptide

<400> SEQUENCE: 38

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asn Thr Thr Lys Ala
                20                  25                  30

Ala Lys Gly Ile Val Glu Gln Cys Cys Thr Ser Ile Cys Ser Leu Tyr
            35                  40                  45

Gln Leu Glu Asn Tyr Cys Asn
    50                  55

<210> SEQ ID NO 39
<211> LENGTH: 56
<212> TYPE: PRT
<213> ORGANISM: Artificial Sequence
<220> FEATURE:
<223> OTHER INFORMATION: RHI-7G B-C-A peptide

<400> SEQUENCE: 39

Asn Thr Thr Phe Val Asn Gln His Leu Cys Gly Ser His Leu Val Glu
1               5                   10                  15

Ala Leu Tyr Leu Val Cys Gly Glu Arg Gly Phe Phe Tyr Thr Pro Lys
                20                  25                  30

Ala Ala Lys Gly Ile Val Glu Gln Cys Cys Thr Ser Ile Cys Ser Leu
            35                  40                  45

Tyr Gln Leu Glu Asn Tyr Cys Asn
    50                  55

<210> SEQ ID NO 40
<211> LENGTH: 56
<212> TYPE: PRT
<213> ORGANISM: Artificial Sequence
<220> FEATURE:
<223> OTHER INFORMATION: RHI-8G B-C-A peptide

```
<400> SEQUENCE: 40

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Ala Ala Lys
            20                  25                  30

Asn Thr Thr Gly Ile Val Glu Gln Cys Cys Thr Ser Ile Cys Ser Leu
        35                  40                  45

Tyr Gln Leu Glu Asn Tyr Cys Asn
    50                  55

<210> SEQ ID NO 41
<211> LENGTH: 58
<212> TYPE: PRT
<213> ORGANISM: Artificial Sequence
<220> FEATURE:
<223> OTHER INFORMATION: RHI-9G2 B-C-A peptide

<400> SEQUENCE: 41

Asn Thr Thr Phe Val Asn Gln His Leu Cys Gly Ser His Leu Val Glu
1               5                   10                  15

Ala Leu Tyr Leu Val Cys Gly Glu Arg Gly Phe Phe Tyr Thr Asn Thr
            20                  25                  30

Thr Lys Ala Ala Lys Gly Ile Val Glu Gln Cys Cys Thr Ser Ile Cys
        35                  40                  45

Ser Leu Tyr Gln Leu Glu Asn Tyr Cys Asn
    50                  55

<210> SEQ ID NO 42
<211> LENGTH: 58
<212> TYPE: PRT
<213> ORGANISM: Artificial Sequence
<220> FEATURE:
<223> OTHER INFORMATION: RHI-10G2 B-C-A peptide

<400> SEQUENCE: 42

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asn Thr Thr Lys Ala
            20                  25                  30

Ala Lys Asn Thr Thr Gly Ile Val Glu Gln Cys Cys Thr Ser Ile Cys
        35                  40                  45

Ser Leu Tyr Gln Leu Glu Asn Tyr Cys Asn
    50                  55

<210> SEQ ID NO 43
<211> LENGTH: 29
<212> TYPE: PRT
<213> ORGANISM: Artificial Sequence
<220> FEATURE:
<223> OTHER INFORMATION: RHI-5G B peptide

<400> SEQUENCE: 43

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asn Lys
            20                  25

<210> SEQ ID NO 44
<211> LENGTH: 31
<212> TYPE: PRT
<213> ORGANISM: Artificial Sequence
```

```
<220> FEATURE:
<223> OTHER INFORMATION: RHI-6G or RHI-10G2 B peptide

<400> SEQUENCE: 44

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asn Thr Thr Lys
            20                  25                  30

<210> SEQ ID NO 45
<211> LENGTH: 32
<212> TYPE: PRT
<213> ORGANISM: Artificial Sequence
<220> FEATURE:
<223> OTHER INFORMATION: RHI-7G B peptide

<400> SEQUENCE: 45

Asn Thr Thr Phe Val Asn Gln His Leu Cys Gly Ser His Leu Val Glu
1               5                   10                  15

Ala Leu Tyr Leu Val Cys Gly Glu Arg Gly Phe Phe Tyr Thr Pro Lys
            20                  25                  30

<210> SEQ ID NO 46
<211> LENGTH: 34
<212> TYPE: PRT
<213> ORGANISM: Artificial Sequence
<220> FEATURE:
<223> OTHER INFORMATION: RHI-9G B peptide

<400> SEQUENCE: 46

Asn Thr Thr Phe Val Asn Gln His Leu Cys Gly Ser His Leu Val Glu
1               5                   10                  15

Ala Leu Tyr Leu Val Cys Gly Glu Arg Gly Phe Phe Tyr Thr Asn Thr
            20                  25                  30

Thr Lys

<210> SEQ ID NO 47
<211> LENGTH: 24
<212> TYPE: PRT
<213> ORGANISM: Artificial Sequence
<220> FEATURE:
<223> OTHER INFORMATION: RHI-8G or RHI-10G2 A peptide

<400> SEQUENCE: 47

Asn Thr Thr Gly Ile Val Glu Gln Cys Cys Thr Ser Ile Cys Ser Leu
1               5                   10                  15

Tyr Gln Leu Glu Asn Tyr Cys Asn
            20

<210> SEQ ID NO 48
<211> LENGTH: 29
<212> TYPE: PRT
<213> ORGANISM: Artificial Sequence
<220> FEATURE:
<223> OTHER INFORMATION: RHI-5G3 B peptide
<220> FEATURE:
<221> NAME/KEY: VARIANT
<222> LOCATION: (1)..(4)
<223> OTHER INFORMATION: Xaa= independently a codable amino acid or
      missing
<220> FEATURE:
<221> NAME/KEY: VARIANT
<222> LOCATION: (5)..(5)
<223> OTHER INFORMATION: Xaa= a codable amino acid
<220> FEATURE:
<221> NAME/KEY: VARIANT
```

```
<222> LOCATION: (9)..(9)
<223> OTHER INFORMATION: Xaa= a codable amino acid
<220> FEATURE:
<221> NAME/KEY: VARIANT
<222> LOCATION: (10)..(10)
<223> OTHER INFORMATION: Xaa= a codable amino acid
<220> FEATURE:
<221> NAME/KEY: VARIANT
<222> LOCATION: (11)..(11)
<223> OTHER INFORMATION: Xaa= a codable amino acid
<220> FEATURE:
<221> NAME/KEY: VARIANT
<222> LOCATION: (12)..(12)
<223> OTHER INFORMATION: Xaa= a codable amino acid
<220> FEATURE:
<221> NAME/KEY: VARIANT
<222> LOCATION: (13)..(13)
<223> OTHER INFORMATION: Xaa= a codable amino acid
<220> FEATURE:
<221> NAME/KEY: VARIANT
<222> LOCATION: (21)..(21)
<223> OTHER INFORMATION: Xaa= a codable amino acid
<220> FEATURE:
<221> NAME/KEY: VARIANT
<222> LOCATION: (26)..(27)
<223> OTHER INFORMATION: Xaa= independently a codable amino acid or
      missing

<400> SEQUENCE: 48

Xaa Xaa Xaa Xaa Xaa Leu Cys Gly Xaa Xaa Xaa Xaa Xaa Ala Leu Tyr
1               5                   10                  15

Leu Val Cys Gly Xaa Arg Gly Phe Phe Xaa Xaa Asn Lys
            20                  25

<210> SEQ ID NO 49
<211> LENGTH: 31
<212> TYPE: PRT
<213> ORGANISM: Artificial Sequence
<220> FEATURE:
<223> OTHER INFORMATION: RHI-6G3 B peptide
<220> FEATURE:
<221> NAME/KEY: VARIANT
<222> LOCATION: (1)..(4)
<223> OTHER INFORMATION: Xaa= independently a codable amino acid or
      missing
<220> FEATURE:
<221> NAME/KEY: VARIANT
<222> LOCATION: (5)..(5)
<223> OTHER INFORMATION: Xaa= a codable amino acid
<220> FEATURE:
<221> NAME/KEY: VARIANT
<222> LOCATION: (9)..(9)
<223> OTHER INFORMATION: Xaa= a codable amino acid
<220> FEATURE:
<221> NAME/KEY: VARIANT
<222> LOCATION: (10)..(10)
<223> OTHER INFORMATION: Xaa= a codable amino acid
<220> FEATURE:
<221> NAME/KEY: VARIANT
<222> LOCATION: (11)..(11)
<223> OTHER INFORMATION: Xaa= a codable amino acid
<220> FEATURE:
<221> NAME/KEY: VARIANT
<222> LOCATION: (12)..(12)
<223> OTHER INFORMATION: Xaa= a codable amino acid
<220> FEATURE:
<221> NAME/KEY: VARIANT
<222> LOCATION: (13)..(13)
<223> OTHER INFORMATION: Xaa= a codable amino acid
<220> FEATURE:
<221> NAME/KEY: VARIANT
<222> LOCATION: (21)..(21)
<223> OTHER INFORMATION: Xaa= a codable amino acid
<220> FEATURE:
<221> NAME/KEY: VARIANT
<222> LOCATION: (26)..(27)
```

-continued

```
<223> OTHER INFORMATION: Xaa= independently a codable amino acid or
      missing

<400> SEQUENCE: 49

Xaa Xaa Xaa Xaa Xaa Leu Cys Gly Xaa Xaa Xaa Xaa Xaa Ala Leu Tyr
1               5                   10                  15

Leu Val Cys Gly Xaa Arg Gly Phe Phe Xaa Xaa Asn Thr Thr Lys
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: RHI-7G3 B peptide
<220> FEATURE:
<221> NAME/KEY: VARIANT
<222> LOCATION: (4)..(7)
<223> OTHER INFORMATION: Xaa= independently a codable amino acid or
      missing
<220> FEATURE:
<221> NAME/KEY: VARIANT
<222> LOCATION: (8)..(8)
<223> OTHER INFORMATION: Xaa= a codable amino acid
<220> FEATURE:
<221> NAME/KEY: VARIANT
<222> LOCATION: (12)..(12)
<223> OTHER INFORMATION: Xaa= a codable amino acid
<220> FEATURE:
<221> NAME/KEY: VARIANT
<222> LOCATION: (13)..(13)
<223> OTHER INFORMATION: Xaa= a codable amino acid
<220> FEATURE:
<221> NAME/KEY: VARIANT
<222> LOCATION: (14)..(14)
<223> OTHER INFORMATION: Xaa= a codable amino acid
<220> FEATURE:
<221> NAME/KEY: VARIANT
<222> LOCATION: (15)..(15)
<223> OTHER INFORMATION: Xaa= a codable amino acid
<220> FEATURE:
<221> NAME/KEY: VARIANT
<222> LOCATION: (16)..(16)
<223> OTHER INFORMATION: Xaa= a codable amino acid
<220> FEATURE:
<221> NAME/KEY: VARIANT
<222> LOCATION: (24)..(24)
<223> OTHER INFORMATION: Xaa= a codable amino acid
<220> FEATURE:
<221> NAME/KEY: VARIANT
<222> LOCATION: (29)..(30)
<223> OTHER INFORMATION: Xaa= a codable amino acid or missing

<400> SEQUENCE: 50

Asn Thr Thr Xaa Xaa Xaa Xaa Xaa Leu Cys Gly Xaa Xaa Xaa Xaa Xaa
1               5                   10                  15

Ala Leu Tyr Leu Val Cys Gly Xaa Arg Gly Phe Phe Xaa Xaa Pro Lys
            20                  25                  30

<210> SEQ ID NO 51
<211> LENGTH: 34
<212> TYPE: PRT
<213> ORGANISM: Artificial Sequence
<220> FEATURE:
<223> OTHER INFORMATION: RHI-9G4 B peptide
<220> FEATURE:
<221> NAME/KEY: VARIANT
<222> LOCATION: (4)..(7)
<223> OTHER INFORMATION: Xaa= independently a codable amino acid or
      missing
<220> FEATURE:
<221> NAME/KEY: VARIANT
<222> LOCATION: (8)..(8)
```

```
<223> OTHER INFORMATION: Xaa= a codable amino acid
<220> FEATURE:
<221> NAME/KEY: VARIANT
<222> LOCATION: (12)..(12)
<223> OTHER INFORMATION: Xaa= a codable amino acid
<220> FEATURE:
<221> NAME/KEY: VARIANT
<222> LOCATION: (13)..(13)
<223> OTHER INFORMATION: Xaa= a codable amino acid
<220> FEATURE:
<221> NAME/KEY: VARIANT
<222> LOCATION: (14)..(14)
<223> OTHER INFORMATION: Xaa= a codable amino acid
<220> FEATURE:
<221> NAME/KEY: VARIANT
<222> LOCATION: (15)..(15)
<223> OTHER INFORMATION: Xaa= a codable amino acid
<220> FEATURE:
<221> NAME/KEY: VARIANT
<222> LOCATION: (16)..(16)
<223> OTHER INFORMATION: Xaa= a codable amino acid
<220> FEATURE:
<221> NAME/KEY: VARIANT
<222> LOCATION: (24)..(24)
<223> OTHER INFORMATION: Xaa= a codable amino acid
<220> FEATURE:
<221> NAME/KEY: VARIANT
<222> LOCATION: (29)..(30)
<223> OTHER INFORMATION: Xaa= independently a codable amino acid or
      missing

<400> SEQUENCE: 51

Asn Thr Thr Xaa Xaa Xaa Xaa Xaa Leu Cys Gly Xaa Xaa Xaa Xaa Xaa
1               5                   10                  15

Ala Leu Tyr Leu Val Cys Gly Xaa Arg Gly Phe Phe Xaa Xaa Asn Thr
            20                  25                  30

Thr Lys

<210> SEQ ID NO 52
<211> LENGTH: 21
<212> TYPE: PRT
<213> ORGANISM: Artificial Sequence
<220> FEATURE:
<223> OTHER INFORMATION: RHI-5G2 A peptide
<220> FEATURE:
<221> NAME/KEY: VARIANT
<222> LOCATION: (8)..(8)
<223> OTHER INFORMATION: Xaa= a codable amino acid; or T or A
<220> FEATURE:
<221> NAME/KEY: VARIANT
<222> LOCATION: (9)..(9)
<223> OTHER INFORMATION: Xaa= a codable amino acid; or S or G
<220> FEATURE:
<221> NAME/KEY: VARIANT
<222> LOCATION: (10)..(10)
<223> OTHER INFORMATION: Xaa= a codable amino acid;  or I or V
<220> FEATURE:
<221> NAME/KEY: VARIANT
<222> LOCATION: (15)..(15)
<223> OTHER INFORMATION: Xaa= a codable amino acid; or Q, D, or E
<220> FEATURE:
<221> NAME/KEY: VARIANT
<222> LOCATION: (18)..(18)
<223> OTHER INFORMATION: Xaa= a codable amino acid; or N, D, or E
<220> FEATURE:
<221> NAME/KEY: VARIANT
<222> LOCATION: (21)..(21)
<223> OTHER INFORMATION: Xaa= a codable amino acid; or N, D, E, G, or A

<400> SEQUENCE: 52

Gly Ile Val Glu Gln Cys Cys Xaa Xaa Xaa Cys Ser Leu Tyr Xaa Leu
1               5                   10                  15

Glu Xaa Tyr Cys Xaa
```

```
<210> SEQ ID NO 53
<211> LENGTH: 24
<212> TYPE: PRT
<213> ORGANISM: Artificial Sequence
<220> FEATURE:
<223> OTHER INFORMATION: RHI-8G3 A peptide
<220> FEATURE:
<221> NAME/KEY: VARIANT
<222> LOCATION: (11)..(11)
<223> OTHER INFORMATION: Xaa= a codable amino acid; or T or A
<220> FEATURE:
<221> NAME/KEY: VARIANT
<222> LOCATION: (12)..(12)
<223> OTHER INFORMATION: Xaa= a codable amino acid; or S or G
<220> FEATURE:
<221> NAME/KEY: VARIANT
<222> LOCATION: (13)..(13)
<223> OTHER INFORMATION: Xaa= a codable amino acid; I or V
<220> FEATURE:
<221> NAME/KEY: VARIANT
<222> LOCATION: (18)..(18)
<223> OTHER INFORMATION: Xaa= a codable amino acid; or Q, D, or E
<220> FEATURE:
<221> NAME/KEY: VARIANT
<222> LOCATION: (21)..(21)
<223> OTHER INFORMATION: Xaa= a codable amino acid; or N, D, or E
<220> FEATURE:
<221> NAME/KEY: VARIANT
<222> LOCATION: (24)..(24)
<223> OTHER INFORMATION: Xaa= a codable amino acid; or N, D, E, G, or A

<400> SEQUENCE: 53

Asn Thr Thr Gly Ile Val Glu Gln Cys Cys Xaa Xaa Xaa Cys Ser Leu
1               5                   10                  15

Tyr Xaa Leu Glu Xaa Tyr Cys Xaa
            20

<210> SEQ ID NO 54
<211> LENGTH: 29
<212> TYPE: PRT
<213> ORGANISM: Artificial Sequence
<220> FEATURE:
<223> OTHER INFORMATION: RHI-8G2 or RHI-8G4 B peptide
<220> FEATURE:
<221> NAME/KEY: VARIANT
<222> LOCATION: (1)..(4)
<223> OTHER INFORMATION: Xaa= independently a codable amino acid or
      missing
<220> FEATURE:
<221> NAME/KEY: VARIANT
<222> LOCATION: (5)..(5)
<223> OTHER INFORMATION: Xaa= a codable amino acid
<220> FEATURE:
<221> NAME/KEY: VARIANT
<222> LOCATION: (9)..(9)
<223> OTHER INFORMATION: Xaa= a codable amino acid
<220> FEATURE:
<221> NAME/KEY: VARIANT
<222> LOCATION: (10)..(10)
<223> OTHER INFORMATION: Xaa= a codable amino acid
<220> FEATURE:
<221> NAME/KEY: VARIANT
<222> LOCATION: (11)..(11)
<223> OTHER INFORMATION: Xaa= a codable amino acid
<220> FEATURE:
<221> NAME/KEY: VARIANT
<222> LOCATION: (12)..(12)
<223> OTHER INFORMATION: Xaa= a codable amino acid
<220> FEATURE:
<221> NAME/KEY: VARIANT
<222> LOCATION: (13)..(13)
<223> OTHER INFORMATION: Xaa= a codable amino acid
<220> FEATURE:
```

-continued

```
<221> NAME/KEY: VARIANT
<222> LOCATION: (21)..(21)
<223> OTHER INFORMATION: Xaa= a codable amino acid
<220> FEATURE:
<221> NAME/KEY: VARIANT
<222> LOCATION: (26)..(29)
<223> OTHER INFORMATION: Xaa= independently a codable amino acid or
      missing

<400> SEQUENCE: 54

Xaa Xaa Xaa Xaa Xaa Leu Cys Gly Xaa Xaa Xaa Xaa Xaa Ala Leu Tyr
1               5                   10                  15

Leu Val Cys Gly Xaa Arg Gly Phe Phe Xaa Xaa Xaa Xaa
            20                  25
```

RECOMBINANTLY EXPRESSED INSULIN POLYPEPTIDES AND USES THEREOF

CROSS REFERENCE TO RELATED APPLICATIONS

This application is a U.S. National Phase application under 35 U.S.C. §371 of PCT Application No. PCT/US2011/045008, filed Jul. 22, 2011 which claims priority under 35 U.S.C. §119(e) from U.S. Provisional Application Ser. No. 61/368,607, filed Jul. 28, 2010.

REFERENCE TO SEQUENCE LISTING SUBMITTED ELECTRONICALLY

The sequence listing of the present application is submitted electronically via EFS-Web as an ASCII formatted sequence listing with a file name "23020-SEQTXT-22MAR2013.TXT", creation date of 22 Mar. 2013, and a size of 35 KB. This sequence listing submitted via EFS-Web is part of the specification and is herein incorporated by reference in its entirety.

BACKGROUND

The majority of "controlled-release" drug delivery systems known in the prior art (e.g., U.S. Pat. No. 4,145,410 to Sears which describes drug release from capsules which are enzymatically labile) are incapable of providing drugs to a patient at intervals and concentrations which are in direct proportion to the amount of a molecular indicator (e.g., a metabolite) present in the human body. The drugs in these prior art systems are thus not literally "controlled," but simply provided in a slow release format which is independent of external or internal factors. The treatment of diabetes mellitus with injectable insulin is a well-known and studied example where uncontrolled, slow release of insulin is undesirable. In fact, it is apparent that the simple replacement of the hormone is not sufficient to prevent the pathological sequelae associated with this disease. The development of these sequelae is believed to reflect an inability to provide exogenous insulin proportional to varying blood glucose concentrations experienced by the patient. To solve this problem several biological and bioengineering approaches have been suggested to develop a more physiological insulin delivery system have been suggested (e.g., see U.S. Pat. No. 4,348,387 to Brownlee et al.; U.S. Pat. Nos. 5,830,506, 5,902,603, and 6,410,053 to Taylor et al. and U.S. Patent Application Publication No. 2004-0202719 to Zion et al.).

Each of these systems relies on the combination of a multivalent glucose binding molecule (e.g., the lectin Con A) and a sugar based component that is reversibly bound by the multivalent glucose binding molecule. Unfortunately, Con A and many of the other readily available lectins have the potential to stimulate lymphocyte proliferation. By binding to carbohydrate receptors on the surfaces of certain types of lymphocytes, these so-called "mitogenic" lectins can potentially induce the mitosis of lymphocytes and thereby cause them to proliferate. Most mitogenic lectins including Con A are selective T-cell mitogens. A few lectins are less selective and stimulate both T-cells and B-cells. Local or systemic in vivo exposure to mitogenic lectins can result in inflammation, cytotoxicity, macrophage digestion, and allergic reactions including anaphylaxis. In addition, plant lectins are known to be particularly immunogenic, giving rise to the production of high titers of anti-lectin specific antibodies. It will be appreciated that mitogenic lectins cannot therefore be used in their native form for in vivo methods and devices unless great care is taken to prevent their release. For example, in U.S. Pat. No. 5,830,506, Taylor highlights the toxic risks that are involved in using Con A and emphasizes the importance and difficulty of containing Con A within a drug delivery device that also requires glucose and insulin molecules to diffuse freely in and out of the device.

The risks and difficulties that are involved with these and other in viva uses of lectins could be significantly diminished if an alternative controlled drug delivery system could be provided that did not require lectins.

SUMMARY

The present disclosure provides recombinantly expressed insulin polypeptides that comprise an N-linked glycan motif. The N-linked glycan motif is not present in wild-type insulins and enables the recombinant expression of glycosylated insulin polypeptides (e.g., in yeast cells). Based on results obtained with synthetic glycosylated insulin conjugates we predict that when these recombinant glycosylated insulin polypeptides are administered to a mammal, at least one pharmacokinetic or pharmacodynamic property of the glycosylated insulin polypeptide will be sensitive to serum concentrations of glucose (or an exogenous saccharide such as alpha-methyl mannose). Exemplary insulin polypeptides, polynucleotides encoding these insulin polypeptides, glycosylated insulin polypeptides, pharmaceutical formulations and sustained release formulations are provided in addition to methods of use and preparation.

BRIEF DESCRIPTION OF THE DRAWINGS

FIG. 20: β-phase elimination half-life results in non-diabetic minipigs during glucose, α-methyl mannose or saline infusion.

FIG. 21: Plots of serum concentrations of (a) recombinant human insulin (RHI) and (b) Di-Sub-AETM-2 insulin conjugate I-11 following a 0.1 U/kg intravenous (i.v.) injection into non-diabetic male Yucatan minipigs equipped with dual vascular access ports (n=3 per study). In each experiment, the animals were infused with (◆) i.v. alpha methyl mannose (a-MM) solution (25% w/v infused at constant rate of 80 ml/h) or (▲) no solution. Data are plotted as the average values fit with a curve derived from the two-compartment, bi-exponential model.

FIG. 22: Blood glucose depression curves in non-diabetic male Yucatan minipigs equipped with dual vascular access ports (n=3 per study) following i.v. injection of conjugates at 0.1 U/kg under conditions of (a) no i.v. sugar infusion or (b) i.v. alpha methyl mannose (a-MM) infusion (25% w/v infused at constant rate of 80 ml/h). (■) RHI (◆) I-6, (○) I-7, (▲) I-15, and (●) I-11.

FIG. 23: Blood glucose levels in (a, —, closed symbols) alloxan-diabetic Yucatan minipigs (n=3 per dose) and (b, - - - -, open symbols) non-diabetic Yucatan minipigs (n=3 per dose) under fasting conditions after a sub-Q injection at time 0 with soluble Di-Sub-AETM-2 insulin conjugate I-11 at doses of 0.25, 0.50, and 1.00 U/kg. Data are plotted as the average values+one standard deviation. FIG. 23(b) scale is enlarged for clarity.

FIG. 24: Blood glucose levels in (a, —, closed symbols) alloxan-diabetic Yucatan minipigs (n=3 per dose) and (b, - - - -, open symbols) non-diabetic Yucatan minipigs (n=3 per dose) under fasting conditions after a sub-Q injection at time 0 with soluble recombinant human insulin (RHI) at doses of (▲,△) 0.063 and (■,□) 0.125 U/kg. Data are plotted as the average values+one standard deviation.

FIG. 25: Summary of i.v. half-life results in minipigs for additional insulin-conjugates.

DETAILED DESCRIPTION OF VARIOUS EMBODIMENTS

This application refers to a number of documents including patent and non-patent documents. The entirety of each of these documents is incorporated herein by reference.

In one aspect, the disclosure provides methods for controlling the pharmacokinetic (PK) and/or pharmacodynamic (PD) profiles of a recombinantly expressed insulin polypeptide in a manner that is responsive to the systemic concentrations of a saccharide such as glucose. As discussed herein, these methods are based in part on the discovery that certain synthetic insulin-conjugates that include high affinity saccharide ligands (e.g., see those in FIGS. 5 and 6) exhibit PK/PD profiles that respond to saccharide concentration changes even in the absence of an exogenous multivalent saccharide-binding molecule such as Con A. This finding was unexpected and provided an unprecedented opportunity to generate simple lectin-free saccharide-responsive drug systems.

Figure 6:
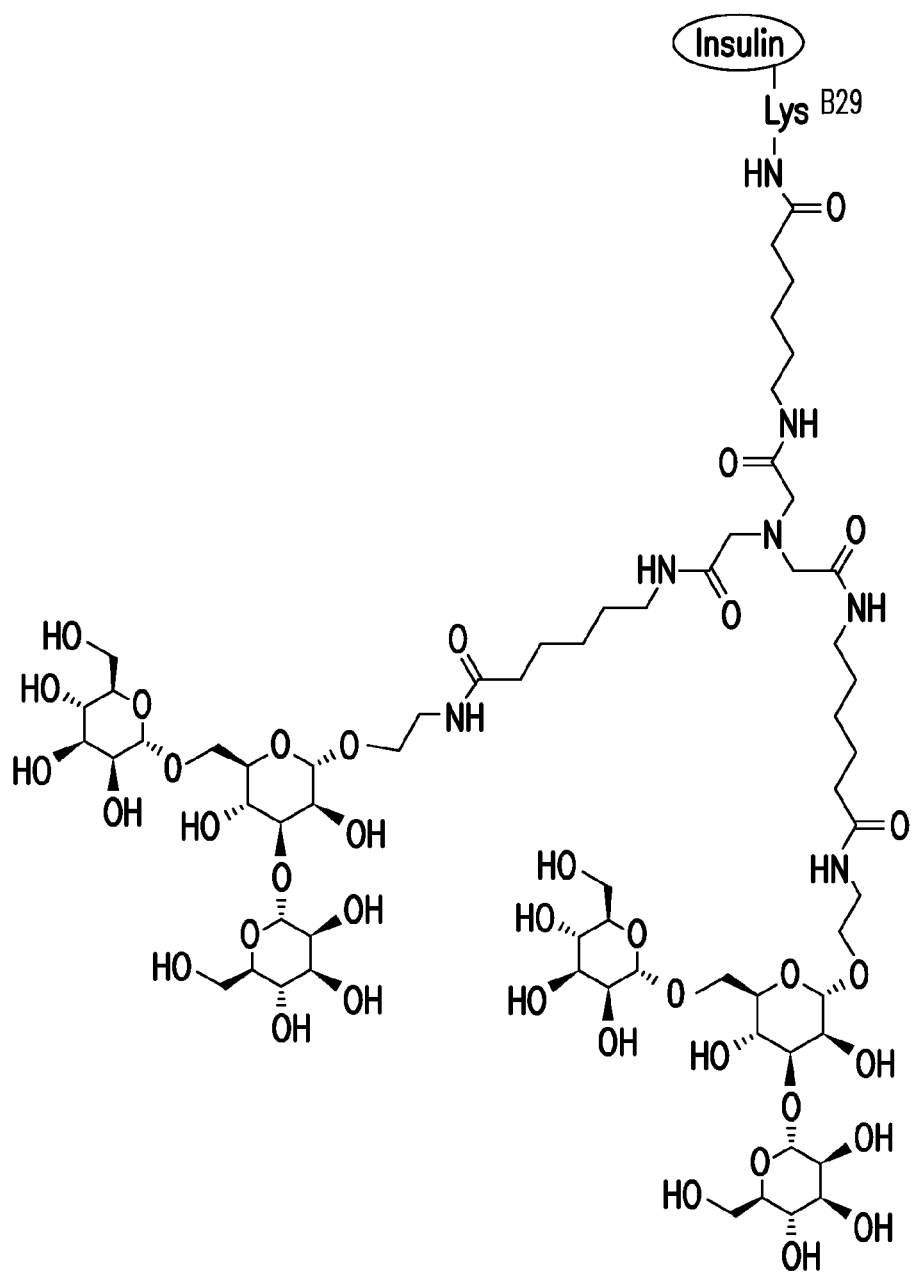
FIG. 6: Chemical structure of synthetic insulin conjugate I-6 (B29 linked TSAT-C6-AETM-2).

One example of such a synthetic insulin-conjugate, known as I-6, is shown in FIG. 6. Conjugate I-6 comprises a discrete, low molecular weight synthetic framework (tris-succinimidyl (6-aminocaproyl)aminotriacetate or TSAT-C6) with two aminoethyltrimannose (AETM) saccharide moieties. The framework is covalently conjugated to insulin via the B29 epsilon-amino group (wild-type human insulin has a lysine residue at position B29). As discussed in the Examples, conjugate I-6 exhibits glucose-responsive pharmacokinetics. As a result, the availability and therefore the bioactivity, of conjugate I-6 varies in response to endogenous glucose levels. We have prepared sustained release formulations of conjugate I-6 using protamine and zinc (PZI formulations) that provide both basal and bolus insulin "delivery" on demand without inducing hypoglycemia. In contrast, conventional insulins are either rapid-acting (e.g., RHI) or slow-acting (e.g., Lantus) and cannot change profiles in response to changes in glucose levels. When compared with conventional insulin in diabetic and normal rats, conjugate I-6 shows a substantially improved therapeutic window, with minimal risk of hypoglycemia at four times the therapeutic dose.

Significantly, our studies have shown that the TSAT-C6 framework employed by conjugate I-6 is not required for glucose-responsive activity. Indeed, we have found that other insulin-conjugated frameworks such as those depicted in FIG. 15A to 15Q can provide similar results (e.g., see Examples 13-17). Our studies also suggest that the type and number of conjugated sugars and, in certain situations, the point of conjugation on the insulin molecule play a more important role in modulating the in vivo glucose-response.

Figure 5A:
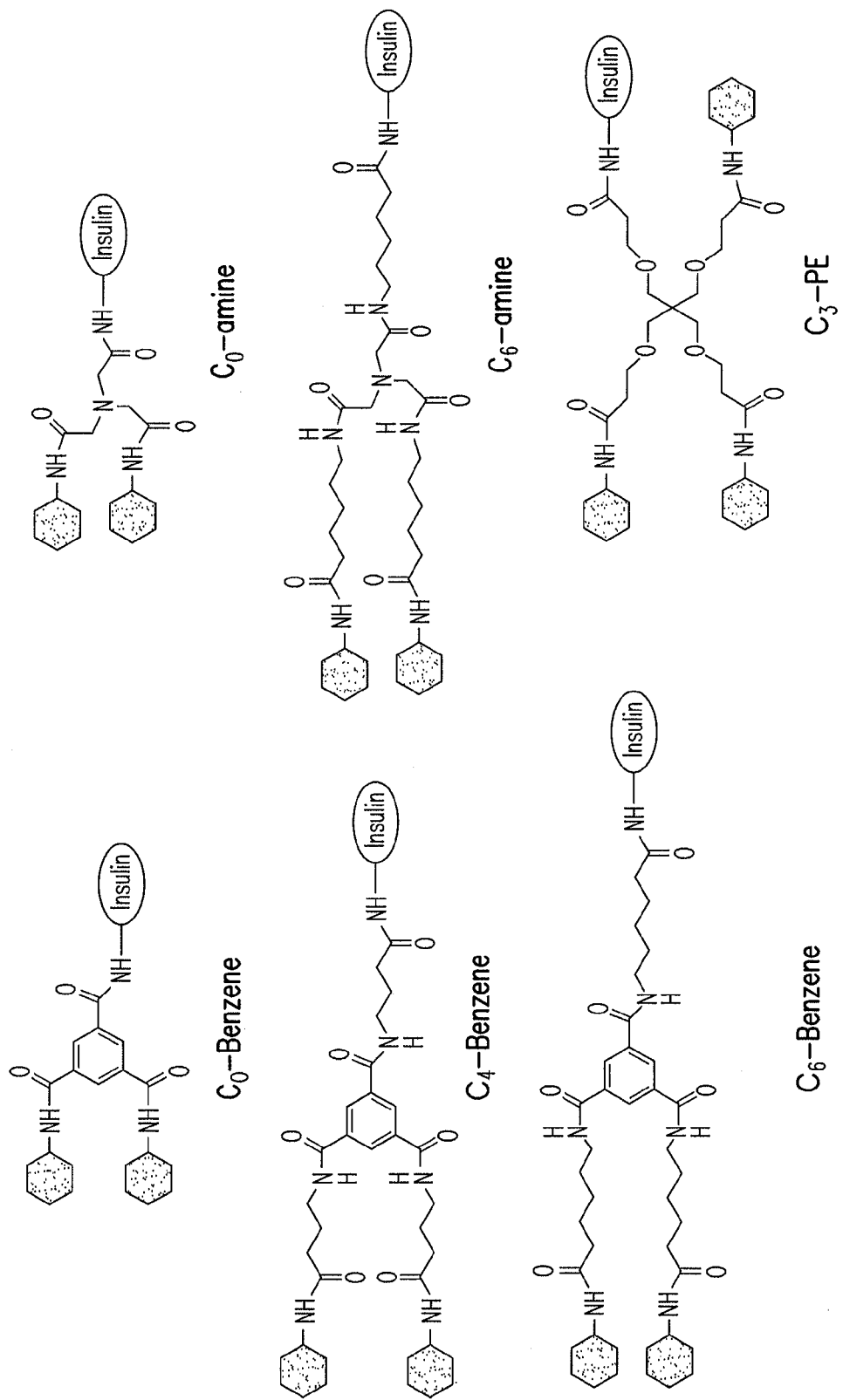
FIG. 5A and FIG. 5B: Chemical structures of some exemplary synthetic insulin conjugates.
Figure 5B:
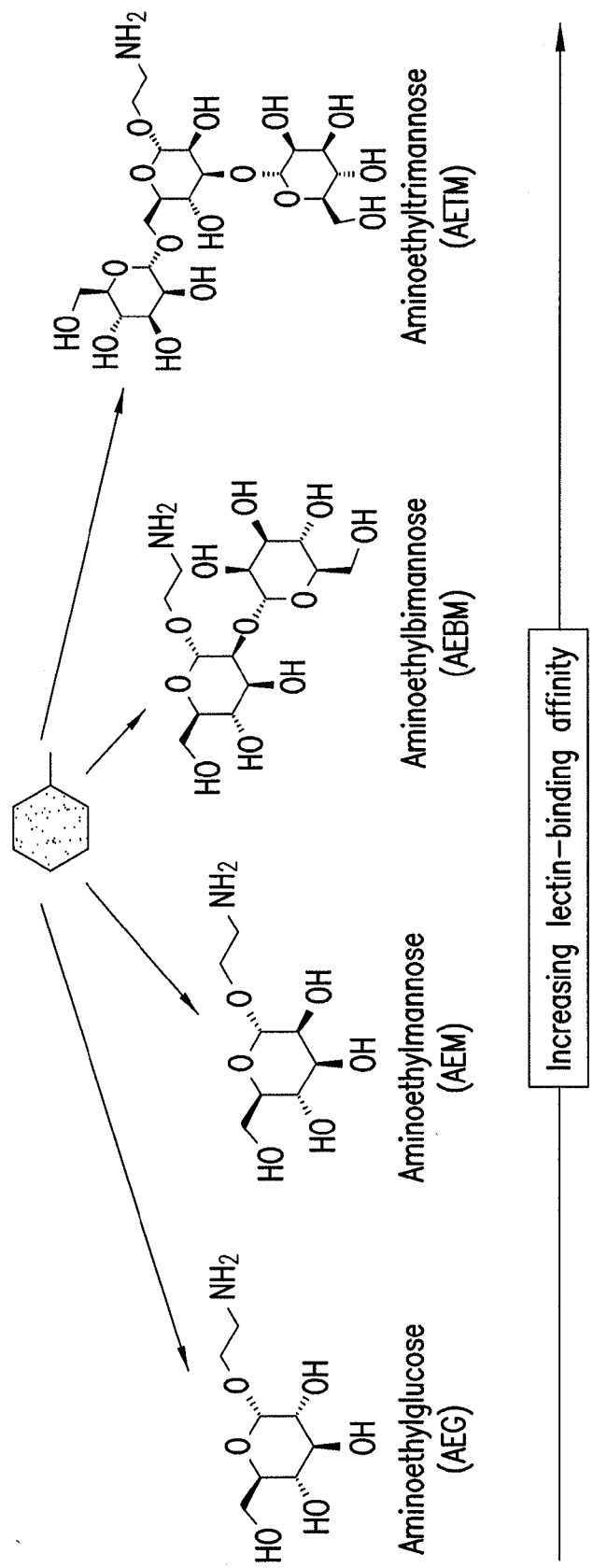

Without wishing to be bound by any particular theory, it is believed that the glucose-responsiveness exhibited by conjugates such as I-6 is mediated by binding to endogenous lectins. Thus, we theorize that when glucose levels in the body are low, the endogenous lectins have glucose binding sites available for binding by the synthetic insulin-conjugate, essentially inactivating the insulin-like activity of the conjugate. Conversely, when glucose levels in the body are high, the binding sites on the lectins are satisfied by endogenous glucose, thus allowing the synthetic insulin-conjugate to circulate and exert its effect. FIGS. 5A and 5B show the relative lectin binding affinities of four sugars; AETM binds lectins with the highest affinity of the four sugars shown. We theorize that the lectin binding affinity of a particular sugar is responsible at least in part for the modulation of in vivo glucose-responsiveness of our synthetic insulin-conjugates.

Conjugates such as I-6 are produced by chemical synthesis. As described in Examples 1-3, the synthetic process is complex and involves a series of steps in which a framework is first conjugated to one or more saccharide ligands and then conjugated to recombinant insulin. In addition, the conjugation process does not produce a pure conjugate. The product is therefore first purified by size exclusion using an appropriate solid phase for separating conjugated and unconjugated materials. The conjugates are then further purified to obtain the desired product using preparative reverse phase HPLC. Once collected, the solution is rotovapped to remove organic solvents and lyophilized. Such a synthetic process presents challenges for large-scale production. The present disclosure stems in part from the realization that alternative methods of producing insulin conjugates via biosynthetic pathways would provide significant advantages over these synthetic methods.

Recombinant Insulin Polypeptides

In one aspect, the present disclosure provides recombinantly expressed insulin polypeptides that have been engineered to include a motif that allows for covalent attachment of N-linked glycans. It will be appreciated that this encompasses insulin polypeptides with one or more of these motifs. As is known in the art, the sequence of these "N-linked glycan motifs" is Asn-Xaa'-[Ser/Thr], where Xaa' is not Pro (e.g., see Marshall, *Annu. Rev. Biochem.* 41:673-702, 1972). N-linked glycans can be covalently attached to the motif via the delta-amino group of the Asn residue.

Insulin

The wild-type sequence of human insulin is shown below and does not include an N-linked glycan motif.

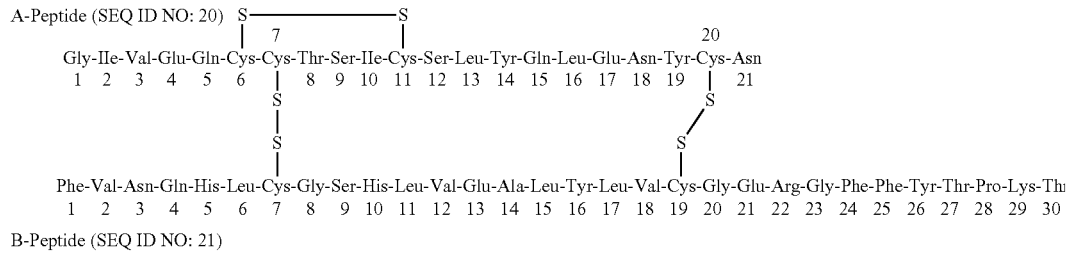

As is well known in the art, the β-cells of the pancreatic islets in humans secrete a single chain precursor of insulin, known as proinsulin. In humans, proinsulin has the sequence:

[B-peptide][C-peptide]-[A-peptide], wherein the C-peptide is a connecting peptide with the sequence of SEQ ID NO:22: Arg-Arg-Glu-Ala-Glu-Asp-Leu-Gln-Val-Gly-Gln-Val-Glu-Leu-Gly-Gly-Gly-Pro-Gly-Ala-Gly-Ser-Leu-Ght-Pro-Leu-Ala-Leu-Glu-Gly-Ser-Leu-Gln-Lys-Arg.

In humans, prior to secretion of the bioactive insulin polypeptide by the β-cells of the pancreatic islets, the C-peptide is removed from proinsulin by cleavage at the two dibasic sites, Arg-Arg and Lys-Arg. As shown above, the cleavage releases the bioactive insulin polypeptide as separate A- and B-peptides that are connected by two disulfide bonds with one disulfide bond within the A-peptide.

Not all organisms recognize and correctly process the human proinsulin sequence. For example, in certain embodiments, yeast may utilize an alternative proinsulin sequence: [Leader peptide]-[B-peptide]-[C-peptide]-[A-peptide].

In the yeast proinsulin sequence, the leader peptide is thought to facilitate appropriate cleavage of the insulin polypeptide in yeast and may, for example, comprise the sequence: Glu-Glu-Ala-Glu-Ala-Glu-Ala-Glu-Pro-Lys (SEQ ID NO:23) or Asp-Asp-Gly-Asp-Pro-Arg (SEQ ID NO:24). In some embodiments, the leader peptide has a sequence of Xaa"-Pro-[Lys/Arg], where Xaa":
  is at least 4, at least 5, at least 6, at least 7, at least 8, at least 9, at least 10, at least 11, at least 12, at least 13, at least 14, at least 15, at least 20, or at least 25 amino acids in length, or
  is no more than 5, no more than 10, no more than 15, no more than 20, no more than 25, no more than 50 amino acids in length; and
  comprises at least about 30%, at least about 40%, at least about 50%, at least about 55%, at least about 60%, at least about 65%, at least about 70%, at least about 75%, at least about 80%, at least about 5%, at least about 90%, or at least about 95% of acidic amino acids (e.g., Asp and/or Glu).

In some embodiments, the leader peptide contains the amino acids Pro-Lys at its C-terminus. In some embodiments, the leader peptide contains the amino acids Pro-Arg at its C-terminus.

Additionally, instead of the long C-peptide connecting segment found in human proinsulin, engineered yeast proinsulin sequences may have a much shorter C-peptide sequence, e.g., Ala-Ala-Lys (SEQ ID NO:16), Asp-Glu-Arg (SEQ ID NO:17), or Thr-Ala-Ala-Lys (SEQ ID NO:25). In some embodiments, the C-peptide has a sequence of Xaa'''-[Lys/Arg], where Xaa''':
  is missing, or is at least 1, at least 2, at least 3, at least 4, at least 5, at least 6, at least 7, at least 8, at least 9, at least 10, at least 15, or at least 20 amino acids in length;
  is no more than 2, no more than 3, no more than 4, no more than 5, no more than 6, no more than 7, no more than 8, no more than 9, no more than 10, no more than 15, no more than 20, or no more than 25 amino acids in length; or
  is exactly 1, 2, 3, 4, 5, 6, 7, 8, 9, 10, 11, 12, 13, 14, 15, 16, 17, 18, 19, 20, 21, 22, 23, 24, or 25 amino acids in length.

In some embodiments, the C-peptide has an amino acid sequence different from that found in human proinsulin. In general, the C-peptide refers to any amino acid sequence in proinsulin that is found between the insulin A-chain and B-chain. In some embodiments, the C-peptide refers to any amino acid sequence in proinsulin that is found between the insulin A-chain and B-chain and that is enzymatically cleaved to produce a bioactive insulin molecule.

Without wishing to be limited to any particular theory, it is thought that the combination of these leader sequences and C-peptide sequences allows for the production of functional insulin from yeast.

As described in more detail below, in some embodiments, proinsulin comprises at least one N-linked glycan motif (e.g., 1, 2, 3 or more N-linked glycan motifs). In some embodiments, a bioactive insulin polypeptide (i.e., separate A- and B-peptides that are connected by two disulfide bonds with one disulfide bond within the A-peptide) comprises at least one N-linked glycan motif (e.g., 1, 2, 3 or more N-linked glycan motifs). In some embodiments, proinsulin comprises at least one N-linked glycan motif, and after enzymatic cleavage, the bioactive insulin polypeptide still comprises the entire N-linked glycan motif that was present in the proinsulin sequence. In some embodiments, proinsulin comprises at least one N-linked glycan motif, and after enzymatic cleavage, the bioactive insulin polypeptide no longer comprises the entire N-linked glycan motif. In some embodiments, proinsulin comprises at least one N-linked glycan motif, and after enzymatic cleavage, the bioactive insulin polypeptide no longer comprises the entire N-linked glycan motif, but still comprises the Asn residue to which an N-linked glycan may be optionally covalently linked. This could happen, for example, if cleavage of proinsulin occurs within the at least one N-linked glycan motif. For example, if Xaa' in the N-linked glycan motif is Lys and cleavage occurs on the C-terminal side of the Lys residue then the bioactive insulin polypeptide will only comprise the Asn-Lys residues from the N-linked glycan motif. Similarly, if Xaa' in the N-linked glycan motif is Arg and cleavage occurs on the C-terminal side of the Arg residue then the bioactive insulin polypeptide will only comprise the Asn-Arg residues from the N-linked glycan motif.

The present disclosure is not limited to human insulin polypeptides (i.e., human proinsulin or bioactive human insulin polypeptides) that include at least one N-linked glycan motif. In general, the present disclosure encompasses any human or non-human insulin that has been modified in accordance with the present disclosure and that retains insulin-like bioactivity (i.e., is capable of causing a detectable reduction in glucose when administered to a suitable species at an appropriate dose in vivo). For example, as discussed below, the present disclosure also encompasses modified porcine insulin, bovine insulin, rabbit insulin, sheep insulin, etc. that include at least one N-linked glycan motif.

As discussed in more detail below, an N-linked glycan motif may be introduced at a variety of sites within a wild-type insulin sequence, by substitution, deletion and/or addition of one or more amino acids (where addition encompasses insertions). It is to be understood that an insulin polypeptide of the present disclosure may include modifications in addition to mutations that have been engineered to introduce an N-linked glycan motif. A variety of modified insulins are known in the art (e.g., see Crotty and Reynolds, *Pediatr. Emerg. Care.* 23:903-905, 2007 and Gerich, *Am. J. Med.* 113:308-16, 2002 and references cited therein). Modified forms of insulin may be chemically modified (e.g., by addition of a chemical moiety such as a PEG group or a fatty acyl chain as described below) and/or mutated (i.e., by addition, deletion or substitution of amino acids besides those that have been mutated to introduce an N-glycan linked motif).

In certain embodiments, an insulin polypeptide of the present disclosure will differ from a wild-type insulin by 1-10 (e.g., 1-9, 1-8, 1-7, 1-6, 1-5, 1-4, 1-3, 1-2, 2-9, 2-8, 2-7, 2-6, 2-5, 2-4, 2-3, 3-9, 3-8, 3-7, 3-6, 3-5, 3-4, 4-9, 4-8, 4-7, 4-6, 4-5, 5-9, 5-8, 5-7, 5-6, 6-9, 6-8, 6-7, 7-9, 7-8, 8-9, 9, 8, 7, 6, 5, 4, 3, 2 or 1) amino acid substitutions, additions and/or deletions. In certain embodiments, an insulin polypeptide of the present disclosure will differ from a wild-type insulin by amino acid substitutions only. In certain embodiments, an insulin polypeptide of the present disclosure will differ from a wild-type insulin by amino acid additions only. In certain embodiments, an insulin polypeptide of the present disclosure will differ from a wild-type insulin by both amino acid substitutions and additions. In certain embodiments, an insulin polypeptide of the present disclosure will differ from a wild-type insulin by both amino acid substitutions and deletions.

In certain embodiments, amino acid substitutions may be made on the basis of similarity in polarity, charge, solubility, hydrophobicity, hydrophilicity, and/or the amphipathic nature of the residues involved. In certain embodiments, a substitution may be conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine. In certain embodiments, the hydrophobic index of amino acids may be considered in choosing suitable mutations. The importance of the hydrophobic amino acid index in conferring interactive biological function on a polypeptide is generally understood in the art. Alternatively, the substitution of like amino acids can be made effectively on the basis of hydrophilicity. The importance of hydrophilicity in conferring interactive biological function of a polypeptide is generally understood in the art. The use of the hydrophobic index or hydrophilicity in designing polypeptides is further discussed in U.S. Pat. No. 5,691, 198.

In certain embodiments, an insulin polypeptide of the present disclosure comprises an amino acid sequence of SEQ ID NO:26 (A-peptide) and an amino acid sequence of SEQ ID NO:27 (B-peptide) as shown below in Formula I:

Asn-Xaa'-[Ser/Thr], where Xaa' is not Pro. In some embodiments, SEQ ID NO:27 includes a motif Asn-Xaa'-[Ser/Thr], where Xaa' is not Pro.

As used herein, a "codable amino acid" is any one of the 20 amino acids that are directly encoded for polypeptide synthesis by the standard genetic code.

In some embodiments, Xaa at each of positions A0, A22, B0 and B31 is independently a codable amino acid, a sequence of 2-50 codable amino acids, or missing.

In some embodiments, Xaa at each of positions A0, A22, B0 and B31 is independently a codable amino acid, a sequence of 2-25 codable amino acids, or missing.

In some embodiments, Xaa at each of positions A0, A22, B0 and B31 is independently a codable amino acid, a sequence of 2-10 codable amino acids, or missing.

In some embodiments, Xaa at each of positions A0, A22, B0 and B31 is independently a codable amino acid, a sequence of 2-9 codable amino acids, or missing.

In some embodiments, Xaa at each of positions A0, A22, B0 and B31 is independently a codable amino acid, a sequence of 2-8 codable amino acids, or missing.

In some embodiments, Xaa at each of positions A0, A22, B0 and B31 is independently a codable amino acid, a sequence of 2-7 codable amino acids, or missing.

In some embodiments, Xaa at each of positions A0, A22, B0 and B31 is independently a codable amino acid, a sequence of 2-6 codable amino acids, or missing.

In some embodiments, Xaa at each of positions A0, A22, B0 and B31 is independently a codable amino acid, a sequence of 2-5 codable amino acids, or missing.

In some embodiments, Xaa at each of positions A0, A22, B0 and B31 is independently a codable amino acid, a sequence of 2-4 codable amino acids, or missing.

In some embodiments, Xaa at each of positions A0, A22, B0 and B31 is independently a codable amino acid, a sequence of 2-3 codable amino acids, or missing.

In some embodiments, Xaa at each of positions A0, A22, B0 and B31 is independently a codable amino acid, a sequence of 2 codable amino acids, or missing.

(I)

```
A-Peptide (SEQ ID NO: 26)
Xaa-Gly-Ile-Val-Glu-Gln-Cys-Cys-Xaa-Xaa-Xaa-Cys-Ser-Leu-Tyr-Xaa-Leu-Glu-Xaa-Tyr-Xaa-Xaa-Xaa
 0   1   2   3   4   5   6   7   8   9  10  11  12  13  14  15  16 17  18  19   20  21  22

B-Peptide (SEQ ID NO: 27)
Xaa-Xaa-Xaa-Xaa-Xaa-Xaa-Leu-Cys-Gly-Xaa-Xaa-Xaa-Xaa-Xaa-Ala-Leu-Tyr-Leu-Val-Cys-Gly-Xaa-Arg-
 0   1   2   3   4   5   6   7   8   9  10  11  12  13  14  15  16  17  18  19  20  21  22

Gly-Phe-Phe-Xaa-Xaa-Xaa-Xaa-Xaa-Xaa
 23  24  25  26  27  28  29  30  31
``` where Xaa at each of positions A0, A22, B0 and B31 is independently a codable amino acid, a sequence of codable amino acids, or missing; Xaa at each of positions A8, A9, A10, A15, A18, A20 and A21 is independently a codable amino acid; Xaa at each of positions B1, B2, B3, B4, B26, B27, B28, B29, and B30 is independently a codable amino acid or missing; and Xaa at each of positions B5, B9, B10, B11, B12, B13 and B21 is independently a codable amino acid, with the proviso that SEQ ID NO:26 and/or SEQ ID NO:27 includes a motif Asn-Xaa'-[Ser/Thr], where Xaa' is not Pro. As used herein, reference to an amino acid sequence that includes "a motif Asn-Xaa'-[Ser/Thr], where Xaa' is not Pro" encompasses amino acid sequence with one or more of the motifs. In certain embodiments the amino acid sequence includes a single "Asn-Xaa'-[Ser/Thr], where Xaa' is not Pro" motif. In some embodiments, SEQ ID NO:26 includes a motif As discussed in more detail below, it is to be understood that the A- and B-peptides may be (a) comprised within a single contiguous amino acid sequence (as in proinsulin) or (b) discontiguous peptides that are linked via one or more disulfide bridges (as in bioactive insulin). In various embodiments, an insulin polypeptide of the present disclosure includes the three disulfide bridges that are found in wild-type insulins (i.e., one between position 7 of the A-peptide and position 7 of the B-peptide, a second between position 20 of the A-peptide and position 19 of the B-peptide, and a third between positions 6 and 11 of the A-peptide).

Thus the present disclosure also specifically encompasses insulin polypeptides of Formula I having discontiguous A-peptide and B-peptide sequences of SEQ ID NO:1 and SEQ ID NO:2 and three disulfide bridges as shown in Formula I':

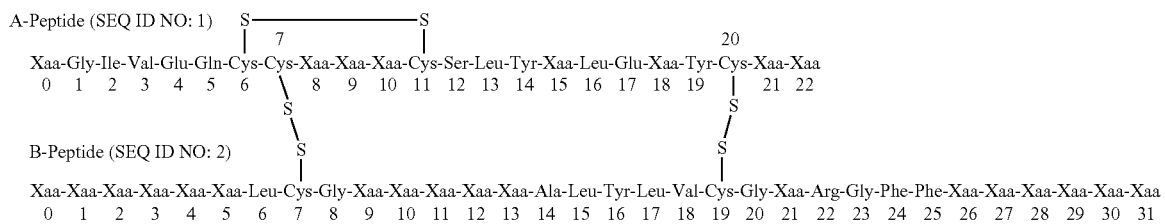

(I')

The present disclosure also encompasses insulin polypeptides of Formula I where the A- and B-peptides are comprised within a single contiguous amino acid sequence. For example, in certain embodiment, the A- and B-peptides may be separated by a "C-peptide" as follows: [B-peptide][C-peptide][A-peptide] (where the C-peptide connects the C-terminus of the B-peptide with the N-terminus of the A-peptide). In certain embodiment, the A- and B-peptides may be separated by a "C-peptide" and include a leader peptide sequence as follows: [Leader peptide]-[B-peptide]-[C-peptide]-[A-peptide] where the leader peptide may be the leader peptide of SEQ ID NO:23, the leader peptide of SEQ ID NO:24, or a leader peptide having a sequence of Xaa"-Pro-[Lys/Arg], where Xaa":

is at least 4, at least 5, at least 6, at least 7, at least 8, at least 9, at least 10, at least 11, at least 12, at least 13, at least 14, at least 15, at least 20, or at least 25 amino acids in length, or is no more than 5, no more than 10, no more than 15, no more than 20, no more than 25, no more than 50 amino acids in length; and comprises at least about 30%, at least about 40%, at least about 50%, at least about 55%, at least about 60%, at least about 65%, at least about 70%, at least about 75%, at least about 80%, at least about 5%, at least about 90%, or at least about 95% of acidic amino acids (e.g., Asp and/or Glu).

In some embodiments, the C-peptide may be the human proinsulin C-peptide of SEQ ID NO:3. In certain organisms, such as *Saccharomyces cerevisiae*, expression of human proinsulin does not result in the production of a cleaved, bioactive insulin polypeptide. Instead, proinsulin precursors expressed in *Saccharomyces cerevisiae* undergo rapid enzymatic cleavage before disulfide bond formation between the A- and B-peptides. In these cases, the non-disulfide bonded peptides are inactive, and therefore non-functional insulin molecules.

In order to harness yeast in the production of bioactive insulin polypeptides, alternative proinsulin sequences have been identified that are not readily digested by proteases, and therefore can be used to generate functional insulin polypeptides. These alternative proinsulin sequences replace the C-peptide with shorter peptide sequences, with even as little as two amino acids of either lysine, and/or arginine. Thus, in some embodiments, the C-peptide may be the C-peptide of SEQ ID NO:16, SEQ ID NO:17, or SEQ ID NO:25. These proinsulin polypeptides are more stable and can be processed in vitro to yield bioactive insulin polypeptides (Thim et al., *Proc. Natl. Acad. Sci. USA* 83:6766-67770, 1986). These and other modified proinsulin polypeptides are described in detail in U.S. Pat. Nos. 5,962,267, 6,521,738, 6,558,924, 6,610,649, 6,777,207, 7,105,314, 7,087,408, and also in WO 95/16708, EP 0055945, EP163529, EP 0347845 and EP 0741188. It is to be understood that the present disclosure encompasses any [B-peptide][C-peptide]-[A-peptide] insulin polypeptide that comprises one of these alternative C-peptide sequences.

In some embodiments, the C-peptide has an amino acid sequence different from that found in human proinsulin. In general, the C-peptide refers to any amino acid sequence in proinsulin that is found between the insulin A-chain and B-chain. In some embodiments, the C-peptide refers to any amino acid sequence in proinsulin that is found between the insulin A-chain and B-chain that is cleaved and removed from the final insulin product. In some embodiments, the C-peptide is a C-peptide having a sequence of Xaa'''-[Lys/Arg], where Xaa''':

is missing, or is at least 1, at least 2, at least 3, at least 4, at least 5, at least 6, at least 7, at least 8, at least 9, at least 10, at least 15, or at least 20 amino acids in length;

is no more than 2, no more than 3, no more than 4, no more than 5, no more than 6, no more than 7, no more than 8, no more than 9, no more than 10, no more than 15, no more than 20, or no more than 25 amino acids in length; or is exactly 1, 2, 3, 4, 5, 6, 7, 8, 9, 10, 11, 12, 13, 14, 15, 16, 17, 18, 19, 20, 21, 22, 23, 24, or 25 amino acids in length.

In some embodiments, the C-peptide sequence will be cleaved from the recombinant insulin polypeptide in a yeast cell. In some embodiments, the C-peptide cleavage site will be two adjacent basic amino acid residues (Lys and/or Arg). In some embodiments, the C-peptide will be cleaved in vitro. In vitro cleavage of the C-peptide may be accomplished using any cleavage site known in the art, e.g., a Met cleavable by cyanogen bromide; a single basic amino acid residue or a pair of basic amino acid residues (Lys or Arg) cleavable by trypsin or trypsin like proteases, *Acromobactor lyticus* protease or by a carboxypeptidase protease. In certain embodiments, the C-peptide cleavage site is a single basic amino acid residue Lys or Arg, preferably Lys.

In certain embodiments, Xaa at one or more of the positions of the A- and B-peptides in Formula I or I' is selected from the choices that are set forth in Table 1 and 2 below.

TABLE 1

| A-peptide | |
|---|---|
| Position | Amino Acid Identity |
| A0 | Any codable amino acid, sequence of codable amino acids, or missing |
| A8 | Thr or Ala |
| A9 | Ser or Gly |
| A10 | Ile or Val |
| A15 | Gln, Asp or Glu |
| A18 | Asn, Asp or Glu |
| A20 | Cys |
| A21 | Asn, Asp, Glu, Gly or Ala |

TABLE 1-continued

A-peptide

| Position | Amino Acid Identity |
|---|---|
| A22 | Any codable amino acid, sequence of codable amino acids, or missing |

TABLE 2

B-peptide

| Position | Amino Acid Identity |
|---|---|
| B0 | Any codable amino acid, sequence of codable amino acids, or missing |
| B1 | Phe, Asp, or missing |
| B2 | Val, or missing |
| B3 | Asn, Lys, Asp or Glu, or missing |
| B4 | Gln, Asp or Glu, or missing |
| B5 | His |
| B9 | Ser or Asp |
| B10 | His or Asp |
| B11 | Leu |
| B12 | Val |
| B13 | Glu or Thr |
| B21 | Glu or Asp |
| B26 | Tyr or Ala, or missing |
| B27 | Thr, or missing |
| B28 | Pro, Ala, Lys, Leu, Val, or Asp, or missing |
| B29 | Lys, Pro, or Glu, or missing |
| B30 | Thr, Ala, Lys, Gln, Ser or Arg, or missing |
| B31 | Any codable amino acid, sequence of codable amino acids, Arg-Arg, or missing |

In certain embodiments, an insulin polypeptide of Formula I comprises an amino acid sequence of SEQ ID NO:28 (A-peptide) and an amino acid sequence of SEQ ID NO:29 (B-peptide) as shown below in Formula II:

In some embodiments, an insulin polypeptide of Formula I, I', II or II' comprises amino acids at positions A8, A9, A10, and B30 selected from those shown in Table 3 below. In some embodiments, an insulin polypeptide of Formula I, I', II or II' comprises amino acids at positions A8, A9, A10, and B30 selected from those shown in Table 3 below for a single species (e.g., from the human sequence or Thr at A8, Ser at A9, Ile at A10 and Thr at B30).

TABLE 3

| | Amino Acid Position | | | |
|---|---|---|---|---|
| Species | A8 | A9 | A10 | B30 |
| Human | Thr | Ser | Ile | Thr |
| Rabbit | Thr | Ser | Ile | Ser |
| Porcine | Thr | Ser | Ile | Ala |
| Bovine | Ala | Ser | Val | Ala |
| Sheep | Ala | Gly | Val | Ala |

In various embodiments, an insulin polypeptide of the present disclosure is mutated at the B28 and/or B29 positions of the B-peptide sequence. For example, insulin lispro (HUMALOG®) is a rapid acting insulin mutant in which the penultimate lysine and proline residues on the C-terminal end of the B-peptide have been reversed ($Lys^{B28}Pro^{B29}$-human insulin). This modification blocks the formation of insulin multimers. Insulin aspart (NOVOLOG®) is another rapid acting insulin mutant in which praline at position B28 has been substituted with aspartic acid ($Asp^{B28}$-human insulin). This mutant also prevents the formation of multimers. In some embodiments, mutation at positions B28 and/or B29 is accompanied by one or more mutations elsewhere in the insulin polypeptide. For example, insulin glulisine (APIDRA®) is yet another rapid acting insulin mutant in which aspartic acid at position B3 has been replaced by a (II)

```
A-Peptide (SEQ ID NO: 28)
Xaa-Gly-Ile-Val-Glu-Gln-Cys-Cys-Xaa-Xaa-Xaa-Cys-Ser-Leu-Tyr-Gln-Leu-Glu-Xaa-Tyr-Cys-Xaa-Xaa
 0   1   2   3   4   5   6   7   8   9   10  11  12  13  14  15  16  17  18  19  20  21  22

B-Peptide (SEQ ID NO: 29)
Xaa-Phe-Val-Xaa-Gln-His-Leu-Cys-Gly-Ser-His-Leu-Val-Glu-Ala-Leu-Tyr-Leu-Val-Cys-Gly-Glu-Arg-
 0   1   2   3   4   5   6   7   8   9   10  11  12  13  14  15  16  17  18  19  20  21  22

Gly-Phe-Phe-Tyr-Thr-Xaa-Xaa-Xaa-Xaa
 23  24  25  26  27  28  29  30  31
```

The present disclosure also specifically encompasses insulin polypeptides of Formula II having discontiguous A- and B-peptide sequences and three disulfide bridges as shown in Formula II':

lysine residue and lysine at position B29 has been replaced with a glutamic acid residue ($Lys^{B3}Glu^{B29}$-human insulin).

In various embodiments, an insulin polypeptide of the present disclosure has an isoelectric point that is shifted rela-

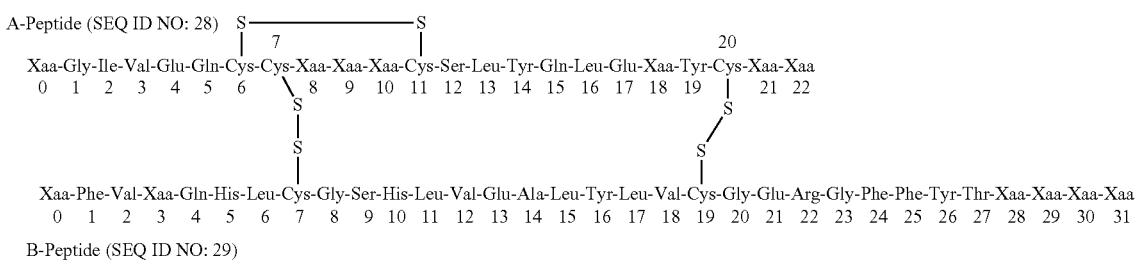
(II')

tive to human insulin. In some embodiments, the shift in isoelectric point is achieved by adding one or more arginine residues to the N-terminus of the insulin A-peptide and/or the C-terminus of the insulin B-peptide. Examples of such insulin polypeptides include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS®) is an exemplary long acting insulin mutant in which $Asp^{A21}$ has been replaced by glycine, and two arginine residues have been added to the C-terminus of the B-peptide. The effect of these changes is to shift the isoelectric point, producing a solution that is completely soluble at pH 4. Thus, in some embodiments, an insulin polypeptide of the present disclosure comprises an A-peptide sequence wherein A21 is Gly and B-peptide sequence wherein B31 is Arg-Arg. It is to be understood that the present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In various embodiments, an insulin molecule of the present disclosure may include a deletion. For example, in certain embodiments, a B-peptide sequence of an insulin polypeptide of the present disclosure is missing B1, B2, B3, B26, B27, B28, B29 and/or B30.

In various embodiments, an insulin polypeptide of the present disclosure may be truncated. For example, the B-peptide sequence may be missing residues B(1-2), B(1-3), B(29-30), B(28-30), B(27-30), and/or B(26-30). In some embodiments, these deletions and/or truncations apply to any of the aforementioned insulin polypeptides (e.g., without limitation to produce ΔB30 insulin lispro, ΔB30 insulin aspart, ΔB30 insulin glulisine, ΔB30 insulin glargine, etc.).

In some embodiments, an insulin polypeptide contains additional amino acid residues on the N- or C-terminus of the A or B-peptide sequences. In some embodiments, one or more amino acid residues are located at positions A0, A22, B0, and/or B31. In some embodiments, one or more amino acid residues are located at position A0. In some embodiments, one or more amino acid residues are located at position A22. In some embodiments, one or more amino acid residues are located at position B0. In some embodiments, one or more amino acid residues are located at position B31. In certain embodiments, an insulin polypeptide does not include any additional amino acid residues at positions A0, A22, B0, or B31.

In certain embodiments, an insulin polypeptide of the present disclosure may have mutations wherein one or more amidated amino acids are replaced with acidic forms. For example, asparagine may be replaced with aspartic acid or glutamic acid. Likewise, glutamine may be replaced with aspartic acid or glutamic acid. In particular, $Asn^{A18}$, $Asn^{A21}$, or $Asn^{B3}$, or any combination of those residues, may be replaced by aspartic acid or glutamic acid. $Gln^{A15}$ or $Gln^{B4}$, or both, may be replaced by aspartic acid or glutamic acid. In certain embodiments, an insulin polypeptide has aspartic acid at position A21 or aspartic acid at position B3, or both.

One skilled in the art will recognize that it is possible to mutate yet other amino acids in the insulin polypeptide while retaining biological activity. For example, without limitation, the following modifications are also widely accepted in the art: replacement of the histidine residue of position B10 with aspartic acid ($His^{B10}{\rightarrow}Asp^{B10}$) replacement of the phenylalanine residue at position B1 with aspartic acid ($Phe^{B1}{\rightarrow}Asp^{B1}$); replacement of the threonine residue at position B30 with alanine) ($Thr^{B30}{\rightarrow}Ala^{B30}$); replacement of the tyrosine residue at position B26 with alanine ($Tyr^{B26}{\rightarrow}Ala^{B26}$); and replacement of the serine residue at position B9 with aspartic acid ($Ser^{B9}{\rightarrow}Asp^{B9}$).

In some embodiments, an insulin polypeptide is modified and/or mutated to reduce its affinity for the insulin receptor. Without wishing to be bound to a particular theory, it is believed that attenuating the receptor affinity of an insulin polypeptide through modification (e.g., acylation) or mutation may decrease the rate at which the insulin polypeptide is eliminated from serum. In some embodiments, a decreased insulin receptor affinity in vitro translates into a superior in vivo activity for an insulin conjugate. In certain other embodiments, an insulin molecule is mutated at position A3, A4, A5, A8, A9, or B30 to reduce its affinity for the insulin receptor (e.g., $Lys^{A4}$, $Lys^{A5}$, $Lys^{A8}$, $Lys^{A9}$, or $Lys^{B30}$).

In various embodiments, an insulin polypeptide of the present disclosure has a protracted profile of action. Thus, in certain embodiments, an insulin polypeptide of the present disclosure may be acylated with a fatty acid. That is, an amide bond is formed between an amino group on the insulin polypeptide and the carboxylic acid group of the fatty acid. The amino group may be the alpha-amino group of an N-terminal amino acid of the insulin polypeptide, or may be the epsilon-amino group of a lysine residue of the insulin polypeptide. An insulin polypeptide of the present disclosure may be acylated at one or more of the three amino groups that are present in wild-type insulin or may be acylated on lysine residue that has been introduced into the wild-type sequence. In certain embodiments, an insulin polypeptide may be acylated at position B1. In certain embodiments, an insulin polypeptide may be acylated at position B29. In certain embodiments, the fatty acid is selected from myristic acid (C14), pentadecylic acid (C15), palmitic acid (C16), heptadecylic acid (C17) and stearic acid (C18). For example, insulin detemir (LEVEMIR®) is a long acting insulin mutant in which $Thr^{B30}$ has been deleted, and a C14 fatty acid chain (myristic acid) has been attached to $Lys^{B29}$.

In some embodiments, the N-terminus of the A-peptide, the N-terminus of the B-peptide, the epsilon-amino group of Lys at position B29 or any other available amino group in an insulin polypeptide of the present disclosure is covalently linked to a moiety of general formula:

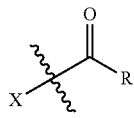

where X is an amino group of the insulin polypeptide and R is H or a $C_{1-30}$ alkyl group. In some embodiments, R is a $C_{1-20}$ alkyl group, a $C_{3-19}$ alkyl group, a $C_{5-18}$ alkyl group, a $C_{6-17}$ alkyl group, a $C_{8-16}$ alkyl group, a $C_{10-15}$ alkyl group, a $C_{12-14}$ alkyl group, etc. In certain embodiments, the insulin polypeptide is conjugated to the moiety at the A1 position. In certain embodiments, the insulin polypeptide is conjugated to the moiety at the B1 position. In certain embodiments, the insulin polypeptide is conjugated to the moiety at the epsilon-amino group of Lys at position B29. In certain embodiments, position B28 of the insulin polypeptide is Lys and the epsilon-amino group of $Lys^{B28}$ is conjugated to the fatty acid moiety. In certain embodiments, position B3 of the insulin polypeptide is Lys and the epsilon-amino group of $Lys^{B3}$ is conjugated to the fatty acid moiety. In some embodiments, the fatty acid chain is 8-20 carbons long. In some embodiments, the fatty acid is octanoic acid (C8), nonanoic acid (C9), decanoic acid (C10), undecanoic acid (C11), dodecanoic acid (C12), or tridecanoic acid (C13). In certain embodiments, the fatty acid is myristic acid (C14), pentadecanoic acid (C15), palmitic acid (C16), heptadecanoic acid (C17), stearic acid (C18), nonadecanoic acid (C19), or arachidic acid (C20).

In certain embodiments, an insulin polypeptide of the present disclosure comprises an N-linked glycan motif and the mutations and/or chemical modifications of one of the following insulin polypeptides: $Lys^{B28}Pro^{B29}$-human insulin (insulin lispro), $Asp^{B28}$-human insulin (insulin aspart), $Lys^{B3}Glu^{B29}$-human insulin (insulin glulisine), $Arg^{B31}Arg^{B32}$-human insulin (insulin glargine), $N^{\epsilon B29}$-myristoyl-des(B30)-human insulin (insulin detemir), $Ala^{B26}$-human insulin, $Asp^{B1}$-human insulin, $Arg^{40}$-human insulin, $Asp^{B1}Glu^{B13}$-human insulin, $Gly^{A21}$-human insulin, $Gly^{A21}Arg^{B31}Arg^{B32}$-human insulin, $Arg^{40}Arg^{B31}Arg^{B32}$-human insulin, $Arg^{40}Gly^{A21}Arg^{B31}Arg^{B32}$-human insulin, des(B30)-human insulin, des(B27)-human insulin, des(B28-B30)-human insulin, des(B1)-human insulin, des(B1-B3)-human insulin.

In certain embodiments, an insulin polypeptide of the present disclosure comprises an N-linked glycan motif and the mutations and/or chemical modifications of one of the following insulin polypeptides: $N^{\epsilon B29}$-palmitoyl-human insulin, $N^{\epsilon B29}$-myrisotyl-human insulin, $N^{\epsilon B28}$-palmitoyl-$Lys^{B28}Pro^{B29}$-human insulin, $N^{\gamma B}28$-myristoyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B29}$-palmitoyl-des(B30)-human insulin, $N^{\epsilon B30}$-myristoyl-$Thr^{B29}Lys^{B30}$-human insulin, $N^{\epsilon B30}$-palmitoyl-$Thr^{B29}Lys^{B30}$-human insulin, $N^{\epsilon B29}$-(N-palmitoyl-γ-glutamyl)-des(B30)-human insulin, $N^{\epsilon B29}$-(N-lithocolyl-γ-glutamyl)-des(B30)-human insulin, $N^{\epsilon B29}$-(ω-carboxyheptadecanoyl)-des(B30)-human insulin, $N^{\epsilon B29}$-(ω-carboxyheptadecanoyl)-human insulin.

In certain embodiments, an insulin polypeptide of the present disclosure comprises an N-linked glycan motif and the mutations and/or chemical modifications of one of the following insulin polypeptides: $N^{\epsilon B29}$-octanoyl-human insulin, $N^{\epsilon B29}$-myristoyl-$Gly^{A21}Arg^{B31}Arg^{B31}$-human insulin, $N^{\epsilon B29}$-myristoyl-$Gly^{A21}Gln^{B3}Arg^{B31}Arg^{B32}$-human insulin, $N^{\epsilon B29}$-myristoyl-$Arg^{40}Gly^{A21}Arg^{B31}Arg^{B32}$-human insulin, $N^{\epsilon B29}$-$Arg^{40}Gly^{A21}Gln^{B3}Arg^{B31}Arg^{B32}$-human insulin, $N^{\epsilon B29}$-myristoyl-$Arg^{40}Gly^{A21}Asp^{B3}Arg^{B31}Arg^{B32}$-human insulin, $N^{\epsilon B29}$-myristoyl-$Arg^{B31}Arg^{B32}$-human insulin, $N^{\epsilon B29}$-myristoyl-$Arg^{40}Arg^{B31}Arg^{B32}$-human insulin, $N^{\epsilon B29}$-octanoyl-$Gly^{A21}Arg^{B31}Arg^{B32}$-human insulin, $N^{\epsilon B29}$-octanoyl-$Gly^{A21}Gln^{B3}Arg^{B31}Arg^{B32}$-human insulin, $N^{\epsilon B29}$-octanoyl-$Arg^{40}Gly^{A21}Arg^{B31}Arg^{B32}$-human insulin, $N^{\epsilon B29}$-octanoyl-$Arg^{40}Gly^{A21}Gln^{B3}Arg^{B31}Arg^{B32}$-human insulin, $N^{\epsilon B29}$-octanoyl-$Arg^{B0}Gly^{A21}Asp^{B3}Arg^{B31}Arg^{B32}$-human insulin, $N^{\epsilon B29}$-octanoyl-$Arg^{B31}Arg^{B32}$-human insulin, $N^{\epsilon B29}$-octanoyl-$Arg^{40}Arg^{B31}Arg^{B32}$-human insulin.

In certain embodiments, an insulin polypeptide of the present disclosure comprises an N-linked glycan motif and the mutations and/or chemical modifications of one of the following insulin polypeptides: $N^{\epsilon B28}$-myristoyl-$Gly^{A21}Lys^{B28}Pro^{B29}Arg^{B31}Arg^{B32}$-human insulin, $N^{\epsilon B28}$-myristoyl-$Gly^{A21}Gln^{B3}Lys^{B28}Pro^{B30}Arg^{B31}Arg^{B32}$-human insulin, $N^{\epsilon B28}$-myristoyl-$Arg^{40}Gly^{A21}Lys^{B28}Pro^{B29}Arg^{B31}Arg^{B32}$-human insulin, $N^{\epsilon B28}$-myristoyl-$Arg^{40}Gly^{A21}Gln^{B3}Lys^{B28}Pro^{B29}Arg^{B31}Arg^{B32}$-human insulin, $N^{\epsilon B28}$-myristoyl-$Arg^{40}Gly^{A21}Asp^{B3}Lys^{B28}Pro^{B29}Arg^{B31}Arg^{B32}$-human insulin, $N^{\epsilon B28}$-myristoyl-$Lys^{B28}Pro^{B29}Arg^{B31}Arg^{B32}$-human insulin, $N^{\epsilon B28}$-myristoyl-$arg^{40}Lys^{B28}Pro^{B29}Arg^{B31}Arg^{B32}$-human insulin, $N^{\epsilon B28}$-octanoyl-$Gly^{A21}Lys^{B28}Pro^{B29}Arg^{B31}Arg^{B32}$-human insulin.

In certain embodiments, an insulin polypeptide of the present disclosure comprises an N-linked glycan motif and the mutations and/or chemical modifications of one of the following insulin polypeptides: $N^{\epsilon B28}$-octanoyl-$Gly^{A21}Gln^{B3}Lys^{B28}Pro^{B29}Arg^{B31}Arg^{B32}$-human insulin, $N^{\epsilon B28}$-octanoyl-$Arg^{40}Gly^{A21}Lys^{B28}Pro^{B29}Arg^{B31}Arg^{B32}$-human insulin, $N^{\epsilon B28}$-octanoyl-$Arg^{40}Gly^{A21}Gln^{B3}Lys^{B28}Pro^{B29}Arg^{B31}Arg^{B32}$-human insulin, $N^{\epsilon B28}$-octanoyl-$Arg^{40}Gly^{A21}Asp^{B3}Lys^{B28}Pro^{B29}Arg^{B31}Arg^{B32}$-human insulin, $N^{\epsilon B28}$-octanoyl-$Lys^{B28}Pro^{B29}Arg^{B31}Arg^{B32}$-human insulin, $N^{\epsilon B28}$-octanoyl-$Arg^{40}Lys^{B28}Pro^{B29}Arg^{B31}Arg^{B32}$-human insulin.

In certain embodiments, an insulin polypeptide of the present disclosure comprises an N-linked glycan motif and the mutations and/or chemical modifications of one of the following insulin polypeptides: $N^{\epsilon B29}$-tridecanoyl-des(B30)-human insulin, $N^{\epsilon B29}$-tetradecanoyl-des(B30)-human insulin, $N^{\epsilon B29}$-decanoyl-des(B30)-human insulin, $N^{\epsilon B29}$-dodecanoyl-des(B30)-human insulin, $N^{\epsilon B29}$-tridecanoyl-$Gly^{A21}$-des(B30)-human insulin, $N^{\epsilon B29}$-tetradecanoyl-$Gly^{A21}$-des(B30)-human insulin, $N^{\epsilon B29}$-decanoyl-$Gly^{A21}$-des(B30)-human insulin, $N^{\epsilon B29}$-dodecanoyl-$Gly^{A21}$-des(B30)-human insulin, $N^{\epsilon B29}$-tridecanoyl-$Gly^{A21}Gln^{B3}$-des(B30)-human insulin, $N^{\epsilon B29}$-tetradecanoyl-$Gly^{A21}Gln^{B3}$-des(B30)-human insulin, $N^{\epsilon B29}$-decanoyl-$Gly^{A21}$-$Gln^{B3}$-des(B30)-human insulin, $N^{\epsilon B29}$-dodecanoyl-$Gly^{A21}$-$Gln^{B3}$-des(B30)-human insulin, $N^{\epsilon B29}$-tridecanoyl-$Ala^{A21}$-des(B30)-human insulin, $N^{\epsilon B29}$-tetradecanoyl-$Ala^{A21}$-des(B30)-human insulin, $N^{\epsilon B29}$-decanoyl-$Ala^{A21}$-des(B30)-human insulin, $N^{\epsilon B29}$-dodecanoyl-$Ala^{A21}$-des(B30)-human insulin, $N^{\epsilon B29}$-tridecanoyl-$Ala^{A21}$-$Gln^{B3}$-des(B30)-human insulin, $N^{\epsilon B29}$-tetradecanoyl-$Ala^{A21}Gln^{B3}$-des(B30)-human insulin, $N^{\epsilon B29}$-decanoyl-$Ala^{A21}Gln^{B3}$-des(B30)-human insulin, $N^{\epsilon B29}$-dodecanoyl-$Ala^{A21}Gln^{B3}$-des(B30)-human insulin, $N^{\epsilon B29}$-tridecanoyl-$Gln^{B3}$-des(B30)-human insulin, $N^{\epsilon B29}$-tetradecanoyl-$Gln^{B3}$-des(B30)-human insulin, $N^{\epsilon B29}$-decanoyl-$Gln^{B3}$-des(B30)-human insulin, $N^{\epsilon B29}$-dodecanoyl-$Gln^{B3}$-des(B30)-human insulin.

In certain embodiments, an insulin polypeptide of the present disclosure comprises an N-linked glycan motif and the mutations and/or chemical modifications of one of the following insulin polypeptides: $N^{\epsilon B29}$-tridecanoyl-$Gly^{A21}$-human insulin, $N^{\epsilon B29}$-tetradecanoyl-$Gly^{A21}$-human insulin, $N^{\epsilon B29}$-decanoyl-$Gly^{A21}$-human insulin, $N^{\epsilon B29}$-dodecanoyl-$Gly^{A21}$-human insulin, $N^{\epsilon B29}$-tridecanoyl-$Ala^{A21}$-human insulin, $N^{\epsilon B29}$-tetradecanoyl-$Ala^{A21}$-human insulin, $N^{\epsilon B29}$-decanoyl-$Ala^{A21}$-human insulin, $N^{\epsilon B29}$-dodecanoyl-$Ala^{A21}$-human insulin.

In certain embodiments, an insulin polypeptide of the present disclosure comprises an N-linked glycan motif and the mutations and/or chemical modifications of one of the following insulin polypeptides: $N^{\epsilon B29}$-tridecanoyl-$Gly^{A21}Gln^{B3}$-human insulin, $N^{\epsilon B29}$-tetradecanoyl-$Gly^{A21}Gln^{B3}$-human insulin, $N^{\epsilon B29}$-decanoyl-$Gly^{A21}Gln^{B3}$-human insulin, $N^{\epsilon B29}$-dodecanoyl-$Gly^{A21}Gln^{B3}$-human insulin, $N^{6329}$-tridecanoyl-$Ala^{A21}Gln^{B3}$-human insulin, $N^{\epsilon B29}$-tetradecanoyl-$Ala^{A21}Gln^{B3}$-human insulin, $N^{\epsilon B29}$-decanoyl-$Ala^{A21}Gln^{B3}$-human insulin, $N^{\epsilon B29}$-dodecanoyl-$Ala^{A21}Gln^{B3}$-human insulin.

In certain embodiments, an insulin polypeptide of the present disclosure comprises an N-linked glycan motif and the mutations and/or chemical modifications of one of the following insulin polypeptides: $N^{\epsilon B29}$-tridecanoyl-Gln$^{B3}$-human insulin, $N^{\epsilon B29}$-tetradecanoyl-Gln$^{B3}$-human insulin, $N^{\epsilon B29}$-decanoyl-Gln$^{B3}$-human insulin, $N^{\epsilon B29}$-dodecanoyl-Gln$^{B3}$-human insulin.

In certain embodiments, an insulin polypeptide of the present disclosure comprises an N-linked glycan motif and the mutations and/or chemical modifications of one of the following insulin polypeptides: $N^{\epsilon B29}$-tridecanoyl-Glu$^{B30}$-human insulin, $N^{\epsilon B29}$-tetradecanoyl-Glu$^{B30}$-human insulin, $N^{\epsilon B29}$-decanoyl-Glu$^{B30}$-human insulin, $N^{\epsilon B29}$-dodecanoyl-Glu$^{B30}$-human insulin.

In certain embodiments, an insulin polypeptide of the present disclosure comprises an N-linked glycan motif and the mutations and/or chemical modifications of one of the following insulin polypeptides: $N^{\epsilon B29}$-tridecanoyl-Gly$^{A21}$Glu$^{B30}$-human insulin, $N^{\epsilon B29}$-tetradecanoyl-Gly$^{A21}$Glu$^{B30}$-human insulin, $N^{\epsilon B29}$-decanoyl-Gly$^{A21}$Glu$^{B30}$-human insulin, $N^{\epsilon B29}$-dodecanoyl-Gly$^{A21}$Glu$^{B30}$-human insulin.

In certain embodiments, an insulin polypeptide of the present disclosure comprises an N-linked glycan motif and the mutations and/or chemical modifications of one of the following insulin polypeptides: $N^{\epsilon B29}$-tridecanoyl-Gly$^{A21}$Gln$^{B3}$Glu$^{B30}$-human insulin, $N^{\epsilon B29}$-tetradecanoyl-Gly$^{A21}$Gln$^{B3}$Glu$^{B30}$-human insulin, $N^{\epsilon B29}$-decanoyl-Gly$^{A21}$Gln$^{B3}$Glu$^{B30}$-human insulin, $N^{\epsilon B29}$-dodecanoyl-Gly$^{A21}$Gln$^{B3}$Glu$^{B30}$-human insulin, $N^{\epsilon B29}$-tridecanoyl-Ala$^{A21}$Glu$^{B30}$-human insulin, $N^{\epsilon B29}$-tetradecanoyl-Ala$^{A21}$Glu$^{B30}$-human insulin, $N^{\epsilon B29}$-decanoyl-Ala$^{A21}$Glu$^{B30}$-human insulin, $N^{\epsilon B29}$-dodecanoyl-Ala$^{A21}$Glu$^{B30}$-human insulin, $N^{\epsilon B29}$-tridecanoyl-Ala$^{A21}$Gln$^{B3}$Glu$^{B30}$-human insulin, $N^{\epsilon B29}$-tetradecanoyl-Ala$^{A21}$Gln$^{B3}$Glu$^{B30}$-human insulin, $N^{\epsilon B29}$-decanoyl-Ala$^{A21}$Gln$^{B3}$Glu$^{30}$-human insulin, $N^{\epsilon B29}$-dodecanoyl-Ala$^{A21}$Gln$^{B3}$Glu$^{B30}$-human insulin.

In certain embodiments, an insulin polypeptide of the present disclosure comprises an N-linked glycan motif and the mutations and/or chemical modifications of one of the following insulin polypeptides: $N^{\epsilon B29}$-tridecanoyl-Gln$^{B3}$Glu$^{B30}$-human insulin, $N^{\epsilon B29}$-tetradecanoyl-Gln$^{B3}$Glu$^{B30}$-human insulin, $N^{\epsilon B29}$-decanoyl-Gln$^{B3}$Glu$^{B30}$-human insulin, $N^{\epsilon B29}$-dodecanoyl-Gln$^{B3}$Glu$^{B30}$-human insulin.

In certain embodiments, an insulin polypeptide of the present disclosure comprises an N-linked glycan motif and the mutations and/or chemical modifications of one of the following insulin polypeptides: $N^{\epsilon B29}$-formyl-human insulin, $N^{\alpha B1}$-formyl-human insulin, $N^{\alpha A1}$-formyl-human insulin, $N^{\epsilon B29}$-formyl-$N^{\alpha B1}$-formyl-human insulin, $N^{\epsilon B29}$-formyl-$N^{\alpha A1}$-formyl-human insulin, $N^{\alpha A1}$-formyl-$N^{\alpha B1}$-formyl-human insulin, $N^{\epsilon B29}$-formyl-$N^{\alpha A1}$-formyl-$N^{\alpha B1}$-formyl-human insulin.

In certain embodiments, an insulin polypeptide of the present disclosure comprises an N-linked glycan motif and the mutations and/or chemical modifications of one of the following insulin polypeptides: $N^{\epsilon B29}$-acetyl-human insulin, $N^{\alpha B1}$-acetyl-human insulin, $N^{\alpha A1}$-acetyl-human insulin, $N^{\epsilon B29}$-acetyl-$N^{\alpha B1}$-acetyl-human insulin, $N^{\epsilon B29}$-acetyl-$N^{\alpha A1}$-acetyl-human insulin, $N^{\alpha A1}$-acetyl-$N^{\alpha B1}$-acetyl-human insulin, $N^{\epsilon B29}$-acetyl-$N^{\alpha A1}$-acetyl-$N^{\alpha B1}$-acetyl-human insulin.

In certain embodiments, an insulin polypeptide of the present disclosure comprises an N-linked glycan motif and the mutations and/or chemical modifications of one of the following insulin polypeptides: $N^{\epsilon B29}$-propionyl-human insulin, $N^{\alpha B1}$-propionyl-human insulin, $N^{\alpha A1}$-propionyl-human insulin, $N^{\epsilon B29}$-acetyl-$N^{\alpha B1}$-propionyl-human insulin, $N^{\epsilon B29}$-propionyl-$N^{\alpha A1}$-propionyl-human insulin, $N^{\alpha A1}$-propionyl-$N^{\alpha B1}$-propionyl-human insulin, $N^{\epsilon B29}$-propionyl-$N^{\alpha A1}$-propionyl-$N^{\alpha B1}$-propionyl-human insulin.

In certain embodiments, an insulin polypeptide of the present disclosure comprises an N-linked glycan motif and the mutations and/or chemical modifications of one of the following insulin polypeptides: $N^{\epsilon B29}$-butyryl-human insulin, $N^{\alpha B1}$-butyryl-human insulin, $N^{\alpha A1}$-butyryl-human insulin, $N^{\epsilon B29}$-butyryl-$N^{\alpha B1}$-butyryl-human insulin, $N^{\epsilon B29}$-butyryl-$N^{\alpha A1}$-butyryl-human insulin, $N^{\alpha A1}$-butyryl-$N^{\alpha B1}$-butyryl-human insulin, $N^{\epsilon B29}$-butyryl-$N^{\alpha A1}$-butyryl-$N^{\alpha B1}$-butyryl-human insulin.

In certain embodiments, an insulin polypeptide of the present disclosure comprises an N-linked glycan motif and the mutations and/or chemical modifications of one of the following insulin polypeptides: $N^{\epsilon B29}$-pentanoyl-human insulin, $N^{\alpha B1}$-pentanoyl-human insulin, $N^{\alpha A1}$-pentanoyl-human insulin, $N^{\epsilon B29}$-pentanoyl-$N^{\alpha B1}$-pentanoyl-human insulin, $N^{\epsilon B29}$-pentanoyl-$N^{\alpha A1}$-pentanoyl-human insulin, $N^{\alpha A1}$-pentanoyl-$N^{\alpha B1}$-pentanoyl-human insulin, $N^{\epsilon B29}$-pentanoyl-$N^{\alpha A1}$-pentanoyl-$N^{\alpha B1}$-pentanoyl-human insulin.

In certain embodiments, an insulin polypeptide of the present disclosure comprises an N-linked glycan motif and the mutations and/or chemical modifications of one of the following insulin polypeptides: $N^{\epsilon B29}$-hexanoyl-human insulin, $N^{\alpha B1}$-hexanoyl-human insulin, $N^{\alpha A1}$-hexanoyl-human insulin, $N^{\epsilon B29}$-hexanoyl-$N^{\alpha B1}$-hexanoyl-human insulin, $N^{\epsilon B29}$-hexanoyl-$N^{\alpha A1}$-hexanoyl-human insulin, $N^{\alpha A1}$-hexanoyl-$N^{\alpha B1}$-hexanoyl-human insulin, $N^{\epsilon B29}$-hexanoyl-$N^{\alpha A1}$-hexanoyl-$N^{\alpha B1}$-hexanoyl-human insulin.

In certain embodiments, an insulin polypeptide of the present disclosure comprises an N-linked glycan motif and the mutations and/or chemical modifications of one of the following insulin polypeptides: $N^{\epsilon B29}$-heptanoyl-human insulin, $N^{\alpha B1}$-heptanoyl-human insulin, $N^{\alpha A1}$-heptanoyl-human insulin, $N^{\epsilon B29}$-heptanoyl-$N^{\alpha B1}$-heptanoyl-human insulin, $N^{\epsilon B29}$-heptanoyl-$N^{\alpha A1}$-heptanoyl-human insulin, $N^{\alpha A1}$-heptanoyl-$N^{\alpha B1}$-heptanoyl-human insulin, $N^{\epsilon B29}$-heptanoyl-$N^{\alpha A1}$-heptanoyl-$N^{\alpha B1}$-heptanoyl-human insulin.

In certain embodiments, an insulin polypeptide of the present disclosure comprises an N-linked glycan motif and the mutations and/or chemical modifications of one of the following insulin polypeptides: $N^{\alpha B1}$-octanoyl-human insulin, $N^{\alpha A1}$-octanoyl-human insulin, $N^{\epsilon B29}$-octanoyl-$N^{\alpha B1}$-octanoyl-human insulin, $N^{\epsilon B29}$-octanoyl-$N^{\alpha A1}$-octanoyl-human insulin, $N^{\alpha A1}$-octanoyl-$N^{\alpha B1}$-octanoyl-human insulin, $N^{\epsilon B29}$-octanoyl-$N^{\alpha A1}$-octanoyl-$N^{\alpha B1}$-octanoyl-human insulin.

In certain embodiments, an insulin polypeptide of the present disclosure comprises an N-linked glycan motif and the mutations and/or chemical modifications of one of the following insulin polypeptides: $N^{\epsilon B29}$-nonanoyl-human insulin, $N^{\alpha B1}$-nonanoyl-human insulin, $N^{\alpha A1}$-nonanoyl-human insulin, $N^{\epsilon B29}$-nonanoyl-$N^{\alpha B1}$-nonanoyl-human insulin, $N^{\epsilon B29}$-nonanoyl-$N^{\alpha A1}$-nonanoyl-human insulin, $N^{\alpha A1}$-nonanoyl-$N^{\alpha B1}$-nonanoyl-human insulin, $N^{\epsilon B29}$-nonanoyl-$N^{\alpha A1}$-nonanoyl-$N^{\alpha B1}$-nonanoyl-human insulin.

In certain embodiments, an insulin polypeptide of the present disclosure comprises an N-linked glycan motif and the mutations and/or chemical modifications of one of the following insulin polypeptides: $N^{\epsilon B29}$-decanoyl-human insulin, $N^{\alpha B1}$-decanoyl-human insulin, $N^{\alpha A1}$-decanoyl-human insulin, $N^{\epsilon B29}$-decanoyl-$N^{\alpha B1}$-decanoyl-human insulin, $N^{\epsilon B29}$-decanoyl-$N^{\alpha A1}$-decanoyl-human insulin, $N^{\alpha A1}$-decanoyl-$N^{\alpha B1}$-decanoyl-human insulin, $N^{\epsilon B29}$-decanoyl-$N^{\alpha A1}$-decanoyl-$N^{\alpha B1}$-decanoyl-human insulin.

In certain embodiments, an insulin polypeptide of the present disclosure comprises an N-linked glycan motif and the mutations and/or chemical modifications of one of the following insulin polypeptides: $N^{\epsilon B28}$-formyl-$Lys^{B28}Pro^{B29}$-human insulin, $N^{\alpha B1}$-formyl-$Lys^{B28}Pro^{B29}$-human insulin, $N^{\alpha A1}$-formyl-$Lys^{B28}Pro^{B29}$-human insulin, $N^{\epsilon B28}$-formyl-$N^{\alpha B1}$-formyl-$Lys^{B28}Pro^{B29}$-human insulin, $N^{\epsilon B28}$-formyl-$N^{\alpha A1}$-formyl-$Lys^{B28}Pro^{B29}$-human insulin, $N^{\alpha A1}$-formyl-$N^{\alpha B1}$-formyl-$Lys^{B28}Pro^{B29}$-human insulin, $N^{\epsilon B28}$-formyl-$N^{\alpha A1}$-formyl-$N^{\alpha B1}$-formyl-$Lys^{B28}Pro^{B29}$-human insulin, $N^{\epsilon B29}$-acetyl-$Lys^{B28}Pro^{B29}$-human insulin, $N^{\alpha A1}$-acetyl-$Lys^{B28}Pro^{B29}$-human insulin, $N^{\alpha A1}$-acetyl-$Lys^{B28}Pro^{B29}$-human insulin, $N^{\epsilon B28}$-acetyl-$N^{\alpha B1}$-acetyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B28}$-acetyl-$N^{\alpha A1}$-acetyl-$Lys^{B28}Pro^{B29}$-human insulin, $N^{\alpha A1}$-acetyl-$N^{\alpha B1}$-acetyl-$Lys^{B28}Pro^{B29}$-human insulin, $N^{\epsilon B28}$-acetyl-$N^{\alpha A1}$-acetyl-$N^{\alpha B1}$-acetyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B28}$-propionyl-$Lys^{B28}Pro^{B29}$-human insulin, $N^{\alpha B1}$-propionyl-$Lys^{B28}Pro^{B29}$-human insulin, $N^{\alpha A1}$-propionyl-$Lys^{B28}Pro^{B29}$-human insulin, $N^{\epsilon B28}$-propionyl-$N^{\alpha B1}$-propionyl-$Lys^{B28}Pro^{B29}$-human insulin, $N^{\epsilon B28}$-propionyl-$N^{\alpha A1}$-propionyl-$Lys^{B28}Pro^{B29}$-human insulin, $N^{\alpha A1}$-propionyl-$N^{\alpha B1}$-propionyl-$Lys^{B28}Pro^{B29}$-human insulin, $N^{\epsilon B28}$-propionyl-$N^{\alpha A1}$-propionyl-$N^{\alpha B1}$-propionyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B28}$-butyryl-$Lys^{B28}Pro^{B29}$-human insulin, $N^{\alpha B1}$-butyryl-$Lys^{B28}Pro^{B29}$-human insulin, $N^{\alpha A1}$-butyryl-$Lys^{B28}Pro^{B29}$-human insulin, $N^{\epsilon B28}$-butyryl-$N^{\alpha B1}$-butyryl-$Lys^{B28}Pro^{B29}$-human insulin, $N^{\epsilon B28}$-butyryl-$N^{\alpha A1}$-butyryl-$Lys^{B28}Pro^{B29}$-human insulin, $N^{\alpha A1}$-butyryl-$N^{\alpha B1}$-butyryl-$Lys^{B28}Pro^{B29}$-human insulin, $N^{\epsilon B28}$-butyryl-$N^{\alpha A1}$-butyryl-$N^{\alpha B1}$-butyryl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B28}$-pentanoyl-$Lys^{B28}Pro^{B29}$-human insulin, $N^{\alpha B1}$-pentanoyl-$Lys^{B28}Pro^{B29}$-human insulin, $N^{\alpha A1}$-pentanoyl-$Lys^{B28}Pro^{B29}$-human insulin, $N^{\epsilon B28}$-pentanoyl-$N^{\alpha B1}$-pentanoyl-$Lys^{B28}Pro^{B29}$-human insulin, $N^{\epsilon B28}$-pentanoyl-$N^{\alpha A1}$-pentanoyl-$Lys^{B28}Pro^{B29}$-human insulin, $N^{\alpha A1}$-pentanoyl-$N^{\alpha B1}$-pentanoyl-$Lys^{B28}Pro^{B29}$-human insulin, $N^{\epsilon B28}$-pentanoyl-$N^{\alpha A1}$-pentanoyl-$N^{\alpha B1}$-pentanoyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B28}$-hexanoyl-$Lys^{B28}Pro^{B29}$-human insulin, $N^{\alpha B1}$-hexanoyl-$Lys^{B28}Pro^{B29}$-human insulin, $N^{\alpha A1}$-hexanoyl-$Lys^{B28}Pro^{B29}$-human insulin, $N^{\epsilon B28}$-hexanoyl-$N^{\alpha B1}$-hexanoyl-$Lys^{B28}Pro^{B29}$-human insulin, $N^{\epsilon B28}$-hexanoyl-$N^{\alpha A1}$-hexanoyl-$Lys^{B28}Pro^{B29}$-human insulin, $N^{\alpha A1}$-hexanoyl-$N^{\alpha B1}$-hexanoyl-$Lys^{B28}Pro^{B29}$-human insulin, $N^{\epsilon B28}$-hexanoyl-$N^{\alpha A1}$-hexanoyl-$N^{\alpha B1}$-hexanoyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B28}$-heptanoyl-$Lys^{B28}Pro^{B29}$-human insulin, $N^{\alpha B1}$-heptanoyl-$Lys^{B28}Pro^{B29}$-human insulin, $N^{\alpha A1}$-heptanoyl-$Lys^{B28}Pro^{B29}$-human insulin, $N^{\epsilon B28}$-heptanoyl-$N^{\alpha B1}$-heptanoyl-$Lys^{B28}Pro^{B29}$-human insulin, $N^{\epsilon B28}$-heptanoyl-$N^{\alpha A1}$-heptanoyl-$Lys^{B28}Pro^{B29}$-human insulin, $N^{\alpha A1}$-heptanoyl-$N^{\alpha B1}$-heptanoyl-$Lys^{B28}Pro^{B29}$-human insulin, $N^{\epsilon B28}$-heptanoyl-$N^{\alpha A1}$-heptanoyl-$N^{\alpha B1}$-heptanoyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B28}$-octanoyl-$Lys^{B28}Pro^{B29}$-human insulin, $N^{\alpha B1}$-octanoyl-$Lys^{B28}Pro^{B29}$-human insulin, $N^{\alpha A1}$-octanoyl-$Lys^{B28}Pro^{B29}$-human insulin, $N^{\epsilon B28}$-octanoyl-$N^{\alpha B1}$-octanoyl-$Lys^{B28}Pro^{B29}$-human insulin, $N^{\epsilon B28}$-octanoyl-$N^{\alpha A1}$-octanoyl-$Lys^{B28}Pro^{B29}$-human insulin, $N^{\alpha A1}$-octanoyl-$N^{\alpha B1}$-octanoyl-$Lys^{B28}Pro^{B29}$-human insulin, $N^{\epsilon B28}$-octanoyl-$N^{\alpha A1}$-octanoyl-$N^{\alpha B1}$-octanoyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B28}$-nonanoyl-$Lys^{B28}Pro^{B29}$-human insulin, $N^{\alpha B1}$-nonanoyl-$Lys^{B28}Pro^{B29}$-human insulin, $N^{\alpha A1}$-nonanoyl-$Lys^{B28}Pro^{B29}$-human insulin, $N^{\epsilon B28}$-nonanoyl-$N^{\alpha B1}$-nonanoyl-$Lys^{B28}Pro^{B29}$-human insulin, $N^{\epsilon B28}$-nonanoyl-$N^{\alpha A1}$-nonanoyl-$Lys^{B28}Pro^{B29}$-human insulin, $N^{\alpha A1}$-nonanoyl-$N^{\alpha B1}$-nonanoyl-$Lys^{B28}Pro^{B29}$-human insulin, $N^{\epsilon B28}$-nonanoyl-$N^{\alpha A1}$-nonanoyl-$N^{\alpha A1}$-nonanoyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B28}$-decanoyl-$Lys^{B28}Pro^{B29}$-human insulin, $N^{\alpha B1}$-decanoyl-$Lys^{B28}Pro^{B29}$-human insulin, $N^{\alpha B1}$-decanoyl-$Lys^{B28}Pro^{B29}$-human insulin, $N^{\epsilon B28}$-decanoyl decanoyl-$Lys^{B28}Pro^{B29}$-human insulin, $N^{\epsilon B28}$-decanoyl-$N^{\alpha A1}$-decanoyl-$Lys^{B28}Pro^{B29}$-human insulin, $N^{\alpha A1}$-decanoyl-$N^{\alpha B1}$-decanoyl-$Lys^{B28}Pro^{B29}$-human insulin, $N^{\epsilon B28}$-decanoyl-$N^{\alpha A1}$-decanoyl-$N^{\alpha B1}$-decanoyl-$Lys^{B28}Pro^{B29}$-human insulin.

In certain embodiments, an insulin polypeptide of the present disclosure comprises an N-linked glycan motif and the mutations and/or chemical modifications of one of the following insulin polypeptides: $N^{\epsilon B29}$-pentanoyl-$Gly^{A21}Arg^{B31}Arg^{B32}$-human insulin, $N^{\alpha B1}$-hexanoyl-$Gly^{A21}Arg^{B31}Arg^{B32}$-human insulin, $N^{\alpha A1}$-heptanoyl-$Gly^{A21}Arg^{B31}Arg^{B32}$-human insulin, $N^{\epsilon B29}$-octanoyl-$N^{\alpha B1}$-octanoyl-$Gly^{A21}Arg^{B31}Arg^{B32}$-human insulin, $N^{\epsilon B29}$-propionyl-$N^{\alpha A1}$-propionyl-$Gly^{A21}Arg^{B31}Arg^{B32}$-human insulin, $N^{\alpha A1}$-acetyl-$N^{\alpha B1}$-acetyl-$Gly^{A21}Arg^{B31}Arg^{B32}$-human insulin, $N^{\epsilon B29}$-formyl-$N^{\alpha A1}$-formyl-$N^{\alpha B1}$-formyl-$Gly^{A21}Arg^{B31}Arg^{B32}$-human insulin, $N^{\epsilon B29}$-formyl-des(B26)-human insulin, $N^{\alpha B1}$-acetyl-$Asp^{B28}$-human insulin, $N^{\epsilon B29}$-propionyl-$N^{\alpha A1}$-propionyl-$N^{\alpha B1}$-propionyl-$Asp^{B1}Asp^{B3}Asp^{B21}$-human insulin, $N^{\epsilon B29}$-pentanoyl-$Gly^{A21}$-human insulin, $N^{\alpha B1}$-hexanoyl-$Gly^{A21}$-human insulin, $N^{\alpha A1}$-heptanoyl-$Gly^{A21}$-human insulin, $N^{\epsilon B29}$-octanoyl-$N^{\alpha B1}$-octanoyl-$Gly^{A21}$-human insulin, $N^{\epsilon B29}$-propionyl-$N^{\alpha A1}$-propionyl-$Gly^{A21}$-human insulin, $N^{\alpha A1}$-acetyl-$N^{\alpha B1}$-acetyl-$Gly^{A21}$-human insulin, $N^{\epsilon B29}$-formyl-$N^{\alpha A1}$-formyl-$N^{\alpha B1}$-formyl-$Gly^{A21}$-human insulin, $N^{\epsilon B29}$-butyryl-des(B30)-human insulin, $N^{\alpha B1}$-butyryl-des(B30)-human insulin, $N^{\alpha A1}$-butyryl-des(B30)-human insulin, $N^{\epsilon B29}$-butyryl-$N^{\alpha B1}$-butyryl-des(B30)-human insulin, $N^{\epsilon B29}$-butyryl- $N^{\alpha A1}$-butyryl-des(B30)-human insulin, $N^{\alpha A1}$-butyryl-$N^{\alpha B1}$-butyryl-des(B30)-human insulin, $N^{\epsilon B29}$-butyryl-$N^{\alpha A1}$-butyryl-$N^{\alpha B1}$-butyryl-des(B30)-human insulin.

The present disclosure also encompasses modified forms of non-human insulins (e.g., porcine insulin, bovine insulin, rabbit insulin, sheep insulin, etc.) that comprise an N-linked glycan motif and any one of the aforementioned mutations and/or chemical modifications.

These and other modified insulin polypeptides are described in detail in U.S. Pat. Nos. 6,906,028; 6,551,992; 6,465,426; 6,444,641; 6,335,316; 6,268,335; 6,051,551; 6,034,054; 5,952,297; 5,922,675; 5,747,642; 5,693,609; 5,650,486; 5,547,929; 5,504,188; 5,474,978; 5,461,031; and 4,421,685; and in U.S. Pat. Nos. 7,387,996; 6,869,930; 6,174,856; 6,011,007; 5,866,538; and 5,750,497.

N-Linked Glycan Motif

In certain embodiments, an insulin polypeptide of the present disclosure comprises one or more N-linked glycan motifs, as characterized by the sequence, Asn-Xaa'-[Ser/Thr], where Xaa' is not Pro. In some embodiments, the N-linked glycan motif is appended to a terminus of an insulin polypeptide. In some embodiments, the N-linked glycan motif is incorporated within the sequence of an insulin polypeptide. In some embodiments, an insulin polypeptide comprises a single N-linked glycan motif. In some embodiments, the single N-linked glycan motif is present on the A-peptide. In some embodiments, the single N-linked glycan motif is present on the B-peptide. In some embodiments, an insulin polypeptide comprises more than one N-linked glycan motif (e.g., 2, 3, or 4 motifs).

It is to be understood that any one of the N-linked glycan motif embodiments that are discussed herein can be included within any one of the insulin polypeptides of Formulas I, I', II or II'.

In some embodiments, in order to avoid enzymatic cleavage that might cleave the Asn residue of the N-linked glycan motif from the insulin polypeptide during enzymatic processing, Xaa' within the N-linked glycan motif is not Pro, Lys or Arg. In some embodiments, Xaa' within the N-linked glycan motif is not Pro or Lys. In some embodiments, Xaa' within the N-linked glycan motif is not Pro or Arg. As discussed below, these motifs may for example be useful when located towards the N-terminus of the A- and/or B-peptides (e.g., N-linked glycan motifs that are encompassed within Xaa at positions A0 or B0 or for N-linked glycan motifs that start at the A8, A10, B0, B1, B2, B3, B9, B10, or B11 positions).

In some embodiments, the N-linked glycan motif may be characterized by the sequence, Asn-[Lys/Arg]-[Ser/Thr]. In some embodiments, this will cause the Ser or Thr residue and any amino acid residues that are on the C-terminal side of the motif to be enzymatically cleaved during processing. In some embodiments, the N-linked glycan motif may be characterized by the sequence, Asn-Lys-[Ser/Thr]. In some embodiments, the N-linked glycan motif may be characterized by the sequence, Asn-Lys-Ser. In some embodiments, the N-linked glycan motif may be characterized by the sequence, Asn-Lys-Thr. In some embodiments, the N-linked glycan motif may be characterized by the sequence, Asn-Arg-[Ser/Thr]. In some embodiments, the N-linked glycan motif may be characterized by the sequence, Asn-Arg-Ser. In some embodiments, the N-linked glycan motif may be characterized by the sequence, Asn-Arg-Thr. As discussed below, these motifs may for example be useful when located towards the C-terminus of the A- and/or B-peptides (e.g., N-linked glycan motifs that are encompassed within Xaa at positions A22 or B31 or for N-linked glycan motifs that start at the A18, A20, A21, A22, B26, B27, B28, B29, B30 or B31 positions). As discussed in more detail below, the present disclosure encompasses insulin polypeptides that include a portion of an N-linked glycan motif (e.g., Asn-[Lys/Arg]) as a result of enzymatic cleavage. Such an insulin polypeptide may still be glycosylated since any N-linked glycan will be covalently attached to the insulin polypeptide via the Asn residue.

i. A-Peptide

In certain embodiments, the A-peptide sequence includes an N-linked glycan motif. For example, in some embodiments an N-linked glycan motif may begin at position A8, A10, A18, A20, A21 or A22 of the A-peptide.

In some embodiments, the N-linked glycan motif that begins at position A8, A10, A18, A20, A21 or A22 of the A-peptide is Asn-Xaa'-[Ser/Thr], where Xaa' is not Pro or Lys. In some embodiments, the N-linked glycan motif that begins at position A8, A10, A18, A20, A21 or A22 of the A-peptide is Asn-Xaa'-[Ser/Thr], where Xaa' is not Pro or Arg. In some embodiments, the N-linked glycan motif that begins at position A8, A10, A18, A20, A21 or A22 of the A-peptide is Asn-Xaa'-[Ser/Thr], where Xaa' is not Pro, Lys or Arg. In some embodiments, the N-linked glycan motif that begins at position A8, A10, A18, A20, A21 or A22 of the A-peptide is Asn-Thr-[Ser/Thr].

In some embodiments, the N-linked glycan motif that begins at position A8, A10, A18, A20, A21 or A22 of the A-peptide is Asn-Xaa'-Ser, where Xaa' is not Pro. In some embodiments, the N-linked glycan motif that begins at position A8, A10, A18, A20, A21 or A22 of the A-peptide is Asn-Xaa'-Ser, where Xaa' is not Pro or Lys. In some embodiments, the N-linked glycan motif that begins at position A8, A10, A18, A20, A21 or A22 of the A-peptide is Asn-Xaa'-Ser, where Xaa' is not Pro or Arg. In some embodiments, the N-linked glycan motif that begins at position A8, A10, A18, A20, A21 or A22 of the A-peptide is Asn-Xaa'-Ser, where Xaa' is not Pro, Lys or Arg. In some embodiments, the N-linked glycan motif that begins at position A8, A10, A18, A20, A21 or A22 of the A-peptide is Asn-Thr-Ser.

In some embodiments, the N-linked glycan motif that begins at position A8, A10, A18, A20, A21 or A22 of the A-peptide is Asn-Xaa'-Thr, where Xaa' is not Pro. In some embodiments, the N-linked glycan motif that begins at position A8, A10, A18, A20, A21 or A22 of the A-peptide is Asn-Xaa'-Thr, where Xaa' is not Pro or Lys. In some embodiments, the N-linked glycan motif that begins at position A8, A10, A18, A20, A21 or A22 of the A-peptide is Asn-Xaa'-Thr, where Xaa' is not Pro or Arg. In some embodiments, the N-linked glycan motif that begins at position A8, A10, A18, A20, A21 or A22 of the A-peptide is Asn-Xaa'-Thr, where Xaa' is not Pro, Lys or Arg. In some embodiments, the N-linked glycan motif that begins at position A8, A10, A18, A20, A21 or A22 of the A-peptide is Asn-Thr-Thr.

In some embodiments, the N-linked glycan motif that begins at position A18, A20, A21 or A22 of the A-peptide is Asn-[Arg/Lys]-[Ser/Thr] (e.g., Asn-Lys-[Ser/Thr], Asn-Lys-Ser, Asn-Lys-Thr, Asn-Arg-[Ser/Thr], Asn-Arg-Ser or Asn-Arg-Thr).

As mentioned above, in some embodiments, an N-linked glycan motif (optionally with additional amino acids) is encompassed within Xaa at position A0 or A22. In some embodiments, Xaa at position A0 or A22 may include spacer amino acids between the N-linked glycan motif and the remainder of the insulin polypeptide (e.g., between the N-linked glycan motif and A1 or between A21 and the N-linked glycan motif). In some embodiments, Xaa at position A0 or A22 includes 1, 1-2, 1-3, 1-4, or 1-5 spacer amino acids. In some embodiments, Xaa at position A0 or A22 includes a single Gly residue as a spacer amino acid.

In some embodiments, the N-linked glycan motif encompassed within Xaa at position A0 is Asn-Xaa'-[Ser/Thr], where Xaa' is not Pro. In some embodiments, the N-linked glycan motif encompassed within Xaa at position A0 is Asn-Xaa'-[Ser/Thr], where Xaa' is not Pro or Lys. In some embodiments, the N-linked glycan motif encompassed within Xaa at position A0 is Asn-Xaa'-[Ser/Thr], where Xaa' is not Pro or Arg. In some embodiments, the N-linked glycan motif encompassed within Xaa at position A0 is Asn-Xaa'-[Ser/Thr], where Xaa' is not Pro, Lys or Arg. In some of these embodiments, Xaa at position A0 corresponds to the N-linked glycan motif (i.e., does not include any additional amino acids). In some of these embodiments, a single Gly residue is included as a spacer amino acid as in: Asn-Xaa'-[Ser/Thr]-Gly where Xaa' is not Pro (and optionally not Lys and/or Arg).

In some embodiments, the N-linked glycan motif encompassed within Xaa at position A0 is Asn-Xaa'-Ser, where Xaa' is not Pro. In some embodiments, the N-linked glycan motif encompassed within Xaa at position A0 is Asn-Xaa'-Ser, where Xaa' is not Pro or Lys. In some embodiments, the N-linked glycan motif encompassed within Xaa at position A0 is Asn-Xaa'-Ser, where Xaa' is not Pro or Arg. In some embodiments, the N-linked glycan motif encompassed within Xaa at position A0 is Asn-Xaa'-Ser, where Xaa' is not Pro, Lys or Arg. In some embodiments, the N-linked glycan motif encompassed within Xaa at position A0 is Asn-Thr-Ser.

In some embodiments, the N-linked glycan motif encompassed within Xaa at position A0 is Asn-Xaa'-Thr, where Xaa' is not Pro. In some embodiments, the N-linked glycan motif encompassed within Xaa at position A0 is Asn-Xaa'-Thr, where Xaa' is not Pro or Lys. In some embodiments, the N-linked glycan motif encompassed within Xaa at position A0 is Asn-Xaa'-Thr, where Xaa' is not Pro or Arg. In some embodiments, the N-linked glycan motif encompassed within Xaa at position A0 is Asn-Xaa'-Thr, where Xaa' is not Pro, Lys or Arg. In some embodiments, the N-linked glycan motif encompassed within Xaa at position A0 is Asn-Thr-Thr.

In some embodiments, the N-linked glycan motif encompassed within Xaa at position A22 is Asn-Xaa'-[Ser/Thr], where Xaa' is not Pro. In some embodiments, the N-linked glycan motif encompassed within Xaa at position A22 is Asn-Xaa'-[Ser/Thr], where Xaa' is not Pro or Lys. In some embodiments, the N-linked glycan motif encompassed within Xaa at position A22 is Asn-Xaa'-[Ser/Thr], where Xaa' is not Pro or Arg. In some embodiments, the N-linked glycan motif encompassed within Xaa at position A22 is Asn-Xaa'-[Ser/Thr], where Xaa' is not Pro, Lys or Arg. In some of these embodiments, Xaa at position A22 corresponds to the N-linked glycan motif (i.e., does not include any additional amino acids). In some of these embodiments, a single Gly residue is included as a spacer amino acid as in: Gly-Asn-Xaa'-[Ser/Thr] where Xaa' is not Pro (and optionally not Lys and/or Arg).

In some embodiments, the N-linked glycan motif encompassed within Xaa at position A22 is Asn-Xaa'-Ser, where Xaa' is not Pro. In some embodiments, the N-linked glycan motif encompassed within Xaa at position A22 is Asn-Xaa'-Ser, where Xaa' is not Pro or Lys. In some embodiments, the N-linked glycan motif encompassed within Xaa at position A22 is Asn-Xaa'-Ser, where Xaa' is not Pro or Arg. In some embodiments, the N-linked glycan motif encompassed within Xaa at position A22 is Asn-Xaa'-Ser, where Xaa' is not Pro, Lys or Arg. In some embodiments, the N-linked glycan motif encompassed within Xaa at position A22 is Asn-Thr-Ser.

In some embodiments, the N-linked glycan motif encompassed within Xaa at position A22 is Asn-Xaa'-Thr, where Xaa' is not Pro. In some embodiments, the N-linked glycan motif encompassed within Xaa at position A22 is Asn-Xaa'-Thr, where Xaa' is not Pro or Lys. In some embodiments, the N-linked glycan motif encompassed within Xaa at position A22 is Asn-Xaa'-Thr, where Xaa' is not Pro or Arg. In some embodiments, the N-linked glycan motif encompassed within Xaa at position A22 is Asn-Xaa'-Thr, where Xaa' is not Pro, Lys or Arg. In some embodiments, the N-linked glycan motif encompassed within Xaa at position A22 is Asn-Thr-Thr.

In some embodiments, Xaa at position A22 is Asn-[Arg/Lys]-[Ser/Thr] (e.g., Asn-Lys-[Ser/Thr], Asn-Lys-Ser, Asn-Lys-Thr, Asn-Arg-[Ser/Thr], Asn-Arg-Ser or Asn-Arg-Thr). In some embodiments an additional Gly residue is included as a spacer amino acid as in: Gly-Asn-[Lys/Arg]-[Ser/Thr] (SEQ ID NO:30).

Those skilled in the art will recognize that these are exemplary variations and the present disclosure encompasses other A0 or A22 amino acid sequences.

ii. B-Peptide

In certain embodiments, the B-peptide sequence includes an N-linked glycan motif. For example, in some embodiments an N-linked glycan motif may begin at position B0, B1, B2, B3, B9, B10, B11, B26, B27, B28, B29, B30 or B31 of the B-peptide.

In some embodiments, the N-linked glycan motif that begins at position B0, B1, B2, B3, B9, B10, B11, B26, B27, B28, B29, B30 or B31 of the B-peptide is Asn-Xaa'-[Ser/Thr], where Xaa' is not Pro or Lys. In some embodiments, the N-linked glycan motif that begins at position B0, B1, B2, B3, B9, B10, B11, B26, B27, B28, B29, B30 or B31 of the B-peptide is Asn-Xaa'-[Ser/Thr], where Xaa' is not Pro or Arg. In some embodiments, the N-linked glycan motif that begins at position B0, B1, B2, B3, B9, B10, B11, B26, B27, B28, B29, B30 or B31 of the B-peptide is Asn-Xaa'-[Ser/Thr], where Xaa' is not Pro, Lys or Arg. In some embodiments, the N-linked glycan motif that begins at position B0, B1, B2, B3, B9, B10, B11, B26, B27, B28, B29, B30 or B31 of the B-peptide is Asn-Thr-[Ser/Thr].

In some embodiments, the N-linked glycan motif that begins at position B0, B1, B2, B3, B9, B10, Bit, B26, B27, B28, B29, B30 or B31 of the B-peptide is Asn-Xaa'-Ser, where Xaa' is not Pro. In some embodiments, the N-linked glycan motif that begins at position B0, B1, B2, B3, B9, B10, B11, B26, B27, B28, B29, B30 or B31 of the B-peptide is Asn-Xaa'-Ser, where Xaa' is not Pro or Lys. In some embodiments, the N-linked glycan motif that begins at position B0, B1, 82, B3, B9, B10, B11, B26, B27, B28, B29, B30 or B31 of the B-peptide is Asn-Xaa'-Ser, where Xaa' is not Pro or Arg. In some embodiments, the N-linked glycan motif that begins at position B0, B1, B2, B3, B9, B10, B11, B26, B27, B28, B29, B30 or 831 of the B-peptide is Asn-Xaa'-Ser, where Xaa' is not Pro, Lys or Arg. In some embodiments, the N-linked glycan motif that begins at position B0, B1, B2, B3, B9, B10, B11, B26, B27, B28, B29, B30 or B31 of the B-peptide is Asn-Thr-Ser.

In some embodiments, the N-linked glycan motif that begins at position B0, B1, B2, B3, B9, B10, B11, B26, B27, B28, B29, B30 or B31 of the B-peptide is Asn-Xaa'-Thr, where Xaa' is not Pro. In some embodiments, the N-linked glycan motif that begins at position B0, B1, B2, B3, B9, B10, B11, B26, B27, B28, B29, B30 or B31 of the B-peptide is Asn-Xaa'-Thr, where Xaa' is not Pro or Lys. In some embodiments, the N-linked glycan motif that begins at position B0, B1, B2, B3, B9, B10, B11, B26, B27, B28, B29, B30 or B31 of the B-peptide is Asn-Xaa'-Thr, where Xaa' is not Pro or Arg. In some embodiments, the N-linked glycan motif that begins at position B0, B1, B2, B3, B9, B10, B11, B26, B27, B28, B29, B30 or B31 of the B-peptide is Asn-Xaa'-Thr, where Xaa' is not Pro, Lys or Arg. In some embodiments, the N-linked glycan motif that begins at position B0, B1, B2, B3, B9, B10, B11, B26, B27, B28, B29, B30 or B31 of the B-peptide is Asn-Thr-Thr.

In some embodiments, the N-linked glycan motif that begins at position B26, B27, B28, B29, 830 or B31 of the B-peptide is Asn-[Arg/Lys]-[Ser/Thr] (e.g., Asn-Lys-[Ser/Thr], Asn-Lys-Ser, Asn-Lys-Thr, Asn-Arg-[Ser/Thr], Asn-Arg-Ser or Asn-Arg-Thr).

As mentioned above, in some embodiments, an N-linked glycan motif (optionally with additional amino acids) is encompassed within Xaa at position B0 or B31. In some embodiments, Xaa at position B0 or B31 may include spacer amino acids between the N-linked glycan motif and the remainder of the insulin polypeptide (e.g., between the N-linked glycan motif and B1 or between B30 and the N-linked glycan motif). In some embodiments, Xaa at position B0 or B31 includes 1, 1-2, 1-3, 1-4, or 1-5 spacer amino acids. In some embodiments, Xaa at position B0 or B31 includes a single Gly residue as a spacer amino acid.

In some embodiments, the N-linked glycan motif encompassed within Xaa at position B0 is Asn-Xaa'-[Ser/Thr], where Xaa' is not Pro. In some embodiments, the N-linked glycan motif encompassed within Xaa at position B0 is Asn-Xaa'-[Ser/Thr], where Xaa' is not Pro or Lys. In some embodiments, the N-linked glycan motif encompassed within Xaa at position B0 is Asn-Xaa'-[Ser/Thr], where Xaa' is not Pro or Arg. In some embodiments, the N-linked glycan motif encompassed within Xaa at position B0 is Asn-Xaa'-[Ser/Thr], where Xaa' is not Pro, Lys or Arg. In some of these embodiments, Xaa at position B0 corresponds to the N-linked glycan motif (i.e., does not include any additional amino acids). In some of these embodiments, a single Gly residue is included as a spacer amino acid as in: Asn-Xaa'-[Ser/Thr]-Gly where Xaa' is not Pro (and optionally not Lys and/or Arg).

In some embodiments, the N-linked glycan motif encompassed within Xaa at position B0 is Asn-Xaa'-Ser, where Xaa' is not Pro. In some embodiments, the N-linked glycan motif encompassed within Xaa at position B0 is Asn-Xaa'-Ser, where Xaa' is not Pro or Lys. In some embodiments, the N-linked glycan motif encompassed within Xaa at position B0 is Asn-Xaa'-Ser, where Xaa' is not Pro or Arg. In some embodiments, the N-linked glycan motif encompassed within Xaa at position B0 is Asn-Xaa'-Ser, where Xaa' is not Pro, Lys or Arg. In some embodiments, the N-linked glycan motif encompassed within Xaa at position B0 is Asn-Thr-Ser.

In some embodiments, the N-linked glycan motif encompassed within Xaa at position B0 is Asn-Xaa'-Thr, where Xaa' is not Pro. In some embodiments, the N-linked glycan motif encompassed within Xaa at position B0 is Asn-Xaa'-Thr, where Xaa' is not Pro or Lys. In some embodiments, the N-linked glycan motif encompassed within Xaa at position B0 is Asn-Xaa'-Thr, where Xaa' is not Pro or Arg. In some embodiments, the N-linked glycan motif encompassed within Xaa at position B0 is Asn-Xaa'-Thr, where Xaa' is not Pro, Lys or Arg. In some embodiments, the N-linked glycan motif encompassed within Xaa at position B0 is Asn-Thr-Thr.

In some embodiments, the N-linked glycan motif encompassed within Xaa at position B31 is Asn-Xaa'-[Ser/Thr], where Xaa' is not Pro. In some embodiments, the N-linked glycan motif encompassed within Xaa at position B31 is Asn-Xaa'-[Ser/Thr], where Xaa' is not Pro or Lys. In some embodiments, the N-linked glycan motif encompassed within Xaa at position B31 is Asn-Xaa'-[Ser/Thr], where Xaa' is not Pro or Arg. In some embodiments, the N-linked glycan motif encompassed within Xaa at position B31 is Asn-Xaa'-[Ser/Thr], where Xaa' is not Pro, Lys or Arg. In some of these embodiments, Xaa at position B31 corresponds to the N-linked glycan motif (i.e., does not include any additional amino acids). In some of these embodiments, a single Gly residue is included as a spacer amino acid as in: Gly-Asn-Xaa'-[Ser/Thr] where Xaa' is not Pro (and optionally not Lys and/or Arg).

In some embodiments, the N-linked glycan motif encompassed within Xaa at position B31 is Asn-Xaa'-Ser, where Xaa' is not Pro. In some embodiments, the N-linked glycan motif encompassed within Xaa at position B31 is Asn-Xaa'-Ser, where Xaa' is not Pro or Lys. In some embodiments, the N-linked glycan motif encompassed within Xaa at position B31 is Asn-Xaa'-Ser, where Xaa' is not Pro or Arg. In some embodiments, the N-linked glycan motif encompassed within Xaa at position B31 is Asn-Xaa'-Ser, where Xaa' is not Pro, Lys or Arg. In some embodiments, the N-linked glycan motif encompassed within Xaa at position B31 is Asn-Thr-Ser.

In some embodiments, the N-linked glycan motif encompassed within Xaa at position B31 is Asn-Xaa'-Thr, where Xaa' is not Pro. In some embodiments, the N-linked glycan motif encompassed within Xaa at position B31 is Asn-Xaa'-Thr, where Xaa' is not Pro or Lys. In some embodiments, the N-linked glycan motif encompassed within Xaa at position B31 is Asn-Xaa'-Thr, where Xaa' is not Pro or Arg. In some embodiments, the N-linked glycan motif encompassed within Xaa at position B31 is Asn-Xaa'-Thr, where Xaa' is not Pro, Lys or Arg. In some embodiments, the N-linked glycan motif encompassed within Xaa at position B31 is Asn-Thr-Thr.

In some embodiments, Xaa at position B31 is Asn-[Arg/Lys]-[Ser/Thr] (e.g., Asn-Lys-[Ser/Thr], Asn-Lys-Ser, Asn-Lys-Thr, Asn-Arg-[Ser/Thr], Asn-Arg-Ser or Asn-Arg-Thr). In some embodiments an additional Gly residue is included as a spacer amino acid as in: Gly-Asn-[Lys/Arg]-[Ser/Thr] (SEQ ID NO:30).

iii. Single and Multiple N-Linked Glycan Motifs

In some embodiments, an insulin polypeptide comprises a single N-linked glycan motif. In some embodiments, the single N-linked glycan motif is present on the A-peptide (e.g., encompassed within Xaa at the A0 or A22 position or starting at the A8, A10, A18, A20, A21, or A22 position). In some embodiments, the single N-linked glycan motif is present on the B-peptide (e.g., encompassed within Xaa at the B0 or B31 position or starting at the B0, B1, B2, B3, B9, B10, B11, B26, B27, B28, B29, B30 or B31 position).

In some embodiments, an insulin polypeptide comprises more than one N-linked glycan motif (e.g., 2, 3, or 4 motifs). In some embodiments, the two or more N-linked glycan motifs are on the A-peptide of the insulin polypeptide (e.g., without limitation a first motif encompassed within Xaa at the A0 position and a second motif encompassed within Xaa at the A22 position or starting at the A18, A20, A21 or A22 position). In some embodiments, the two or more N-linked glycan motifs are on the B-peptide of the insulin polypeptide (e.g., without limitation a first motif encompassed within Xaa at the B0 position or starting at the B0, B1, B2, B3, B9, B10, or B11 position and a second motif encompassed within Xaa at the B31 position or starting at the B26, B27, B28, B29, B30 or B31 position). In some embodiments, the two or more N-linked glycan motifs are on the A-peptide and/or B-peptide of the insulin polypeptide. In some embodiments, an insulin polypeptide of the present disclosure comprises an N-linked glycan motif on the A-peptide and an N-linked glycan motif on the B-peptide (e.g., without limitation a first motif encompassed within Xaa at the A0 position and a second motif encompassed within Xaa at the B31 position or starting at the B26, B27, B28, B29, B30 or B31 position; a first motif encompassed within Xaa at the B0 position or starting at the B0, B1, B2, B3, B9, B10, or B11 position and a second motif encompassed within Xaa at the A22 position or starting at the A18, A20, A21 or A22 position; a first motif encompassed within Xaa at the A0 position and a second motif encompassed within Xaa at the B0 position or starting at the B0, B1, B2, B3, B9, B10, or B11 position; or a first motif encompassed within Xaa at the A22 position or starting at the A18, A20, A21 or A22 position and a second motif encompassed within Xaa at the B31 position or starting at the B26, B27, B28, B29, B30 or B31 position). For example, studies that we have performed with various synthetic insulin-conjugates have shown that having saccharide ligands conjugated at more than one insulin amino acid position (e.g., at positions A1 and B29) can be advantageous in certain circumstances.

iv. N-Linked Glycan Motifs Located on Termini

In certain embodiments, a recombinant insulin polypeptide of the present disclosure comprises N-linked glycan motifs that are located on one or more termini of the A- and/or B-peptide.

In certain embodiments, Asn in an N-linked glycan motif is located on the N-terminus of the A-peptide (e.g., within Xaa at position A0).

In certain embodiments, Asn in an N-linked glycan motif is located on the N-terminus of the B-peptide (e.g., within Xaa at position B0, at position B0, at position B1 when B0 is missing, at position B2 when B(0-1) are missing, or at position B3 when B(0-2) are missing).

In certain embodiments, an N-linked glycan motif is located on the C-terminus of the A-peptide (e.g., starting at position A20, A21 or A22 or encompassed within Xaa at position A22). In certain embodiments, only a portion of an N-linked glycan motif is located on the C-terminus of the A-peptide (e.g., Asn or Asn-Xaa' where Xaa' is not Pro). As discussed herein, this may happen when an N-linked glycan motif that was present in proinsulin is cleaved during enzymatic processing, e.g., when Xaa' in the N-linked glycan motif is Lys or Arg the C-terminus of the A-peptide may end with Asn-[Lys/Arg].

In certain embodiments, an N-linked glycan motif is located on the C-terminus of the B-peptide (e.g., starting at position B26 when B(29-31) are missing, starting at position B27 when B(30-31) are missing, starting at position B28 when B31 is missing, starting at position B29, starting at position B30, starting at position B31 or encompassed within Xaa at position B31). In certain embodiments, only a portion of an N-linked glycan motif is located on the C-terminus of the B-peptide (e.g., Asn or Asn-Xaa' where Xaa' is not Pro). As discussed herein, this may happen when an N-linked glycan motif that was present in proinsulin is cleaved during enzymatic processing, e.g., when Xaa' in the N-linked glycan motif is Lys or Arg the C-terminus of the B-peptide may end with Asn-[Lys/Arg].

In the following embodiments, references to a "portion" of an N-linked glycan motif mean Asn or Asn-Xaa' where Xaa' is not Pro. In some embodiments, a "portion" of an N-linked glycan motif means Asn-[Lys/Arg].

In certain embodiments, a first N-linked glycan motif is located on the N-terminus of the A-peptide (e.g., within Xaa at position A0) and a second N-linked glycan motif (or portion thereof) is located on the C-terminus of the A-peptide (e.g., starting at position A20, A21 or A22 or encompassed within Xaa at position A22).

In certain embodiments, a first N-linked glycan motif is located on the N-terminus of the B-peptide (e.g., within Xaa at position B0, at position B0, at position B1 when B0 is missing, at position B2 when B(0-1) are missing, or at position B3 when B(0-2) are missing) and a second N-linked glycan motif (or portion thereof) is located on the C-terminus of the B-peptide (e.g., starting at position B26 when B(29-31) are missing, starting at position B27 when B(30-31) are missing, starting at position B28 when B31 is missing, starting at position B29, starting at position B30, starting at position B31 or encompassed within Xaa at position B31).

In certain embodiments, a first N-linked glycan motif is located on the N-terminus of the A-peptide (e.g., within Xaa at position A0) and a second N-linked glycan motif is located on the N-terminus of the B-peptide (e.g., within Xaa at position B0, at position B0, at position B1 when B0 is missing, at position B2 when B(0-1) are missing, or at position B3 when B(0-2) are missing).

In certain embodiments, a first N-linked glycan motif is located on the N-terminus of the A-peptide (e.g., within Xaa at position A0) and a second N-linked glycan motif (or portion thereof) is located on the C-terminus of the B-peptide (e.g., starting at position B26 when B(29-31) are missing, starting at position B27 when B(30-31) are missing, starting at position B28 when B31 is missing, starting at position B29, starting at position B30, starting at position B31 or encompassed within Xaa at position B31).

In certain embodiments, a first N-linked glycan motif (or portion thereof) is located on the C-terminus of the A-peptide (e.g., starting at position A20, A21 or A22 or encompassed within Xaa at position A22) and a second N-linked glycan motif (or portion thereof) is located on the C-terminus of the B-peptide (e.g., starting at position B26 when B(29-31) are missing, starting at position B27 when B(30-31) are missing, starting at position B28 when B31 is missing, starting at position B29, starting at position B30, starting at position B31 or encompassed within Xaa at position B31).

In certain embodiments, a first N-linked glycan motif (or portion thereof) is located on the C-terminus of the A-peptide (e.g., starting at position A20, A21 or A22 or encompassed within Xaa at position A22) and a second N-linked glycan motif is located on the N-terminus of the B-peptide (e.g., within Xaa at position B0, at position B0, at position B1 when B0 is missing, at position B2 when B(0-1) are missing, or at position B3 when B(0-2) are missing).

v. N-Linked Glycan Motifs Located Towards C-Termini

In certain embodiments, a recombinant insulin polypeptide of the present disclosure comprises N-linked glycan motifs that are located towards one or more termini of the A- and/or B-peptide.

In certain embodiments, Asn in an N-linked glycan motif is located within 1-3 amino acids of the N-terminus of the A-peptide (e.g., within 1, 2 or 3 amino acids).

In certain embodiments, Asn in an N-linked glycan motif is located within 1-3 amino acids of the N-terminus of the B-peptide (e.g., within 1, 2 or 3 amino acids).

In certain embodiments, [Ser/Thr] in an N-linked glycan motif is separated from the C-terminus of the A-peptide by no more than 1-3 amino acids (e.g., 1, 2 or 3 amino acids). In certain embodiments, the C-terminus of the A-peptide ends with the sequence Asn-Xaa'-[Ser/Thr]-[Arg/Lys] where Xaa' is not Pro, Lys or Arg.

In certain embodiments, [Ser/Thr] in an N-linked glycan motif is separated from the C-terminus of the B-peptide by no more than 1-3 amino acids (e.g., 1, 2 or 3 amino acids). In certain embodiments, the C-terminus of the B-peptide ends with the sequence Asn-Xaa'-[Ser/Thr]-[Arg/Lys] where Xaa' is not Pro, Lys or Arg.

In certain embodiments, Asn in a first N-linked glycan motif is located within 1-3 amino acids of the N-terminus of the A-peptide (e.g., within 1, 2 or 3 amino acids) and [Ser/Thr] in a second N-linked glycan motif is separated from the C-terminus of the A-peptide by no more than 1-3 amino acids (e.g., no more than 1, 2 or 3 amino acids).

In certain embodiments, Asn in a first N-linked glycan motif is located within 1-3 amino acids of the N-terminus of the B-peptide (e.g., within 1, 2 or 3 amino acids) and [Ser/Thr] in a second N-linked glycan motif is separated from the C-terminus of the B-peptide by no more than 1-3 amino acids (e.g., no more than 1, 2 or 3 amino acids).

In certain embodiments, Asn in a first N-linked glycan motif is located within 1-3 amino acids of the N-terminus of the A-peptide (e.g., within 1, 2 or 3 amino acids) and Asn in a second N-linked glycan motif is located within 1-3 amino acids of the N-terminus of the B-peptide (e.g., within 1, 2 or 3 amino acids).

In certain embodiments, Asn in a first N-linked glycan motif is located within 1-3 amino acids of the N-terminus of the A-peptide (e.g., within 1, 2 or 3 amino acids) and [Ser/Thr] in a second N-linked glycan motif is separated from the C-terminus of the B-peptide by no more than 1-3 amino acids (e.g., no more than 1, 2 or 3 amino acids).

In certain embodiments, [Ser/Thr] in a first N-linked glycan motif is separated from the C-terminus of the A-peptide by no more than 1-3 amino acids (e.g., 1, 2 or 3 amino acids) and [Ser/Thr] in a second N-linked glycan motif is separated from the C-terminus of the B-peptide by no more than 1-3 amino acids (e.g., no more than 1, 2 or 3 amino acids).

In certain embodiments, [Ser/Thr] in a first N-linked glycan motif is separated from the C-terminus of the A-peptide by no more than 1-3 amino acids (e.g., no more than 1, 2 or 3 amino acids) and Asn in a second N-linked glycan motif is located within 1-3 amino acids of the N-terminus of the B-peptide (e.g., within 1, 2 or 3 amino acids).

In any one of these embodiments, the C-terminus of the A- and/or B-peptides may end with the sequence Asn-Xaa'-[Ser/Thr]-[Arg/Lys] where Xaa' is not Pro, Lys or Arg.

vi. N-Linked Glycan Motifs Located on and Towards Termini

In certain embodiments, a recombinant insulin polypeptide of the present disclosure comprises two or more N-linked glycan motifs that are located on or towards two or more termini of the A- and/or B-peptide. It is to be understood that the present disclosure encompasses all combinations and permutations of the individual embodiments that were presented above (e.g., motif on N-terminus of A-peptide and towards C-terminus of B-peptide, motif towards N-terminus of A-peptide and on C-terminus of B-peptide, etc.).

As discussed in the previous section it is to be understood that, in certain embodiments, the mutations needed to introduce the one or more N-linked glycan motifs into a wild-type insulin or proinsulin sequence may be accompanied by one or more mutations elsewhere in the insulin polypeptide and/or chemical modifications. In some embodiments, the mutations elsewhere in the insulin polypeptide are selected from the choices that are set forth in Tables 1-3. In some embodiments, the mutations needed to introduce the one or more N-linked glycan motifs into a wild-type insulin or proinsulin sequence are the only mutations in the insulin polypeptide.

In some embodiments, a pro-leader peptide sequence may also be included in the sequence of an insulin polypeptide of the present disclosure (e.g., within the definition of Xaa at B0 in Formula I or II). A pro-leader peptide directs the polypeptide sequence from the endoplasmic reticulum to the Golgi apparatus and further to a secretory vesicle for secretion into the culture medium (i.e., exportation of the polypeptide across the cell wall or at least through the cellular membrane into the periplasmic space of the yeast cell). The pro-leader peptide may be the yeast α-factor pro-leader peptide, as disclosed in U.S. Pat. Nos. 4,546,082 and 4,870,008. Alternatively, the pro-leader peptide may be a synthetic pro-leader peptide, which is to say a pro-leader peptide not found in nature. Suitable synthetic pro-leader peptides are disclosed in U.S. Pat. Nos. 5,395,922; 5,795,746; 5,162,498 and WO 98/32867. In some embodiments, the pro-leader peptide will comprise an endopeptidase processing site at the C-terminal end, such as a Lys-Arg sequence or any functional analog thereof. An exemplary pro-leader peptide that was used in the Examples has the sequence: Ala-Pro-Val-Asn-Thr-Thr-Thr-Glu-Asp-Glu-Thr-Ala-Gln-Ile-Pro-Ala-Glu-Ala-Val-Ile-Gly-Tyr-Ser-Asp-Leu-Glu-Gly-Asp-Phe-Asp-Val-Ala-Val-Leu-Pro-Phe-Ser-Asn-Ser-Thr-Asn-Asn-Gly-Leu-Leu-Phe-Ile-Asn-Thr-Thr-Ile-Ala-Ser-Ile-Ala-Ala-Lys-Glu-Glu-Gly-Val-Ser-Met-Ala-Lys-Arg (SEQ ID NO:8).

Recombinant Insulin Polynucleotides

In one aspect, polynucleotides that encode insulin polypeptides of the present disclosure are provided. A polynucleotide is said to "encode" a polypeptide if, in its native state or when manipulated by methods well known to those skilled in the art, it can be transcribed and/or translated to produce the mRNA for and/or the polypeptide. The anti-sense strand is the complement of such a nucleic acid, and the encoding sequence can be deduced therefrom.

The polynucleotides may be prepared by any manner. For example, in certain embodiments a polynucleotide may be prepared synthetically by established standard methods, e.g., the phosphoamidite method described by Beaucage et al., *Tetrahedron Letters* 22:1859-1869, 1981 or the method described by Matthes et al., *EMBO Journal* 3:801-805, 1984. According to the phosphoamidite method, oligonucleotides are synthesized, for example, in an automatic DNA synthesizer, purified, duplexed and ligated to form the synthetic polynucleotide construct. A currently preferred way of preparing the DNA construct is by polymerase chain reaction (PCR).

The polynucleotide sequence of the invention may also be of cDNA origin. For example, a cDNA sequence encoding a leader peptide may be joined to a cDNA sequence encoding the wild-type A- and B-peptides, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The present disclosure also provides recombinant vectors that are capable of replicating in a cell (e.g., a yeast cell) which carry one or more polynucleotide sequences encoding an insulin polypeptide of the present disclosure. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome. In a preferred embodiment, the recombinant vector is capable of replicating in yeast.

The vectors of the present disclosure may contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, and URA3. A preferred selectable marker for yeast is the *Schizosaecharomyces pombe* TPI gene (see Russell, *Gene* 40:125-130, 1985).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell. Examples of suitable promoters for directing the transcription in a yeast host are the Mal, TPI, ADH or PGK promoters. In some embodiments, the promoter sequence used to direct the transcription of a gene in a yeast cell is regulated by an external yeast stimuli and/or fermentation conditions. In some embodiments, the promoter sequence is regulated by the administration of methanol to methylotrophic yeast (e.g., *P. pastoris*, etc). In some embodiments, the use of promoters responsive to external yeast stimuli and/or fermentation conditions results in an increased yield of a desired insulin polypeptide.

A polynucleotide vector of the disclosure may also be operably connected to a suitable terminator. In yeast a suitable terminator is the TPI terminator (see Alber et al., *J. Mol. Appl. Genet.* 1:419-434, 1982).

The procedures used to ligate a polynucleotide of the disclosure, promoter and terminator, and insert them into suitable yeast vectors containing the information necessary for yeast replication, are well known to persons skilled in the art. It will be understood that the vector may be constructed either by first preparing a DNA construct containing the entire DNA sequence encoding a proinsulin of the present disclosure, and subsequently inserting this sequence into a suitable expression vector, or by sequentially inserting DNA fragments containing genetic information followed by ligation.

N-Linked Glycans

Figure 1A:
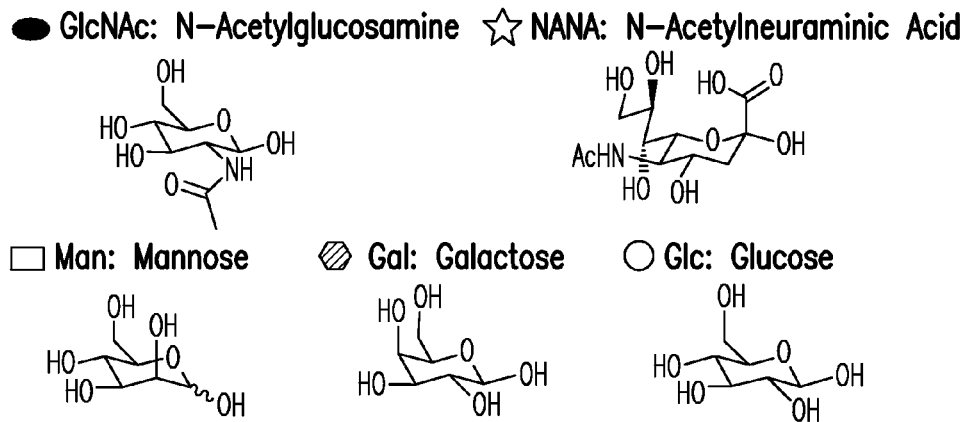
FIG. 1: (A) Structures of different saccharides, including N-acetylglucosamine (GlcNAc), N-acetylneuraminic Acid (NANA), mannose (Man), galactose (Gal), and glucose (Glc). (B) Representative N-glycan structures that can be appended to an N-linked glycan motif.

N-linked glycans are an important class of branched sugars that are covalently linked to polypeptides via a nitrogen (as opposed to O-linked glycans that are covalently linked to polypeptides via an oxygen). In humans, N-linked glycans share a conserved core pentasaccharide $GlcNAc_2Man_3$ structure with variations in the branching and substitutions of the sugar residues (see FIG. 1). Polypeptide glycosylation is central in regulating key biological processes, including polypeptide folding, polypeptide stability, oligomerization and trafficking.

Figure 2:
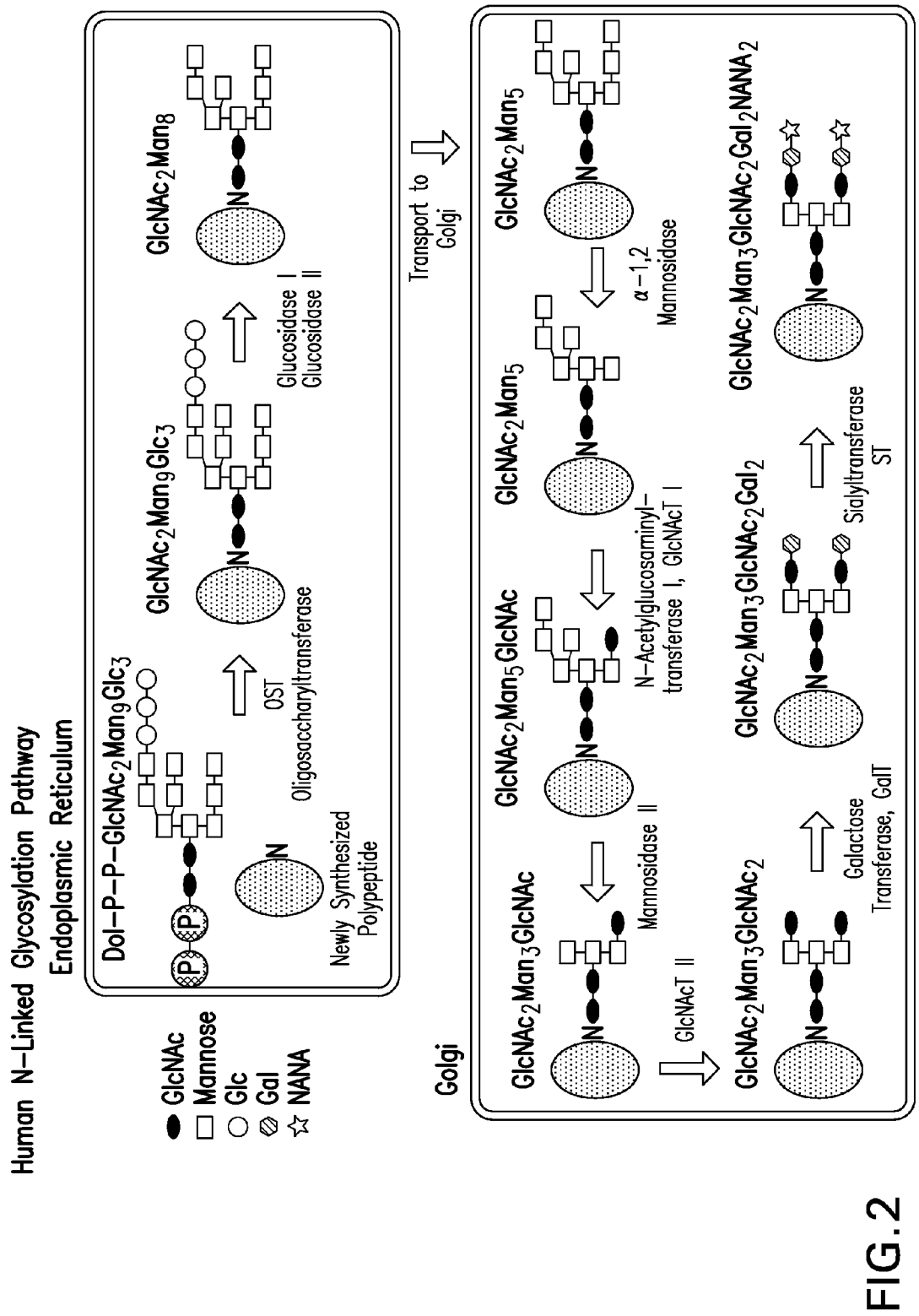
FIG. 2: Representative N-glycosylation pathway in humans.

N-linked glycans are covalently attached to polypeptide targets in the endoplasmic reticulum and the Golgi apparatus via a series of enzymes (see FIG. 2). Typically, in humans, glycans are added to the polypeptide in the lumen of the endoplasmic reticulum. The glycan is added to the amino group on the side chain of an asparagine residue contained within N-linked glycan motif Asn-Xaa'-[Ser/Thr], where Xaa' may be any amino acid except Pro. The initial glycan chain is usually trimmed by specific glycosidase enzymes in the endoplasmic reticulum, resulting in the short, branched $GlcNAc_2Man_3$ core comprised of two N-acetylglucosamine and three mannose residues. After initial processing in the endoplasmic reticulum, the glycosylated polypeptide is then transported to the Golgi where further processing may take place. The trimmed N-linked glycan moiety may be modified by the addition of several mannose residues, resulting in a "high-mannose" N-linked glycan. Additionally or alternatively, one or more monosaccharides units of N-acetylglucosamine may be added to the core mannose subunits to form "complex" N-linked glycans. Galactose may be added to the N-acetylglucosamine subunits, and sialic acid subunits may be added to the galactose subunits, resulting in a chain that terminates with any of a sialic acid, a galactose or an N-acetylglucosamine residue (see FIG. 2). Additionally, a fucose residue may be added to an N-acetylglucosamine residue of the glycan core. Each of these additions is catalyzed by specific glycosyl transferases.

In one aspect, the present disclosure provides recombinant insulin polypeptides that comprise an N-linked glycan motif, Asn-Xaa'-[Ser/Thr], where Xaa' is not Pro, wherein the delta-amino group of Asn in the motif is covalently bonded to a glycan.

In general, the N-linked glycan will comprise at least one β-linked N-acetylglucosamine. In some embodiments, the N-linked glycan comprises a $GlcNAc_2$ structure where GlcNAc is β-linked N-acetyl glucosamine.

In some embodiments, the N-linked glycan comprises at least one mannose residue. In some embodiments, the glycan comprises a bimannose, trimannose, or higher conjugated mannose. In some embodiments, the trimannose is a linear trimannose. In some embodiments, the trimannose is a branched trimannose.

In some embodiments, the N-linked glycan comprises a structure of the general formula: $GlcNAc_2Man_n$ where $Man_n$ is an integer number of mannose residues. In some embodiments the n of $Man_n$ is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or greater. In some embodiments, n is 3, 4, 5, 6, 7, 8, or 9. In some embodiments, n is 3. In some embodiments, n is 5. In some embodiments, n is 8. In some embodiments, n is 9. In some embodiments, the mannose residues from the general formula $GlcNAc_2Man_n$ are covalently linked in a linear array. In some embodiments, the mannose residues are covalently linked in a branched array. In some embodiments, the linkages of the saccharide residues are β1-N-GlcNAc, β1-4-GlcNAc, β1-2-GlcNAc, β1-4-Man, α1-6-Man, α1-2-Man, and/or α1-3-Man.

These mannosylated N-glycans are of particular interest based on our experience with synthetic insulin-conjugates such as I-6. Of note, these N-glycans differ from the traditional "humanized" N-glycans that others have attempted to produce in yeast (e.g., when attempting to reproduce a glycosylated human therapeutic protein in yeast).

In some embodiments, the N-linked glycan comprises a group of the general formula, $GlcNAc_2Man_9Glc_3$, where Glc is glucose. Again, the inclusion of terminal glucose residues within an N-glycan is of particular interest based on our studies with synthetic insulin-conjugates. However, it is to be understood that the present disclosure also encompasses situations where the N-glycan is $GlcNAc_2Man_3GlcNAc$, $GlcNAc_2Man_5GlcNAc$, or $GlcNAc_2Man_3GlcNAc_2$. In some embodiments, the glycan is $GlcNAc_2Man_3GlcNAc_2Gal_2$ where Gal is galactose. In some embodiments, the glycan is GlcNAc$_2$Man$_3$GlcNAc$_2$Gal$_2$NANA$_2$ where Gal is galactose and NANA is α-2,3-linked and/or α-2,6-linked N-acetyl neuraminic acid. In some embodiments, the saccharide residues are covalently linked in a linear array. In some embodiments, the saccharide residues are covalently linked in a branched array. In some embodiments, the linkages of the saccharide residues are β1,N-GlcNAc, β1,4-GlcNAc, β1,2-GlcNAc, β1,4-Man, α1,6-Man, α1,2-Man, α1,3-Man, β1,4-Gal, α2,3-NANA and/or α2-6-NANA. In some embodiments, N-glycans of the present invention can include different types of linkages (e.g., α1,6-Man and α1,3-Man, etc.).

In some embodiments, the present invention provides compositions comprising a homogeneous population of glycosylated insulin polypeptides (i.e., compositions that comprise a significant proportion of glycosylated insulin polypeptides with the same N-linked glycans). In some embodiments, the present invention provides compositions comprising a population of insulin polypeptides, wherein at least 30%, at least 35%, at least 40%, at least 45%, at least 50%, at least 55%, at least 60%, at least 65%, at least 70%, at least 75%, at least 80%, at least 85%, at least 90%, or at least 95% of the insulin polypeptides comprise the same N-linked glycans (e.g., the same single N-linked glycan when a single N-linked glycan motif is present or the same two or more N-linked glycans when two or more N-linked glycan motifs are present in the insulin polypeptide).

Yeast Production of Recombinant Insulin Polypeptides

Yeast are used in industry for polypeptide production (including the production of recombinant insulin) because of the ability to grow yeast in high-yielding fermentation systems. Fermentation-based processes offer (a) rapid production of high concentrations of polypeptide; (b) the ability to use sterile, well-controlled production conditions; (c) the ability to use simple, chemically defined (and polypeptide-free) growth media; (d) ease of genetic manipulation; (e) the absence of contaminating human or animal pathogens such as viruses; (f) the ability to express a wide variety of polypeptides, including those poorly expressed in cell culture owing to toxicity etc.; and (g) ease of polypeptide recovery (e.g., via secretion into the medium). In addition, fermentation facilities for yeast are generally far less costly to construct than cell culture facilities.

Figure 3:
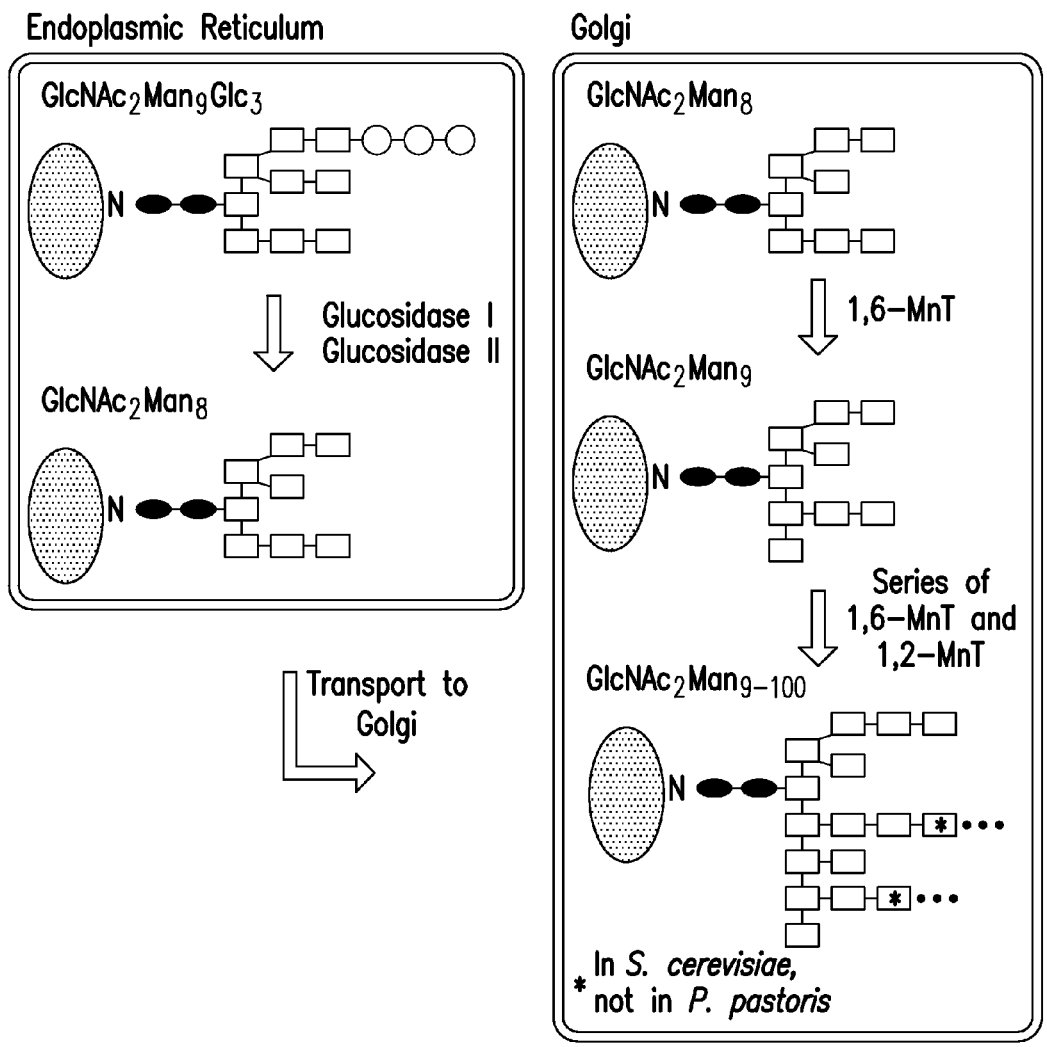
FIG. 3: Representative N-glycosylation pathway in yeast that leads to complex N-glycosylation. MnT is mannosyltransferase.
Figure 4A:
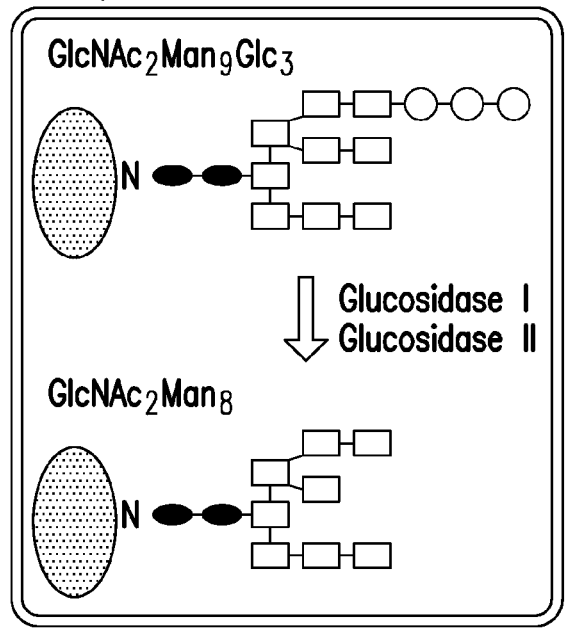
FIG. 4: Representative modified N-glycosylation pathways in yeast. (A) Modified pathway in yeast with a deletion of the 1,6-mannosyltransferase, Och1p gene. (B) Modified pathway in yeast with a deletion of the 1,6-mannosyltransferase, Och1p gene and the 1,3-mannosyltransferase, ALG3 gene. MnS is mannosidase.
Figure 4A:
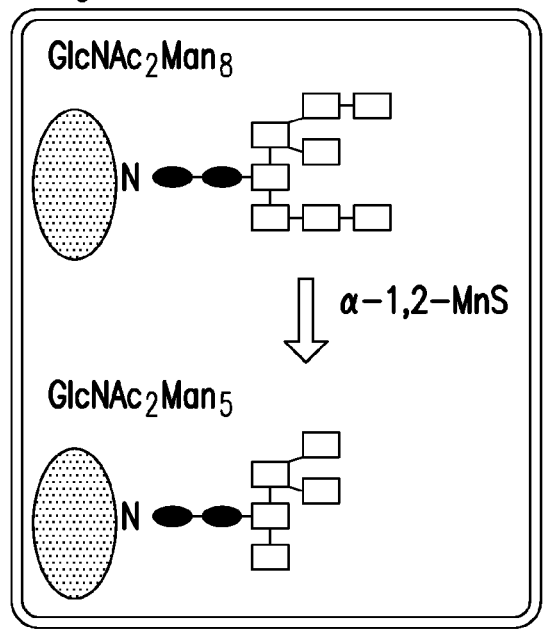
Figure 4B:
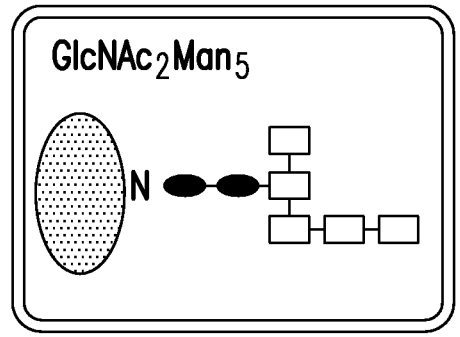
Figure 4B:
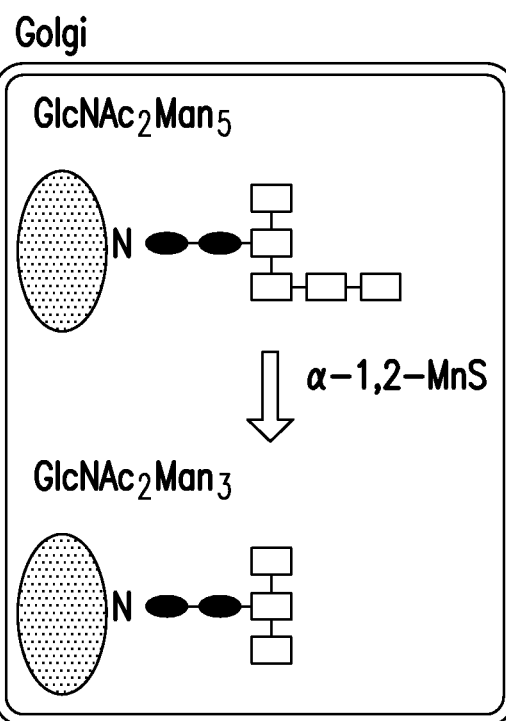

Despite the significant advantages of yeast for efficiently generating high yields of recombinant polypeptides, yeast have one disadvantage when it comes to the production of glycosylated polypeptides. Yeast have a significantly different glycosylation pathway as compared to the glycosylation pathway in humans (e.g., compare FIGS. 2 and 3). Historically, the differences in the glycosylation pathways have prevented the use of yeast as hosts for the production of recombinant human glycosylated polypeptides despite the otherwise notable advantages over mammalian expression systems.

Although yeast and humans have some key differences in their glycosylation pathways, some of the initials steps in the pathways are shared. For example, the first step, the transfer of the core oligosaccharide structure to the nascent polypeptide, is highly conserved in all eukaryotes including yeast, fungi, plants and humans (see FIGS. 2 and 3). Subsequent processing of the core oligosaccharide, however, differs significantly between yeast and humans. In yeast, the oligosaccharide proceeds to be modified by the addition of mannose sugars. The addition of the mannose sugars to the core oligosaccharide is catalyzed by mannosyltransferases residing in the Golgi (e.g., OCH1, MNT1, MNN1, etc.). In S. cerevisiae, OCHI encodes a 1,6-mannosyltransferase, which adds a mannose to the glycan structure GlcNAc$_2$Man$_8$ to yield GlcNAc$_2$Man$_9$. The GlcNAc$_2$Man$_9$ structure, which contains three 1,6-mannose residues, is a substrate for further 1,2-, 1,6-, and 1,3-mannosyltransferases in vivo, leading to the hypermannosylated glycosylated polypeptides that are characteristic for S. cerevisiae and which typically may have 30-40 mannose residues per N-glycan (see FIG. 3).

Significant progress has been made in the development of alternative yeast strains with genetic modifications that provide glycosylated polypeptides with human-like glycosylation patterns. The development of these yeast strains has been an important advance for the generation of functional human glycosylated polypeptide therapeutic agents.

Some of the yeast genetic modifications include the deletion of an OCH1 homolog in Pichia pastoris, which is disclosed in WO02/00856 and the Japanese Patent Application Publication No. 8-336387. Additionally, mutants of S. cerevisiae deficient in mannosyltransferase activity (e.g., OCH1 or MNN9 mutants) have shown to be non-lethal and display a reduced mannose content in the oligosaccharide of yeast glycosylated polypeptides (see FIG. 4). For additional modifications of the glycosylation pathways in yeast refer to U.S. Pat. Nos. 5,135,854, 5,834,251, 7,388,081, 7,326,681 and U.S. Publication Nos. 2006/0177898, 2007/0178551, 2007/0184063, and 2008/0274498.

In one aspect, methods are provided that use yeast cells to express insulin polypeptides of the present disclosure. A yeast cell will be transformed with a polynucleotide sequence encoding an insulin polypeptide of the present disclosure. In some embodiments, the yeast cell will be selected from the *Pichia pastoris, Hansenula polymorpha, Saccharomyces cerevisiae*, and/or *Kluyveromyces lactis* species. In some embodiments, the yeast cell will be a *Pichia pastoris* cell.

In some embodiments, the yeast cell is a wild-type yeast cell. In some embodiments, the yeast cell is a genetically engineered yeast cell. In some embodiments, the yeast cell is genetically modified by the addition, deletion or mutation of one or more genes. In some embodiments, the yeast cell is genetically modified to incorporate one or more new genes. Genetic modifications can be accomplished by methods known in the art and as described above.

In some embodiments the yeast cell has a normal glycosylation pathway. In some embodiments, the yeast cell will have a genetically modified glycosylation pathway as described above. In some embodiments, the yeast cell has one or more modifications in the normal yeast glycosylation pathway, so that it produces a polypeptide end product with a different N-glycan structure from the N-glycan structure that would be produced by the traditional yeast glycosylation pathway. For example, in some embodiments, transfer of additional mannose residues onto the glycan core may be prevented by the mutation and/or deletion of a mannosyltransferase. In some embodiments, the yeast cell has been genetically engineered so that it does not express an α-1,2-mannosyltransferase, α-1,3-mannosyltransferase and/or an α-1,6-mannosyltransferase. In some embodiments, the yeast cell harbors an insertion, deletion and/or mutation in α-1,2-mannosyltransferase, α-1,3-mannosyltransferase and/or an α-1,6-mannosyltransferase that renders the mannosyltransferase non-functional.

Methods for transforming yeast strains for the expression of polypeptides are well known in the art (e.g., see European Patent Publication Nos. EP 0088632, EP 0116201, EP 0123294, EP 0123544, EP 0163529, EP 0123289, EP 0100561, EP 0189998 and EP 0195986, PCT Patent Publications WO 95/01421, WO 95/02059 and WO 90/10075, and U.S. Pat. Nos. 4,546,082 and 6,358,705).

The medium used to cultivate the transformed yeast cells may be any conventional medium suitable for growing yeast organisms. In some embodiments, an insulin polypeptide of the present disclosure will be directly harvested from the yeast cell. In some embodiments, the yeast cell will be lysed and the target insulin polypeptide will be isolated and purified using methods known in the art.

In some embodiments, an insulin polypeptide of the present disclosure will be excreted from the yeast cell into the medium. These insulin polypeptides may be recovered from the medium by conventional procedures including separating the yeast cells from the medium by centrifugation or filtration, precipitating the polypeptide components of the supernatant or filtrate by means of a salt, e.g., ammonium sulphate, followed by purification by a variety of chromatographic procedures, e.g., ion exchange chromatography, affinity chromatography, or the like.

In some embodiments, after recovery of the insulin polypeptide of the present disclosure from the culture medium, an insulin polypeptide may be subjected to various in vitro procedures to remove a possible leader peptide and/or C-peptide to provide a desired insulin polypeptide. Such methods include enzymatic conversion by means of trypsin or an *Achromobacter lyticus* protease in the presence of an L-threonine ester followed by conversion of the threonine ester by basic or acid hydrolysis as described in U.S. Pat. No. 4,343,898 or 4,916,212.

Figure 1B:
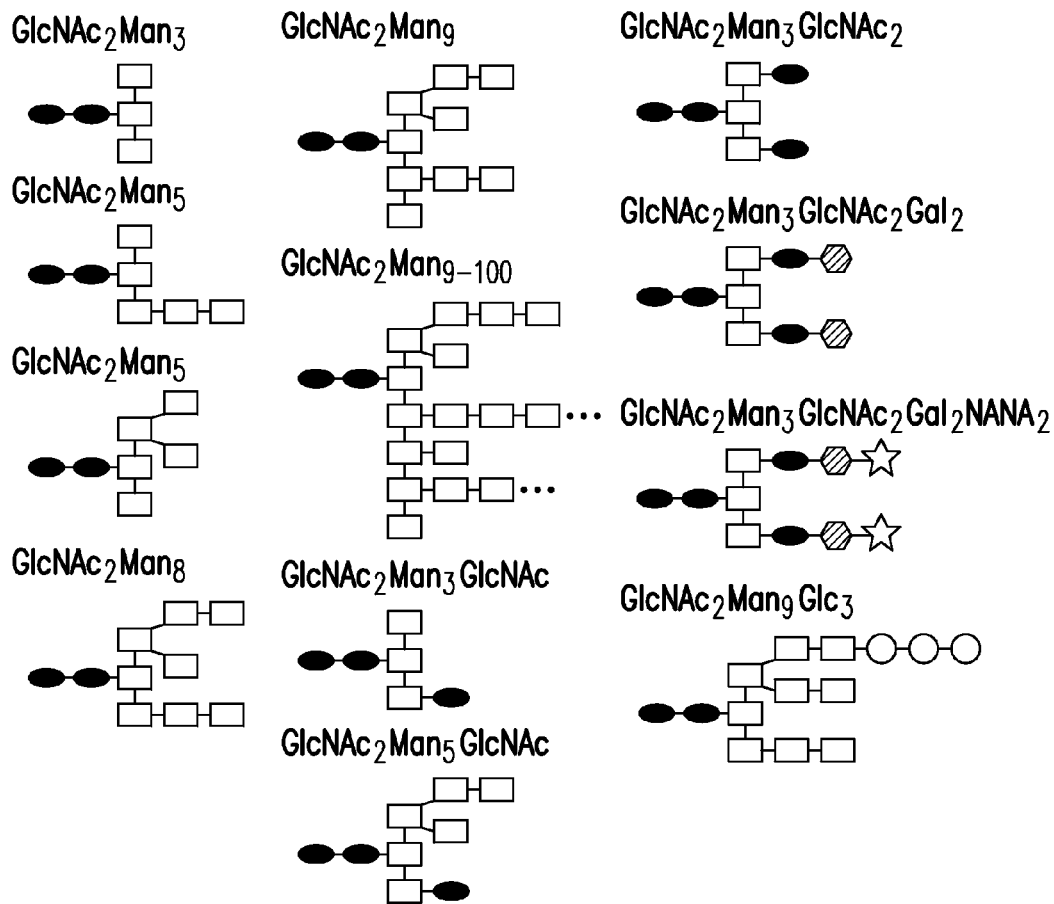

In some embodiments, an insulin polypeptide comprising at least one N-linked glycan (e.g., as shown in FIG. 1B) may be trimmed using an exoglycosidase. In some embodiments, the exoglycosidase is an α-1,2-mannosidase, an α-1,3-mannosidase, an α-1,6-mannosidase, an α-(1-2,3)-mannosidase and/or an α-(1-2,3,6)-mannosidase. In some embodiments the exoglycosidase is expressed by the yeast cell and the trimming occurs in vivo. In some embodiments, after purification from a yeast cell, the insulin polypeptide of the present disclosure is treated with an exoglycosidase in vitro. In some embodiments, an insulin polypeptide of the present invention comprising at least one N-linked glycan (e.g., as shown in FIG. 1B) is used as is and not trimmed using an exoglycosidase.

Sustained Release Formulations

As discussed in the Examples, in certain embodiments it may be advantageous to administer a glycosylated insulin polypeptide of the present disclosure in a sustained fashion (i.e., in a form that exhibits an absorption profile that is more sustained than soluble recombinant human insulin). This will provide a sustained level of glycosylated insulin polypeptide that can respond to fluctuations in glucose on a timescale that it more closely related to the typical glucose fluctuation timescale (i.e., hours rather than minutes). In certain embodiments, the sustained release formulation may exhibit a zero-order release of the glycosylated insulin polypeptide when administered to a mammal under non-hyperglycemic conditions (i.e., fasted conditions).

It will be appreciated that any formulation that provides a sustained absorption profile may be used. In certain embodiments this may be achieved by combining the glycosylated insulin polypeptide with other ingredients that slow its release properties into systemic circulation.

For example, PZI (protamine zinc insulin) formulations may be used for this purpose. As described in the Examples, we have found that in certain embodiments the absorption profile and stability of PZI formulations prepared with our synthetic insulin-conjugates are sensitive to the absolute and relative amounts of protamine and zinc included in the formulation. For example, whereas commercial PZI and NPH insulin formulations require only about 0.05 to about 0.2 mg protamine/mg insulin, some PZI-conjugate preparations required about 1 to about 5 mg protamine/mg conjugate in order to effectively sustain the absorption profile. Furthermore, while commercial protamine insulin preparations contain about 0.006 mg zinc/mg insulin, we have found that increasing the zinc concentration along with the protamine concentration can, in certain embodiments, lead to more stable, easily dispersible formulations of synthetic insulin-conjugates. In some cases, the zinc content was in the range of about 0.05 to about 0.5 mg zinc/mg conjugate.

Thus, by extrapolation, in certain embodiments, a PZI formulation of the present disclosure may include from about 0.05 to about 10 mg protamine/mg glycosylated insulin polypeptide. For example, from about 0.2 to about 10 mg protamine/mg glycosylated insulin polypeptide, e.g., about 1 to about 5 mg protamine/mg glycosylated insulin polypeptide. In certain embodiments, a PZI formulation of the present disclosure may include from about 0.006 to about 0.5 mg zinc/mg glycosylated insulin polypeptide. For example, from about 0.05 to about 0.5 mg zinc/mg glycosylated insulin polypeptide, e.g., about 0.1 to about 0.25 mg zinc/mg glycosylated insulin polypeptide.

In certain embodiments, a PZI formulation of the present disclosure may include protamine and zinc in a ratio (w/w) in the range of about 100:1 to about 5:1. For example, from about 50:1 to about 5:1, e.g., about 40:1 to about 10:1.

The Examples also describe the benefits of including one or more of the following components in a PZI formulation: an antimicrobial preservative, an isotonic agent, and a non-glycosylated insulin polypeptide.

In certain embodiments a PZI formulation of the present disclosure includes an antimicrobial preservative (e.g., m-cresol, phenol, methylparaben, or propylparaben). In certain embodiments the antimicrobial preservative is m-cresol. For example, in certain embodiments, a PZI formulation may include from about 0.1 to about 1.0% v/v m-cresol. For example, from about 0.1 to about 0.5% v/v m-cresol, e.g., about 0.15 to about 0.35% v/v m-cresol.

In certain embodiments a PZI formulation of the present disclosure includes a polyol as isotonic agent (e.g., mannitol, propylene glycol or glycerol). In certain embodiments the isotonic agent is glycerol. In certain embodiments, the isotonic agent is a salt, e.g., NaCl. For example, a PZI formulation may comprise from about 0.05 to about 0.5 M NaCl, e.g., from about 0.05 to about 0.25 M NaCl or from about 0.1 to about 0.2 M NaCl.

In certain embodiments a PZI formulation of the present disclosure includes an amount of a non-glycosylated insulin polypeptide. In certain embodiments, a PZI formulation includes a molar ratio of glycosylated insulin polypeptide to non-glycosylated insulin polypeptide in the range of about 100:1 to 1:1, e.g., about 50:1 to 2:1 or about 25:1 to 2:1.

The present disclosure also encompasses the use of standard sustained (also called extended) release formulations that are well known in the art of small molecule formulation (e.g., see *Remington's Pharmaceutical Sciences*, 19$^{th}$ ed., Mack Publishing Co., Easton, Pa., 1995). The present disclosure also encompasses the use of devices that rely on pumps or hindered diffusion to deliver a glycosylated insulin polypeptide on a gradual basis. In certain embodiments, a long acting formulation may (additionally or alternatively) be provided by including certain mutations and/or chemical modification in the glycosylated insulin polypeptide. For example, one could include the mutations of insulin glargine (LANTUS®) or insulin detemir (LEVEMIR®). As noted previously, insulin glargine is an exemplary long acting insulin analog in which Asp-A21 has been replaced by glycine, and two arginine residues have been added to the C-terminus of the B-peptide. The effect of these changes is to shift the isoelectric point, producing a solution that is completely soluble at pH 4. Insulin detemir is another long acting insulin analog in which Thr-B30 has been deleted, and a C14 fatty acid chain has been attached to Lys-B29.

Uses of Insulin Polypeptides

In another aspect, methods of using glycosylated insulin polypeptides of the present disclosure are provided. In general, the glycosylated insulin polypeptides can be used to controllably provide insulin in response to a saccharide (e.g., glucose or an exogenous saccharide such as mannose, alpha-methyl mannose, L-fucose, etc. as described herein). The disclosure encompasses treating a disease or condition by administering glycosylated insulin polypeptides of the present disclosure. Although the glycosylated insulin polypeptides can be used to treat any patient (e.g., dogs, cats, cows, horses, sheep, pigs, mice, etc.), they are most preferably used in the treatment of humans. As used herein, the term "treat" (or "treating", "treated", "treatment", etc.) refers to the administration of a glycosylated insulin polypeptide of the present disclosure to a subject in need thereof with the purpose to alleviate, relieve, alter, ameliorate, improve or affect a condition (e.g., diabetes), a symptom or symptoms of a condition (e.g., uncontrolled glucose levels), or the predisposition toward a condition.

A glycosylated insulin polypeptide can be administered to a patient by any route. In general the most appropriate route of administration will depend upon a variety of factors including the nature of the disease or condition being treated, the condition of the patient, etc. In general, the present disclosure encompasses administration by oral, intravenous, intramuscular, intra-arterial, subcutaneous, intraventricular, pulmonary, transdermal, rectal, intravaginal, intraperitoneal, topical (as by powders, ointments, or drops), buccal, or as an oral or nasal spray or aerosol. General considerations in the preparation of pharmaceutical formulations for these different routes may be found, for example, in *Remington's Pharmaceutical Sciences*, 19th ed., Mack Publishing Co., Easton, Pa., 1995. In various embodiments, the glycosylated insulin polypeptide may be administered subcutaneously, e.g., by injection. The glycosylated insulin polypeptide can be dissolved in a carrier for ease of delivery. For example, the carrier can be an aqueous solution including, but not limited to, sterile water, saline or buffered saline.

In general, a therapeutically effective amount of glycosylated insulin polypeptide will be administered. By a "therapeutically effective amount" of glycosylated insulin polypeptide is meant a sufficient amount to treat the disease or condition at a reasonable benefit/risk ratio, which involves a balancing of the efficacy and toxicity of the glycosylated insulin polypeptide. In general, therapeutic efficacy and toxicity may be determined by standard pharmacological procedures in cell cultures or with experimental animals, e.g., by calculating the $ED_{50}$ (the dose that is therapeutically effective in 50% of the treated subjects) and the $LD_{50}$ (the dose that is lethal to 50% of treated subjects). The $ED_{50}/LD_{50}$ represents the therapeutic index of the glycosylated insulin polypeptide. Ultimate selection of an appropriate range of doses for administration to humans is determined in the course of clinical trials.

In various embodiments, the average daily dose of glycosylated insulin polypeptide is in the range of 10 to 200 U, e.g., 25 to 100 U (where 1 Unit of non-glycosylated insulin is ~0.04 mg and a simple upward adjustment can be applied based on the molar mass of the additional N-linked glycan(s)). In certain embodiments, an amount of glycosylated insulin polypeptide with these doses is administered on a daily basis. In certain embodiments, an amount of glycosylated insulin polypeptide with 5 to 10 times these doses is administered on a weekly basis. In certain embodiments, an amount of glycosylated insulin polypeptide with 10 to 20 times these doses is administered on a bi-weekly basis. In certain embodiments, an amount of glycosylated insulin polypeptide with 20 to 40 times these doses is administered on a monthly basis.

In certain embodiments, a glycosylated insulin polypeptide of the present disclosure may be used to treat hyperglycemia in a patient (e.g., a mammalian patient). In certain embodiments, the patient is diabetic. However, the present methods are not limited to treating diabetic patients. For example, in certain embodiments, a glycosylated insulin polypeptide may be used to treat hyperglycemia in a patient with an infection associated with impaired glycemic control. In certain embodiments, a glycosylated insulin polypeptide may be used to treat diabetes.

In certain embodiments, when a glycosylated insulin polypeptide or formulation of the present disclosure is administered to a patient (e.g., a mammalian patient) it induces less hypoglycemia than a non-glycosylated version of the insulin polypeptide. In certain embodiments, a glycosylated insulin polypeptide or formulation of the present disclosure also induces an HbA1c value within a normal range for the species in question. In certain embodiments, the formulation leads to an HbA1c value of less than 7%, e.g., in the range of about 4 to about 6%.

In various embodiments, a glycosylated insulin polypeptide of the present disclosure may be administered to a patient who is receiving at least one additional therapy. In various embodiments, the at least one additional therapy is intended to treat the same disease or disorder as the administered glycosylated insulin polypeptide. In various embodiments, the at least one additional therapy is intended to treat a side-effect of the glycosylated insulin polypeptide. The two or more therapies may be administered within the same, overlapping or non-overlapping timeframes as long as there is a period when the patient is receiving a benefit from both therapies. The two or more therapies may be administered on the same or different schedules as long as there is a period when the patient is receiving a benefit from both therapies. The two or more therapies may be administered within the same or different formulations as long as there is a period when the patient is receiving a benefit from both therapies. In certain embodiments, a drug may be admixed with a glycosylated insulin polypeptide of the present disclosure (i.e., a drug which is simply combined with the glycosylated insulin polypeptide in a pharmaceutical formulation). For example, in certain embodiments, any of these approaches may be used to administer more than one anti-diabetic drug to a subject. Certain exemplary embodiments of this approach are described in more detail below.

Insulin sensitizers (e.g., biguanides such as metformin, glitazones) act by increasing a patient's response to a given amount of insulin. A patient receiving an insulin sensitizer will therefore require a lower dose of a glycosylated insulin polypeptide of the present disclosure than an otherwise identical patient would. Thus, in certain embodiments, a glycosylated insulin polypeptide may be administered to a patient who is also being treated with an insulin sensitizer. In various embodiments, the glycosylated insulin polypeptide of the present disclosure may be administered at up to 75% of the normal dose required in the absence of the insulin sensitizer.

In various embodiments, up to 50, 40, 30 or 20% of the normal dose may be administered.

Insulin resistance is a disorder in which normal amounts of insulin are inadequate to produce a normal insulin response. For example, insulin-resistant patients may require high doses of insulin in order to overcome their resistance and provide a sufficient glucose-lowering effect. In these cases, insulin doses that would normally induce hypoglycemia in less resistant patients fail to even exert a glucose-lowering effect in highly resistant patients. Similarly, the glycosylated insulin polypeptides of the present disclosure are only effective for this subclass of patients when they provide high levels of bioactive insulin in a suitable timeframe. In certain embodiments, the treatment of this subclass of patients may be facilitated by combining the two approaches. Thus in certain embodiments, a traditional insulin-based therapy is used to provide a baseline level of insulin and a glycosylated insulin polypeptide of the present invention is administered to provide a controlled supplement of bioactive insulin when needed by the patient. Thus, in certain embodiments, glycosylated insulin polypeptides may be administered to a patient who is also being treated with insulin. In various embodiments, the insulin may be administered at up to 75% of the normal dose required in the absence of a glycosylated insulin polypeptide of the present disclosure. In various embodiments, up to 50, 40, 30 or 20% of the normal dose may be administered. It will be appreciated that this combination approach may also be used with insulin resistant patients who are receiving an insulin secretagogue (e.g., a sulfonylurea, GLP-1, exendin-4, etc.) and/or an insulin sensitizer (e.g., a biguanide such as metformin, a glitazone).

PK and PD Properties

In various embodiments, the pharmacokinetic and/or pharmacodynamic behavior of a glycosylated insulin polypeptide of the present disclosure may be modified by variations in the serum concentration of a saccharide.

For example, from a pharmacokinetic (PK) perspective, the serum concentration curve may shift upward when the serum concentration of the saccharide (e.g., glucose) increases or when the serum concentration of the saccharide crosses a threshold (e.g., is higher than normal glucose levels).

In certain embodiments, the serum concentration curve of a glycosylated insulin polypeptide is substantially different when administered to the mammal under fasted and hyperglycemic conditions. As used herein, the term "substantially different" means that the two curves are statistically different as determined by a student t-test ($p<0.05$). As used herein, the term "fasted conditions" means that the serum concentration curve was obtained by combining data from five or more fasted non-diabetic individuals. In certain embodiments, a fasted non-diabetic individual is a randomly selected 18-30 year old who presents with no diabetic symptoms at the time blood is drawn and who has not eaten within 12 hours of the time blood is drawn. As used herein, the term "hyperglycemic conditions" means that the serum concentration curve was obtained by combining data from five or more fasted non-diabetic individuals in which hyperglycemic conditions (glucose $C_{max}$ at least 100 mg/dL above the mean glucose concentration observed under fasted conditions) were induced by concurrent administration of glycosylated insulin polypeptide and glucose. Concurrent administration of glycosylated insulin polypeptide and glucose simply requires that the glucose $C_{max}$ occur during the period when the glycosylated insulin polypeptide is present at a detectable level in the serum. For example, a glucose injection (or ingestion) could be timed to occur shortly before, at the same time or shortly after the glycosylated insulin polypeptide is administered. In certain embodiments, the glycosylated insulin polypeptide and glucose are administered by different routes or at different locations. For example, in certain embodiments, the glycosylated insulin polypeptide is administered subcutaneously while glucose is administered orally or intravenously.

In certain embodiments, the serum $C_{max}$ of the glycosylated insulin polypeptide is higher under hyperglycemic conditions as compared to fasted conditions. Additionally or alternatively, in certain embodiments, the serum area under the curve (AUC) of the glycosylated insulin polypeptide is higher under hyperglycemic conditions as compared to fasted conditions. In various embodiments, the serum elimination rate of the glycosylated insulin polypeptide is slower under hyperglycemic conditions as compared to fasted conditions. As discussed in the Examples, we have found that in certain embodiments, the serum concentration curve of synthetic insulin-conjugates can be fit using a two-compartment bi-exponential model with one short and one long half-life. The long half-life appears to be particularly sensitive to glucose concentration. Thus, in certain embodiments, the long half-life of a glycosylated insulin polypeptide is longer under hyperglycemic conditions as compared to fasted conditions. In certain embodiments, the fasted conditions involve a glucose $C_{max}$ of less than 100 mg/dL (e.g., 80 mg/dL, 70 mg/dL, 60 mg/dL, 50 mg/dL, etc.). In certain embodiments, the hyperglycemic conditions involve a glucose $C_{max}$ in excess of 200 mg/dL (e.g., 300 mg/dL, 400 mg/dL, 500 mg/dL, 600 mg/dL, etc.). It will be appreciated that other PK parameters such as mean serum residence time (MRT), mean serum absorption time (MAT), etc. could be used instead of or in conjunction with any of the aforementioned parameters.

The normal range of glucose concentrations in humans, dogs, cats, and rats is 60 to 200 mg/dL. One skilled in the art will be able to extrapolate the following values for species with different normal ranges (e.g., the normal range of glucose concentrations in miniature pigs is 40 to 150 mg/di). Glucose concentrations below 60 mg/dL are considered hypoglycemic. Glucose concentrations above 200 mg/dL are considered hyperglycemic. In certain embodiments, the PK properties of the glycosylated insulin polypeptide may be tested using a glucose clamp method (see Examples) and the serum concentration curve of the glycosylated insulin polypeptide may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Additionally or alternatively, the serum $T_{max}$, serum $C_{max}$, mean serum residence time (MRT), mean serum absorption time (MAT) and/or serum half-life may be substantially different at the two glucose concentrations. As discussed below, in certain embodiments, 100 mg/dL and 300 mg/dL may be used as comparative glucose concentrations. It is to be understood however that the present disclosure encompasses each of these embodiments with an alternative pair of comparative glucose concentrations including, without limitation, any one of the following pairs: 50 and 200 mg/dL, 50 and 300 mg/dL, 50 and 400 mg/dL, 50 and 500 mg/dL, 50 and 600 mg/dL, 100 and 200 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc.

Thus, in certain embodiments, the $C_{max}$ of the glycosylated insulin polypeptide is higher when administered to the mammal at the higher of the two glucose concentrations (e.g., 300 vs. 100 mg/dL glucose). In certain embodiments, the $C_{max}$ of the glycosylated insulin polypeptide is at least 50% (e.g., at least 100%, at least 200% or at least 400%) higher when administered to the mammal at the higher of the two glucose concentrations (e.g., 300 vs. 100 mg/dL glucose).

In certain embodiments, the AUC of the glycosylated insulin polypeptide is higher when administered to the mammal at the higher of the two glucose concentrations (e.g., 300 vs. 100 mg/dL glucose). In certain embodiments, the AUC of the glycosylated insulin polypeptide is at least 50% (e.g., at least e.g., at least 100%, at least 200% or at least 400%) higher when administered to the mammal at the higher of the two glucose concentrations (e.g., 300 vs. 100 mg/dL glucose).

In certain embodiments, the serum elimination rate of the glycosylated insulin polypeptide is slower when administered to the mammal at the higher of the two glucose concentrations (e.g., 300 vs. 100 mg/dL glucose). In certain embodiments, the serum elimination rate of the glycosylated insulin polypeptide is at least 25% (e.g., at least 50% or at least 100%) faster when administered to the mammal at the lower of the two glucose concentrations (e.g., 100 vs. 300 mg/dL glucose).

As discussed in the Examples, we have found that in certain embodiments the serum concentration curve of synthetic insulin-conjugates can be fit using a two-compartment bi-exponential model with one short and one long half-life. The long half-life appears to be particularly sensitive to glucose concentration. Thus, in certain embodiments, the long half-life of a glycosylated insulin polypeptide is longer when administered to the mammal at the higher of the two glucose concentrations (e.g., 300 vs. 100 mg/dL glucose). In certain embodiments, the long half-life is at least 50% (e.g., at least 100%, at least 200% or at least 400%) longer when administered to the mammal at the higher of the two glucose concentrations (e.g., 300 vs. 100 mg/dL glucose).

In certain embodiments, the serum concentration curve of a glycosylated insulin polypeptide is substantially the same as the serum concentration curve of a non-glycosylated version of the insulin polypeptide when administered to the mammal under hyperglycemic conditions. As used herein, the term "substantially the same" means that there is no statistical difference between the two curves as determined by a student t-test (p>0.05). In certain embodiments, the serum concentration curve of the glycosylated insulin polypeptide is substantially different from the serum concentration curve of a non-glycosylated version of the insulin polypeptide when administered under fasted conditions. In certain embodiments, the serum concentration curve of the conjugate is substantially the same as the serum concentration curve of a non-glycosylated version of the insulin polypeptide when administered under hyperglycemic conditions and substantially different when administered under fasted conditions. In certain embodiments, the hyperglycemic conditions involve a glucose $C_{max}$ in excess of 200 mg/dL (e.g., 300 mg/dL, 400 mg/dL, 500 mg/dL, 600 mg/dL, etc.). In certain embodiments, the fasted conditions involve a glucose $C_{max}$ of less than 100 mg/dL (e.g., 80 mg/dL, 70 mg/dL, 60 mg/dL, 50 mg/dL, etc.). It will be appreciated that any of the aforementioned PK parameters such as serum $T_{max}$, serum $C_{max}$, AUC, mean serum residence time (MRT), mean serum absorption time (MAT) and/or serum half-life could be compared.

From a pharmacodynamic (PD) perspective, the bioactivity of a glycosylated insulin polypeptide may increase when the glucose concentration increases or when the glucose concentration crosses a threshold, e.g., is higher than normal glucose levels. In certain embodiments, the bioactivity of a glycosylated insulin polypeptide is lower when administered under fasted conditions as compared to hyperglycemic conditions. In certain embodiments, the fasted conditions involve a glucose $C_{max}$ of less than 100 mg/dL (e.g., 80 mg/dL, 70 mg/dL, 60 mg/dL, 50 mg/dL, etc.). In certain embodiments, the hyperglycemic conditions involve a glucose $C_{max}$ in excess of 200 mg/dL (e.g., 300 mg/dL, 400 mg/dL, 500 mg/dL, 600 mg/dL, etc.).

In certain embodiments, the PD properties of a glycosylated insulin polypeptide may be tested by measuring the glucose infusion rate (GIR) required to maintain a steady glucose concentration. According to such embodiments, the bioactivity of a glycosylated insulin polypeptide may be substantially different when administered at glucose concentrations of 50 and 200 mg/dL, 50 and 300 mg/dL, 50 and 400 mg/dL, 50 and 500 mg/dL, 50 and 600 mg/dL, 100 and 200 mg/dL, 100 and 300 mg/dL, 100 and 400 mg/dL, 100 and 500 mg/dL, 100 and 600 mg/dL, 200 and 300 mg/dL, 200 and 400 mg/dL, 200 and 500 mg/dL, 200 and 600 mg/dL, etc. Thus, in certain embodiments, the bioactivity of a glycosylated insulin polypeptide is higher when administered to the mammal at the higher of the two glucose concentrations (e.g., 300 vs. 100 mg/dL glucose). In certain embodiments, the bioactivity of a glycosylated insulin polypeptide is at least 25% (e.g., at least 50% or at least 100%) higher when administered to the mammal at the higher of the two glucose concentrations (e.g., 300 vs. 100 mg/dL glucose).

In certain embodiments, the PD behavior can be observed by comparing the time to reach minimum blood glucose concentration ($T_{nadir}$), the duration over which the blood glucose level remains below a certain percentage of the initial value (e.g., 70% of initial value or $T_{70\% \, BQL}$), etc.

In general, it will be appreciated that any of the PK and PD characteristics discussed in this section can be determined according to any of a variety of published pharmacokinetic and pharmacodynamic methods (e.g., see Baudys et al., *Bioconjugate Chem.* 9:176-183, 1998 for methods suitable for subcutaneous delivery).

It will also be appreciated that while the foregoing was described in the context of glucose-responsive glycosylated insulin polypeptides, the same properties and assays apply to glycosylated insulin polypeptides that are responsive to other saccharides including exogenous saccharides, e.g., mannose, L-fucose, N-acetyl glucosamine, alpha-methyl mannose, etc. As discussed in more detail above and in the Examples, instead of comparing PK and/or PD properties under fasted and hyperglycemic conditions, the PK and/or PD properties may be compared under fasted conditions with and without administration of the exogenous saccharide. It will be appreciated that glycosylated insulin polypeptides can be designed that respond to different $C_{max}$ values of a given exogenous saccharide.

Exogenous Trigger

As mentioned previously, the methods, glycosylated insulin polypeptides and compositions that are described herein are not limited to glucose responsive glycosylated insulin polypeptides. As demonstrated in the Examples, several exemplary synthetic glucose-responsive conjugates were also responsive to exogenous saccharides such as alpha-methyl mannose. It will therefore be appreciated that in certain embodiments a glycosylated insulin polypeptide may be triggered by exogenous administration of a saccharide other than glucose such as alpha-methyl mannose and L-fucose or any other saccharide that can alter the PK or PD properties of the glycosylated insulin polypeptide. As used herein, an "exogenous" saccharide is one which is not present at significant levels in a patient unless administered to the patient. In certain embodiments the patient is a mammal, e.g., a human, a dog, a cat, a rat, etc. As used herein, a saccharide is not present at significant levels in a patient if normal serum for that type of patient includes less than 0.1 mM of the saccharide. In certain embodiments normal serum for the patient may include less than 0.08 mM, less than 0.06 mM, or less than 0.04 mM of the saccharide.

Once a glycosylated insulin polypeptide has been administered as described above (e.g., as a sustained release formulation) it can be triggered by administration of a suitable exogenous saccharide. In a certain embodiment, a triggering amount of the exogenous saccharide is administered. As used herein, a "triggering amount" of exogenous saccharide is an amount sufficient to cause a change in at least one PK and/or PD property of the glycosylated insulin polypeptide (e.g., $C_{max}$, AUC, half-life, etc. as discussed previously). It is to be understood that any of the aforementioned methods of administration for the glycosylated insulin polypeptide apply equally to the exogenous saccharide. It is also be to be understood that the methods of administration for the glycosylated insulin polypeptide and exogenous saccharide may be the same or different. In various embodiments, the methods of administration are different (e.g., for purposes of illustration the glycosylated insulin polypeptide may be administered by subcutaneous injection on a weekly basis while the exogenous saccharide is administered orally on a daily basis). The oral administration of an exogenous saccharide is of particular value since it facilitates patient compliance. In general, it will be appreciated that the PK and PD properties of the glycosylated insulin polypeptide will be related to the PK profile of the exogenous saccharide. Thus, the glycosylated insulin polypeptide PK and PD properties can be tailored by controlling the PK profile of the exogenous saccharide. As is well known in the art, the PK profile of the exogenous saccharide can be tailored based on the dose, route, frequency and formulation used. For example, if a short and intense activation of the glycosylated insulin polypeptide is desired then an oral immediate release formulation might be used. In contrast, if a longer less intense activation of glycosylated insulin polypeptide is desired then an oral extended release formulation might be used instead. General considerations in the formulation and manufacture of immediate and extended release formulation may be found, for example, in *Remington's Pharmaceutical Sciences*, 19$^{th}$ ed., Mack Publishing Co., Easton, Pa., 1995.

It will also be appreciated that the relative frequency of administration of a glycosylated insulin polypeptide of the present disclosure and an exogenous saccharide may be the same or different. In certain embodiments, the exogenous saccharide is administered more frequently than the glycosylated insulin polypeptide. In some embodiments, the glycosylated insulin polypeptide of the present invention may be administered twice, or thrice, or more times daily. In certain embodiment, the glycosylated insulin polypeptide may be administered daily while the exogenous saccharide is administered more than once a day. In certain embodiment, the glycosylated insulin polypeptide may be administered twice weekly, weekly, biweekly or monthly while the exogenous saccharide is administered daily. In certain embodiments, the glycosylated insulin polypeptide is administered monthly and the exogenous saccharide is administered twice weekly, weekly, or biweekly. Other variations on these schemes will be recognized by those skilled in the art and will vary depending on the nature of the glycosylated insulin polypeptide and formulation used.

EXAMPLES

Examples 1-3 describe processes used to prepare an exemplary synthetic insulin-conjugate I-6 (see FIG. 6 for the structure of the conjugate). Examples 4-7 also describe experiments that were performed to demonstrate how the PK and PD properties of this exemplary synthetic insulin-conjugate are sensitive to saccharide concentrations (e.g., endogenous glucose levels). Examples 8 and 9 describe how these experiments would be performed with glycosylated insulin polypeptides of the present disclosure. Example 10 describes the small- and large-scale production, purification, and in vitro enzyme processing of exemplary insulin polypeptides that have not been engineered to include N-linked glycan motifs in two different yeast strains. Example 11 describes the small- and large-scale production, purification, and in vitro enzyme processing of exemplary insulin polypeptides that have been engineered to include N-linked glycan motifs in two different yeast strains. Example 12 describes the sequences of some exemplary insulin polypeptides that have been engineered to include N-linked glycan motifs. Examples 13-17 describe experiments that were performed with some of the exemplary synthetic conjugates of FIG. 15A to 15Q.

Example 1

Amine-Functionalized Drug Conjugation with Multivalent Activated Esters in Organic Solvent A framework containing N-terminal activated esters is dissolved at 60 mM in 1 ml of anhydrous DMSO followed by the addition of 400 µl (excess) of triethylamine (TEA). The solution is stirred rapidly for 10 minutes at room temperature. In parallel, a 122 mM solution of ligand is prepared in an appropriate volume of anhydrous DMSO. Once dissolved, enough ligand solution is added dropwise over the course of ten minutes to provide a number of reactive equivalents equal to exactly the number of activated ester groups on the framework, N, minus one. For example, if there are N=3 activated ester groups on the framework, then (1×(3−1)×60 mM/122 mM)=0.98 ml of ligand solution are added. If there are N=4 activated ester groups on the framework, then (1×(4−1)×60 mM/122 mM)=1.5 ml of ligand solution are added, and so on. After the ligand solution is added, the solution is stirred for two hours at room temperature.

The amine-bearing drug is then dissolved separately in 7.5 ml of anhydrous DMSO at a concentration of 8.1 mM. Once dissolved, the entire drug solution is added over the course of one minute to the framework/DMSO/ligand/TEA solution followed by room temperature mixing for an additional two hours to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 10 ml. This solution is further purified to obtain the desired product using preparative reverse phase HPLC on a Waters SymmetryPrep C18, 7 µm column, 19×150 mm. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltraPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and ligand used. Once collected, the solution is rotovapped to remove acetonitrile and lyophilized to obtain pure conjugate whose identity may be verified by LC-MS (HT Laboratories, San Diego, Calif.).

Example 2

B29-Insulin Conjugates with Multivalent Saccharides Produced in Organic Solvent from Unprotected Insulin This example makes use of the fact that in the unprotected insulin case, the Lys-B29 epsilon-amino moiety is the most reactive amine, followed by the A1 and then the B1 alpha-amino moieties. Therefore, when unprotected insulin is used as the amine-containing drug the resulting conjugate should be predominantly substituted at the Lys-B29 position. Using the method described in Example 1 and recombinant human insulin (MW=5808 Da, Sigma Aldrich, St. Louis, Mo.) as the amine-containing drug, synthetic insulin-conjugate I-6 was prepared using the TSAT-C6 activated ester framework purchased from Molecular Biosciences (Boulder, Colo.) and AETM as the ligand. The appropriately sized size exclusion medium was Biogel P2 (Bio-Rad Laboratories, Hercules, Calif.), and the appropriately sized ultrafiltration membrane molecular weight cutoff was 3 kDa.

According to N-terminal sequencing, approximately 87% of the AETM-containing framework was conjugated to insulin via the Lys-B29 (85% purity, MW (LC-MS) 7378).

Example 3

Amine-Functionalized Drug Conjugation with Multivalent Activated Esters in Aqueous Solvent This example describes an alternative to the method described in Example 1 in which the reaction is performed in aqueous solvent instead of organic solvent.

The framework containing N terminal activated esters is dissolved at 60 mM in 6.25 ml of anhydrous DMSO followed by the addition of 2 ml (excess) of triethylamine (TEA). The solution is stirred rapidly for 10 minutes at room temperature. In parallel, a 448 mM solution of ligand is prepared in an appropriate volume of anhydrous DMSO. Once dissolved, enough ligand solution is added dropwise over the course of ten minutes to provide a number of reactive equivalents equal to 1.5 times the number of activated ester groups on the framework, N, minus one. For example, if there are N=3 activated ester groups on the framework, then (1.5×(3−1)×60 mM/448 mM)×6.25 ml=2.5 ml of ligand solution are added. If there are N=4 activated ester groups on the framework, then (1.5×(4−1)×60 mM/448 mM)×6.25 ml=3.8 ml of ligand solution are added, and so on. After the ligand solution is added, the solution is stirred for one hour at room temperature.

The amine-bearing drug is then dissolved separately at 17.2 mM in 2.67 ml of a 0.1 M, pH 11 sodium carbonate buffer and the pH subsequently adjusted to 10.8 with 1.0 N sodium hydroxide. Once dissolved, the entire framework/DMSO/ligand/TEA solution is added dropwise over the course of 75 minutes to the drug/carbonate buffer solution. During the addition, the pH of the resulting mixture is adjusted every 5 minutes to 10.8 if necessary using dilute HCl or NaOH. The solution is allowed to stir for an additional 15 minutes after the dropwise addition to ensure complete reaction.

The resulting solution is then superdiluted by 10× into a 20 mM pH 5.0 HEPES buffered saline solution containing 0.150 M NaCl followed by pH adjustment with dilute HCl to a final pH of 8.0. The aqueous solution is first purified by size exclusion using an appropriate solid phase for the desired separation of conjugated and unconjugated materials. The solution passing through the column void volume is then concentrated using an appropriately sized ultrafiltration membrane to approximately 40 ml. This solution is further purified to obtain the desired product using preparative reverse phase HPLC on a Waters SymmetryPrep C18, 7 μm, 19×150 mm column. Buffer A is deionized water containing 0.1% TFA and Buffer B is acetonitrile containing 0.1% TFA. Before purification, the column is equilibrated at 15 ml/minutes with a 80% A/20% B mobile phase using a Waters DeltaPrep 600 system. Approximately 5 ml of the crude solution is injected onto the column over the course of 2 minutes at a flow rate of 15 ml/minutes after which a linear gradient is employed from 80% A/20% B to 75% A/25% B over the next 5 minutes followed by a slower linear gradient from 75% A/25% B to 62% A/38% B over the next 22 minutes. The retention time of the desired peak will vary depending on the drug, framework, and ligand used. Once collected, the solution is rotovapped to remove acetonitrile and lyophilized to obtain pure conjugate whose identity may be verified by LC-MS (HT Laboratories, San Diego, Calif.).

Example 4

Long Acting Insulin Conjugate Dose Response Effect

In order to generate a long acting conjugate, a PZI (protamine zinc insulin) formulation was prepared from a solution of synthetic insulin-conjugate I-6 that was prepared according to the methods described in Example 3. The excipients used in the formulation included protamine, zinc, m-cresol, and salt all of which were obtained commercially from Sigma-Aldrich (St. Louis, Mo.).

TABLE 4

| Component | Variable | Volume (ml) |
|---|---|---|
| I-6 solution at 2.7 mg/ml | unmodified insulin = 16.7% | 1.000 |
| 250 mM HEPES buffered saline | NaCl concentration = 1.5 M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

Once the formulation was prepared after addition of the components in the order described in Table 4, they were gently mixed for 30 minutes prior to in vivo testing.

To test the sustained release profile as well as the glucose-responsive PK profile, the following experiment was conducted. The formulation was injected at 5 or 15 U/kg (body weight in grams/1.87=microliters of injection volume) of the formulation behind the neck of fasted normal non-diabetic rats (Male Sprague-Dawley, 400-500 gm, n=3). After a 240 minute delay, a glucose dose (4 g/kg) was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4° C. to collect the serum. Serum insulin concentrations were subsequently measured with a commercially available ELISA kit (Iso-Insulin ELISA, Mercodia, Uppsala, Sweden).

Figure 7:
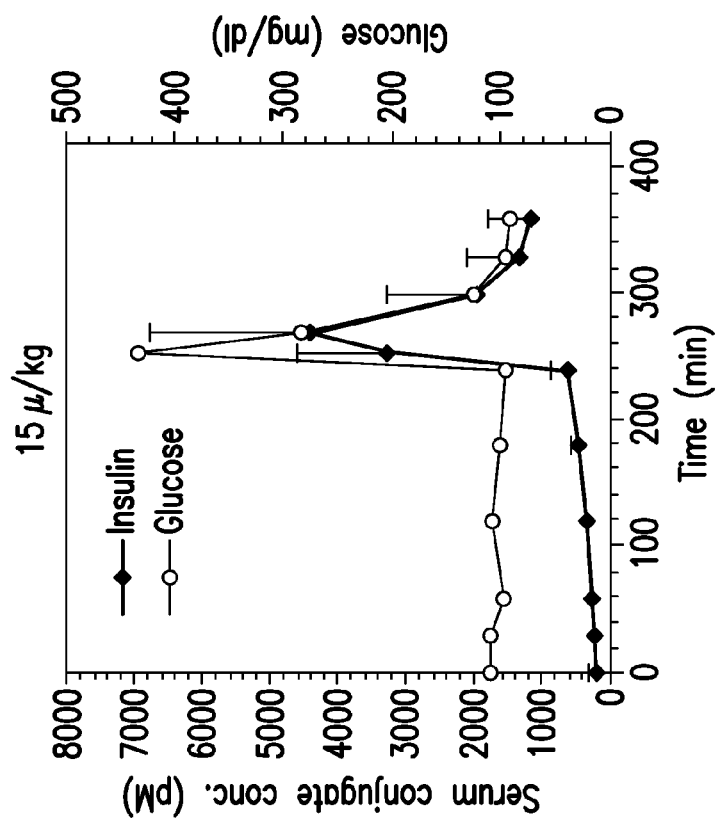
FIG. 7: Plot of serum insulin (♦) and blood glucose (○) levels following subcutaneous injection in non-diabetic, male SD rats (n=3 per dose) at time 0 with a long-acting protamine zinc (PZI) formulation of synthetic conjugate I-6 followed by IP injection of glucose (4 g/kg) at 240 minutes. As shown, no hypoglycemia is observed as early or late time points. A comparison of the response with 5 U/kg (left) and 15 U/kg (right) doses shows a dramatic dose-dependent glucose response.
Figure 7:
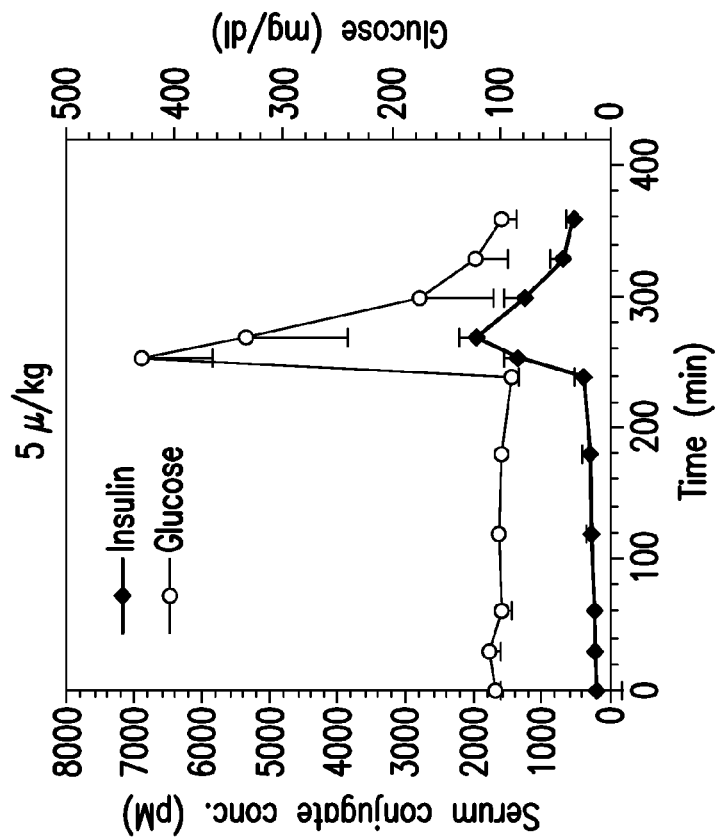

As shown in FIG. 7, the synthetic insulin-conjugate exhibited a flat PK profile until the glucose was injected. The glucose response was dramatic and dose-dependent (compare data obtained with a 5 U/kg (left) and 15 U/kg (right) dose of synthetic insulin-conjugate). No hypoglycemia was observed at early or late time points.

Example 5

Long Acting Conjugate in Diabetics and Non-Diabetics

In order to confirm the in vivo utility of the long acting synthetic insulin-conjugate formulation, we administered it (5, 10 and 20 U/kg) to normal and STZ-induced diabetic rats (Male Sprague-Dawley, 400-500 gm, n=6). The formulation was prepared using the procedure in Table 5.

TABLE 5

| Component | Variable | Volume (ml) |
| --- | --- | --- |
| I-6 solution at 2.7 mg/ml | unmodified insulin = 0% | 1.000 |
| 250 mM HEPES buffered saline | NaCl concentration = 1.5 M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

Figure 8A:
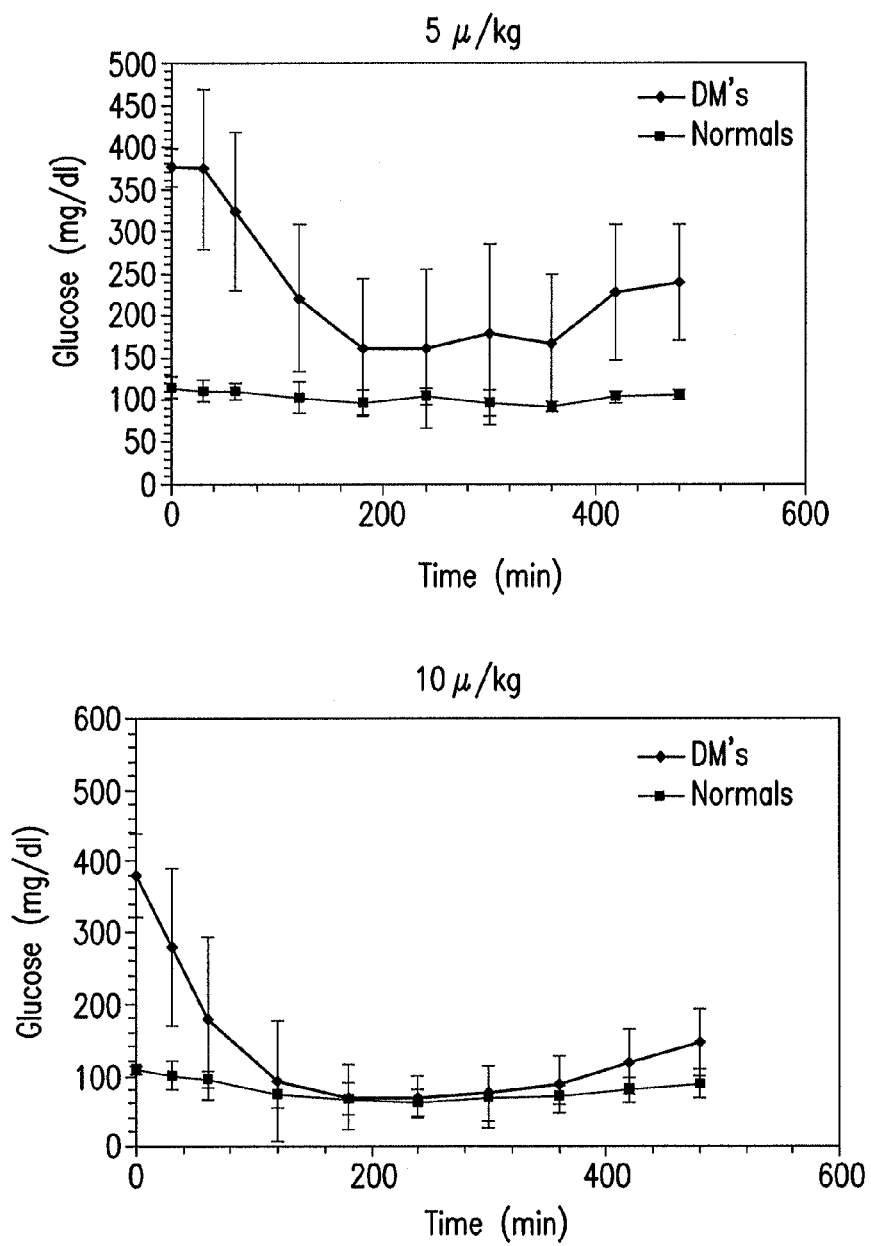
FIG. 8A and FIG. 8B: Plot of blood glucose levels following subcutaneous injection in non-diabetic (normals) and diabetic (DM's) male SD rats at time 0 with a long-acting PZI formulation of synthetic conjugate I-6. The conjugate was administered at 5, 10 and 20 U/kg. As shown, the non-diabetic male SD rats did not show any hypoglycemia while the glucose levels in diabetic male SD rats showed a clear dose proportional response that lasted for over 8 hours at the highest dose.
Figure 8B:
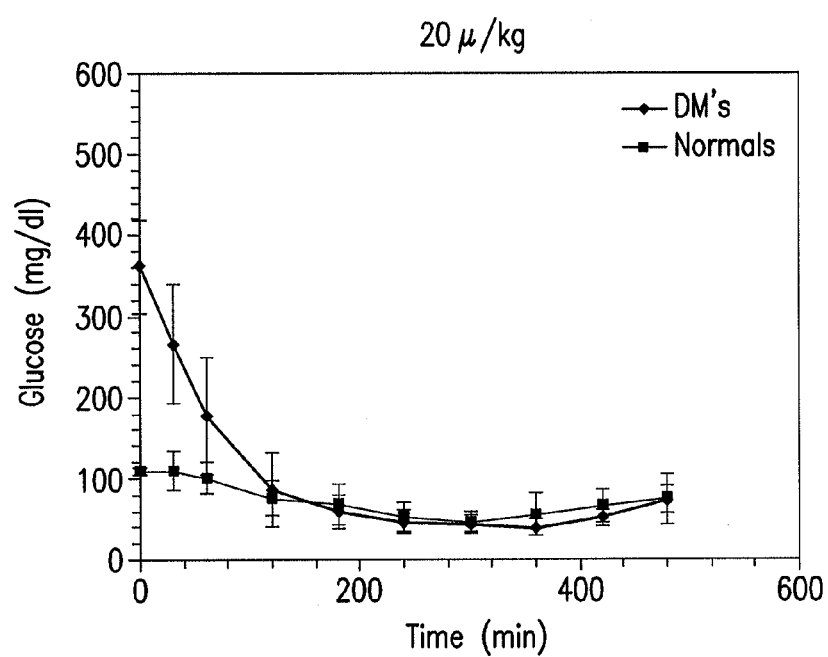

No external IP injections of glucose were used to trigger the bioactivity of the conjugates. Instead we relied on the endogenous levels of glucose in the rats to control the PK and PD profile of the conjugate formulation. Blood samples were collected via tail vein bleeding at various time points after the initial conjugate injection. Blood glucose values were measured using commercially available test strips (Precision Xtra, Abbott Laboratories, Abbott Park, Ill.). As shown in FIGS. 8A and 8B, no hypoglycemia was observed at early or late time points for the normal or diabetic rats. The glucose profiles observed with the diabetic rats are dramatic and demonstrate that the conjugates were activated by the higher glucose concentrations and exerted their glucose-lowering effect in a dose proportional manner over a long time period (over 8 hours at the highest dose).

Example 6

In Vivo Half Life/Elimination Rate Comparison

In order to determine the rate at which conjugate I-6 was cleared from serum in vivo in the presence or absence of inhibitory sugars such as glucose or alpha-methyl mannose (a-MM), the following experiment was conducted. In each case conjugate I-6 (or RHI as a control) was dosed at 0.4 mg conjugate/kg body weight into dual jugular vein cannulated male Sprague-Dawley rats (Taconic, JV/JV, 350-400 g, n=3).

To determine the elimination rate in the presence of elevated glucose levels, one hour before the start of the experiment one rat cannula was connected to a syringe infusion pump containing a sterile 50% w/v glucose solution. The pump infusion rate was adjusted by the experimenter to ensure that the blood glucose levels in the animal remained above 300 mg/dL at all times during the experiment. Blood glucose was measured using commercially available test strips (Precision Xtra, Abbott Laboratories, Abbott Park, Ill.). In a typical experiment, it was found that the infusion pump rate required to keep the animals above 300 mg/dL was typically greater than 85 µL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

To determine the elimination rate in the presence of a-MM, one hour before the start of the experiment one rat cannula was connected to a syringe infusion pump containing a sterile 25% w/v a-MM solution. The pump infusion rate was adjusted by the experimenter, but was typically set at 85 µL/min. A blood sample was taken at t=0 min, after which a sterile conjugate solution or control insulin was injected intravenously via the second rat cannula, followed immediately by a chase solution of heparin-saline to ensure that all of the conjugate dose was administered into the animal. After an additional flush of the cannula line with heparin-saline, the second cannula was used to collect blood samples at t=1, 2, 4, 8, 15, 30, 60, 90, 120, and 180 minutes post-dose.

Figure 9:
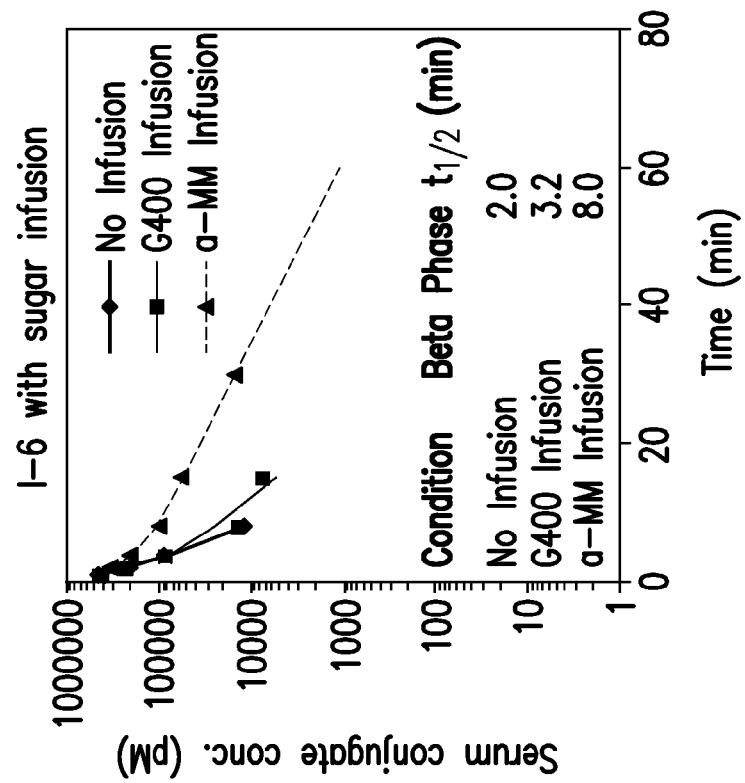
FIG. 9: Plots of serum insulin concentration as a function of time following injection of synthetic conjugate I-6 or recombinant human insulin (RHI) (left) and following injection of synthetic I-6 with and without glucose or α-methyl mannose (right).
Figure 9:
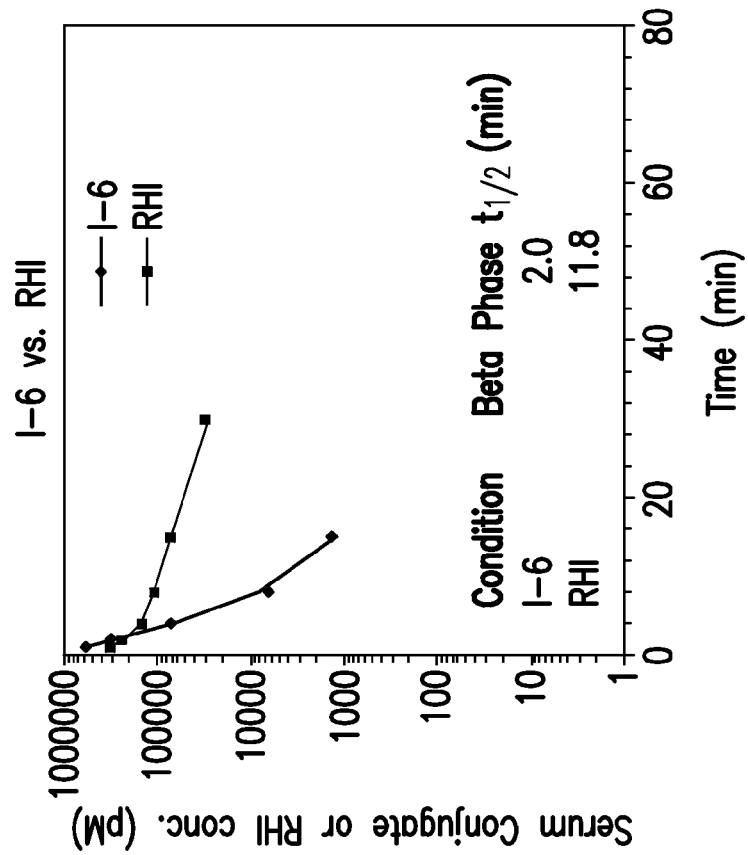

Throughout the experiment, blood glucose was measured using commercially available test strips (Precision Xtra, Abbott Laboratories, Abbott Park, Ill.). Blood from each timepoint was centrifuged at 4° C. to collect the serum, and serum insulin or serum conjugate concentrations were subsequently measured with a commercially available ELISA kit (Iso-Insulin ELISA, Mercodia, Uppsala, Sweden). Insulin or conjugate serum concentration vs. time data was best fit with the sum of two independent decaying exponentials ($C(t)=a \exp(-k_a t)+b \exp(-k_b t)$) according to the two-compartment model, where $t\frac{1}{2}(a)=(\ln 2)/k_a$ and $t\frac{1}{2}(b)=(\ln 2)/k_b$. Results are shown in FIG. 9. The left panel demonstrates the significantly higher (>5×) elimination rate for conjugate I-6 versus RHI in the absence of a-MM or glucose. The right panel shows that the elimination rate decreases somewhat (~50%) in the presence of glucose (G400 infusion) and quite substantially (~400%) in the presence of a-MM (a-MM infusion).

Example 7

Glucose-Responsive PK for Conjugate I-6 Intravenous (i.v.) Infusion

In this example, the i.v. elimination rate experiment described in Example 6 was modified from a single i.v. bolus of 0.4 mg conjugate/kg body weight to a continuous i.v. infusion. The goal of the experiment was to maintain a constant input rate of conjugate (or RHI as a control) for six hours with an intraperitoneal (i.p.) injection of glucose administered at the four hour time point to determine the resulting effect on serum conjugate (or RHI) concentration. Dual jugular vein cannulated male Sprague-Dawley rats (Taconic, JV/JV, 350-400 g, n=3) were used in each experiment such that one jugular vein line was used for conjugate or RHI infusion and the other for blood collection.

For RHI, a 50 mU/ml solution was sterile filtered through a 0.2 µm filtration membrane and infused at 0.07 ml/min to provide a constant input rate of 3.5 mU/min for the entire six hour experiment. A blood sample was taken at t=0 min, after which the constant i.v. infusion was initiated. The second cannula was used to collect blood samples at t=30, 60, 120, 180 and 240 min. At t=240 min, a 4 g/kg dose of glucose was administered via i.p. injection followed by blood collection at t=255, 270, 300, 330 and 360 min.

For conjugate I-6, a 150 mU/ml solution was sterile filtered through a 0.2 μm filtration membrane and infused at 0.10 ml/min to provide a constant input rate of 15 mU/min for the entire six hour experiment. A blood sample was taken at t=0 min, after which the constant i.v. infusion was initiated. The second cannula was used to collect blood samples at t 30, 60, 120, 180 and 240 min. At t=240 min, a 1, 2, or 4 g/kg dose of glucose was administered via i.p. injection followed by blood collection at t=255, 270, 300, 330 and 360 min.

Throughout the experiments, blood glucose was measured using commercially available test strips (Precision Xtra, Abbott Laboratories, Abbott Park, Ill.). Blood from each timepoint was centrifuged at 4° C. to collect the serum, and serum insulin or serum conjugate concentrations were subsequently measured with a commercially available ELISA kit (Iso-Insulin ELISA, Mercodia, Uppsala, Sweden).

Figure 10A:
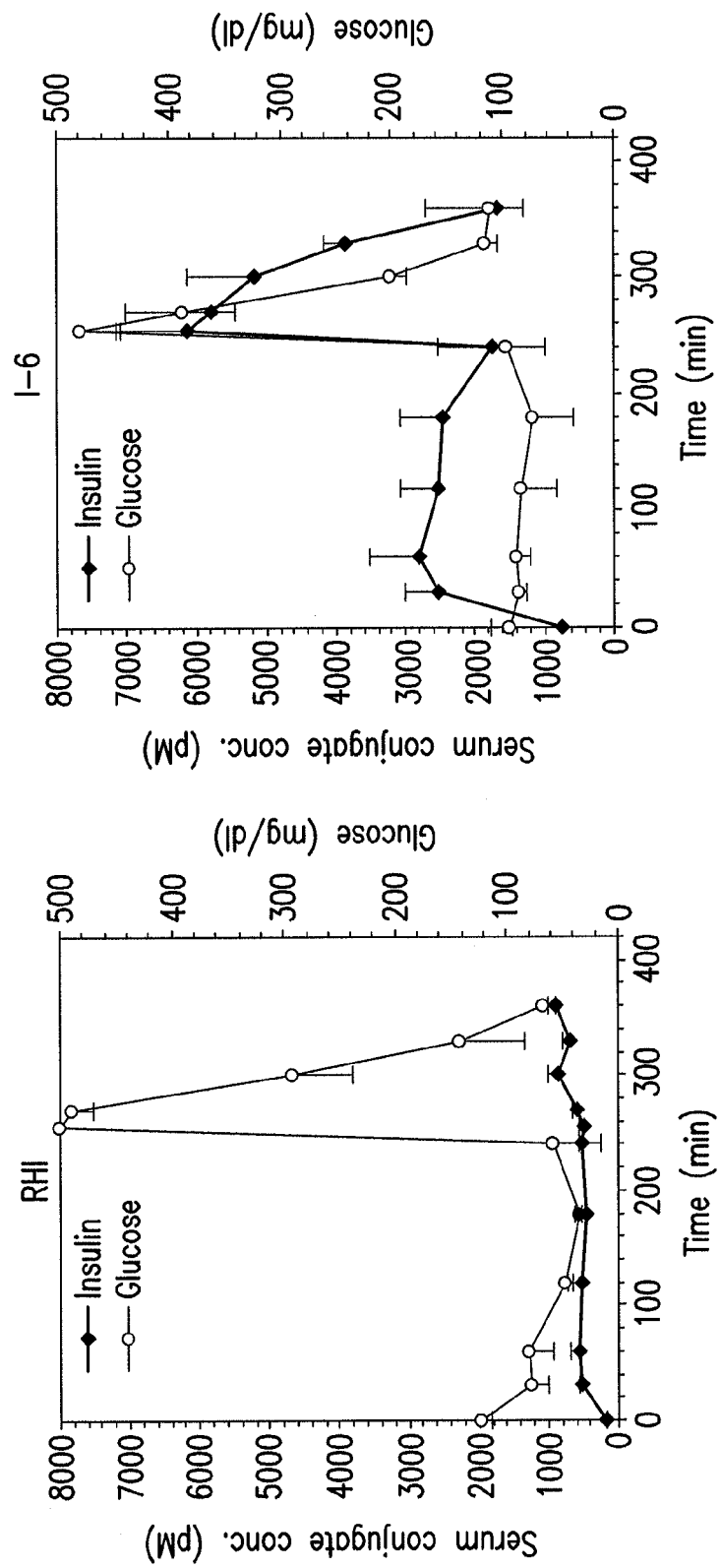
FIG. 10A, FIG. 10B, and FIG. 10C: Plots of serum insulin (◆) and blood glucose (○) levels following constant intravenous (i.v.) infusion of RHI (3.5 mU/min) or synthetic conjugate I-6 (15 mU/min) in non-diabetic, male SD rats (n=3). An IP injection of glucose (1, 2 or 4 g/kg) was given at 240 minutes.
Figure 10B:
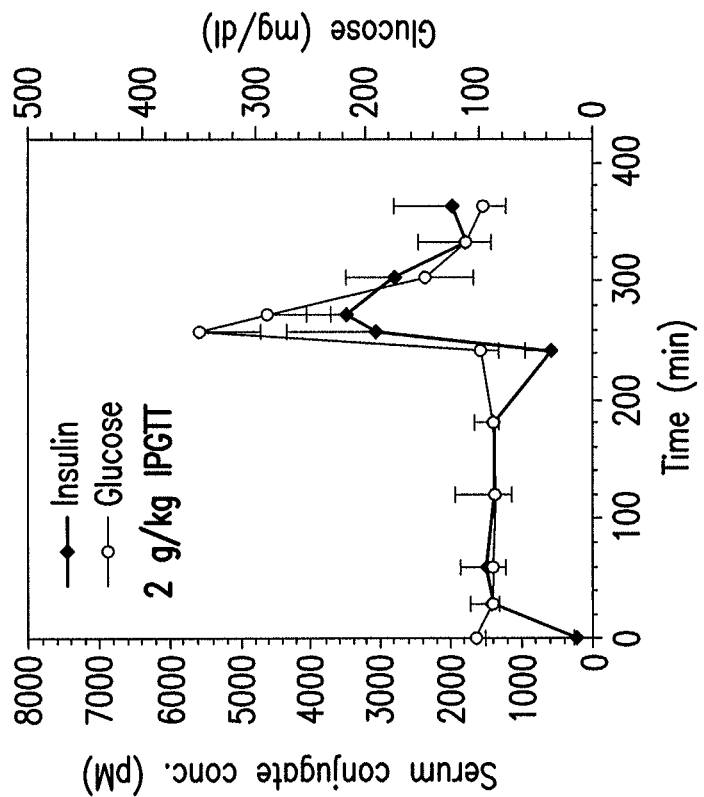
Figure 10B:
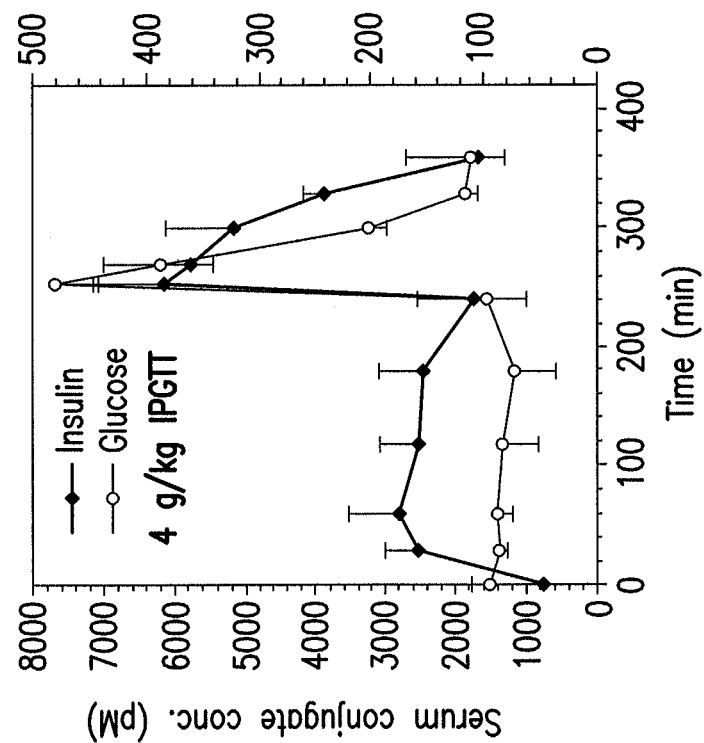
Figure 10C:
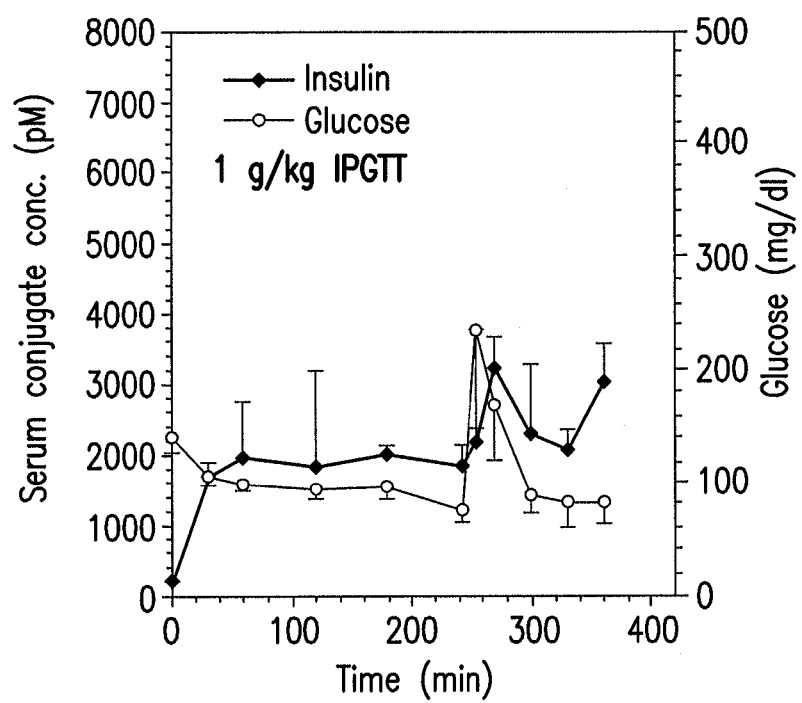

The two panels of FIG. 10A compare the blood glucose and serum insulin/conjugate concentration profiles for a 3.5 mU/min infusion of RHI and 15 mU/min infusion of conjugate I-6 before and after a 4 g/kg i.p. glucose injection. RHI infusion causes significant hypoglycemia prior to glucose injection compared to the I-6 infusion. Following the i.p. glucose injection, the serum concentration of conjugate I-6 immediately increases by over 300% as the blood glucose concentration increases followed by a rapid return to baseline levels as the glucose concentration decreases. On the other hand, there is no significant change in serum RHI concentration after i.p. glucose injection. The three panels of FIGS. 10B and 10C show that the extent to which the serum conjugate concentration increases during i.p. glucose injection is directly related to the dose of glucose administered and the resulting blood glucose levels. For example, only a 50% peak to baseline change in serum conjugate concentration is observed for the 1 g/kg glucose injection while a 300% peak to baseline change is observed for the 4 g/kg dose.

Example 8

In Vivo Half Life/Elimination Rate Comparison

In order to determine the rate at which a glycosylated insulin polypeptide of the present disclosure is cleared from serum in vivo in the presence or absence of inhibitory sugars such as glucose or alpha-methyl mannose (a-MM), the following experiment is conducted. In each case the glycosylated insulin polypeptide (or RHI as a control) is dosed at 0.4 mg/kg body weight into dual jugular vein cannulated male Sprague-Dawley rats (Taconic, JV/JV, 350-400 g, n=3).

To determine the elimination rate in the presence of elevated glucose levels, one hour before the start of the experiment one rat cannula is connected to a syringe infusion pump containing a sterile 50% w/v glucose solution. The pump infusion rate is adjusted by the experimenter to ensure that the blood glucose levels in the animal remained above 300 mg/dL at all times during the experiment. Blood glucose is measured using commercially available test strips (Precision Xtra, Abbott Laboratories, Abbott Park, Ill.). A blood sample is taken at t=0 min, after which a sterile glycosylated insulin polypeptide solution or control RHI solution is injected intravenously via the second rat cannula, followed immediately by a chase solution of heparin-saline to ensure that all of the glycosylated insulin polypeptide dose was administered into the animal. After an additional flush of the cannula line with heparin-saline, the second cannula is used to collect blood samples at t=1, 2, 4, 8, 15, 30, 60, 90, 120, and 180 minutes post-dose.

To determine the elimination rate in the presence of a-MM, one hour before the start of the experiment one rat cannula is connected to a syringe infusion pump containing a sterile 25% w/v a-MM solution. The pump infusion rate is adjusted by the experimenter. A blood sample is taken at t=0 min, after which a sterile conjugate solution or control insulin is injected intravenously via the second rat cannula, followed immediately by a chase solution of heparin-saline to ensure that all of the conjugate dose is administered into the animal. After an additional flush of the cannula line with heparin-saline, the second cannula is used to collect blood samples at t=1, 2, 4, 8, 15, 30, 60, 90, 120, and 180 minutes post-dose.

Throughout the experiment, blood glucose is measured using commercially available test strips (Precision Xtra, Abbott Laboratories, Abbott Park, Ill.). Blood from each timepoint is centrifuged at 4° C. to collect the serum, and serum insulin or serum conjugate concentrations are subsequently measured with a commercially available ELISA kit (Iso-Insulin ELISA, Mercodia, Uppsala, Sweden). RHI or glycosylated insulin polypeptide serum concentration vs. time data is best fit with the sum of two independent decaying exponentials ($C(t)=a\exp(-k_a t)+b\exp(-k_b t)$) according to the two-compartment model, where $t\frac{1}{2}(a)=(\ln 2)/k_a$ and $t\frac{1}{2}(b)=(\ln 2)/k_b$. A higher elimination rate for the glycosylated insulin polypeptide versus RHI in the absence of a-MM or glucose is expected. The addition of high concentrations of glucose or a-MM are expected to slow the elimination rate of the glycosylated insulin polypeptide.

Example 9

Glucose-Responsive PK for Glycosylated Insulin Polypeptide i.v. Infusion

In this example, the i.v. elimination rate experiment described in Example 8 is modified from a single i.v. bolus of 0.4 mg/kg body weight to a continuous i.v. infusion. The goal of the experiment is to maintain a constant input rate of glycosylated insulin polypeptide (or RHI as a control) for six hours with an i.p. injection of glucose administered at the four hour time point to determine the resulting effect on serum glycosylated insulin polypeptide (or RHI) concentration. Dual jugular vein cannulated male Sprague-Dawley rats (Taconic, JV/JV, 350-400 g, n=3) are used in each experiment such that one jugular vein line is used for glycosylated insulin polypeptide or RHI infusion and the other for blood collection.

For RHI, a 50 mU/ml solution is sterile filtered through a 0.2 μm filtration membrane and infused at 0.07 ml/min to provide a constant input rate of 3.5 mU/min for the entire six hour experiment. A blood sample is taken at t=0 min, after which the constant i.v. infusion is initiated. The second cannula is used to collect blood samples at t=30, 60, 120, 180 and 240 min. At t=240 min, a 4 g/kg dose of glucose is administered via i.p. injection followed by blood collection at t=255, 270, 300, 330 and 360 min.

For glycosylated insulin polypeptide, a 150 mU/ml solution is sterile filtered through a 0.2 μm filtration membrane and infused at 0.10 ml/min to provide a constant input rate of 15 mU/min for the entire six hour experiment. A blood sample is taken at t=0 min, after which the constant i.v. infusion is initiated. The second cannula is used to collect blood samples at t=30, 60, 120, 180 and 240 min. At t=240 min, a 1, 2, or 4 g/kg dose of glucose is administered via i.p. injection followed by blood collection at t=255, 270, 300, 330 and 360 min.

Throughout the experiments, blood glucose is measured using commercially available test strips (Precision Xtra, Abbott Laboratories, Abbott Park, Ill.). Blood from each timepoint is centrifuged at 4° C. to collect the serum, and serum RHI or serum glycosylated insulin polypeptide concentrations are subsequently measured with a commercially available ELISA kit (Iso-Insulin ELISA, Mercodia, Uppsala, Sweden).

RHI infusion is expected to cause significant hypoglycemia prior to glucose injection compared to the glycosylated insulin polypeptide infusion. Following the i.p. glucose injection, the serum concentration of glycosylated insulin polypeptide is expected to increase as the blood glucose concentration increases followed by a rapid return to baseline levels as the glucose concentration decreases. No significant change in serum RHI concentration after i.p. glucose injection is expected. The extent to which the serum conjugate concentration increases during i.p. glucose injection is expected to be directly related to the dose of glucose administered and the resulting blood glucose levels.

Example 10

Recombinant Insulin Polypeptides: Production in Yeast, Protein Purification, and In Vitro Enzyme Processing This example demonstrates the recombinant production of several exemplary insulin polypeptides in two different yeast strains (KM71 and GS115) on both small- and large-scales. These insulin polypeptides were not engineered to include N-linked glycan motifs. The recombinantly-produced insulin polypeptides had the expected molecular weight and were recognized by anti-insulin antibodies. The experiments described in this example demonstrate that insulin polypeptides manufactured in yeast generated commercial scale yields. This example also describes procedures that were used for in vitro enzyme processing of recombinantly produced insulin polypeptides (to remove the C-peptide and leader peptide).

Materials and Methods

Preparation of Electrocompetent *P. pastoris* Strains

KM71 (Invitrogen, Carlsbad, Calif.) was cultured at 30° C. in YPD broth (per liter: 10 g yeast extract, 20 g peptone, and 20 g glucose, pH 6.5). After successful revival of the strain, electrocompetent KM71 was prepared as described by Wu and Letchworth (*Biotechniques* 36:152-4). Electrocompetent KM71 were stored in a −80° C. freezer. Electrocompetent *P. pastoris* GS115 (Invitrogen, Carlsbad, Calif.) was prepared by the same procedure.

Preparation of Insulin Polypeptide Expressing Gene Constructs

Gene synthesis of insulin polypeptide constructs was performed at GeneArt (Regensburg, Germany). Briefly, genes of interest coding for the expression of insulin polypeptides are listed in Table 6. The genes were synthesized at GeneArt, then cut with BamI (5' site) and EcoR1 (3' site) enzymes and then inserted into the same sites in the pPIC3.5K vector (Invitrogen, Carlsbad, Calif.). The resulting plasmid was then amplified in *E. coli* in culture flasks and then extracted, purified, giving a 1 mg/mL solution of the plasmid DNA in TE buffer.

TABLE 6

| Construct ID | DNA sequence |
|---|---|
| RHI-1 | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGAAGAAGCTGAAGCT GAAGCTGAACCAAAGTTTGTTAACCAACACTTGTGTGGTTCTCAC TTGGTTGAAGCTTTGTACTTGGTTTGTGGTGAAAGAGGTTTCTTC TACACTCCAAAGGCTGCTAAGGGTATCGTTGAACAATGTTGTACT TCTATCTGTTCTTTGTACCAATTGGAAAACTACTGTAACTAA (SEQ ID NO: 3) |
| RHI-2 | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGACGACGGTGACCCA AGATTTGTTAACCAACACTTGTGTGGTTCTCACTTGGTTGAAGCT TTGTACTTGGTTTGTGGTGAAAGAGGTTTCTTCTACACTCCAAAG GACGAAAGAGGTATCGTTGAACAATGTTGTACTTCTATCTGTTCT TTGTACCAATTGGAAAACTACTGTAACTAA (SEQ ID NO: 4) |
| RHI-3 | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGAAGAAGCTGAAGCT GAAGCTGAACCAAAGTTTGTTAACCAACACTTGTGTGGTTCTCAC TTGGTTGAAGCTTTGTACTTGGTTTGTGGTGAAAGAGGTTTCTTC TACACTCCAAAGGACGAAAGAGGTATCGTTGAACAATGTTGTACT TCTATCTGTTCTTTGTACCAATTGGAAAACTACTGTAACTAA (SEQ ID NO: 5) |
| RAT-1 | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGAAGAAGCTGAAGCT GAAGCTGAACCAAAGTTTGTTAAGCAACACTTGTGTGGTTCTCAC TTGGTTGAAGCTTTGTACTTGGTTTGTGGTGAAAGAGGTTTCTTC TACACTCCAAAGGCTGCTAAGGGTATCGTTGACCAATGTTGTACT TCTATCTGTTCTTTGTACCAATTGGAAAACTACTGTAACTAA (SEQ ID NO: 6) |
| RHI-4 | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGACGACGGTGACCCA AGATTTGTTAACCAACACTTGTGTGGTTCTCACTTGGTTGAAGCT TTGTACTTGGTTTGTGGTGAAAGAGGTTTCTTCTACACTCCAAAG GCTGCTAAGGGTATCGTTGAACAATGTTGTACTTCTATCTGTTCT TTGTACCAATTGGAAAACTACTGTAACTAA (SEQ ID NO: 7) |

DNA Preparation for *P. pastoris* Transformation

Four genetic constructs were initially used for transforming GS115 and KM71. Prior to transformation by electroporation, each construct was linearized by SalI. Complete linearization of each construct was confirmed by agarose gel electrophoresis. QiaQuick PCR purification spin columns (Qiagen) were then used to remove SalI and salts from the linearized plasmids. Linearized plasmids were eluted from the spin columns using autoclaved, deionized water.

Once the DNA has been transformed into the yeast strains, the resulting gene constructs code for the amino acid sequences shown in Table 7. The Pro-leader peptide sequence is designed to be cleaved by Kex-2 endoprotease within the yeast prior to protein secretion into the media (Kjeldsen et al., 1999, *Biotechnol. Appl. Biochem.* 29:79-86). Thus the resulting insulin polypeptide secreted into the media includes only the leader peptide sequence attached to the [B-peptide]-[C-peptide]-[A-peptide] sequence.

TABLE 7

| Construct ID | Pro-leader peptide | Leader peptide | B-C-A peptides |
|---|---|---|---|
| RHI-1 | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | FVNQHLCGSHLVEALY LVCGERGFFYTPKAAK GIVEQCCTSICSLYQL ENYCN (SEQ ID NO: 11) |
| RHI-2 | APVNTTTEDETAQIPAEAVI GYSDLEGDFDVAVLPFSNST NNGLLFINTTIASIAAKEEG VSMAKR (SEQ ID NO: 8) | DDGDPR (SEQ ID NO: 10) | FVNQHLCGSHLVEALY LVCGERGFFYTPKDER GIVEQCCTSICSLYQL ENYCN (SEQ ID NO: 12) |
| RHI-3 | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | FVNQHLCGSHLVEALY LVCGERGFFYTPKDER GIVEQCCTSICSLYQL ENYCN (SEQ ID NO: 12) |
| RAT-4 | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | FVKQHLCGPHLVEALY LVCGERGFFYTPKAAK GIVDQCCTSICSLYQL ENYCN (SEQ ID NO: 12) |
| RHI-4 | APVNTTTEDETAQIPAEAVI GYSDLEGDFDVAVLPFSNST NNGLLFINTTIASIAAKEEG VSMAKR (SEQ ID NO: 8) | DDGDPR (SEQ ID NO: 10) | FVNQHLCGSHLVEALY LVCGERGFFYTPKAAK GIVEQCCTSICSLYQL ENYCN (SEQ ID NO: 11) |

*P. pastoris* Transformation

The linearized plasmids were individually transformed into electrocompetent *P. pastoris* GS115 and KM71 (both are His⁻ strains) according to the procedure reported by Wu and Letchworth (*Biotechniques* 36:152-4). The electroporated cells were re-suspended in 1 mL ice-cold, 1 M sorbitol and plated on minimal dextrose-sorbitol agar (1.34% yeast nitrogen base without ammonium and amino acids, $4\times10^{-5}$% biotin, 2% dextrose, 1 M sorbitol, and 2% agar) plates. The agar plates were incubated at 30° C. for 4-7 days. Expression plasmids integrated into GS115 and KM71 genomes render a His⁺ phenotype to the transformants and allow the transformants to grow on minimal dextrose-sorbitol agar without histidine supplementation.

Screening for *P. pastoris* Transformants for Clones with High-Copy Number of Expression Cassettes The clones derived in 2 strains of *P. pastoris* with 4 expression plasmids in the above steps were individually screened for incorporation of high-copy number of the gene constructs. All the transformants were selected on minimal dextrose-sorbitol agar without histidine supplementation. Each transformation generated over 500 His⁺ transformants. Some of these transformants are expected to contain multiple copies of the expression plasmid since multiple integration events happen naturally in *P. pastoris*. These high-copy number transformants could produce higher levels of insulin polypeptides. Therefore, all transformants were screened based on their resistance to geneticin in order to select for those with the highest copy number, since all of the expression plasmids are pPIC3.5K-deriviatives and contain a geneticin-resistant marker (i.e., higher copy number clones should lead to higher incorporation of geneticin resistance).

His⁺ transformants were grown on minimal dextrose-sorbitol agar and were pooled together and plated on YPD agar (1% yeast extract, 2% peptone, 2% dextrose, and 2% agar) containing geneticin by the following procedure:

1 to 2 ml of sterile water was pipetted over the His⁺ transformants (from each expression plasmid-strain combination) on each minimal dextrose-sorbitol plate.

His⁺ transformants were resuspended into the water by using a sterile spreader and running it across the top of the agar.

The cell suspension was transferred and pooled into a sterile, 50 ml conical centrifuge tube and vortexed briefly.

Cell density of the cell suspension was determined by using a spectrophotometer (1 $OD_{600}$ unit≈$5\times10^7$ cells/ml).

$10^5$ cells were plated on YPD plates containing geneticin at a final concentration of 0.25, 0.5, 1.0, 1.5, 2.0, 3.0, and 4.0 mg/ml.

Plates were incubated at 30° C. and checked daily. Geneticin-resistant colonies took 3 to 5 days to appear.

Colonies that grew on YPD-geneticin plates were streaked for purity on YPD agar containing the same concentration of geneticin to ensure the isolated colonies are resistant to high concentration of geneticin. Several clones at various genecitin concentration levels were then selected for insulin polypeptide expression studies in shake flasks.

Shake-Flask Studies

Shake flask studies were conducted on the 40 geneticin-resistant clones (4 expression plasmids×2 strains×5 transformants) at 2 buffer conditions (buffered vs. unbuffered media) for a total of 80 shake culture flasks.

Half of the transformants were KM71 derivatives, which have Mut$^S$ phenotypes. Isolated KM71 transformant colonies from streaked plates prepared above were used to inoculate 100 mL non-buffered MGY broth (1% yeast extract, 2% peptone, 1.34% yeast nitrogen base, $4\times10^{-5}$% biotin, and 1% glycerol) or 100 mL BMGY broth (same as MGY, but with 100 mM potassium phosphate, pH 6). These seed cultures were incubated at 30° C. with orbital shaking at 250 rpm for 16 hours or until $OD_{600}$ values reached 2-6. Then, a small aliquot of each MGY culture was used to prepare glycerol stocks. The remaining MGY cultures were then harvested by centrifugation at 4000×g for 5 min. Culture supernatants were discarded and each cell pellet was re-suspended with 20 mL MMY broth (same as MGY except glycerol was replaced by 0.5% methanol). Similarly, BMGY seed cultures were harvested by centrifugation at 4000×g for 5 min. Culture supernatants were discarded and each cell pellet was re-suspended with 20 mL BMMY broth (same as BMGY except glycerol was replaced by 0.5% methanol).

Methanol in the MMY and BMMY broths induce protein expression. The MMY and BMMY cultures were incubated at 30° C. with orbital shaking at 250 rpm for 96 hours. Every 24 hours, methanol was added to each culture to a final concentration of 0.5%. A 0.5-mL aliquot of culture was also removed from each shake flasks every 24 hours after the start of induction. For these samples, cells were separated from culture supernatants by micro-centrifugation and both fractions were stored at −80° C.

The second half of the transformants were GS115 derivatives, which were expected to be Mut$^+$. Isolated GS115 transformant colonies from streaked plates prepared as described previously were used to inoculate 25 mL MGY broth and 25 mL BMGY broth. These seed cultures were incubated at 30° C. with orbital shaking at 250 rpm for 16 hours or until $OD_{600}$ values reached 2-6. Then, a small aliquot of each MGY culture was used to prepare glycerol stocks. Another aliquot of the remaining cells was harvested by centrifugation for inoculating 20 mL MMY broth, such that the starting $OD_{600}$ value was about 1. Similarly, the BMGY seed cultures were used to inoculate 20 mL BMMY broth, such that the starting $OD_{600}$ value was about 1. The MMY and BMMY cultures were incubated at 30° C. with orbital shaking at 250 rpm for 96 hours. Every 24 hours, methanol was added to each culture to a final concentration of 0.5%. A 0.5-mL aliquot of culture was removed from each shake flask every 24 hours after the start of induction. Cells were separated from culture supernatants by micro-centrifugation and both fractions were stored at −80° C.

After 96-hour of induction, all cultures were harvested by centrifugation. Cell pellets were discarded. The final culture supernatants plus culture supernatants collected at various time points during induction were analyzed for insulin polypeptide expression yields by denaturing polyacrylamide gel electrophoresis (SDS-PAGE, BioRad, Hercules, Calif.; Standard Ladder: SeeBlue@Plus2 Prestain Standard (1×); Stain: SimplyBlue SafeStain; Precast gels: Criterion Precast Gel 16.5% Tris-Tricine/Peptide; Running buffer: 1× Tris/Tricine/SDS Buffer; Loading Buffer: Tricine Sample Buffer) or enzyme-linked immunosorbent assay (ELISA, Mercodia Iso-Insulin ELISA, Uppsala, Sweden).

Media for Large-Scale Insulin Polypeptide Expression in Yeast

BM_Y=BM_Y Base Medium (Teknova, Cat# B8001)
BMGY=BM_Y+0.1% Glycerol (v/v)
BMMY=BM_Y+Methanol Preparation of MDS Agar Plates for Large-Scale Insulin Polypeptide Expression in Yeast 319 g of sorbitol and 35 g of agar were dissolved in 1.4 L of di-$H_2O$. The mixture was autoclaved for 30 minutes. The temperature was allowed to drop to 60° C. before proceeding. Next, 175 mL of sterile 13.4% (w/v) Yeast-Nitrogen Base (YNB) containing ammonium sulfate in deionized water was added. To this mixture was added a portion of 175 mL of sterile 20% glucose in deionized water and 3.5 mL of sterile 0.02% biotin solution in deionized water. The solution was mixed to homogeneity and then poured into plates.

Large-Scale Expression and Culture of Insulin Polypeptide in Yeast

Using a sterile loop, an aliquot of frozen cells were transferred to a MDS plate, and streaked in order to obtain single colonies. The plate was incubated at 30° C. for 2-4 days to elucidate yeast colonies. One colony was picked at random with a sterile loop and used to inoculate 25 mL of BMGY medium (24.17 mL of BM_Y+0.83 mL of 30% glycerol). This medium was incubated for 24 hrs in an incubator/shaker (~150 rpm) at 30° C.

After this time, 75 mL BMGY (72.5 mL of BM_Y 2.5 mL of 30% glycerol) was added to the culture to give a final volume of ~100 mL. The incubation was continued for another 24 hr under the same conditions. The next day, the Optical Density (OD) was assayed to determine how much preculture was needed to obtain a 1000 OD aliquot (e.g., if OD=15, then 1000 OD/15 OD*mL$^{-1}$=>66.7 mL of preculture were needed to get 1000 OD).

Then the calculated volume of preculture was centrifuged (4000 rpm, 4° C. for 10 min) and the supernatant decanted. The pellet was resuspended in 990 mL of BM_Y medium. The OD was rechecked (it should be around 1.0) and the culture volume was adjusted accordingly if needed. 10 mL of biochemical grade methanol (Sigma-Aldrich, St. Louis, Mo. #494437) was then added to the flask, and the flask was incubated at 30° C., in a incubator/shaker at ~150 rpm for 24 hr. Methanol was added every 24 hr for 2-6 days depending on the desired level of protein expression.

After the desired level of yeast growth was achieved, the culture is centrifuged (10,000 rpm, 4° C. for 30 min). The supernatant was decanted and kept in clean container and frozen at −80° C. until needed.

Large-Scale Purification of Insulin Polypeptide

Cells from the culture flasks were spun down via centrifuge at 4000×g for 10 min at 4° C. The resulting supernatant was decanted into a clean flask. The pH of supernatant was adjusted to ~3.3 using 1 N HCl or 1 N NaOH, followed by a dilution of the supernatant with an equal volume of deionized water (Milli-Q, Millipore, Billerica, Mass.).

The resulting culture supernatant was clarified via filtration through a 0.2 micron, low binding filter unit (Millipore, Billerica, Mass.). Separately, an ion-exchange column (1.42 cm×1.42 cm×5.0 cm) was prepared SP Sepharose Fast-Flow media (GE Healthcare) that was prepared in 25 mM Citrate buffer, pH 3.3 (Wash Buffer). Once the column had been appropriately packed, the column was connected to a peristaltic pump to allow for loading of the culture supernatant onto the ion exchange column (~10 ml/minute). Once all of the culture supernatant had been loaded onto the column, approximately 10 column volumes (CV) of Wash Buffer was passed through the column using the peristaltic pump. After this was done, the purified insulin polypeptide was eluted from the column using approximately 2-5 CVs of elution buffer (50 mM, pH 7.6 and 200 mM NaCl).

The resulting purified insulin polypeptide solution was concentrated and desalted using a diafiltration setup (88 cm$^2$ and 0.11 m$^2$ Cassette holder, 5 kDa MWCO Pellicon3 0.11 m$^2$ Cassette filter, Millipore, Billerica, Mass.) connected to a MasterFlex Model 7523-80 pump (ColePalmer, Vernon Hills, Ill.). The solution was first concentrated or diluted to approximately 250 mL of volume and then diafiltered against Milli-Q deionized water for approximately 8-10 diavolumes.

The desalted, purified insulin polypeptide solution was then either lyophilized or used directly in a subsequent enzymatic processing step.

In Vitro Enzyme Processing

*Achromobacter lyticus* protease (ALP) was prepared by dissolving 2 U of enzyme in 1 mL of Milli-Q H$_2$O. A working solution was prepared by further diluting the enzyme stock solution 1:9 with Milli-Q H2O for a concentration of 0.2 U/mL.

Broth from all 10 RHI-1 mutants was used (GS115 RHI-1 A-E and KM71 RHI-1 A-E). Two 200 µL aliquots of each broth sample were prepared and adjusted to pH ~10 by addition of 40 µL of 2 M Tris. Two aliquots of ~540 µg/mL human RHI were prepared in the same manner to act as controls. 2.4 µL working enzyme solution was added to one of each pair of aliquots. 2.4 µL Milli-Q H$_2$O was added to the other to serve as a control. Samples were incubated at room temperature for 4.5 hours on a rocker and then frozen at −80° C. until analysis.

Samples were prepared for SDS-PAGE and western blotting by adding 20 µL Tricine sample buffer (Bio-rad) to 10 µL of prepared broth and boiling for 5 minutes. Samples, along with peptide and protein ladders, were resolved on 16.5% Tris-Tricine gels run at 125 V for 1.75 hours at room temperature. Proteins were then transferred to nitrocellulose membranes using an iBlot dry transfer system (Invitrogen), program P3 for 5.5 minutes. Membranes were fixed for 15 minutes with 0.25% gluteraldehyde in PBS and then washed 3×5 minutes with TBS. Blocking was carried out in 5% powdered milk in PBS 0.05% Tween-20 (PBST) for 1 hour on a rocker at room temperature. Blots were then incubated in mouse anti-human pro-insulin/insulin antibody (Abcam) diluted 1:1000 in 1% powdered milk in PBST overnight at 4° C. on a shaker. Blots were washed 2×10 minutes with PBST and incubated for two hours at room temperature in HRP conjugated goat anti-mouse IgG diluted 1:3000 in 1% milk in PBST. Blots were washed 2×10 minutes in PBST followed by a 2 minute wash in dH$_2$O. Bands were developed by incubating for 2 hours at room temperature in TMB substrate (Pierce), followed by extensive washing with dH$_2$O.

Results

Production of Insulin Polypeptides in Yeast

This example demonstrates insulin polypeptide production in yeast. In particular, this example explicitly demonstrates insulin polypeptide (specifically, production of RHI-1, RHI-2, RHI-3, and RAT-1) production in two different yeast strains. The present disclosure encompasses the recognition that these procedures can be useful for expressing and purifying any other recombinant insulin polypeptide, such as insulin polypeptides that have been mutated to contain at least one N-linked glycan motif (described in further detail in Example 11). The present disclosure n also encompasses the recognition that other strains of yeast might be suitable for expression of insulin polypeptides.

Figures 11A, 11B:
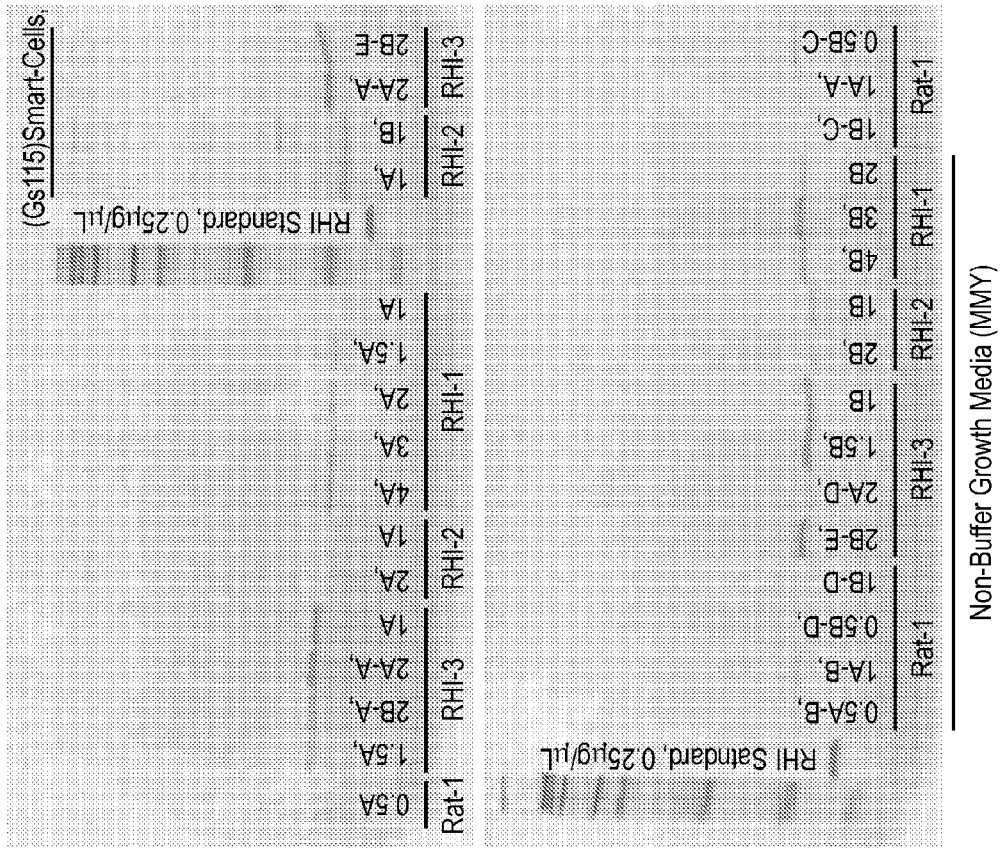
FIG. 11: Unpurified culture supernatant yields from GS115 strain clones grown under buffered (BMMY) and unbuffered (MMY) conditions. (A) Insulin polypeptide yield in mg/L from various clones ("Clone#" refers to clones obtained from different geneticin plate resistance levels) using ELISA analysis (ISO-Insulin ELISA, Mercodia, Uppsala, Sweden). (B) SDS-PAGE of clones showing the molecular weights of the produced insulin polypeptides. Recombinant human insulin standard (RHI standard) is shown in lane 14 of the top right gel and in lane 2 of the bottom right gel at 250 mg/L for yield comparison purposes.

FIG. 11 presents unpurified culture supernatant yields from the GS115 strain clones grown under buffered (BMMY) and unbuffered (MMY) conditions. The left panel of FIG. 11 presents the insulin polypeptide yield in mg/L from various clones ("Clone#" refers to clones obtained from different geneticin plate resistance levels) using ELISA analysis (ISO-Insulin ELISA, Mercodia, Uppsala, Sweden). The right panel of FIG. 11 presents SDS-PAGE of the clones, showing the molecular weights of the produced insulin polypeptides. Recombinant human insulin standard (RHI standard) is shown in lane 14 of the top right gel and in lane 2 of the bottom right gel at 250 mg/L for yield comparison purposes. As expected, the insulin polypeptides have a higher MW than that of the RHI standard due to the leader peptide and the connecting peptide ("C-peptide").

Figures 12A, 12B:
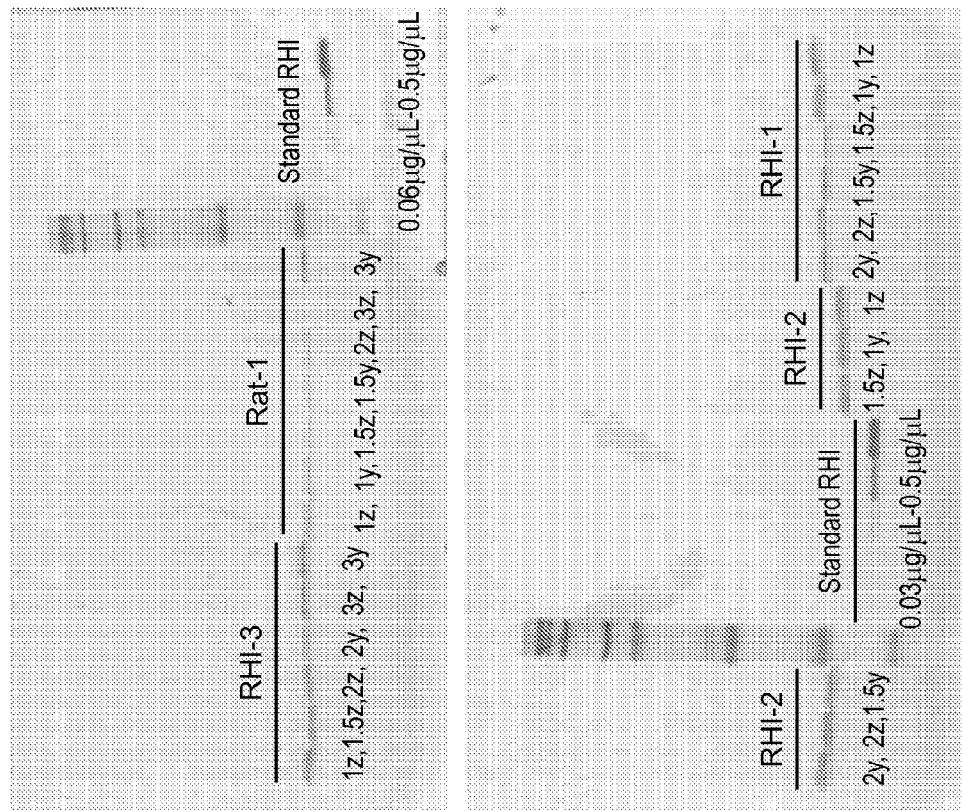
FIG. 12: Unpurified culture supernatant yields from KM71 strain clones grown under buffered conditions. (A) Insulin polypeptide yield in mg/L from various clones ("Clone#" refers to clones obtained from different geneticin plate resistance levels) using ELISA analysis (ISO-Insulin ELISA, Mercodia, Uppsala, Sweden). (B) SDS-PAGE of clones showing the molecular weights of the produced insulin polypeptides. Recombinant human insulin standard (RHI standard) is shown in lanes 15-18 of the top right gel (60-500 mg/L) and in lanes 5-9 of the bottom right gel (30-500 mg/L) for yield comparison purposes.

FIG. 12 presents unpurified culture supernatant yields from the KM71 strain clones grown under buffered conditions. The left panel of FIG. 12 presents the insulin polypeptide yield in mg/L from various clones ("Clone#" refers to clones obtained from different geneticin plate resistance levels) using ELISA analysis (ISO-Insulin ELISA, Mercodia, Uppsala, Sweden). The right panel of FIG. 12 presents SDS-PAGE of the clones, showing the molecular weights of the produced insulin polypeptides. Recombinant human insulin standard (RHI standard) is shown in lanes 15-18 of the top right gel (60-500 mg/L) and in lanes 5-9 of the bottom right gel (30-500 mg/L) for yield comparison purposes. As expected, the insulin polypeptides have a higher MW than that of the RHI standard due to the leader peptide and the connecting peptide ("C-peptide").

Figures 13A, 13B:
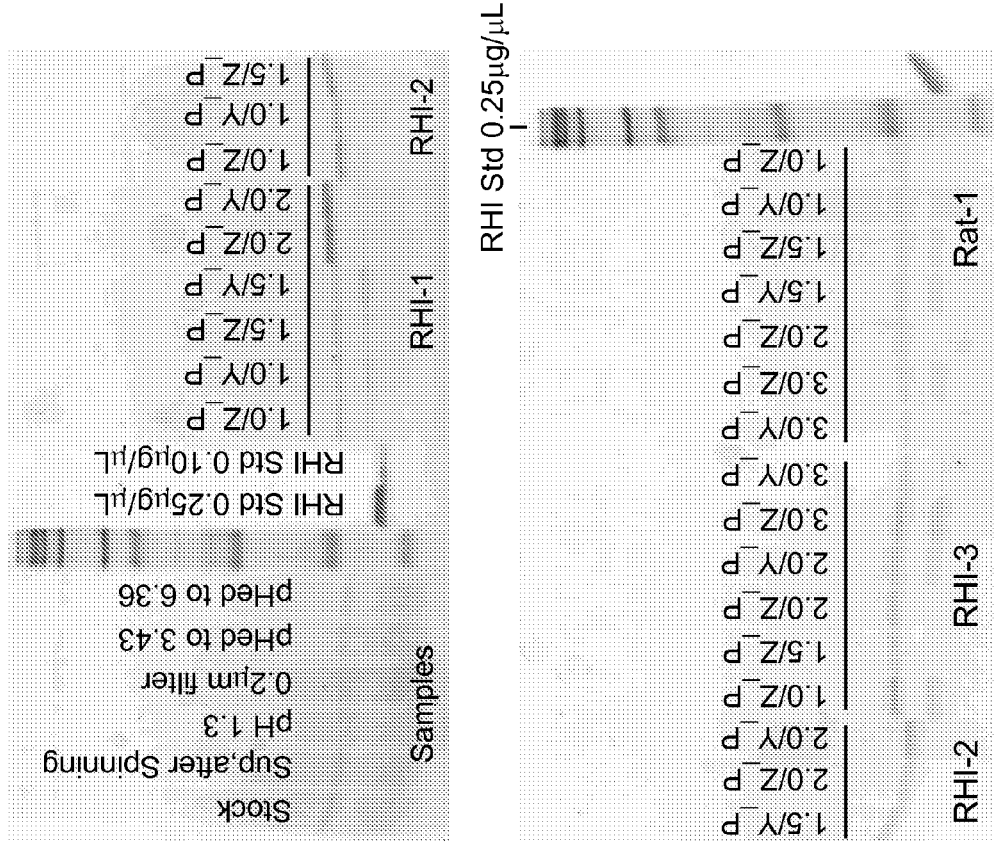
FIG. 13: Unpurified culture supernatant yields from KM71 strain clones grown under unbuffered conditions. (A) Insulin polypeptide yield in mg/L from various clones ("Clone#" refers to clones obtained from different geneticin plate resistance levels) using ELISA analysis (ISO-Insulin ELISA, Mercodia, Uppsala, Sweden). (B) SDS-PAGE of clones showing the molecular weights of the produced insulin polypeptides. Recombinant human insulin standard (RHI Standard) is shown in lanes 8 and 9 of the top right gel (250 and 100 mg/L) and in lane 18 of the bottom right gel (250 mg/L) for yield comparison purposes.

FIG. 13 presents unpurified culture supernatant yields from the KM71 strain clones grown under unbuffered conditions. The left panel of FIG. 13 presents the insulin polypeptide yield in mg/L from various clones ("Clone#" refers to clones obtained from different geneticin plate resistance levels) using ELISA analysis (ISO-Insulin ELISA, Mercodia, Uppsala, Sweden). The right panel of FIG. 13 presents SDS-PAGE of the clones, showing the molecular weights of the produced insulin polypeptides. Recombinant human insulin standard (RHI Standard) is shown in lanes 8 and 9 of the top right gel (250 and 100 mg/L) and in lane 18 of the bottom right gel (250 mg/L) for yield comparison purposes. As expected, the insulin polypeptides have a higher MW than that of the RHI standard due to the leader peptide and the connecting peptide ("C-peptide").

The results presented in FIGS. 11-13 demonstrate that the insulin polypeptides produced by the various plasmid constructs were of the correct MW. In addition, these data show that the insulin polypeptides are insulin-like, as they were measurable and detectable by a commercial insulin ELISA kit that uses antibodies that are specific for human insulin. These data further demonstrate that insulin polypeptides could be expressed in yeast at commercially-useful levels (e.g., >25 mg/L). Finally, these data demonstrated a good correlation between ELISA-measured yields and SDS-PAGE-measured yields from crude culture supernatants. In other words, when SDS-PAGE band intensity increased, ELISA measurements also tended to increase. This correlation further demonstrates that the band of interest at the appropriate molecular weight on the SDS-PAGE gel was indeed the insulin polypeptide.

In Vitro Enzyme Processing of Purified Insulin Polypeptides

This example also describes procedures that were used for in vitro enzyme processing of recombinantly produced insulin polypeptides (to remove the C-peptide and leader peptide). The present disclosure encompasses the recognition that these procedures can be utilized for purification of insulin polypeptides at any step of the production process, e.g., from crude cell culture broth, from clarified supernatant, from purified insulin polypeptide product, etc.

Figure 14A:
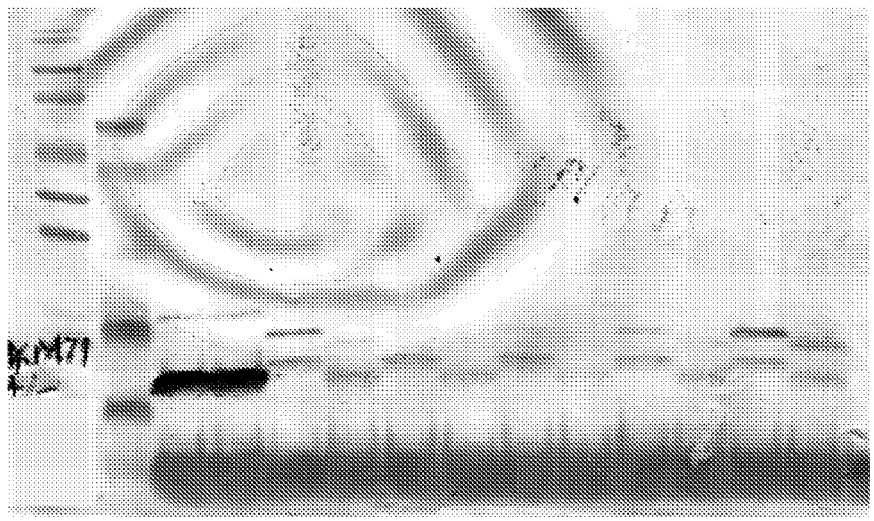
FIG. 14: Western blot of (A) KM71 RHI-1 A-E broth and (B) GS115 RHI-1 A-E broth before and after ALP digestion. "−" indicates no enzyme, "+" indicates with enzyme digestion. Lanes: 1 protein ladder, 2 peptide ladder, 3 RHI−, 4 RHI+, 5 RHI-1 A−, 6 RHI-1 A+, 7 RHI-1 B−, 8 RHI-1 B+, 9 RHI-1 C−, 10 RHI-1 C+, 11 RHI-1 D−, 12 RHI-1 D+, 13 RHI-1 E−, 14 RHI-1 E+.
Figure 14B:
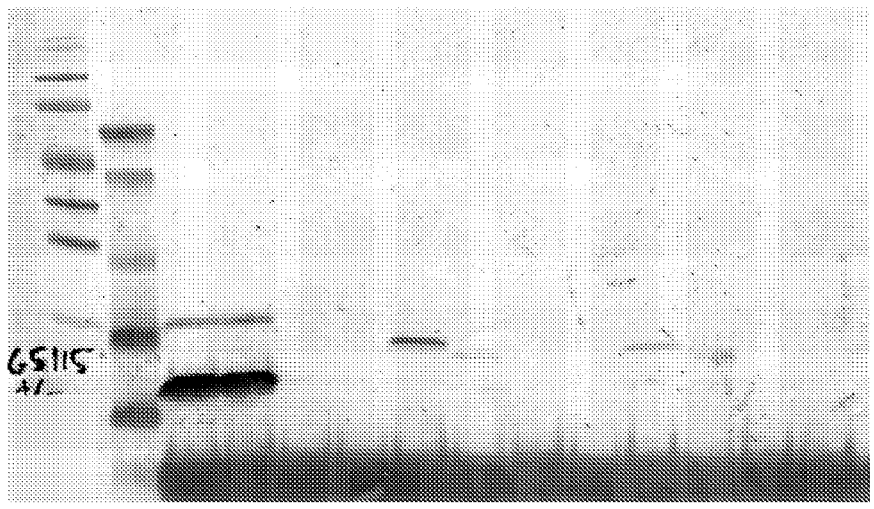

Broth from methanol induced mutants containing gene RHI-1 was digested with *Achromobacter lyticus* protease (ALP). ALP is a C-terminal lysine protease, and as such was expected to cleave the peptide linker between the A- and B-peptides of the insulin polypeptide as well as the leader peptide sequence linked to the N-terminus of the B-peptide. Dried membranes were scanned and are presented in FIG. 14. Two bands were present in most lanes containing broth, and both bands were shifted to a lower molecular weight after enzyme digestion compared to the controls. The lower MW band in each digested pair is at approximately the same location as the RHI control. The RHI control did not change MW following digestion. These results demonstrate that insulin polypeptides of the appropriate size were generated after enzyme processing. Digestion of the insulin polypeptides with ALP would be predicted to produce the products presented in Table 8 (where the A- and B-peptides in the product are connected via three disulfide bridges as shown in Formulas I' and II').

TABLE 8

| Construct ID | B-peptide | C-peptide | A-peptide |
|---|---|---|---|
| RSI-1 | FVNQHLCGSHLVEALYLVCG ERGFFYTPK (SEQ ID NO: 13) | AAK (SEQ ID NO: 16) | GIVEQCCTSICSLYQLENY CN (SEQ ID NO: 18) |
| RHI-2 | DGGDPRFVNQHLCGSHLVEA LYLVCGERGFFYTPK (SEQ ID NO: 14) | DER (SEQ ID NO: 17) | GIVEQCCTSICSLYQLENY CN (SEQ ID NO: 18) |
| RHI-3 | FVNQHLCGSHLVEALYLVCG ERGFFYTPK (SEQ ID NO:13) | DER (SEQ ID NO: 17) | GIVEQCCTSICSLYQLENY CN (SEQ ID NO: 18) |
| RHI-4 | DGGDPRFVNQHLCGSHLVEA LYLVCGERGFFYTPK (SEQ ID NO: 14) | AAK (SEQ ID NO: 16) | GIVEQCCTSICSLYQLENY CN (SEQ ID NO: 18) |
| RAT-1 | FVKQHLCGPHLVEALYLVCG ERGFFYTPK (SEQ ID NO: 15) | AAK (SEQ ID NO: 16) | GIVDQCCTSICSLYQLENY CN (SEQ ID NO: 19) |

Example 11

Recombinant Insulin Containing N-Linked Glycan Motifs: Production in Yeast, Protein Purification, and In Vitro Enzyme Processing This example describes the recombinant production of exemplary insulin polypeptides which include at least one N-linked glycan motif in two different yeast strains (KM71 and GS115) on both small- and large-scales. In certain embodiments, these insulin polypeptides are glycosylated. This example also describes procedures that are used for in vitro enzyme processing of recombinantly produced insulin polypeptides (to remove the C-peptide and leader peptide).

Materials and Methods

Gene synthesis of insulin polypeptide constructs is carried out essentially as described in Example 10. Briefly, genes of interest coding for the expression of insulin polypeptides are listed in Table 9.

TABLE 9

| Construct ID | DNA sequence |
|---|---|
| RHI-5G | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGAAGAAGCTGAAGCT GAAGCTGAACCAAAGTTTGTTAACCAACACTTGTGTGGTTCTCAC TTGGTTGAAGCTTTGTACTTGGTTTGTGGTGAAAGAGGTTTCTTC TACACTAACAAGACTGCTGCTAAGGGTATCGTTGAACAATGTTGT ACTTCTATCTGTTCTTTGTACCAATTGGAAAACTACTGTAACTAA (SEQ ID NO: 31) |
| RHI-6G | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGAAGAAGCTGAAGCT GAAGCTGAACCAAAGTTTGTTAACCAACACTTGTGTGGTTCTCAC TTGGTTGAAGCTTTGTACTTGGTTTGTGGTGAAAGAGGTTTCTTC TACACTAACACTACTAAGGCTGCTAAGGGTATCGTTGAACAATGT TGTACTTCTATCTGTTCTTTGTACCAATTGGAAAACTACTGTAAC TAA (SEQ ID NO: 32) |
| RHI-7G | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGAAGAAGCTGAAGCT GAAGCTGAACCAAAGAACACTACTTTTGTTAACCAACACTTGTGT GGTTCTCACTTGGTTGAAGCTTTGTACTTGGTTTGTGGTGAAAGA GGTTTCTTCTACACTCCAAAGGCTGCTAAGGGTATCGTTGAACAA TGTTGTACTTCTATCTGTTCTTTGTACCAATTGGAAAACTACTGT AACTAA (SEQ ID NO: 33) |
| RHI-8G | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGAAGAAGCTGAAGCT GAAGCTGAACCAAAGTTTGTTAACCAACACTTGTGTGGTTCTCAC TTGGTTGAAGCTTTGTACTTGGTTTGTGGTGAAAGAGGTTTCTTC TACACTCCAAAGGCTGCTAAGAACACTACTGGTATCGTTGAACAA TGTTGTACTTCTATCTGTTCTTTGTACCAATTGGAAAACTACTGT AACTAA (SEQ ID NO: 34) |
| RHI-9G2 | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGAAGAAGCTGAAGCT GAAGCTGAACCAAAGAACACTACTTTTGTTAACCAACACTTGTGT GGTTCTCACTTGGTTGAAGCTTTGTACTTGGTTTGTGGTGAAAGA GGTTTCTTCTACACTAACAACACTACTAAGGCTGCTAAGGGTATCGTT GAACAATGTTGTACTTCTATCTGTTCTTTGTACCAATTGGAAAAC TACTGTAACTAA (SEQ ID NO: 35) |
| RHI-10G2 | ATGAGATTCCCATCTATCTTCACTGCTGTTTTGTTCGCTGCTTCT TCTGCTTTGGCTGCTCCTGTTAACACTACTACTGAAGACGAAACT GCTCAAATCCCAGCTGAAGCGGTTATCGGTTACTCTGACTTGGAA GGTGACTTCGACGTTGCTGTTTTGCCTTTCTCTAACTCTACTAAT AATGGTTTGTTGTTCATCAACACTACTATCGCTTCTATCGCTGCT AAGGAAGAGGGTGTTTCTATGGCTAAGAGAGAAGAAGCTGAAGCT GAAGCTGAACCAAAGTTTGTTAACCAACACTTGTGTGGTTCTCAC TTGGTTGAAGCTTTGTACTTGGTTTGTGGTGAAAGAGGTTTCTTC TACACTAACACTACTAAGGCTGCTAAGAACACTACTGGTATCGTT GAACAATGTTGTACTTCTATCTGTTCTTTGTACCAATTGGAAAAC TACTGTAACTAA (SEQ ID NO: 36) |

DNA preparation for *P. pastoris* transformation is carried out essentially as described in Example 10. Once the DNA has been transformed into the yeast strains, the resulting gene constructs code for the amino acid sequences shown in Table 10. The Pro-leader peptide is designed to be cleaved by Kex-2 endoprotease within the yeast prior to protein secretion into the media (Kjeldsen et al., 1999, *Biotechnol. Appl. Biochem.* 29:79-86). Thus the resulting insulin polypeptide secreted into the media includes only the leader peptide sequence attached to the [B-peptide][C-peptide]-[A-peptide] sequence.

different amino acid sequences that result in addition of other or additional N-linked glycan motifs).

Results from these procedures are expected to demonstrate that the insulin polypeptides produced by the various plasmid constructs are of the correct MW. In addition, results from these procedures are expected to show that the insulin polypeptides are insulin-like (i.e., measurable and detectable by a commercial insulin ELISA kit that uses antibodies that are specific for human insulin). These data are further expected to demonstrate that insulin polypeptides can be expressed in yeast at commercially-interesting levels (e.g.,

TABLE 10

| Construct ID | Pro-leader peptide | Leader peptide | B-C-A peptides |
|---|---|---|---|
| RHI-5G | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | FVNQHLCGSHLVEALYLVC GERGFFYTNKTAAKGIVEQ CCTSICSLYQLENYCN (SEQ ID NO: 37) |
| RHI-6G | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | FVNQHLCGSHLVEALYLVC GERGFFYTNTTKAAKGIVE QCCTSICSLYQLENYCN (SEQ ID NO: 38) |
| RHI-7G | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | NTTFVNQHLCGSHLVEALY LVCGERGFFYTPKAAKGIV EQCCTSICSLYQLENYCN (SEQ ID NO: 39) |
| RHI-8G | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | FVNQHLCGSHLVEALYLVC GERGFFYTPKAAKNTTGIV EQCCTSICSLYQLENYCN (SEQ ID NO: 40) |
| RHI-9G2 | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | NTTFVNQHLCGSHLVEALY LVCGERGFFYTNTTKAAKG IVEQCCTSICSLYQLENYC N (SEQ ID NO: 41) |
| RHI-10G2 | APVNTTTEDETAQIPAEAVI GYSDLEGDFDVAVLPFSNST NNGLLFINTTIASIAAKEEG VSMAKR (SEQ ID NO: 8) | EEAEAEAEPK (SEQ ID NO: 9) | FVNQHLCGSHLVEALYLVC GERGFFYTNTTKAAKNTTG IVEQCCTSICSLYQLENYC N (SEQ ID NO: 42) |

Electrocompetent *P. pastoris* strains are produced essentially as described in Example 10. *P. pastoris* transformation with insulin polypeptide constructs is carried out essentially as described in Example 10. Screening for *P. pastoris* transformants for clones with high-copy number of expression cassettes is carried out essentially as described in Example 10. Shake-flask studies are carried out essentially as described in Example 10.

Large-scale insulin polypeptide expression is carried out essentially as described in Example 10. Glycosylated insulin polypeptide purification is carried out essentially as described in Example 10. In vitro enzyme processing is carried out essentially as described in Example 10.

Results

Production of Insulin Polypeptides in Yeast

This example describes the production from two different yeast strains of insulin polypeptides containing one or more N-linked glycan motifs. This example provides a few representative examples of insulin polypeptides, but the present invention encompasses the recognition that these procedures can be useful for expressing and purifying any other recombinant insulin polypeptide (e.g., insulin polypeptides with >25 mg/L). Finally, these data are expected to demonstrate a good correlation between ELISA-measured yields and SDS-PAGE-measured yields from crude culture supernatants. In other words, when SDS-PAGE band intensity increases, ELISA measurements also tend to increase.

In Vitro Enzyme Processing of Purified Insulin Polypeptides

This example describes procedures that are used for in vitro enzyme processing of recombinantly produced insulin polypeptides (to remove the C-peptide and leader peptide). The present disclosure encompasses the recognition that these procedures can be utilized for purification of insulin polypeptides at any step of the production process, e.g., from crude cell culture broth, from clarified supernatant, from purified insulin polypeptide product, etc. Digestion of the insulin polypeptides with ALP is expected to generate the products presented in Table 11 where N-linked glycan motifs are shown underlined. In the RHI-5G construct, the N-linked glycan motif Asn-Lys-Thr straddles the B- and C-peptides (and is therefore cleaved when proinsulin is converted into bioactive insulin leaving Asn-Lys on the C-terminus of the B-peptide).

TABLE 11

| Construct ID | B-peptide | C-peptide | A-peptide |
|---|---|---|---|
| RHI-5G | FVNQHLCGSHLVEALYLVCG ERGFFYT<u>NK</u> (SEQ ID NO: 43) | TAAK (SEQ ID NO: 25) | GIVEQCCTSICSLYQLENY CN (SEQ ID NO: 18) |
| RHI-6G | FVNQHLCGSHLVEALYLVCG ERGFFYT<u>NTTK</u> (SEQ ID NO: 44) | AAK (SEQ ID NO: 16) | GIVEQCCTSICSLYQLENY CN (SEQ ID NO: 18) |
| RHI-7G | <u>NTT</u>FVNQHLCGSHLVEALYL VCGERGFFYTPK (SEQ ID NO: 45) | AAK (SEQ ID NO: 16) | GIVEQCCTSICSLYQLENY CN (SEQ ID NO: 18) |
| RHI-8G | FVNQHLCGSHLVEALYLVCG ERGFFYTPK (SEQ ID NO: 13) | AAK (SEQ ID NO: 16) | <u>NTT</u>GIVEQCCTSICSLYQL ENYCN (SEQ ID NO: 47) |
| RHI-9G2 | <u>NTT</u>FVNQHLCGSHLVEALYL VCGERGFFYT<u>NTT</u>K (SEQ ID NO: 46) | AAK (SEQ ID NO: 16) | GIVEQCCTSICSLYQLENY CN (SEQ ID N0: 18) |
| RHI-10G2 | FVNQHLCGSHLVEALYLVCG ERGFFYT<u>NTTK</u> (SEQ ID NO: 44) | AAK (SEQ ID NO: 16) | <u>NTT</u>GIVEQCCTSICSLYQL ENYCN (SEQ ID NO: 47) |

It is to be understood that the present disclosure encompasses insulin polypeptides where the A- and B-peptides of Table 11 are comprised within a single contiguous amino acid sequence (as in proinsulin) separated by the corresponding C-peptide as follows: [B-peptide]-[C-peptide]-[A-peptide] (where the C-peptide connects the C-terminus of the B-peptide with the N-terminus of the A-peptide). It is also to be understood that the present disclosure encompasses insulin polypeptides where the A- and B-peptides of Table 11 are separated by the corresponding C-peptide and include a leader peptide sequence as follows: [Leader peptide]-[B-peptide]-[C-peptide]-[A-peptide] (where the leader peptide may be any one of the leader peptide sequences described herein). It is also to be understood that the present disclosure encompasses insulin polypeptides where the A- and B-peptides of Table 11 are discontiguous peptides that are linked via one or more disulfide bridges (as in bioactive insulin). In various embodiments, an insulin polypeptide of the present disclosure includes the three disulfide bridges that are found in wild-type insulins (as shown in Formula I' and II').

Example 12

Sequences of Exemplary Insulin Polypeptides with N-Linked Glycan Motifs

This example describes the sequences of some exemplary insulin polypeptides with N-linked glycan motifs. The B-, C- and A-peptide sequences of individual constructs are presented in Table 12 where N-linked glycan motifs are shown underlined. In the RHI-5G series, the N-linked glycan motif straddles the B- and C-peptides and is therefore cleaved when proinsulin is converted into bioactive insulin. It is to be understood that the present disclosure encompasses insulin polypeptides where the A- and B-peptides of Table 12 are comprised within a single contiguous amino acid sequence (as in proinsulin) separated by the corresponding C-peptide as follows: [B-peptide][C-peptide]-[A-peptide] (where the C-peptide connects the C-terminus of the B-peptide with the N-terminus of the A-peptide). It is also to be understood that the present disclosure encompasses insulin polypeptides where the A- and B-peptides of Table 12 are separated by the corresponding C-peptide and include a leader peptide sequence as follows: [Leader peptide]-[B-peptide]-[C-peptide]-[A-peptide] (where the leader peptide may be any one of the leader peptide sequences described herein). It is also to be understood that the present disclosure encompasses insulin polypeptides where the A- and B-peptides of Table 12 are discontiguous peptides that are linked via one or more disulfide bridges (as in bioactive insulin). In various embodiments, an insulin polypeptide of the present disclosure includes the three disulfide bridges that are found in wild-type insulins (as shown in Formula I' and II').

TABLE 12

| Construct ID | B-peptide | C-peptide | A-peptide |
|---|---|---|---|
| RHI-5G2 | FVNQHLCGSHLVEALYLVCG ERGFFYT<u>NK</u> (SEQ ID NO: 43) | TAAK (SEQ ID NO: 25) | GIVEQCCXXXCSLYXLEXY CX (SEQ ID NO: 52) |
| RHI-5G3 | XXXXXLCGXXXXXALYLVCG XRGFFXX<u>NK</u> (SEQ ID NO: 48) | TAAK (SEQ ID NO: 25) | GIVEQCCTSICSLYQLENY CN (SEQ ID NO: 18) |
| RHI-5G4 | XXXXXLCGXXXXXALYLVCG XRGFFXX<u>NK</u> (SEQ ID NO: 48) | TAAK SEQ ID NO: 25) | GIVEQCCXXXCSLYXLEXY CX (SEQ ID NO: 52) |

TABLE 12-continued

| Construct ID | B-peptide | C-peptide | A-peptide |
|---|---|---|---|
| RHI-6G2 | FVNQHLCGSHLVEALYLVCG ERGFFYT<u>NTT</u>K (SEQ ID NO: 44) | AAK (SEQ ID NO: 16) | GIVEQCCXXXCSLYXLEXY CX (SEQ ID NO: 52) |
| RHI-6G3 | XXXXXLCGXXXXXALYLVCG XRGFFXX<u>NTT</u>K (SEQ ID NO: 49) | AAK (SEQ ID NO: 16) | GIVEQCCTSICSLYQLENY CN (SEQ ID NO: 18) |
| RHI-6G4 | XXXXXLCGXXXXXALYLVCG XRGFFXX<u>NTT</u>K (SEQ ID NO: 49) | AAK (SEQ ID NO: 16) | GIVEQCCXXXCSLYXLEXY CX (SEQ ID NO: 52) |
| RHI-7G2 | <u>NTT</u>FVNQHLCGSHLVEALYL VCGERGFFYTPK (SEQ ID NO: 45) | AAK (SEQ ID NO: 16) | GIVEQCCXXXCSLYXLEXY CX (SEQ ID NO: 52) |
| RHI-7G3 | <u>NTT</u>XXXXXLCGXXXXXALYL VCGXRGFFXXPK (SEQ ID NO: 50) | AAK (SEQ ID NO: 16) | GIVEQCCTSICSLYQLENY CN (SEQ ID NO: 18) |
| RHI-7G4 | <u>NTT</u>XXXXXLCGXXXXXALYL VCGXRGFFXXPK (SEQ ID NO: 50) | AAK (SEQ ID NO: 16) | GIVEQCCXXXCSLYXLEXY CX (SEQ ID NO: 52) |
| RHI-8G2 | XXXXXLCGXXXXXALYLVCG XRGFFXXXX (SEQ ID NO: 50) | AAK (SEQ ID NO: 16) | <u>NTT</u>GIVEQCCTSICSLYQL ENYCN (SEQ ID NO: 47) |
| RHI-8G3 | FVNQHLCGSHLVEALYLVCG ERGFFYTPK (SEQ ID NO: 13) | AAK (SEQ ID NO: 16) | <u>NTT</u>GIVEQCCXXXCSLYXL EXYCX (SEQ ID NO: 53) |
| RHI-8G4 | XXXXXLCGXXXXXALYLVCG XRGFFXXXX (SEQ ID NO: 50) | AAK (SEQ ID NO: 16) | <u>NTT</u>GIVEQCCXXXCSLYXL EXYCX (SEQ ID NO: 53) |
| RHI-9G3 | <u>NTT</u>FVNQHLCGSHLVEALYL VCGERGFFYT<u>NTT</u>K (SEQ ID NO: 46) | AAK (SEQ ID NO: 16) | GIVEQCCXXXCSLYXLEXY CX (SEQ ID NO: 52) |
| RHI-9G4 | <u>NTT</u>XXXXXLCGXXXXXALYL VCGXRGFFXX<u>NTT</u>K (SEQ ID NO: 51) | AAK (SEQ ID NO: 16) | GIVEQCCTSICSLYQLENY CN (SEQ ID NO: 18) |
| RHI-9G5 | <u>NTT</u>XXXXXLCGXXXXXALYL VCGXRGFFXX<u>NTT</u>K (SEQ ID NO: 51) | AAK (SEQ ID NO: 16) | GIVEQCCXXXCSLYXLEXY CX (SEQ ID NO: 52) |
| RHI-10G3 | FVNQHLCGSHLVEALYLVCG ERGFFYT<u>NTT</u>K (SEQ ID NO: 44) | AAK (SEQ ID NO: 16) | <u>NTT</u>GIVEQCCXXXCSLYXL EXYCX (SEQ ID NO: 53) |
| RHI-10G4 | XXXXXLCGXXXXXALYLVCG XRGFFXX<u>NTT</u>K (SEQ ID NO: 49) | AAK (SEQ ID NO: 16) | <u>NTT</u>GIVEQCCTSICSLYQL ENYCN (SEQ ID NO: 47) |
| MHI-10G5 | XXXXXLCGXXXXXALYLVCG XRGFFXX<u>NTT</u>K (SEQ ID NO: 49) | AAK (SEQ ID NO: 16) | <u>NTT</u>GIVEQCCXXXCSLYXL EXYCX (SEQ ID NO: 53) |

In certain embodiments, X at each of positions A8, A9, A10, A15, A18, A20 and A21 is independently a codable amino acid; X at each of positions B1, B2, B3, 84, B26, B27, B28, B29, and B30 is independently a codable amino acid or missing; and X at each of positions B5, B9, B10, B11, B12, B13 and B21 is independently a codable amino acid. In certain embodiments, X at each of positions A8, A9, A10, A15, A18, A20, A21 are selected from the choices that are set forth in Tables 1 and/or 3. In certain embodiments, X at each of positions B1, B2, B3, B4, B5, B9, B10, B11, B12, B13, B21, B26, B27, B28, B29, and B30 are selected from the choices that are set forth in Tables 2 and/or 3. It is to be understood that this numbering scheme takes into account the fact that in certain constructs an N-linked glycan motif is encompassed within position A0 (e.g., in the case of RHI-8 and RHI-10 series) and/or within position B0 (e.g., in the case of RHI-7 and RHI-9 series).

Figure 15A:
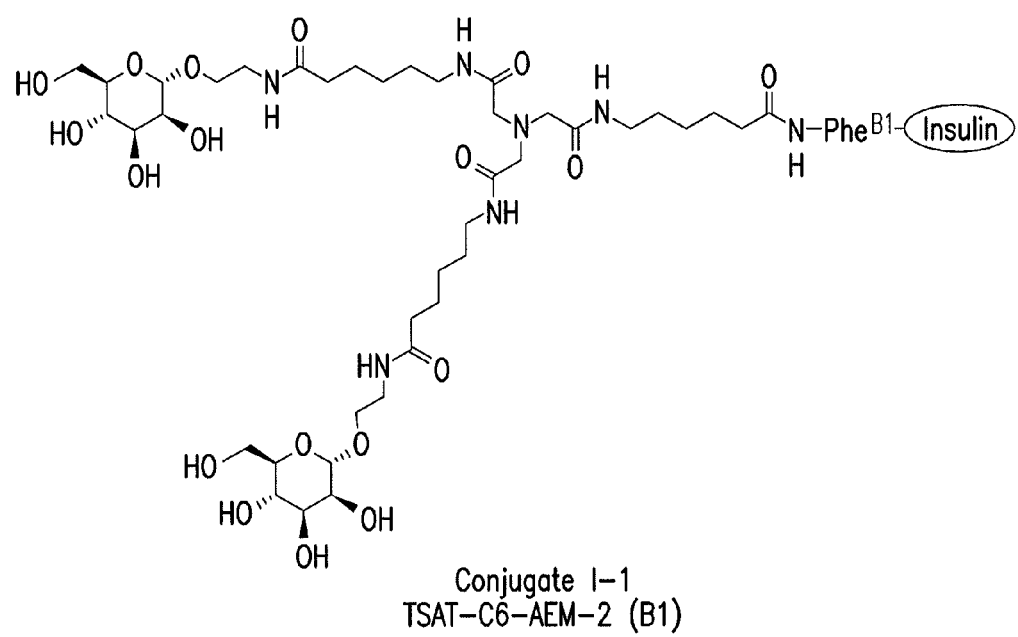
FIG. 15A to FIG. 15Q: Chemical structure of other exemplary synthetic insulin conjugates I-1 to I-5 and I-7 to I-18. Experimental results obtained with some of these exemplary synthetic insulin conjugates are shown in FIG. 16 onwards.
Figure 15B:
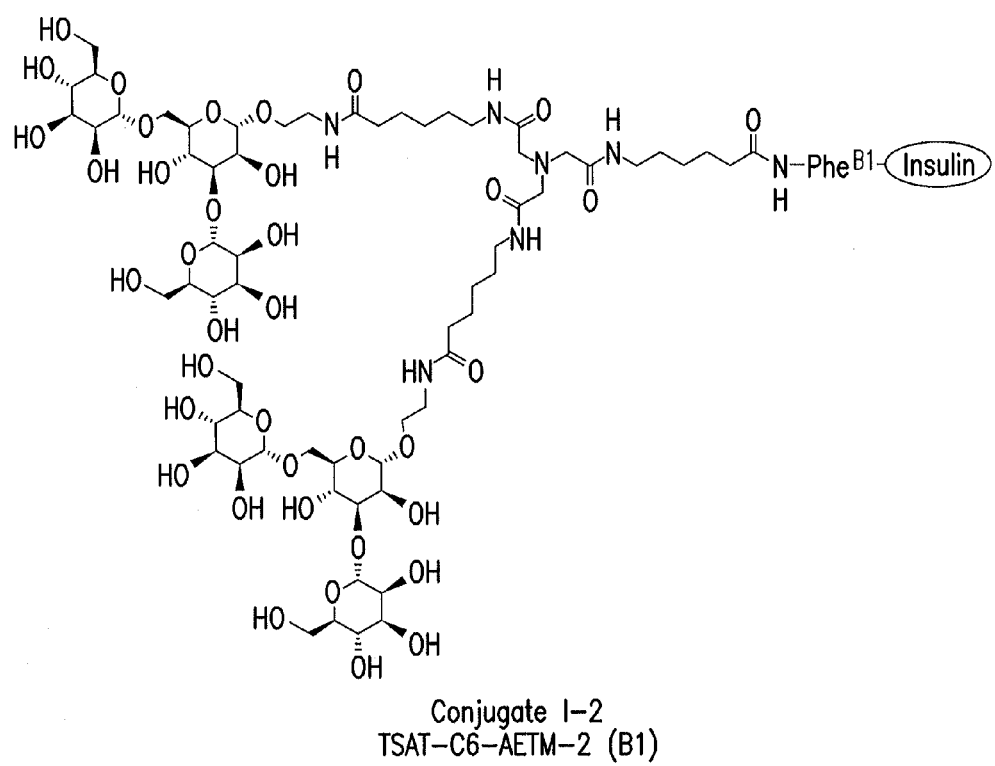
Figure 15C:
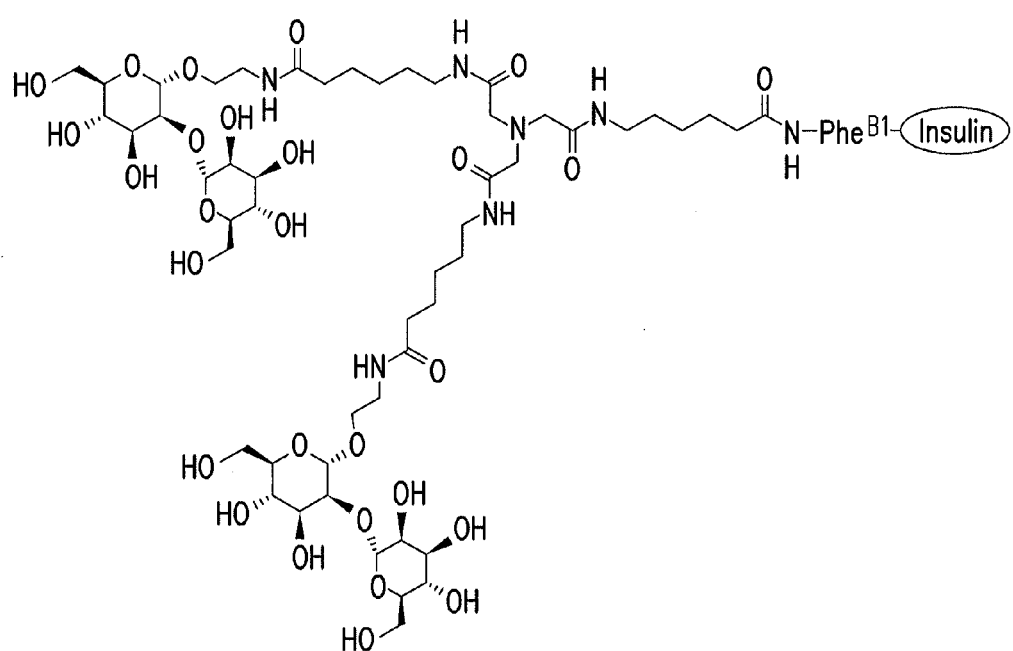
Figure 15D:
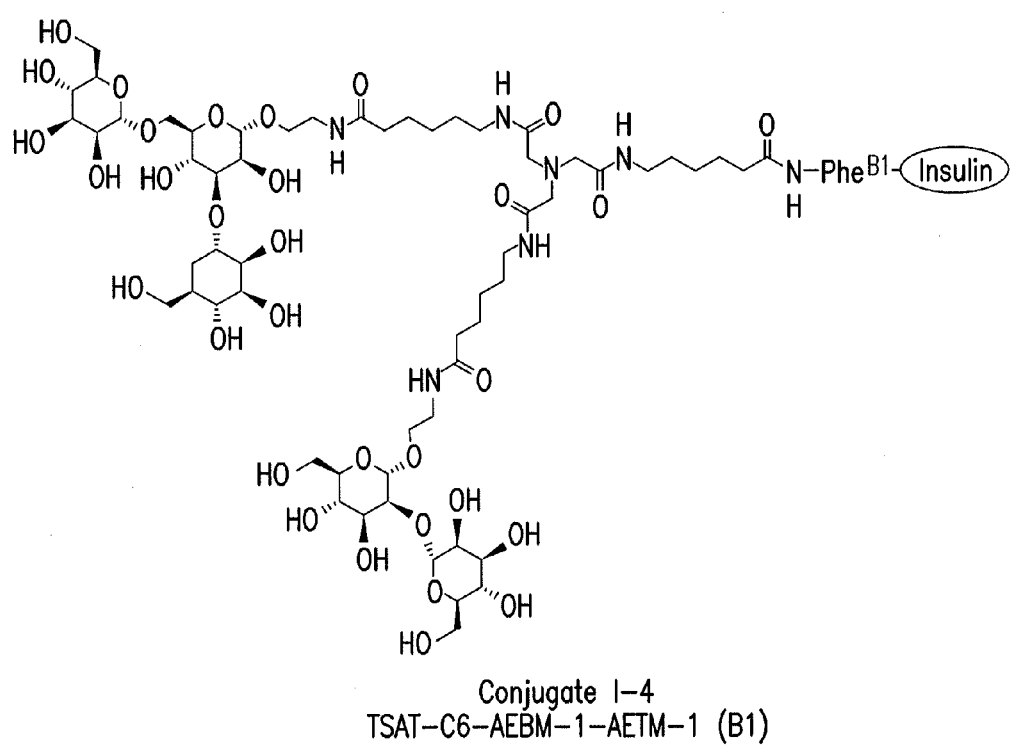
Figure 15E:
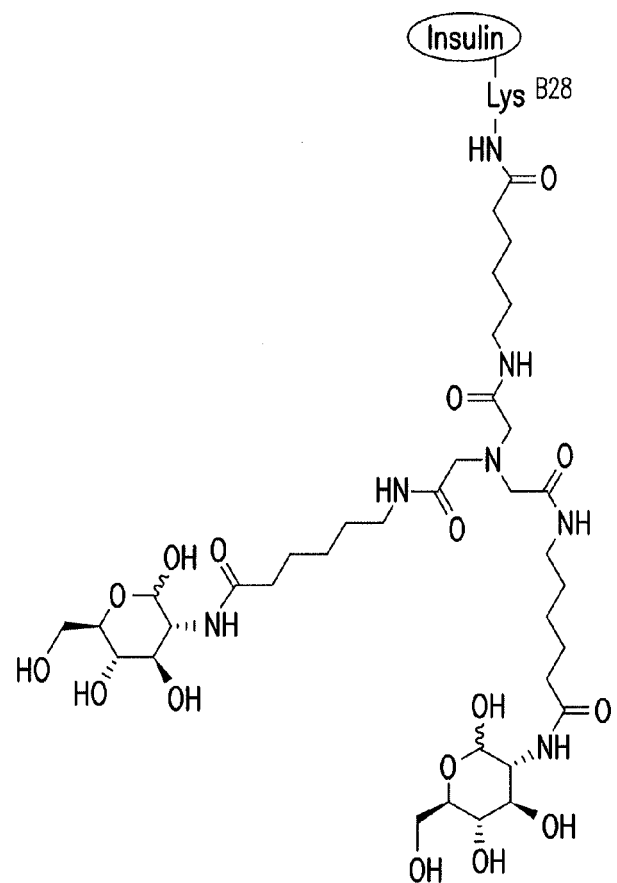
Figure 15F:
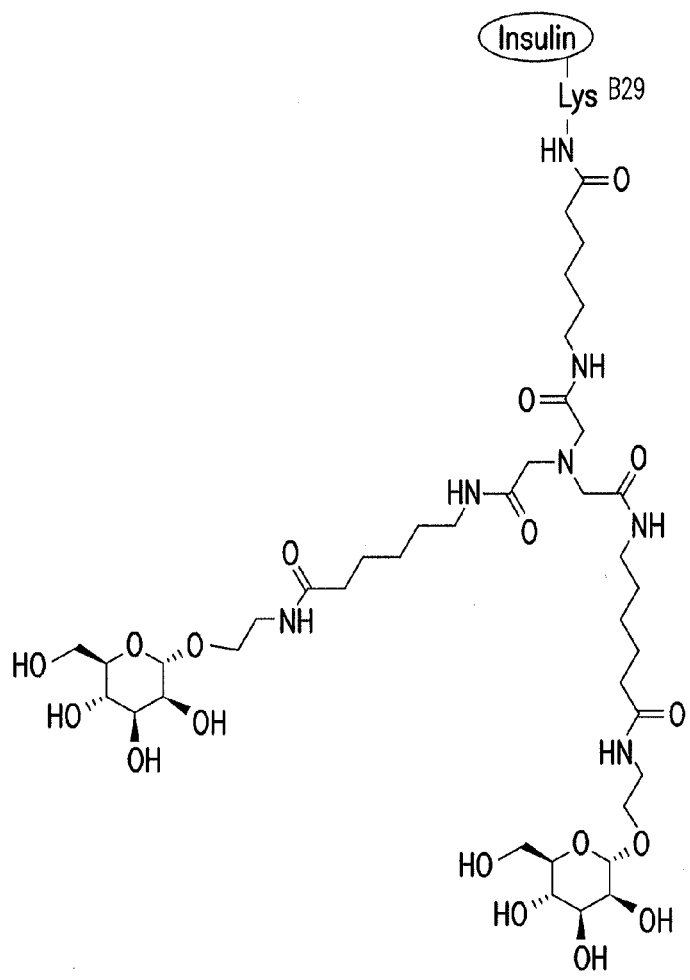
Figure 15G:
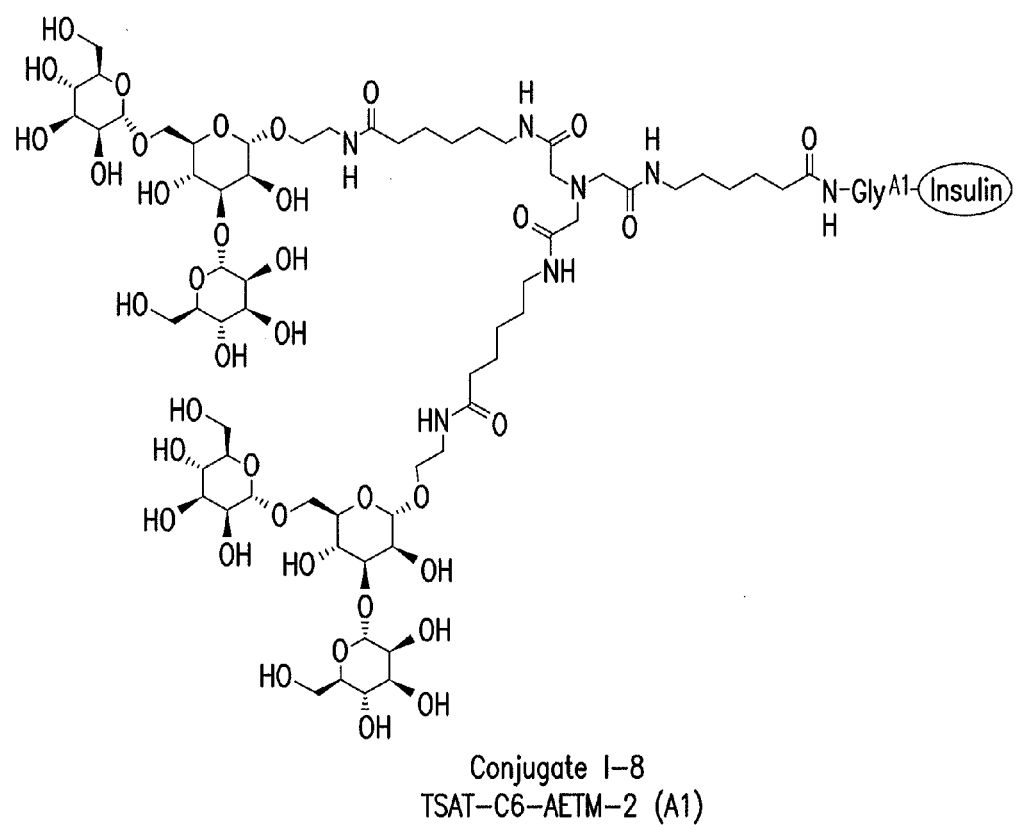
Figure 15H:
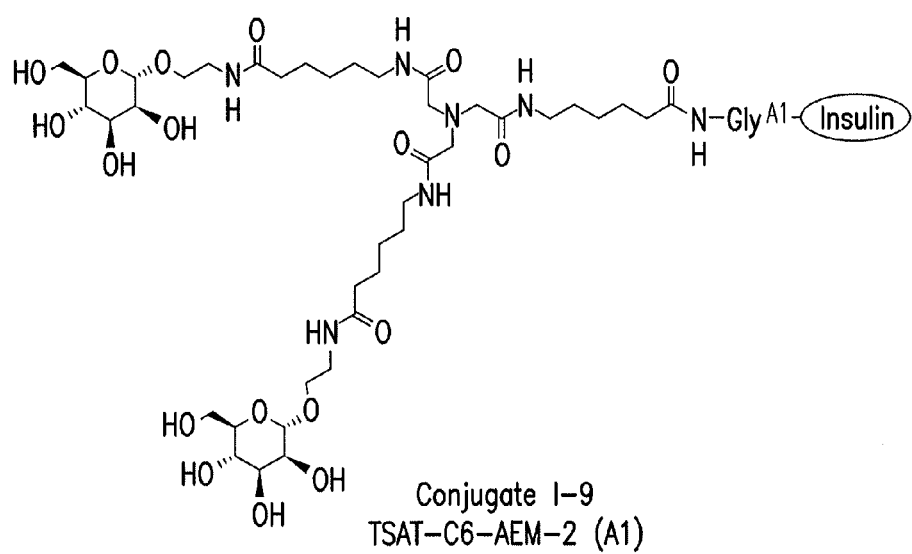
Figure 15I:
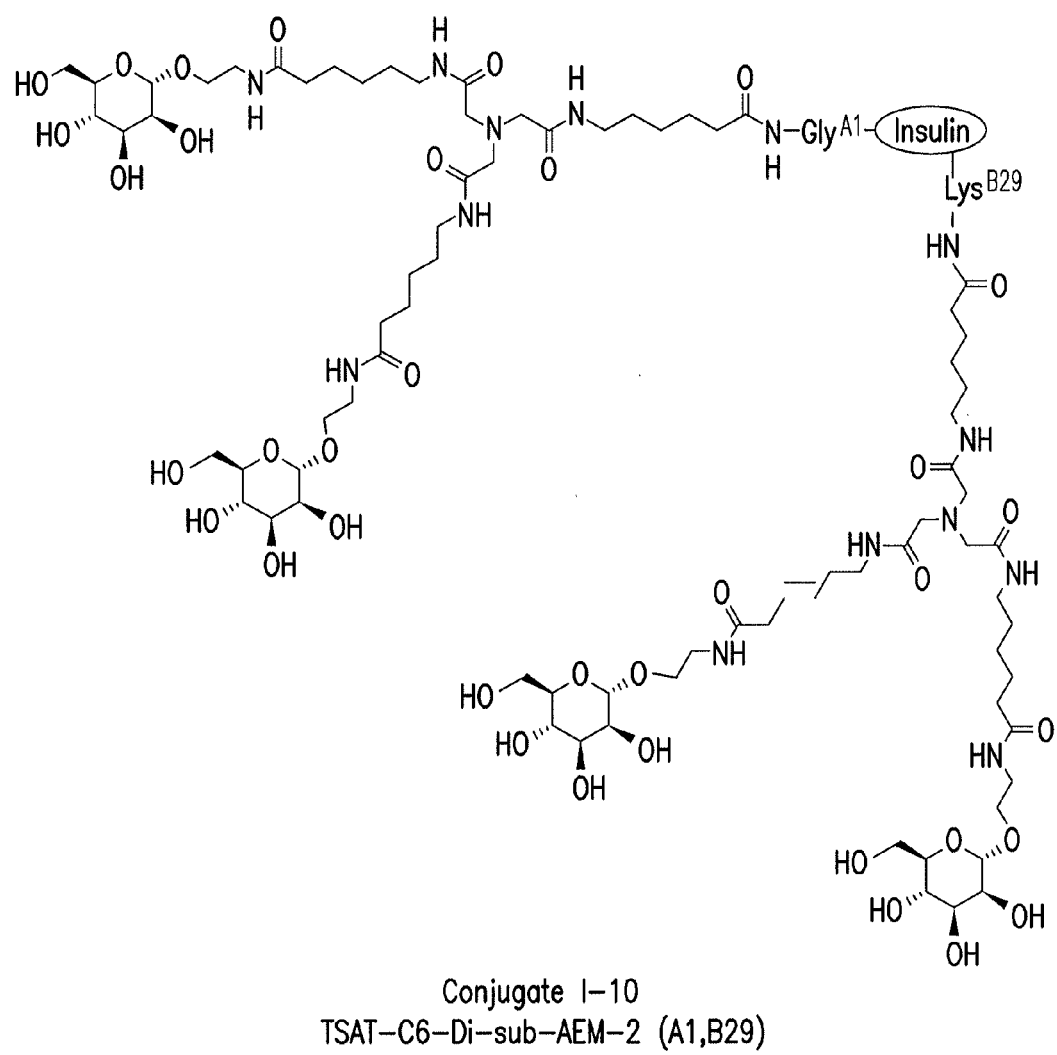
Figure 15J:
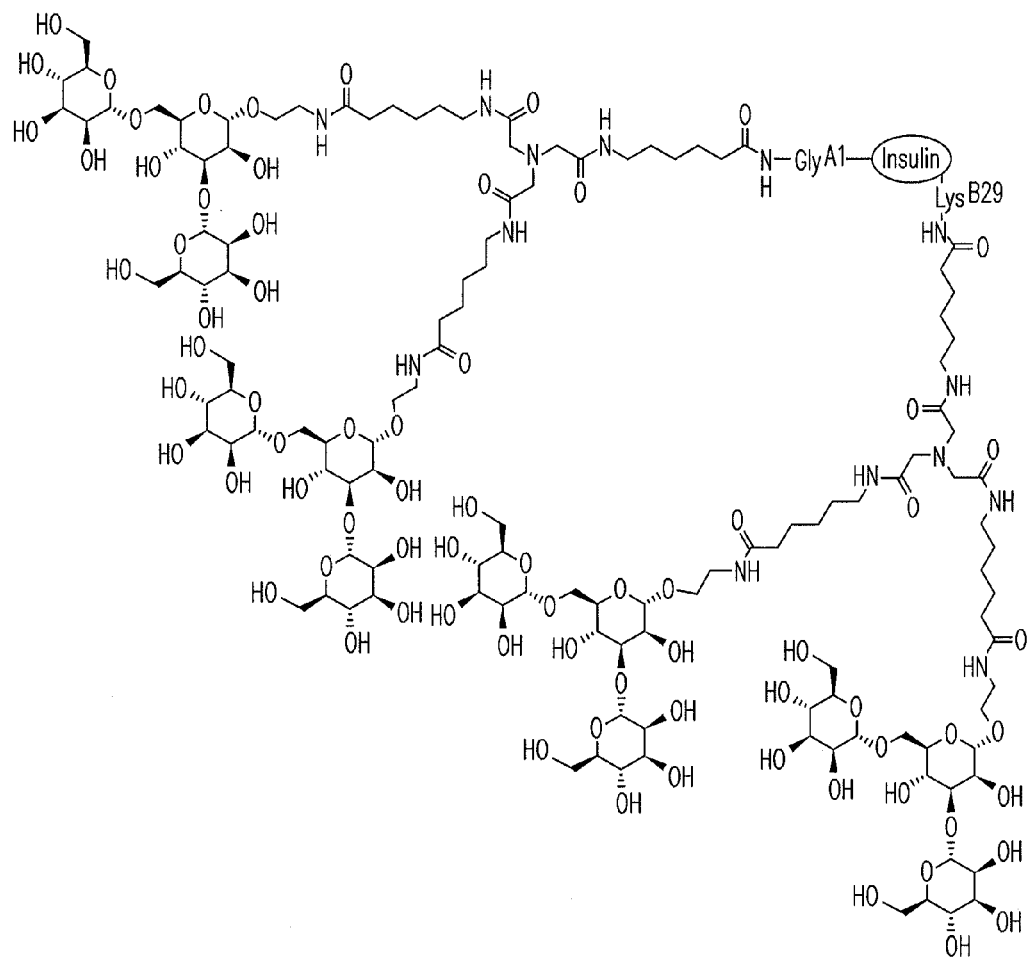
Figure 15K:
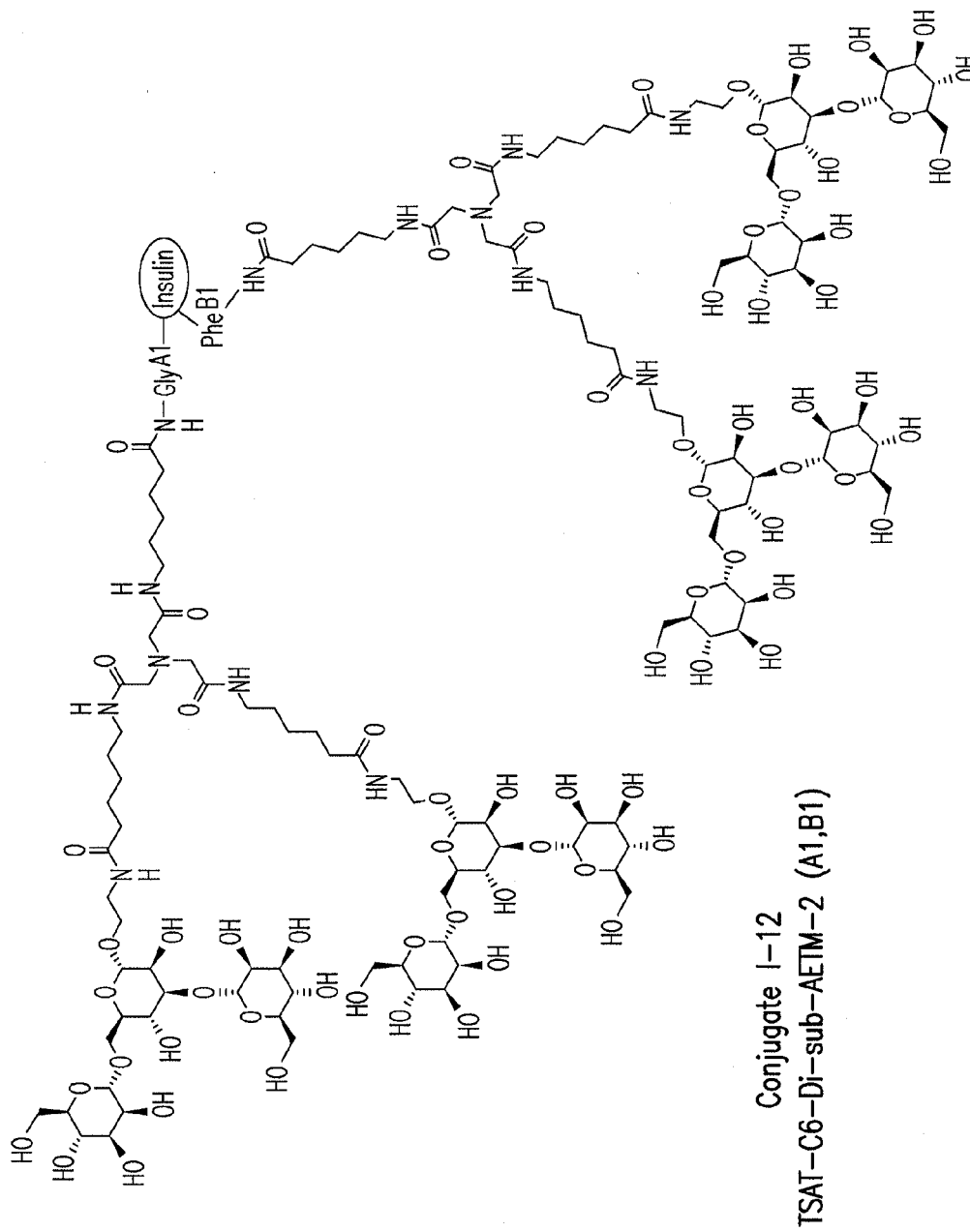
Figure 15L:
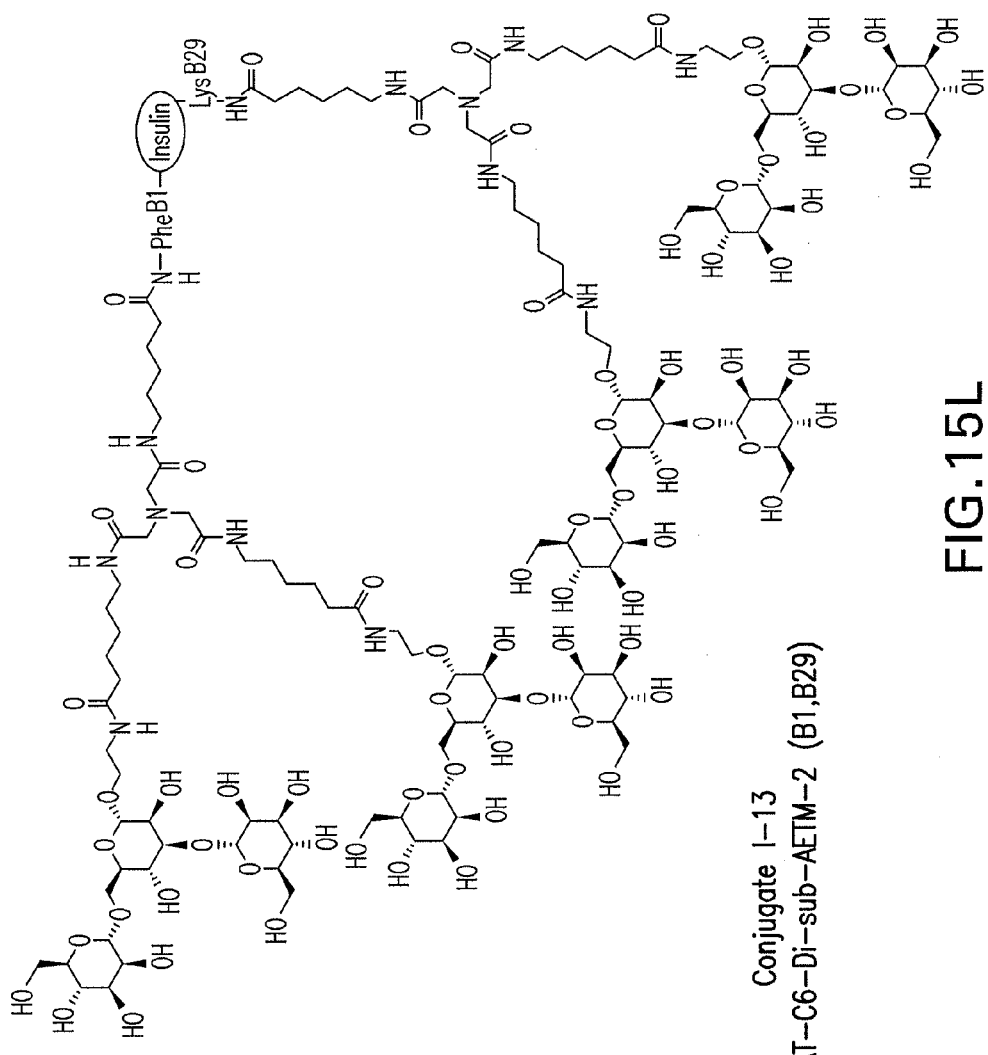
Figure 15M:
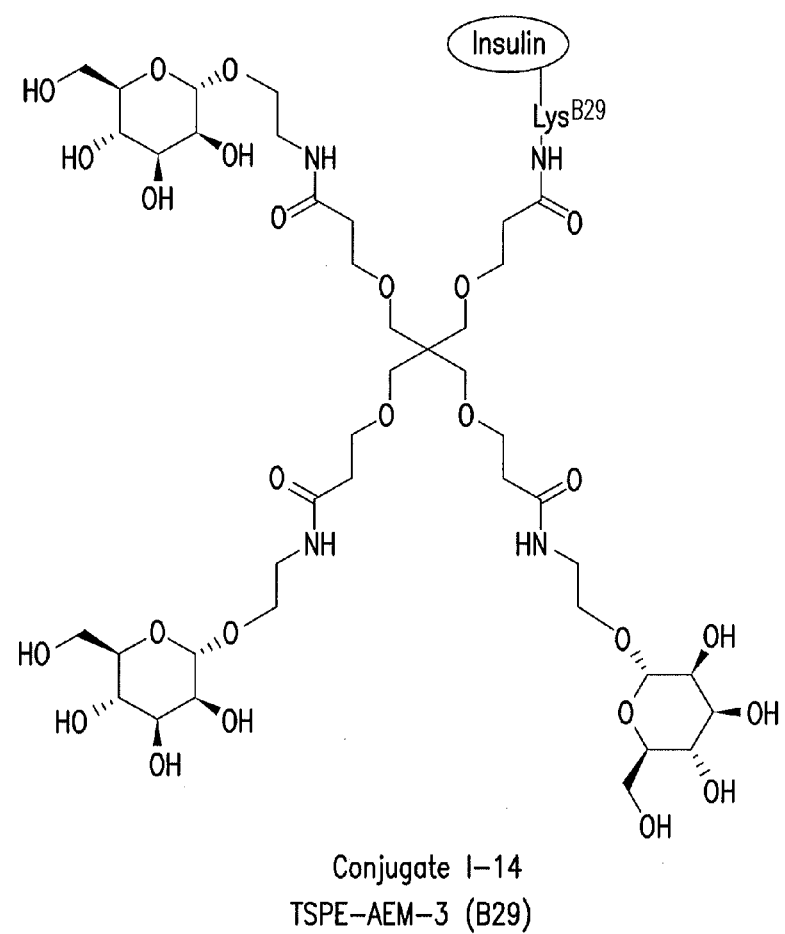
Figure 15N:
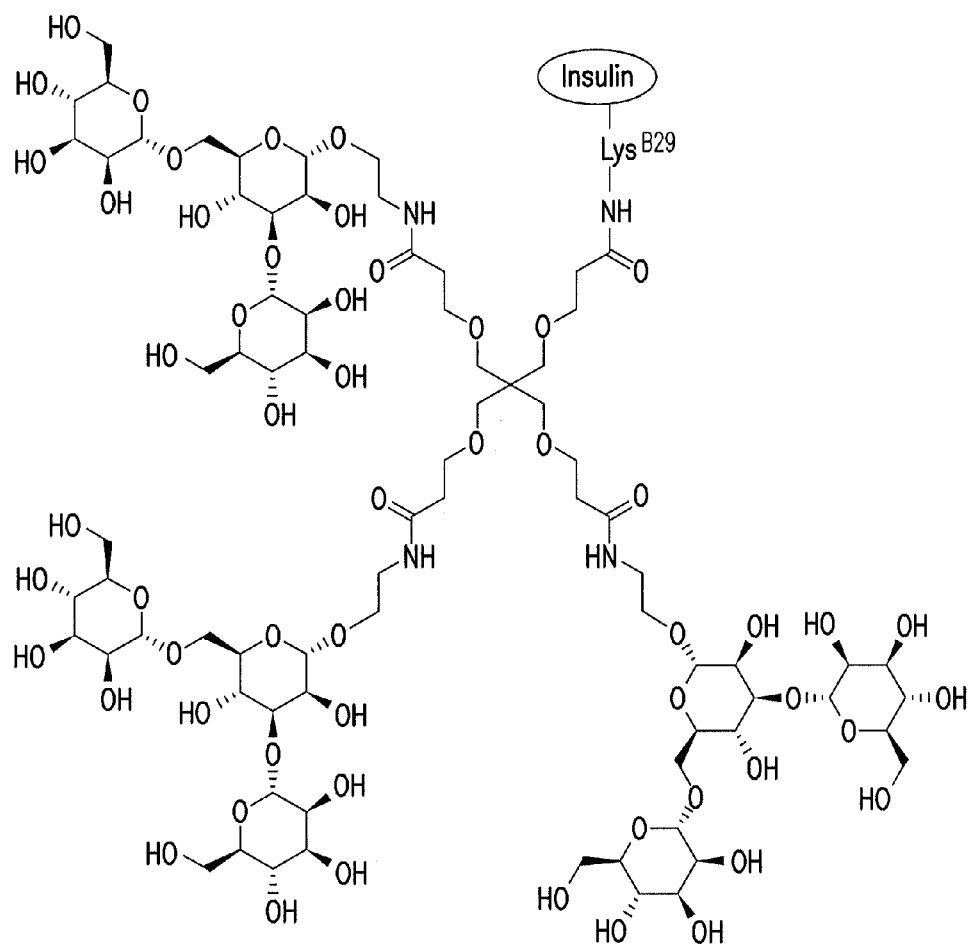
Figure 15O:
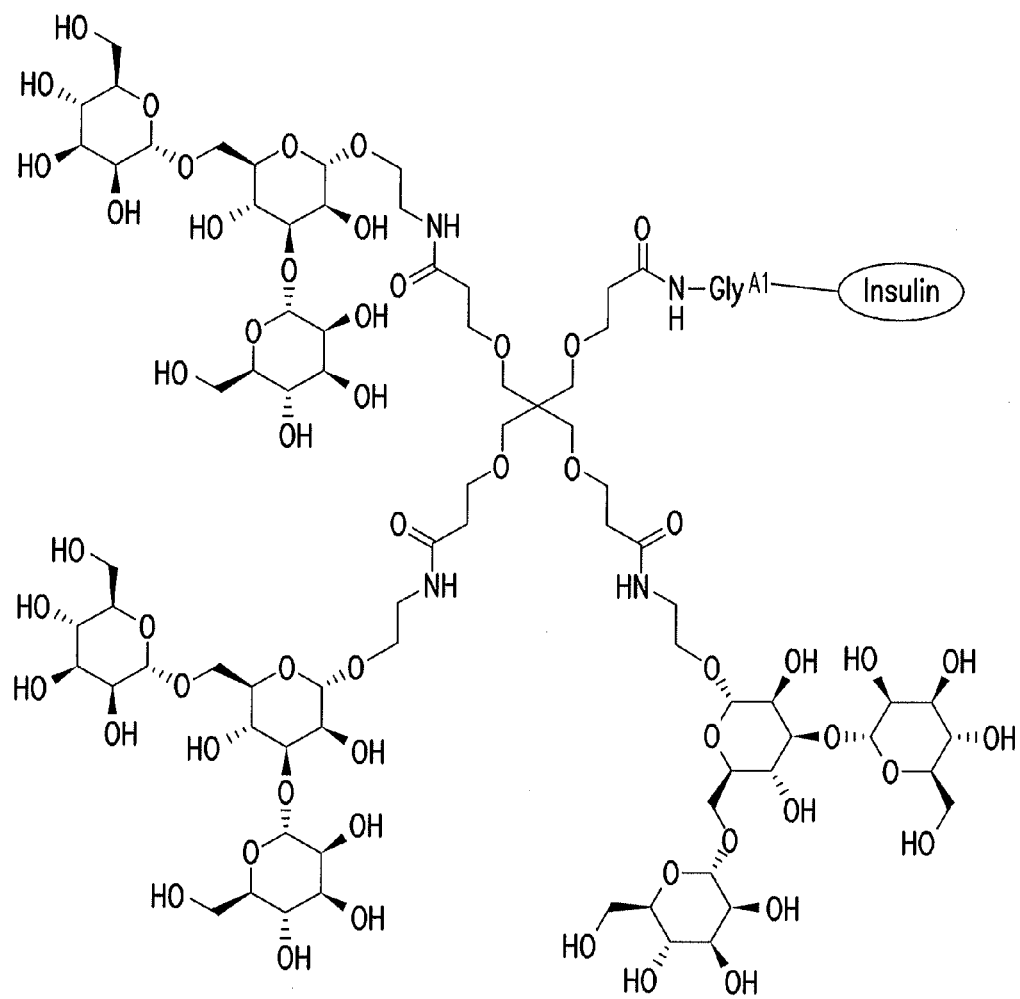
Figure 15P:
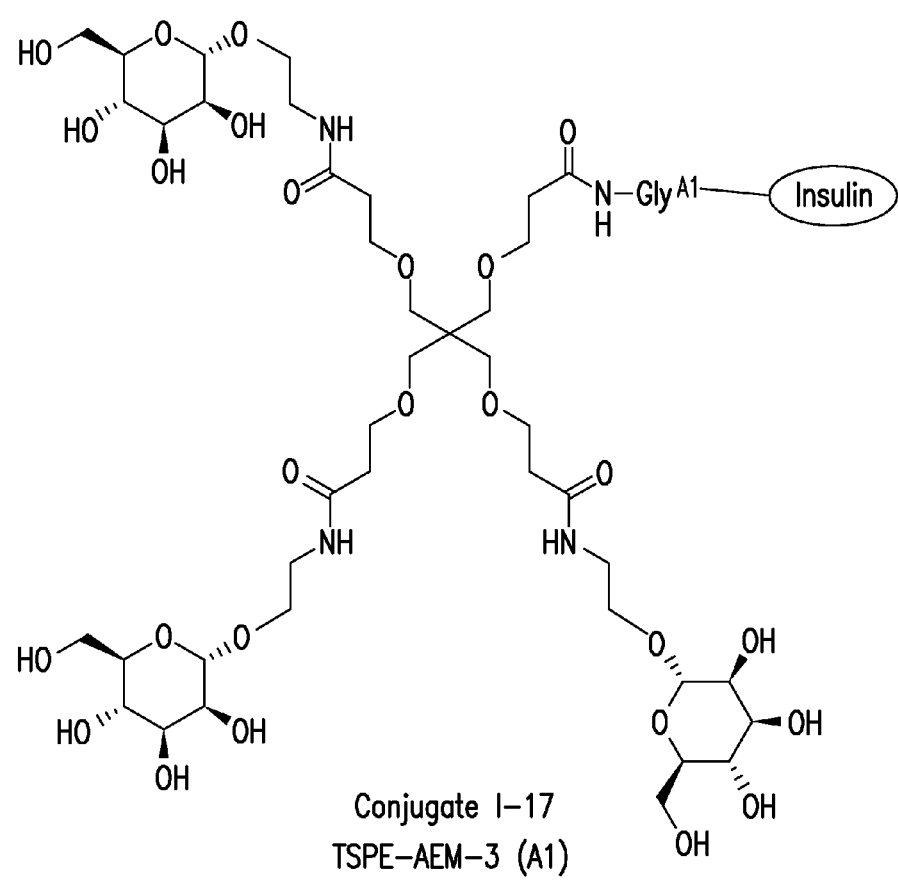
Figure 15Q:
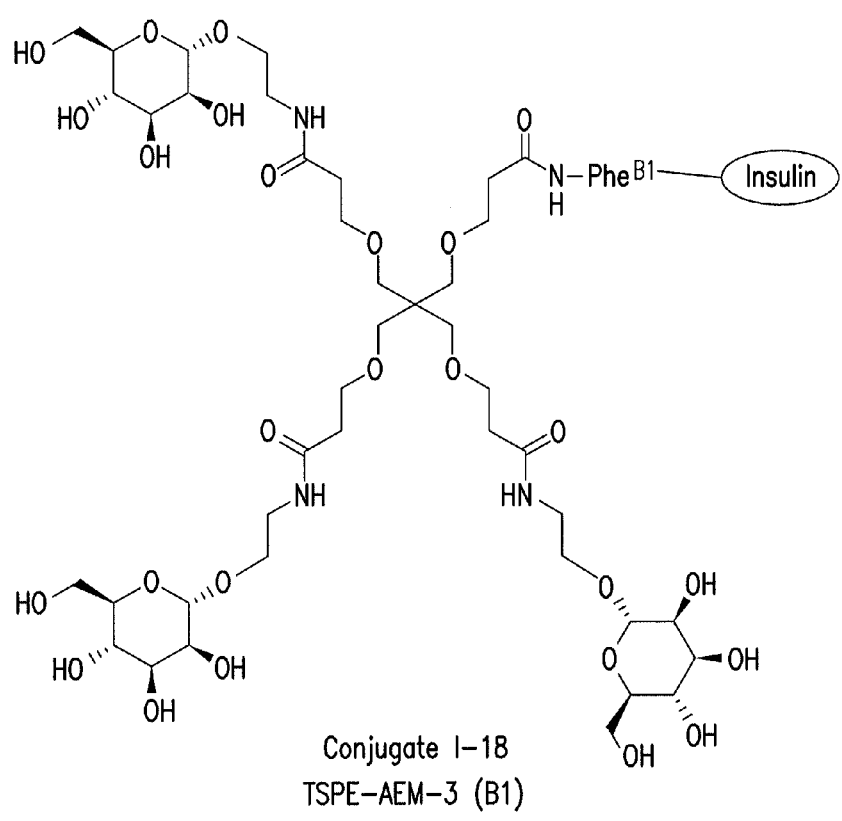
Figure 16:
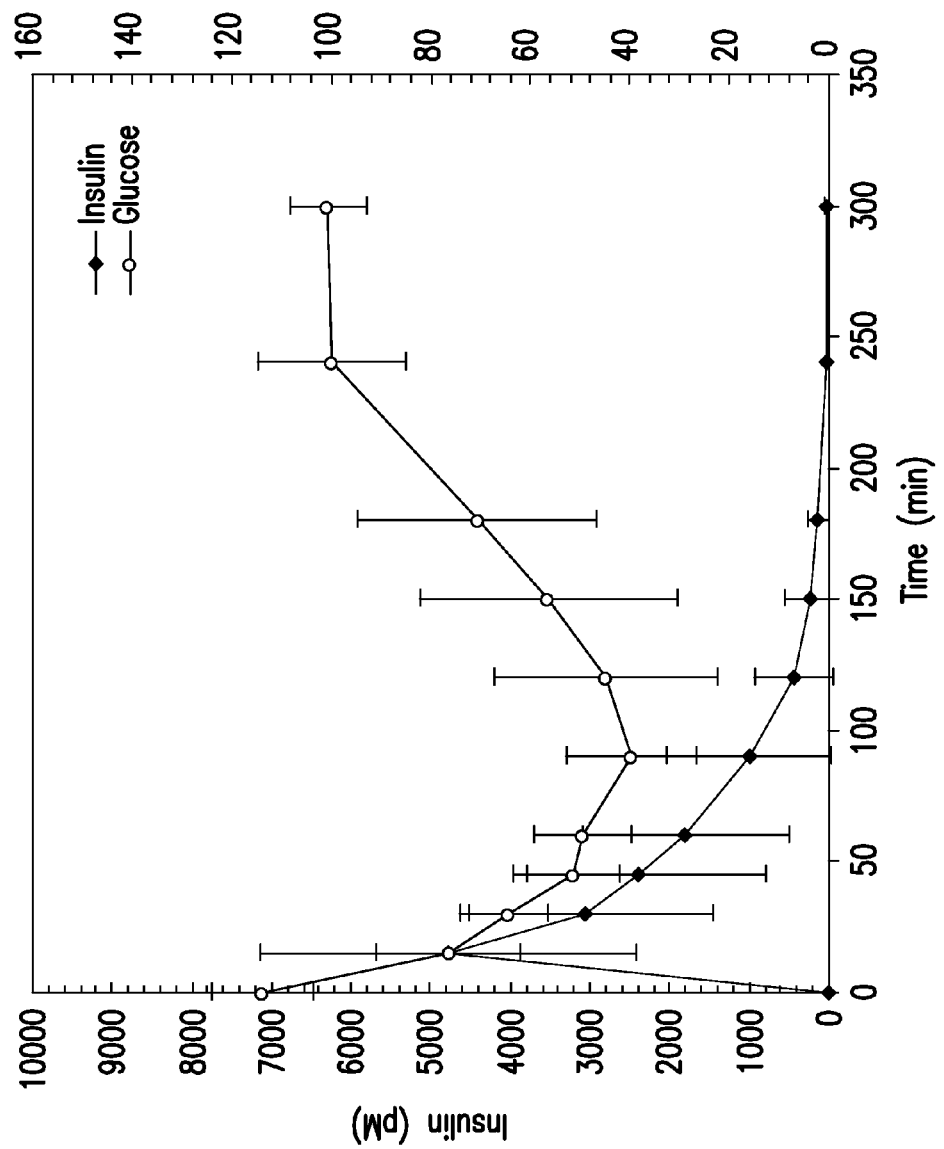
FIG. 16: Plot of serum insulin (left) and blood glucose (right) levels following subcutaneous injection in non-diabetic, male SD rats (n=3) at time 0 with TSAT-C6-AEM-2 conjugate I-1 (3.5 U/kg).
Figure 17:
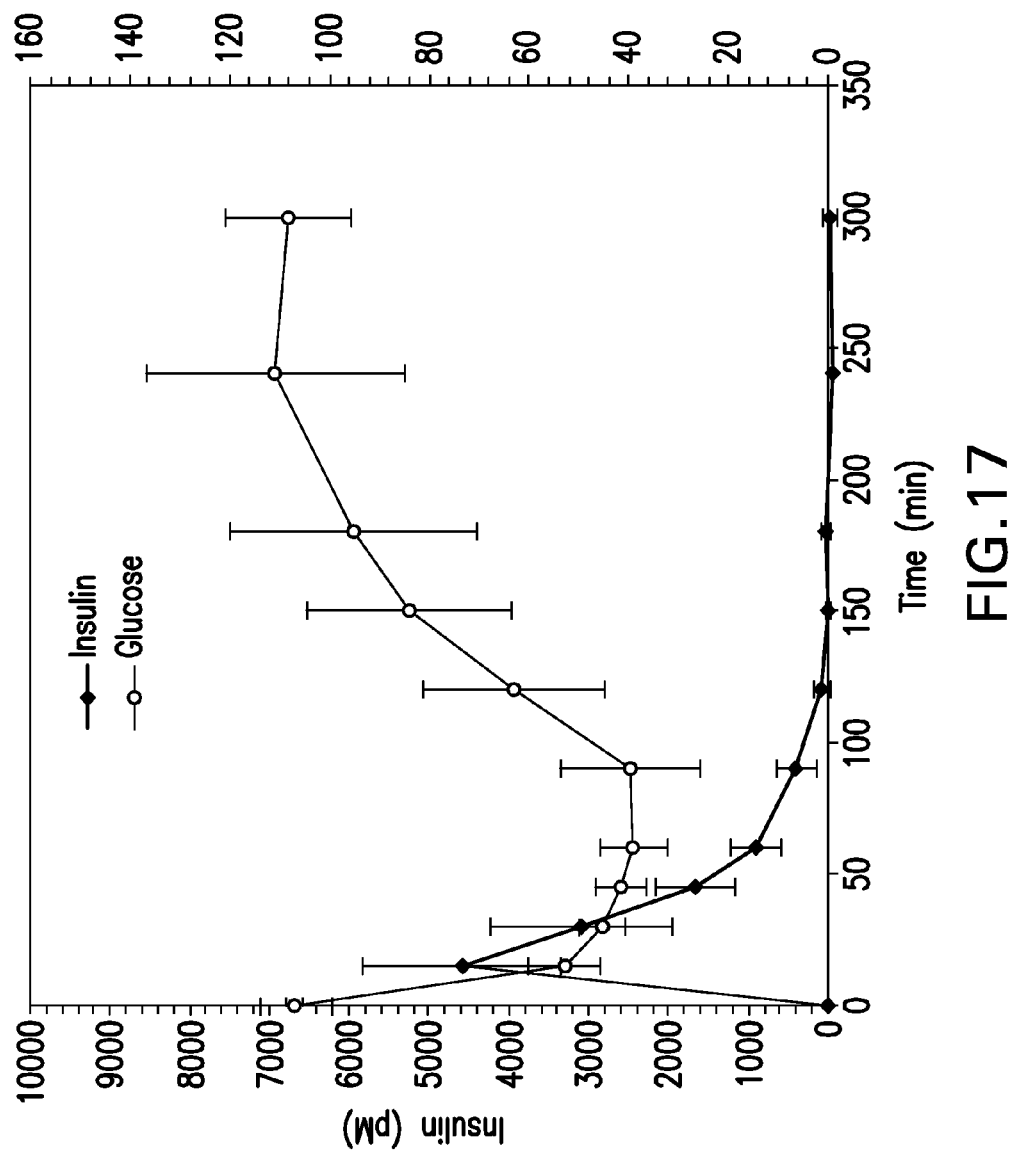
FIG. 17: Plot of serum insulin (left) and blood glucose (right) levels following subcutaneous injection in non-diabetic, male SD rats (n=3) at time 0 with TSAT-C6-AEBM-2 I-3 conjugate (5 U/kg).
Figure 18:
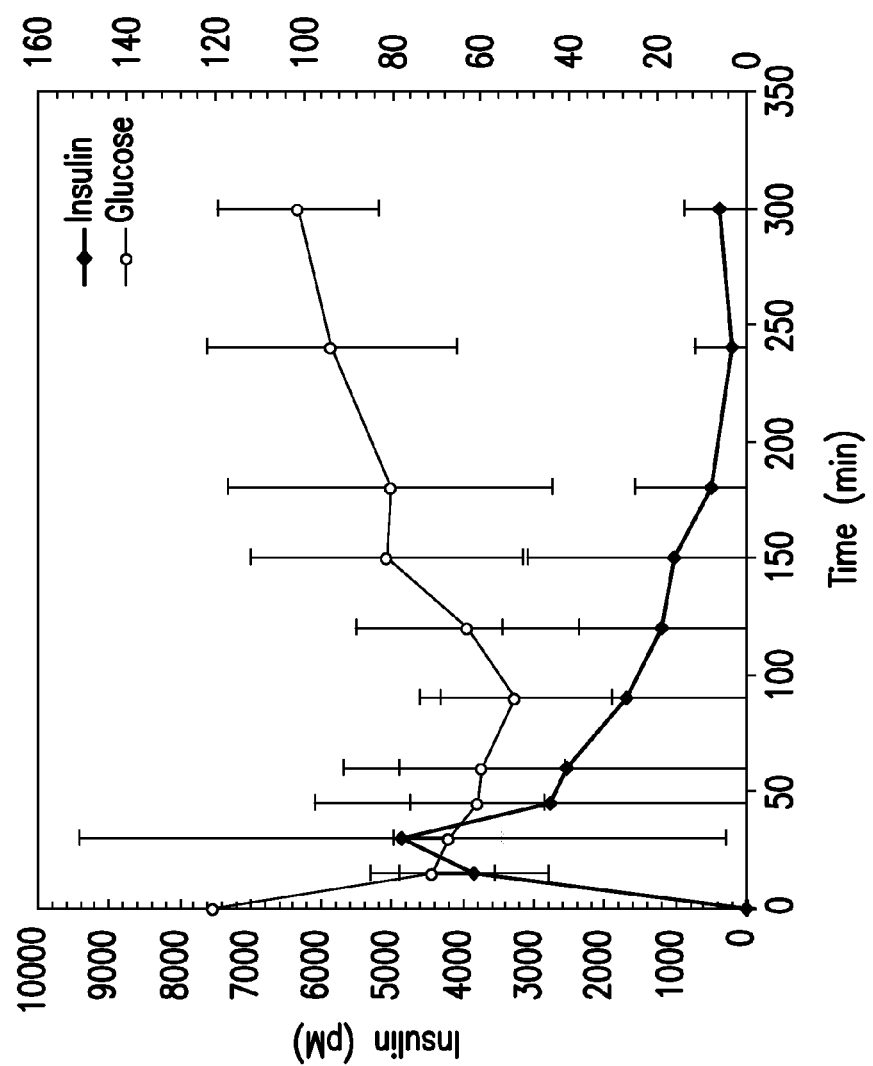
FIG. 18: Plot of serum insulin (left) and blood glucose (right) levels following subcutaneous injection in non-diabetic, male SD rats (n=3) at time 0 with TSAT-C6-AEBM-1 AETM-1 conjugate I-4 (5 U/kg).
Figure 19:
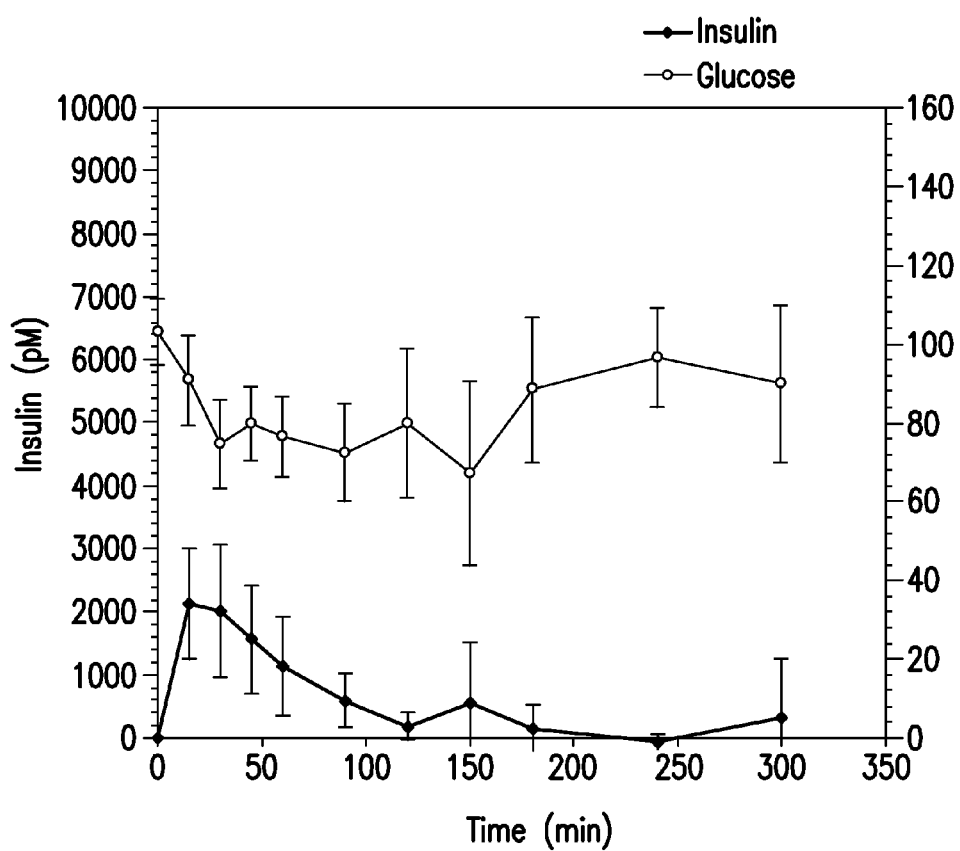
FIG. 19: Plot of serum insulin (left) and blood glucose (right) levels following subcutaneous injection in non-diabetic, male SD rats (n=3) at time 0 with TSAT-C6-AETM-2 conjugate I-2 (5 U/kg).

Examples 13-17 describe experiments that were performed with some of the exemplary synthetic conjugates of FIG. 15A to 15Q.

Example 13

Effect of Ligand on Bioactivity

This example compares the blood glucose profiles obtained for a series of subcutaneously administered exemplary conjugates. The ligand composition varies across the conjugates to cover a range of affinities: AEM-2, AEBM-2, AETM-1-AEBM-1 and AETM-2 (from lowest to highest affinity). The insulin conjugates are shown as I-1, I-2, I-3, and I-4 in FIG. 15A to 15C, respectively. In each case, the conjugates were injected at 5 U/kg (3.5 U/kg for AEM-2) behind the neck of fasted normal non-diabetic rats (Male Sprague-Dawley, 400-500 gm, n=6). Blood samples were collected via tail vein bleeding at 0 minutes and at 30, 60, 90, 120, 150, 180, 210, 240, and 300 minutes after injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (Human Insulin ELISA, Mercodia, Uppsala, Sweden).

FIGS. 16-19 show the blood glucose levels alongside the serum insulin levels for each of the four conjugates tested. These results show quite clearly that the reduced glucose response for conjugates with higher affinity ligands results from the reduced PK profile of the conjugate (compare FIG. 16 for AEM-2 with FIG. 19 for AETM-2).

Example 14

Mechanism Verification and Glucose-Responsive Performance in Miniature Swine

This example investigates the sugar-dependent in vivo elimination rate of certain exemplary conjugates in human-representative, non-diabetic, male miniature swine (Yucatan strain), also called "minipigs" herein. A subset of insulin-conjugates summarized in FIG. 1 were tested to initially determine the effects of sugar affinity and multivalency on sugar-dependent elimination rates. The conjugates are shown in FIGS. 6 and 15 as I-6, I-7 and I-11.

In each experiment, the insulin-conjugate was dosed i.v. at 0.1 U/kg into non-diabetic, dual-vascular access ported minipigs and blood was collected at frequent time intervals post-injection. To determine the serum elimination rate in the presence of glucose, a sterile 50% w/v glucose solution was infused i.v. into one port using a syringe pump one hour prior to administering the insulin-conjugate, and the rate was adjusted throughout the entire experiment to ensure that the blood glucose levels in the animal remained at or near 400 mg/dl (typically 80-150 ml/h). To determine the serum elimination rate in the presence of a-MM, the glucose solution was replaced with a sterile 25% w/v a-MM solution and the pump infusion rate held constant throughout the experiment at 80 ml/h. In each case, the resulting insulin-conjugate concentration vs. time data was fit with the sum of two independent decaying exponentials (C(t)=a exp(-$k_a$t) (3 exp(-$k_p$t)) according to the two-compartment model.

At 400 mg/dl the high levels of endogenous glucose-induced porcine insulin crossreacted with our insulin-conjugate immunoassay. As such, the PK results from the glucose infusion experiments required subtraction of values obtained from a porcine insulin-only assay leading to a particularly "noisy" set of data. Since a-MM does not induce endogenous porcine insulin secretion, data from the a-MM infusion studies were used as our primary indicator of sugar-responsive changes in insulin-conjugate half-life. Interestingly, in the pigs, the AETM-2 insulin-conjugate (I-6) showed only a modest 1.7× increase in $t_{1/2}$ in the presence of a-MM compared to a 4.0× increase in the rats (data not shown). However, in the pigs, the A1,B29-di-substituted AETM-2 insulin-conjugate (I-11) demonstrated an almost 10-fold increase in $t_{1/2}$ in the presence of a-MM (FIGS. 20 and 21). Tabular results for other conjugates are shown in FIG. 25.

The area over the glucose lowering curve for the i.v. dose of di-substituted AETM-2 insulin-conjugate (I-11) in the presence of a-MM was approximately 2.6× higher than in the absence of sugar (FIG. 22).

Figures 24A, 24B:
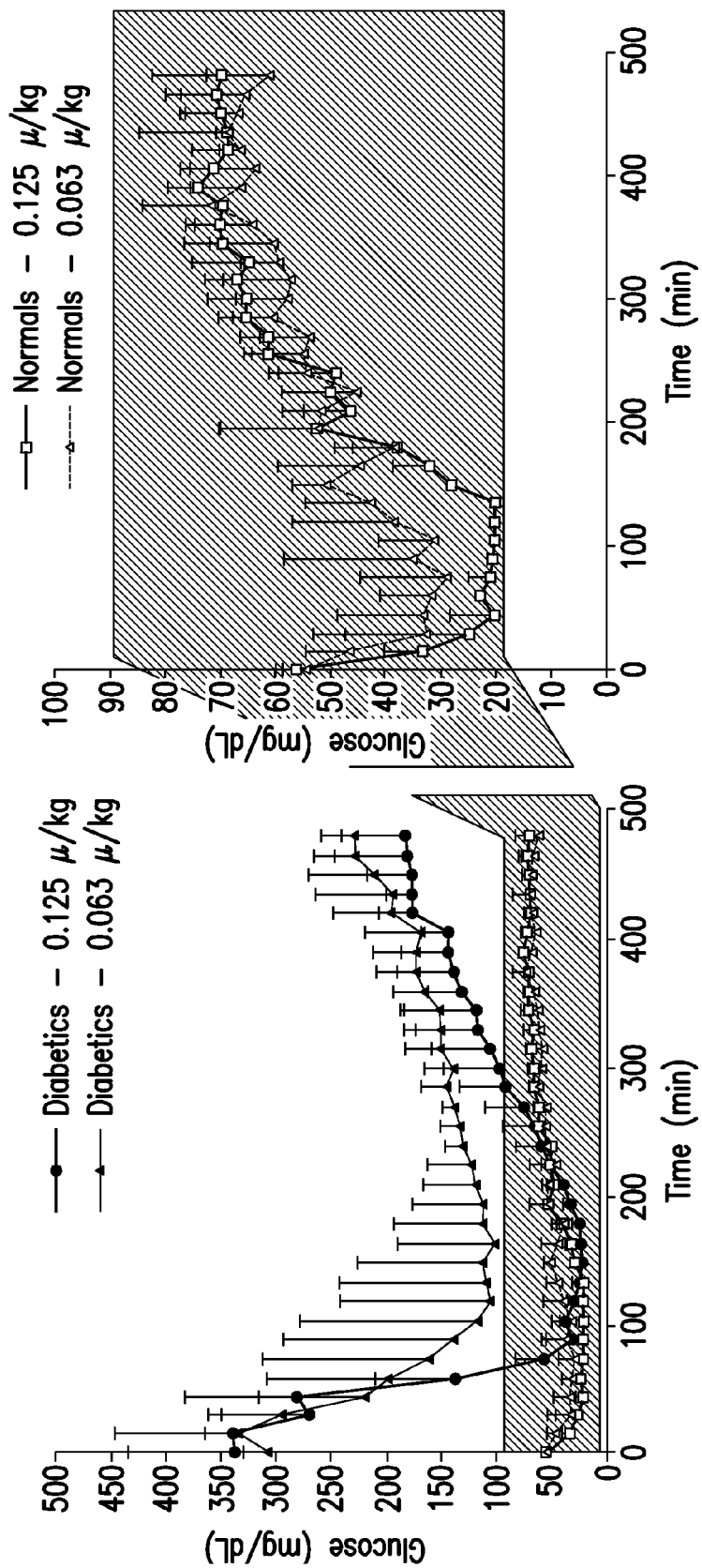
FIG. 24(b) scale is enlarged for clarity.
Figure 26:
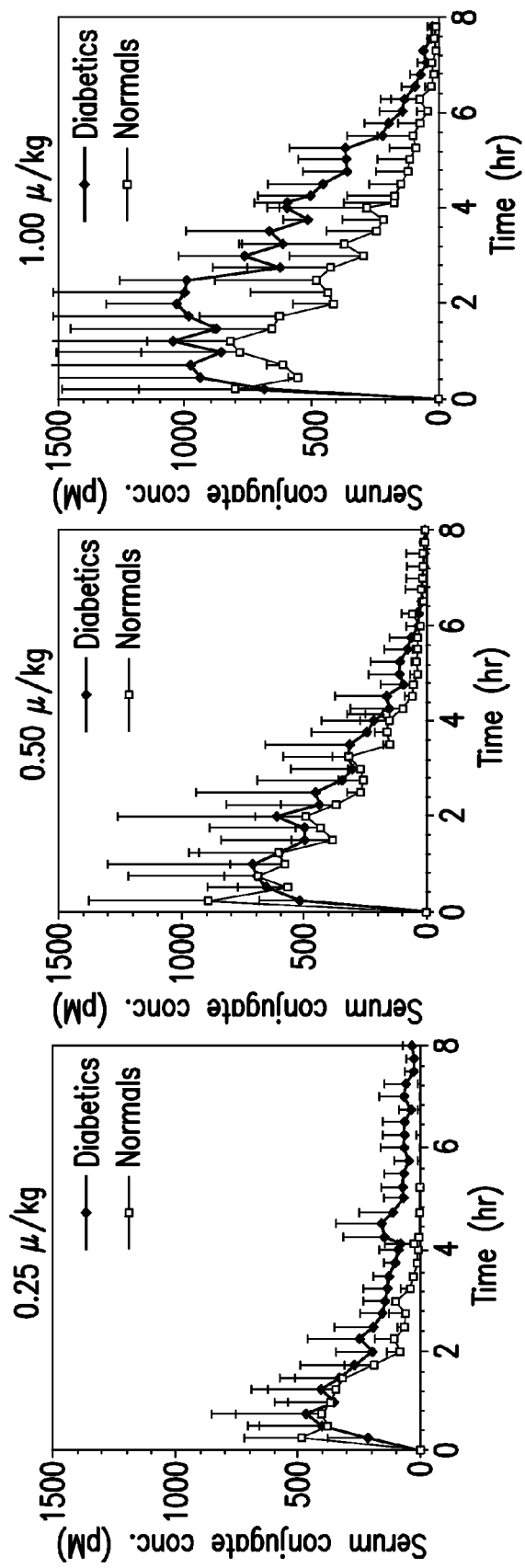
FIG. 26: Plot of serum insulin levels after a single subcutaneous injection of 0.25, 0.5 and 1 U/kg insulin conjugate I-11 in diabetic and normal minipigs.

Conjugate I-11 was injected sub-Q as a soluble solution at doses of 0.25, 0.50, and 1.00 U/kg in both non-diabetic, normoglycemic and alloxan-diabetic, hyperglycemic minipigs to determine its ability to lower glucose in diabetics without causing hypoglycemia in non-diabetic animals. The insulin-conjugate demonstrated a significant dose-dependent reduction in blood glucose levels in the diabetics with absolutely no hypoglycemia or signs of glucose-lowering in the non-diabetics (FIG. 23). In comparison, RHI injected at 0.063 and 0.125 U/kg caused significant glucose-lowering in the diabetic animals with noticeable hypoglycemia and significant glucose-lowering and hypoglycemia in the non-diabetic animals (FIG. 24). Based on these preliminary results, a single injection of approximately 0.5 U/kg of soluble insulin-conjugate I-11 provided hypoglycemia-free glucose control for 6-8 hours in diabetic minipigs. Serum elimination rates of sub-Q injected I-11 were determined in diabetic and normal minipigs (FIG. 26). Similar PK profiles were observed between diabetics and normals for all doses.

Taken together, these results demonstrate that an endogenous lectin-based mechanism exists in the minipigs that can be exploited through selection of sugar affinity and multivalency. It appears that insulin-conjugates with higher affinities and multivalencies provide improved hypoglycemia-free glycemic control in minipigs as compared to rats.

Example 15

Effect of a-MM on PK and Bioactivity of Conjugates I-14 and I-15

In this example, we set out to determine the pharmacokinetic and pharmacodynamic behavior of conjugates I-14 and I-15 (see FIGS. 15M and 15N, respectively, for conjugate structures). In each case, the same dose of conjugate (5 U/kg) was injected behind the neck of fasted normal non-diabetic rats (Male Sprague-Dawley, 400-500 gm, n=3). After a 15 minute delay a 4 g/kg dose of a-MM was injected IP. Blood samples were collected via tail vein bleeding at 0 minutes and at 30, 60, 90, 120, 150, 180, 210, 240, and 300 minutes after the initial conjugate injection. Blood glucose values were measured using commercially available test strips (Precision Xtra, Abbott Laboratories, Abbott Park, Ill.). In addition, blood from each timepoint was centrifuged at 4 C to collect the serum. Serum insulin concentrations were subsequently measured with a commercially available ELISA kit (ISO Insulin ELISA, Mercodia, Uppsala, Sweden). A control was performed by injecting saline instead of a-MM after 15 minutes.

Figure 27:
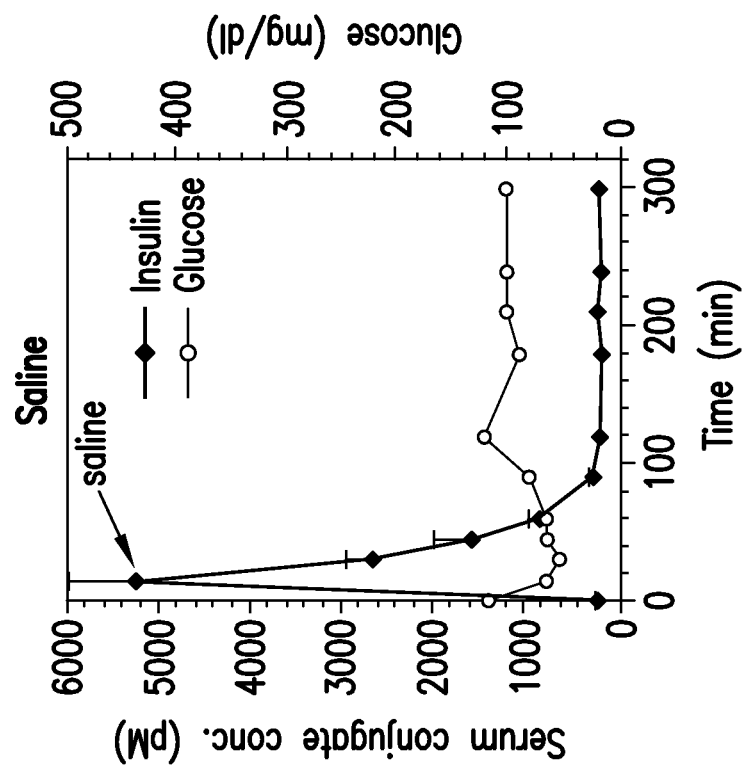
FIG. 27: Plot of serum insulin and blood glucose levels following subcutaneous injection in non-diabetic, male SD rats (n=3) at time 0 with TSPE-AEM-3 conjugate I-14 followed by IP injection of alpha-methyl mannose (left) or saline (right) after 15 minutes. Alpha-methyl mannose is a very high affinity saccharide which is capable of competing with AEM for binding to lectins such as Con A. As shown, the change in PK/PD profile that results from injection of alpha-methyl mannose is significant (p<0.05).
Figure 27:
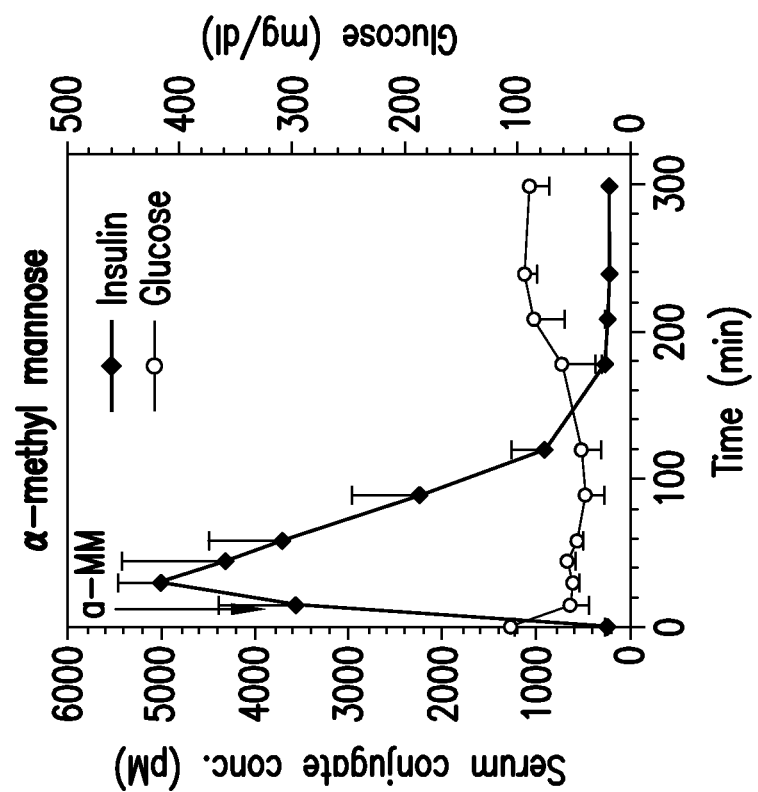

FIG. 27 shows the results obtained when a-MM was administered by IP injection 15 minutes after the sub-Q injection of I-14. As shown, the increase in PK/PD profile that resulted from injection of a-MM was very significant ($p<0.05$) for I-14 when compared to the saline injection control group.

Figure 28:
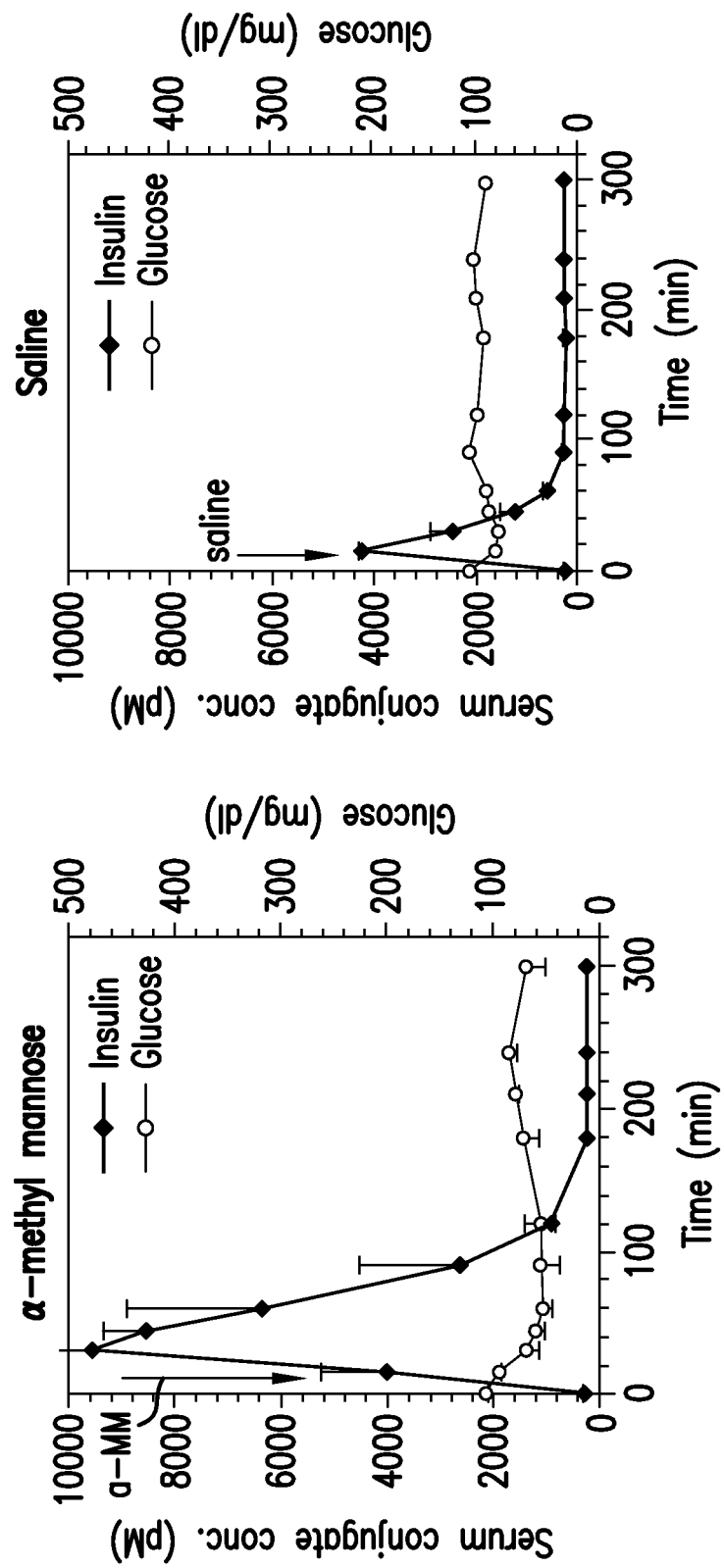
FIG. 28: Plot of serum insulin and blood glucose levels following subcutaneous injection in non-diabetic, male SD rats (n=3) at time 0 with TSPE-AETM-3 conjugate I-15 followed by IP injection of alpha-methyl mannose (left) or saline (right) after 15 minutes. Alpha-methyl mannose is a very high affinity saccharide which is capable of competing with AEM for binding to lectins such as Con A. As shown, the change in PK/PD profile that results from injection of alpha-methyl mannose is significant (p<0.05).

FIG. 28 shows the results obtained when a-MM was administered by IP injection 15 minutes after the sub-Q injection of I-15. As shown, the increase in PK/PD profile that resulted from injection of a-MM was very significant (p<0.05) for I-15 when compared to the saline injection control group.

Example 16

In Vivo Half Life/Elimination Rate Comparison

The results obtained in Example 15 are consistent with the exemplary conjugates being eliminated from the body via a lectin dependent mechanism that can be disrupted by the presence of a competitive saccharide. In order to explore this mechanism in more detail, we conducted the following experiments on exemplary conjugates to determine the rate at which they were cleared from serum in vivo versus unconjugated insulin.

In each case the soluble conjugate was dosed at 0.4 mg conjugate/kg body weight into dual jugular vein cannulated male Sprague-Dawley rats (Taconic, JV/JV, 350-400 g, n=3). A sterile conjugate solution or control insulin was injected intravenously via one JV cannula, followed immediately by a chase solution of heparin-saline to ensure that all of the conjugate dose was administered into the animal. The second cannula was used to collect blood samples at t=0 (pre-dose), and at 1, 2, 4, 8, 15, 30, 60, 90, 120, and 180 minutes post-dose.

Blood glucose values were measured using commercially available test strips (Precision Xtra, Abbott Laboratories, Abbott Park, Ill.). In addition, blood from each timepoint was centrifuged at 4 C to collect the serum. Serum insulin or serum conjugate concentrations were subsequently measured with a commercially available ELISA kit (Iso-Insulin ELISA, Mercodia, Uppsala, Sweden).

The serum concentration of either RHI or the conjugates were plotted as a function of time following the intravenous injection. The data was fit using a two-compartment bi-exponential model with the following general formula: $C(t)=A_o \text{EXP}(-at)+B_o \text{EXP}(-bt)$ where t is time, C(t) is the concentration in serum as a function of time, $A_o$ is the first compartment concentration constant, a is the first compartment exponential time constant, $B_o$ is the second compartment concentration constant, and b is the second compartment exponential time constant.

The following table summarizes the t½ parameters for RHI and the conjugates tested:

| Formulation | t1/2 (a) | t1/2 (b) | Ratio to RHI t1/2 (a) | Ratio to RHI t1/2 (b) |
|---|---|---|---|---|
| RHI | 0.76 | 11.46 | 1.00 | 1.00 |
| I-14: TSPE-AEM-3 | 0.66 | 2.62 | 0.87 | 0.23 |
| I-15: TSPE-AETM-3 | 0.22 | 1.33 | 0.29 | 0.12 |

This data is consistent with the hypothesis that the exemplary conjugates are eliminated from serum more rapidly than unconjugated insulin, the extent of which is governed by the affinity of the particular conjugate for the endogenous lectin and the number of ligands substituted per conjugate. Furthermore, the a-MM induced increase in PK/PD profiles demonstrated in Example 15 correlates well with the reduction in Phase b half-life for each of the conjugates tested.

Example 17

Performance of Long Acting Conjugates Prepared from Conjugates with Varying Ligand Affinity and Multivalency In this example, we set out to determine the time action and glucose-responsive PK profile of long-acting formulations of conjugates I-14 and I-15 (see FIGS. 15M and N, respectively, for conjugate structures). The following long-acting formulation was used for each conjugate:

| Component | Variable | Volume (ml) |
|---|---|---|
| Conjugate solution at 2.7 mg/ml | unmodified insulin = 16.7% | 1.000 |
| 250 mM HEPES buffered saline | NaCl concentration = 1.5 M | 0.111 |
| Zinc acetate solution | Zinc concentration = 4.6 mg/ml | 0.124 |
| Cresol solution in water | 3% v/v | 0.159 |
| pH 7.2 Protamine solution in 25 mM HEPES buffered saline | Protamine concentration = 12.5 mg/ml | 4 × 0.194 aliquots |

Figure 29:
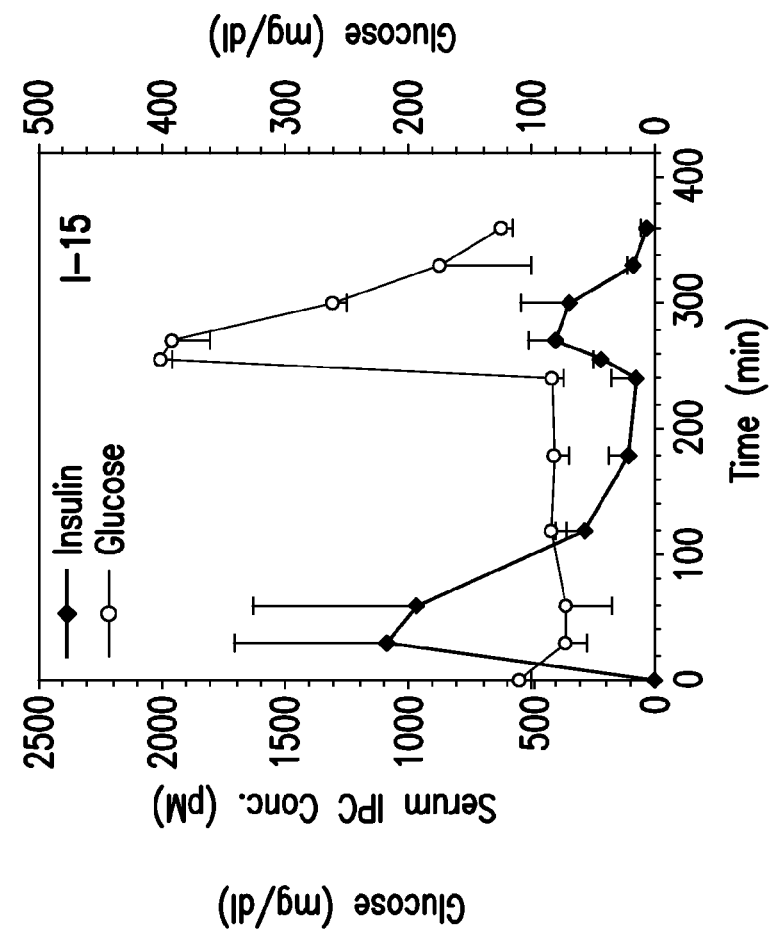
FIG. 29: Plot of serum insulin (♦) and blood glucose (○) levels following subcutaneous injection in non-diabetic, male SD rats (n=3 per dose) at time 0 with long-acting conjugate formulations followed by IP injection of glucose (4 g/kg) at 240 minutes. The conjugates are TSPE-AEM-3 (I-14) and TSPE-AETM-3 (I-15).
Figure 29:
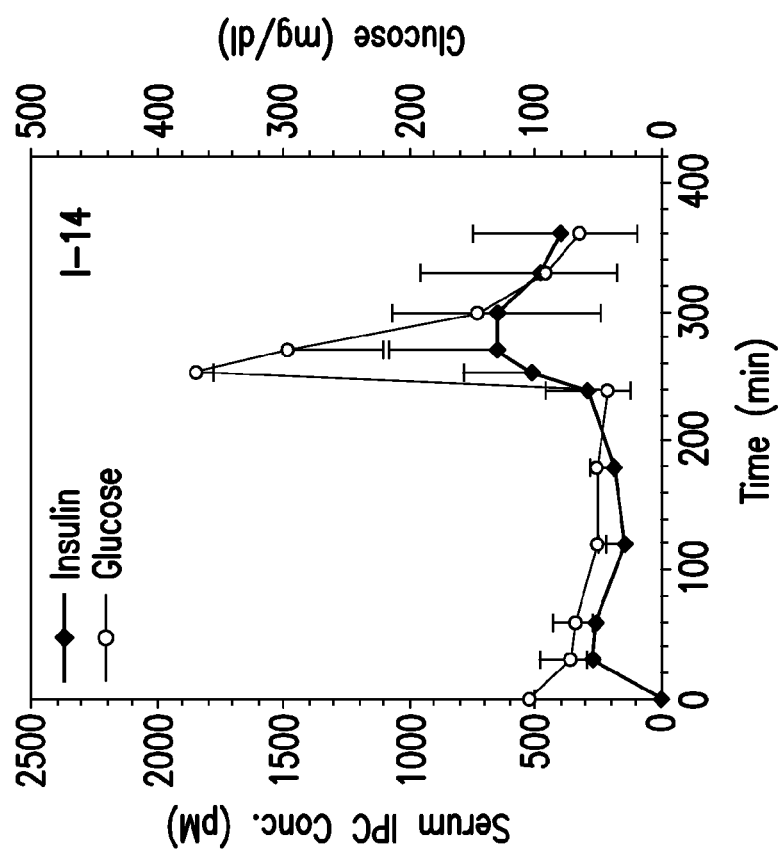

The four hour IP glucose injection (4 g/kg) experiments were performed by dosing 15 U/kg (body weight in grams/1.87=microliters of injection volume) of each of the conjugates described above. As shown in FIG. 29, both conjugates exhibited a protracted absorption profile with some element of increase in measured serum insulin concentration following the 4 hour glucose injection. It appears that there was some significant conjugate absorption in the first four hours after injection of the long acting TSPE-AETM-3 conjugate I-15. The TSPE-AEM-3 conjugate I-14 exhibited a flat absorption profile. These results correlate well with the fact that the half-lives of these conjugates are all less than unmodified insulin as described in Example 16 and that each of them demonstrates an a-MM-induced increase in PK/PD profile as described in Example 15.

OTHER EMBODIMENTS

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A recombinantly expressed insulin polypeptide comprising
   (a) an A-peptide comprising the amino acid sequence of SEQ ID NO:18 or 47, and;
   (b) a B-peptide comprising the amino acid sequence of SEQ ID NO: 43, 44, 45, or 46,
   wherein the insulin polypeptide includes a disulfide bridge between positions 6 and 11 of the A-peptide, a disulfide bridge between position 7 of the A-peptide and position 7 of the B-peptide, and a disulfide bridge between position 20 of the A-peptide and position 19 of the B-peptide, wherein the asparagine (Asn) residue at position 28 of SEQ ID NO:43, position 28 of SEQ ID NO:44, position 1 of SEQ ID NO:45, position 1 and 28 of SEQ ID NO:46, and position 1 of SEQ ID NO:47 is conjugated to an N-glycan.

2. The polypeptide of claim 1, wherein the A-peptide and B-peptide are comprised within a contiguous amino acid sequence.

3. The polypeptide of claim 1, wherein the N-linked glycan is a branched trimannose.

4. A pharmaceutical formulation comprising a recombinantly expressed insulin polypeptide comprising
   (a) an A-peptide comprising the amino acid sequence of SEQ ID NO:18 or 47, and;
   (b) a B-peptide comprising the amino acid sequence of SEQ ID NO: 43, 44, 45, or 46,
   wherein the insulin polypeptide includes a disulfide bridge between positions 6 and 11 of the A-peptide, a disulfide bridge between position 7 of the A-peptide and position 7 of the B-peptide, and a disulfide bridge between position 20 of the A-peptide and position 19 of the B-peptide, wherein the asparagine (Asn) residue at position 28 of SEQ ID NO:43, position 28 of SEQ ID NO:44, position 1 of SEQ ID NO:45, position 1 and 31 of SEQ ID NO:46, and position 1 of SEQ ID NO:47 is conjugated to an N-glycan; and a pharmaceutically acceptable carrier.

5. The pharmaceutical formulation of claim 4, wherein the A-peptide and B-peptide are comprised within a contiguous amino acid sequence.

6. The pharmaceutical formulation of claim 4, wherein the N-linked glycan is a branched trimannose.

7. The pharmaceutical formulation of claim 4, wherein the N-linked glycan is $GlcNAc_2Man_5$ where GlcNAc is β-linked N-acetyl glucosamine and Man is mannose.

* * * * *